US012662677B2

(12) United States Patent
Barbas, III et al.

(10) Patent No.: US 12,662,677 B2
(45) Date of Patent: Jun. 23, 2026

(54) CHIMERIC POLYPEPTIDES HAVING TARGETED BINDING SPECIFICITY

(71) Applicant: The Scripps Research Institute, La Jolla, CA (US)

(72) Inventors: Carlos F. Barbas, III, La Jolla, CA (US); Andrew Mercer, Poolesville, MD (US); Brian M. Lamb, San Diego, CA (US); Thomas Gaj, Solana Beach, CA (US)

(73) Assignee: The Scripps Research Institute, La Jolla, CA (US)

( * ) Notice: Subject to any disclaimer, the term of this patent is extended or adjusted under 35 U.S.C. 154(b) by 808 days.

(21) Appl. No.: 17/951,849

(22) Filed: Sep. 23, 2022

(65) Prior Publication Data

US 2023/0304022 A1 Sep. 28, 2023

Related U.S. Application Data

(62) Division of application No. 17/031,149, filed on Sep. 24, 2020, now Pat. No. 11,466,277, which is a division of application No. 15/878,043, filed on Jan. 23, 2018, now Pat. No. 10,829,766, which is a division of application No. 14/425,944, filed as application No. PCT/US2013/058100 on Sep. 4, 2013, now Pat. No. 9,902,962.

(60) Provisional application No. 61/818,364, filed on May 1, 2013, provisional application No. 61/753,763, filed on Jan. 17, 2013, provisional application No. 61/696,689, filed on Sep. 4, 2012.

(51) Int. Cl.
| | |
|---|---|
| *C12N 15/62* | (2006.01) |
| *C12N 9/16* | (2006.01) |
| *C12N 9/22* | (2006.01) |
| *C12N 15/63* | (2006.01) |

(52) U.S. Cl.
CPC .............. *C12N 15/62* (2013.01); *C12N 9/16* (2013.01); *C12N 9/22* (2013.01); *C12N 15/63* (2013.01); *C07K 2319/80* (2013.01)

(58) Field of Classification Search
CPC . C12N 15/62; C12N 9/16; C12N 9/22; C12N 15/63; C07K 2319/80
See application file for complete search history.

(56) References Cited

U.S. PATENT DOCUMENTS

| | | |
|---|---|---|
| 9,902,962 B2 | 2/2018 | Barbas, III |
| 10,829,766 B2 | 11/2020 | Barbas, III |
| 2010/0086532 A1 | 4/2010 | Barbas, III |
| 2011/0301073 A1 | 12/2011 | Gregory |
| 2012/0178131 A1 | 7/2012 | Zhang |
| 2012/0270273 A1 | 10/2012 | Gregory |
| 2013/0196373 A1 | 8/2013 | Gregory |
| 2018/0230474 A1 | 8/2018 | Barbas, III |
| 2021/0147854 A1 | 5/2021 | Barbas |

FOREIGN PATENT DOCUMENTS

| | | |
|---|---|---|
| WO | 2008/006028 A1 | 1/2010 |
| WO | 2011/072246 A1 | 6/2011 |
| WO | 2011/146121 A1 | 11/2011 |
| WO | 2012/033462 A1 | 3/2012 |
| WO | 2013/074999 A1 | 5/2013 |
| WO | 2013/101877 A2 | 7/2013 |
| WO | 2014039585 A1 | 3/2014 |
| WO | PCT/US2013/058100 | 3/2014 |

OTHER PUBLICATIONS

Mukaihara, et al., Genetic screening of Hrp type III-related pathogenicity genes controlled by the HrpB transcriptional activator in Ralstonia solanacearum, Molecular Microbiology, Jul. 28, 2004, pp. 863-875, vol. 54(4).
Ochiai et al., Genome Sequence of *Xanthomonas oryzae* pv. *oryzae* Suggests Contributions of Large Numbers of Effector Genes and Insertion Sequences to its Race Diversity, JARQ, 2005, pp. 275-287, vol. 39(4).
Yu et al., Colonization of Rice Leaf Blades by an African Strain of *Xanthomonas oryzae* pv. *oryzae* Depends on a New TAL Effector That Induces the Rice Nodulin-3 Os11N3 Gene, Molecular Plant-Microrobe Interactions, 2011, pp. 1102-1113, vol. 24(9).
Cermak et al., Nucl. Acids Res. 39(12): e82, 2011.
Gaj, et al., ZFN, TALEN, and CRISPR/Cas-based methods for genome engineering, Trends in Biotechnology, 397-405, Jul. 3, 2013.
Hopkins et al., Mol. Plant-Microbe Interactions 1992.
De Lange et al., New Phytologist 199:773, 2013.
Lamb, et al., Directed evolution of the TALE N-Terminal domain for recognition of all 5' bases, Nucleic Acids Research, 9779-9785, Nov. 2013.
Lamb, et al., Supplemental Materials, Nucleic Acids Research, 9779-9785, Nov. 2013.
Meckler et al., Nucl. Acids Res. 2013.
Mercer, et al., Chimeric TALE recombinases with programmable DNA sequence specificity, Nucleic Acids Research, 11163-11172, Nov. 1, 2012.

(Continued)

*Primary Examiner* — Suzanne M Noakes
*Assistant Examiner* — Ciara A McKnight
(74) *Attorney, Agent, or Firm* — Hugh Wang; Thomas Fitting

(57) ABSTRACT

Disclosed herein are chimeric polypeptides, including compositions thereof, expression vectors, and methods of use thereof, for the generation of transgenic cells, tissues, plants, and animals. The compositions, vectors, and methods of the present invention are also useful in gene therapy techniques.

10 Claims, 38 Drawing Sheets

Specification includes a Sequence Listing.

(56) References Cited

OTHER PUBLICATIONS

Miller, et al., A TALE nuclease architecture for efficient genome editing, Nature Biotechnology, 143-148, Feb. 2011.

Miller et al., 2011 Suppl. Information.

Mukaihara, et al., Genetic screening of Hrp type III-related pathogenicity genes controlled by the HrpB transcriptional activator in Ralstonia solanacearum, Molecular Microbio.

Mussolino, et al., A novel TALE nuclease scaffold enables high genome editing activity in combination with low toxicity, Nucleic Acids Research, 9283-9293, Aug. 3, 2011.

Nga-Sze Mak et al., Science 2012.

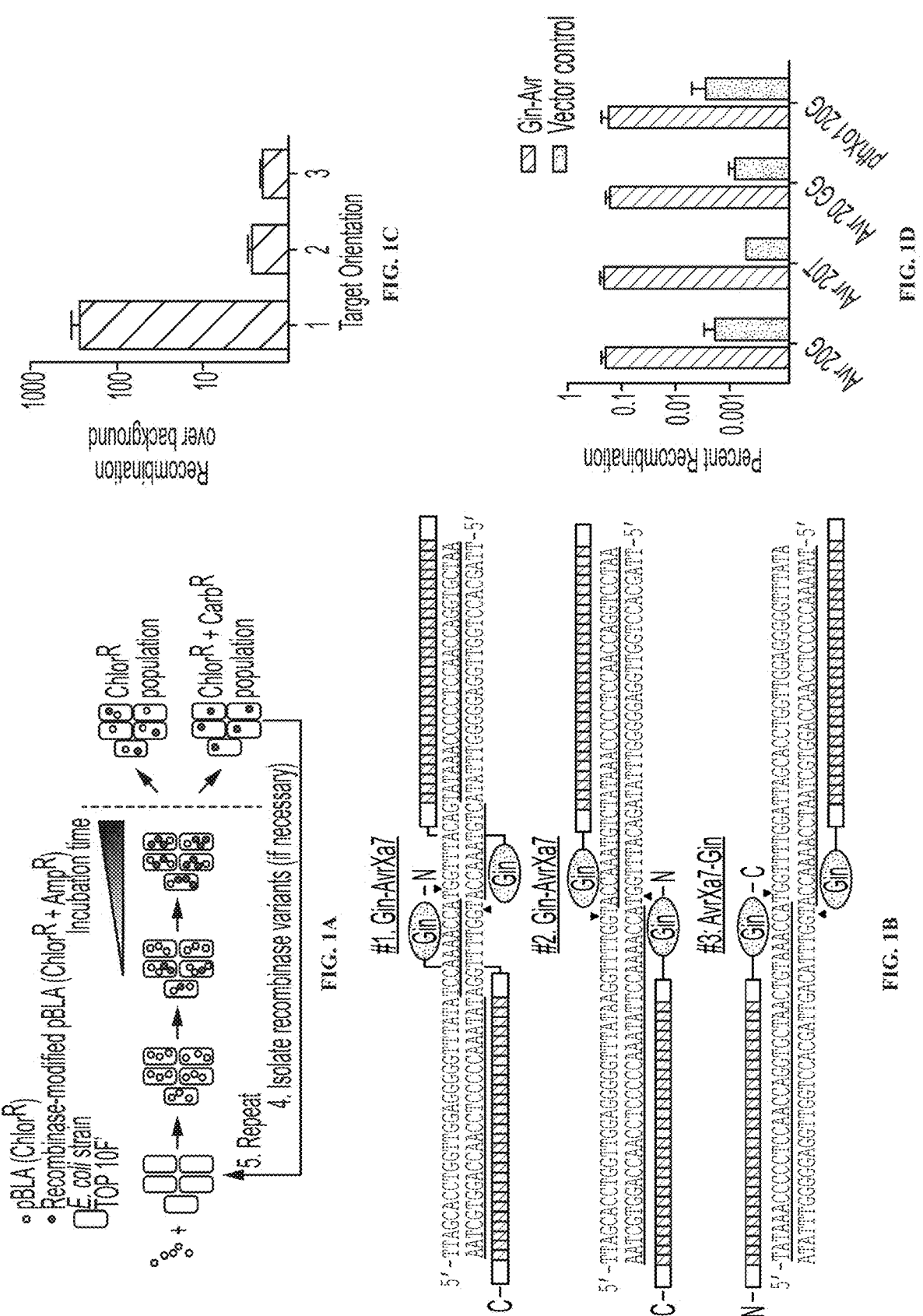

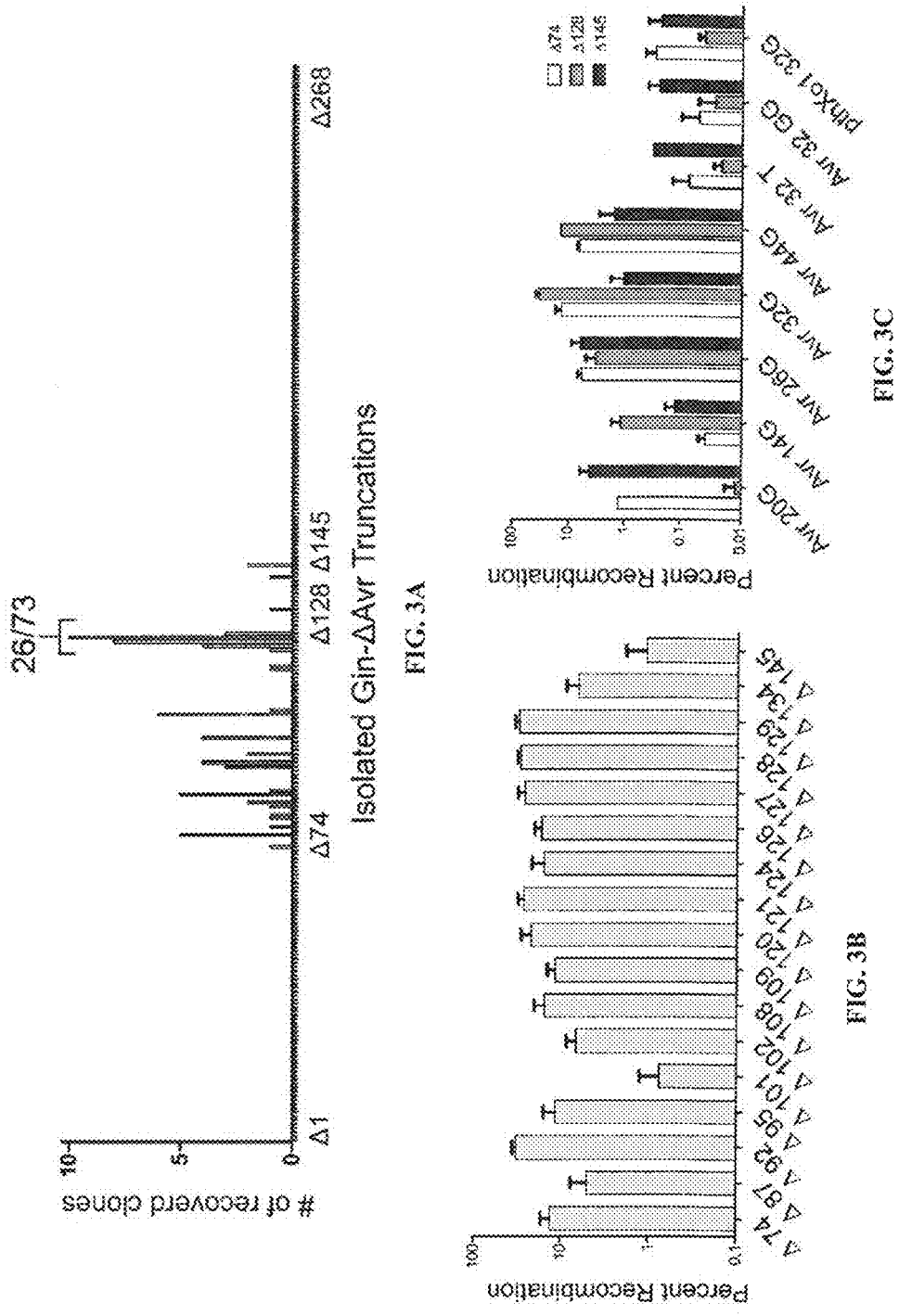

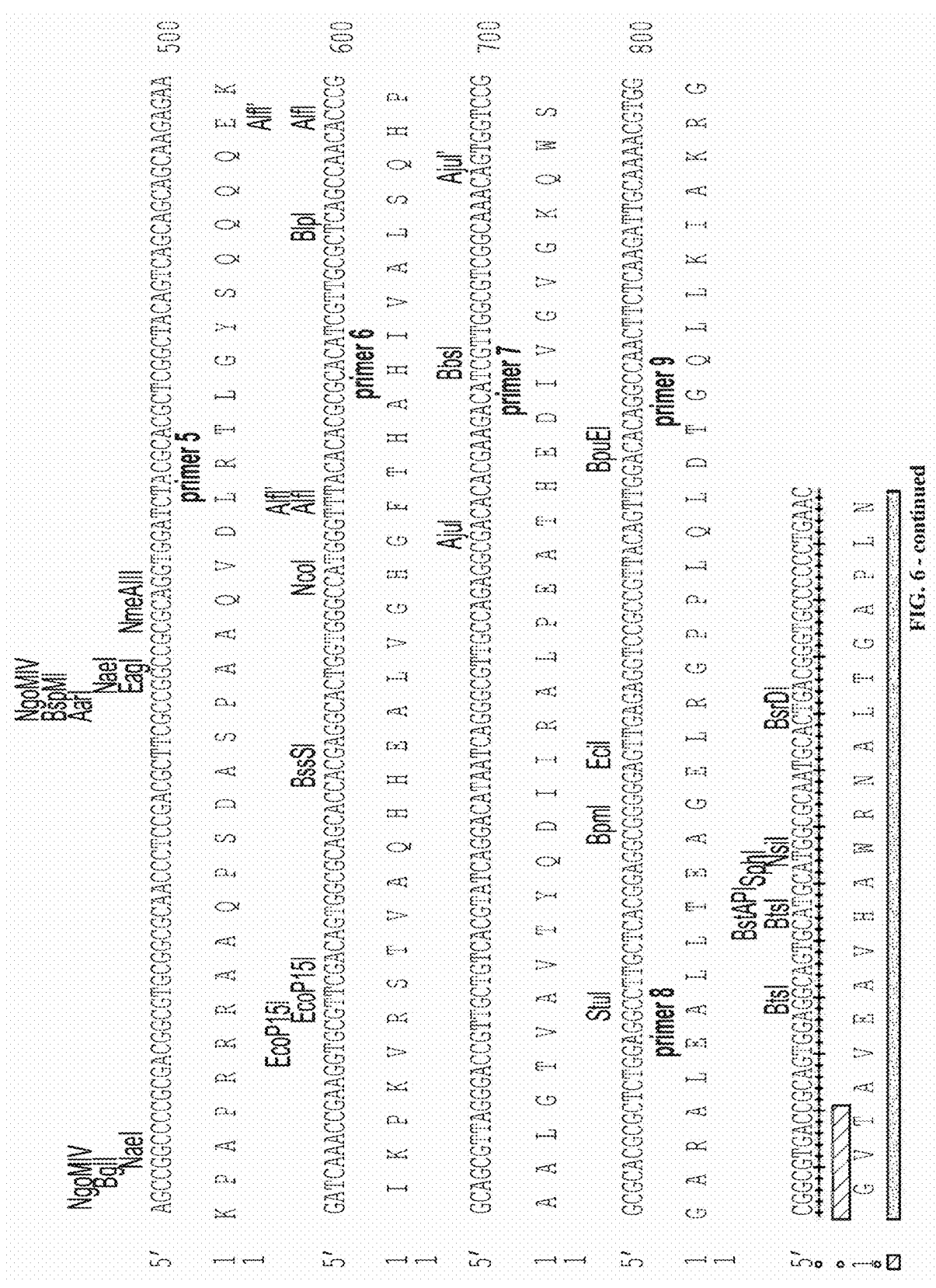
FIG. 6 – continued

FIG. 7

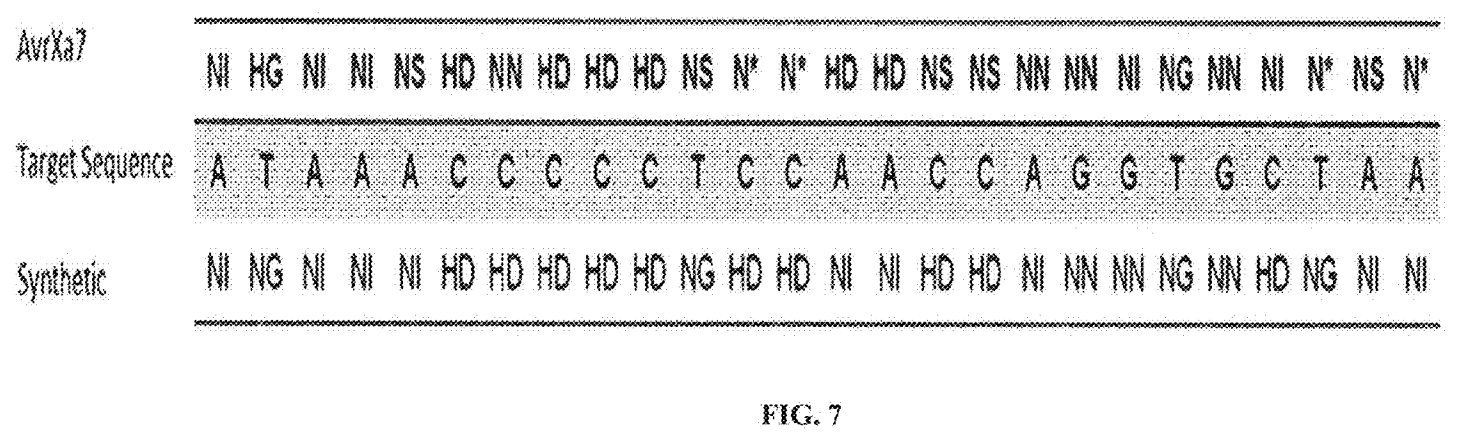

TALE and TALER sequences
AvrXa7 protein:

MDPIRSRTPSPARELLPGPQPDRVQPTADRGGAPPAGGPLDGLPARRTMSRTRLPSPPAPSPA
FSAGSFSDLLRQFDPSLLDTSLLDSMPAVGTPHTAAAPAECDEVQSGLRAADDPPPTVRVAV
TAARPPRAKPAPRRRAAQPSDASPAAQVDLRTLGYSQQQQEKIKPKVRSTVAQHHEALVGH
GFTHAHIVALSQHPAALGTVAVTYQDIIRALPEATHEDIVGVGKQWSGARALEALLTEAGEL
RGPPLQLDTGQLLKIAKRGGVTAVEAVHAWRNALTGAPLNLTPDQVVAIASNIGGKQALET
VQRLLPVLCQDHGLTPDQVVAIASHGGGKQALETVQRLLPVLCQDHGLTPDQVVAIASNIG
GKQALETVQRLLPVLCQAHGLTPDQVVAIASNIGGKQALETVQRLLPVLCQDHGLTPAQVV
AIASNSGGKQALETVQRLLPVLCQDHGLTPDQVVAIASHDGGKQALETLQRLLPVLCQDHG
LTPDQVVAIANNNGGKQALETLQRLLPVLCQDHGLTPDQVVAIASHDGGKQALETVQRLLP
VLCQDHGLTPDQVVAIASHDGGKQALETVQRLLPVLCQDHGLTPAQVVAIASHDGGKQAL
ETVQRLLPVLCQDHGLTPDQVVAIASNSGGKQALETVQRLLPVLCQDHGLTPDQVVAIASN
GGKQALETVQRLLPVLCQDHGLTPDQVVAIASNGGKQALETVQRLLPVQRLLPVLCQDHG
LTQDQVVAIASHDGGKQALETVQRLLPVLCQDHGLTPDQVVAIASHDGGKQALETVQRLLP
VLCQDHGLTPDQVVAIASNSGGKQALETVQRLLPVLCQDHGLTPDQVVAIASNSGGKQALE
TVQRLLPVLCQDHGLTPDQVVAIASNNGGKQALETVQRLLPVLCQDHGLTPDQVVAIANN
NGGKQALETVQRLLPVLCQDHGLTPAQVVAIASNIGGKQALETVQRLLPVLCQDHGLTLDQ
VVAIASNGGSKQALETVQRLLPVLCQDHGLTPDQVVAIANNNGGKQALETVQRLLPVLCQ
DHGLTPDQVVAIASNIGGKQALETVQRLLPVLCQDHGLTLDQVVAIASNGGKQALETVQRL
LPVLCQDHGLTPNQVVAIASNSGGKQALETVQRLLPVLCQDHGLTPNQVVAIASNGGKQAL
ESIVAQLSRPDPALAALTNDHLVALACLGGRPALDAVKKGLPHAPELIRRINRRIPERTSHRV
PDLAHVVRVLGFFQSHSHPAQAFDDAMTQFEMSRHGLVQLFRRVGVTEFEARYGTLPPASQ
RWDRILQASGMKRAKPSPTSAQTPDQASLHAFADSLERDLDAPSPMHEGDQTRASSRKRSR
SDRAVTGPSTQQSFEVRVPEQQDALHLPLSWRVKRPRTRIGGGLPDPGTPIAADLAASSTVM
WEQDAAPFAGAADDFPAFNEEELAWLMELLPQSGSVGGTI

FIG. 8

AvrXa7 gene:

ATGGATCCCATTCGTTCGCGCACGCCAAGTCCTGCCCGCGAGCTTCTGCCCGGACCCCA
ACCGGATAGGGTTCAGCCGACTGCAGATCGGGGGGGGGCTCCGCCTGCTGGCGGCCCC
CTGGATGGCTTGCCCGCTCGGCGGACGATGTCCCGGACCCGGCTGCCATCTCCCCCTGC
GCCCTCGCCTGCGTTCTCGGCGGGCAGCTTCAGCGATCTGCTCCGTCAGTTCGATCCGTC
GCTTCTTGATACATCGCTTCTTGATTCGATGCCTGCCGTCGGCACGCCGCATACAGCGGC
TGCCCCAGCAGAGTGCGATGAGGTGCAATCGGGTCTGCGTGCAGCCGATGACCCGCCAC
CCACCGTGCGTGTCGCTGTCACTgcgGCGCGGCCGCCGCGCGCCAAGCCGGCCCCGCGAC
GGCGTGCGGCGCAACCCTCCGACGCTTCGCCGGCCGCGCAGGTGGATCTACGCACGCTC
GGCTACAGTCAGCAGCAGCAAGAGAAGATCAAACCGAAGGTGCGTTCGACAGTGGCGC
AGCACCACGAGGCACTGGTGGGCCATGGGTTTACACACGCGCACATCGTTGCGCTCAGC
CAACACCCGGCAGCGTTAGGGACCGTTGCTGTCACGTATCAGGACATAATCAGGGCGTT
GCCAGAGGCGACACGAAGACATCGTTGGCGTCGGCAAACAGTGGTCCGGCGCACGC
GCTCTGGAGGCCTTGCTCACGGAGGCGGGGGAGTTGAGAGGTCCGCCGTTACAGTTGGA
CACAGGCCAACTTCTCAAGATTGCAAAACGTGGCGGCGTGACCGCAGTGGAGGCAGTG
CATGCATGGCGCAATGCACTGACGGGTGCCCCCCTGAACCTGACCCCGGACCAAGTGGT
GGCCATCGCCAGCAATATTGGCGGCAAGCAGGCGCTGGAGACGGTACAGCGGCTGTTG
CCGGTGCTGTGCCAGGACCATGGCCTGACCCCGGACCAGGTCGTGGCCATCGCCAGCCA
TGGCGGCGGCAAGCAGGCGCTGGAGACGGTGC

FIG. 9

```
AGCGGCTGTTGCCGGTGCTGTGCCAGGACCATGGCCTGACCCCGGACCAGGTGGTGGCC
ATCGCCAGCAATATTGGCGGCAAGCAGGCGCTAGAGACGGTGCAGCGGCTGTTGCCGG
TGCTGTGCCAGGCCCATGGCCTGACCCCGGACCAGGTCGTGGCCATCGCCAGCAATATT
GGCGGCAAGCAGGCGCTGGAGACGGTGCAGCGGCTGTTGCCGGTGCTGTGCCAGGACC
ATGGCCTGACCCCGGCCCAGGTGGTGGCCATCGCCAGCAATAGTGGCGGCAAGCAGGC
GCTGGAGACGGTGCAGCGGCTGTTGCCGGTGCTGTGCCAGGACCATGGCCTGACCCCGG
ACCAAGTCGTGGCCATCGCCAGCCACGATGGCGGCAAGCAGGCGCTGGAGACGCTGCA
GCGGCTGTTGCCGGTGCTGTGCCAGGACCATGGCCTGACCCCGGACCAGGTCGTGGCCA
TCGCCAACAATAACGGCGGCAAGCAGGCGCTGGAGACGCTGCAGCGGCTGTTGCCGGT
GCTGTGCCAGGACCATGGCCTGACCCCGGACCAAGTGGTGGCCATCGCCAGCCACGATG
GCGGCAAGCAGGCGCTGGAGACGGTGCAGCGGCTGTTGCCGGTGCTGTGCCAGGACCA
TGGCCTGACCCCGGACCAGGTGGTGGCCATCGCCAGCCACGATGGCGGCAAGCAGGCG
CTGGAGACGGTGCAGCGGCTGTTGCCGGTGCTGTGCCAGGACCATGGCCTGACCCCGGC
CCAAGTGGTGGCCATCGCCAGCCACGATGGCGGCAAGCAGGCGCTGGAGACGGTGCAG
CGGCTGTTGCCGGTGCTGTGCCAGGACCATGGCCTGACCCCGGACCAGGTGGTGGCCAT
CGCCAGCAATAGCGGCGGCAAGCAGGCGCTGGAGACGGTACAGCGGCTGTTGCCGGTG
CTGTGCCAGGACCATGGACTGACCCCGGACCAGGTCGTGGCCATCGCCAGCAATGGCG
GCAAGCAGGCGCTGGAGACGGTACAGCGGCTGTTGCCGGTGCTGTGCCAGGACCATGG
CCTGACCCCGGACCAGGTCGTGGCCATCGCCAGCAATGGCGGCAAGCAGGCGCTGGAG
ACGGTGCAGCGGCTGTTGCCGGTACAGCGGCTGTTGCCGGTGCTGTGCCAGGACCATGG
CCTGACCCAGGACCAGGTGGTGGCCATCGCCAGCCACGATGGCGGCAAGCAGGCGCTG
GAGACGGTGCAGCGGCTGTTGCCGGTGCTGTGCCAGGACCATGGCCTGACCCCGGACCA
AGTGGTGGCCATCGCCAGCCACGATGGCGGCAAACAGGCGCTGGAGACGGTGCAGCGG
CTGTTGCCGGTGCTGTGCCAGGACCATGGCCTGACCCCGGACCAGGTGGTGGCCATCGC
CAGCAATAGTGGCGGCAAGCAGGCGCTGGAGACGGTGCAGCGGCTGTTGCCGGTGCTG
TGCCAGGACCATGGCCTGACCCCGGACCAAGTGGTGGCCATCGCCAGCAATAGTGGCG
GCAAGCAGGCGCTGGAGACGGTGCAGCGGCTGTTGCCGGTGCTGTGCCAGGACCATGG
CCTGACCCCGGACCAGGTGGTGGCCATCGCCAGCAATAACGGCGGCAAGCAGGCGCTG
GAGACGGTGCAGCGGCTGTTGCCGGTGCTGTGCCAGGACCATGGCCTGACCCCGGACCA
GGTCGTGGCCATCGCCAACAATAACGGCGGCAAGCAGGCGCTGGAGACGGTGCAGCGG
CTGTTGCCGGTGCTGTGCCAGGACCATGGCCTGACCCCGGCGCAGGTGGTGGCCATCGC
CAGCAATATTGGCGGCAAGCAGGCGCTGGAGACGGTGCAGCGGCTGTTGCCGGTGCTGT
GCCAGGACCATGGCCTGACCCTGGACCAGGTGGTGGCCATTGCCAGCAATGGCGGCAG
CAAACAGGCGCTAGAGACGGTGCAGCGGCTGTTGCCGGTGCTGTGCCAGGACCATGGC
CTGACCCCGGACCAAGTGGTGGCCATCGCCAACAATAACGGCGGCAAGCAGGCGCTGG
AGACGGTGCAGCGGCTGTTGCCGGTGCTGTGCCAGGACCATGGCCTGACCCCGGACCAG
GTCGTGGCCATCGCCAGCAATATTGGCGGCAAGCAGGCGCTGGAGACGGTGCAGCGGC
TGTTGCCGGTGCTGTGCCAGGACCATGGCCTGACCCTGGACCAGGTGGTGGCCATCGCC
AGCAATGGCGGCAAGCAGGCGCTGGAGACGGTGCAGCGGCTGTTGCCGGTGCTGTGCC
AGGACCATGGCCTGACCCCGAACCAGGTGGTGGCCATCGCCAGCAATAGTGGCGGCAA
GCAGGCGCTGGAGACGGTGCAGCGGCTGTTGCCGGTGCTGTGCCAGGACCATGGCCTGA
CCCCGAACCAGGTGGTGGCCATCGCCAGCAATGGCGGCAAGCAGGCGCTGGAGAGCAT
TGTTGCCCAGTTATCTCGCCCTGATCCGGCGTTGGCCGCGTTGACCAACGACCACCTCGT
CGCCTTGGCCTGCCTCGGCGGACGTCCTGCCCTGGATGCAGTGAAAAAGGGATTGCCGC
ACGCGCCGGAATTGATCAGAAGAATCAATCGCCGCATTCCCGAACGCACGTCCCATCGC
GTTCCCGACCTCGCGCACGTGGTTCGCGTGCTTGGTTTTTTCCAGAGCCACTCCCACCCA
GCGCAAGCATTCGATGACGCCATGACGCAGTTCGAGATGAGCAGGCACGGCTTGGTAC
AGCTCTTTCGCAGAGTGGGCGTCACCGAATTCGAAGCCCGCTACGGAACGCTCCCCCCA
GCCTCGCAGCGTTGGGACCGTATCCTCCAGGCATCAGGG
```

FIG. 9 - continued

ATGAAAAGGGCCAAACCGTCCCCTACTTCAGCTCAAACACCGGATCAGGCGTCTTTGCA
TGCATTCGCCGATTCGCTGGAGCGTGACCTTGATGCGCCCAGCCCAATGCACGAGGGAG
ATCAGACGCGGGCAAGCAGCCGTAAACGGTCCCGATCGGATCGTGCTGTCACCGGCCCC
TCCACACAGCAATCTTTCGAGGTGCGCGTTCCCGAACAGCAAGATGCGCTGCATTTGCC
CCTCAGCTGGAGGGTAAAACGCCCGCGTACCAGGATCGGGGGCGGCCTCCCGGATCCT
GGTACGCCCATCGCTGCCGACCTGGCAGCGTCCAGCACCGTGATGTGGGAACAAGATGC
GGCCCCCTTCGCAGGGGCAGCGGATGATTTCCCGGCATTCAACGAAGAGGAGCTCGCAT
GGTTGATGGAGCTATTGCCTCAGTCAGGCTCAGTCGGAGGGACGATCTGA

FIG. 9 - continued

Gin-AvrΔ74

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSPRQFDPSLLDTSLLDSMPAVGTPHTAAAPAECDEVQS
GLRAADDPPPTVRVAVTAARPPRAKPAPRRRAAQPSDASPAAQVDLRTLGYSQQQEKIKP
KVRSTVAQHHEALVGHGFTHAHIVALSQHPAALGTVAVTYQDIIRALPEATHEDIVGVGKQ
WSGARALEALLTEAGELRGPPLQLDTGQLLKIAKRGGVTAVEAVHAWRNALTGAPLNLTP
DQVVAIASNIGGKQALETVQRLLPVLCQDHGLTPDQVVAIASHGGGKQALETVQRLLPVLC
QDHGLTPDQVVAIASNIGGKQALETVQRLLPVLCQAHGLTPDQVVAIASNIGGKQALETVQ
RLLPVLCQDHGLTPAQVVAIASNSGGKQALETVQRLLPVLCQDHGLTPDQVVAIASHDGGK
QALETLQRLLPVLCQDHGLTPDQVVAIANNNGGKQALETLQRLLPVLCQDHGLTPDQVVAI
ASHDGGKQALETVQRLLPVLCQDHGLTPDQVVAIASHDGGKQALETVQRLLPVLCQDHGL
TPAQVVAIASHDGGKQALETVQRLLPVLCQDHGLTPDQVVAIASNSGGKQALETVQRLLPV
LCQDHGLTPDQVVAIASNGGKQALETVQRLLPVLCQDHGLTPDQVVAIASNGGKQALETV
QRLLPVQRLLPVLCQDHGLTQDQVVAIASHDGGKQALETVQRLLPVLCQDHGLTPDQVVAI
ASHDGGKQALETVQRLLPVLCQDHGLTPDQVVAIASNSGGKQALETVQRLLPVLCQDHGL
TPDQVVAIASNSGGKQALETVQRLLPVLCQDHGLTPDQVVAIASNNGGKQALETVQRLLPV
LCQDHGLTPDQVVAIANNNGGKQALETVQRLLPVLCQDHGLTPAQVVAIASNIGGKQALET
VQRLLPVLCQDHGLTLDQVVAIASNGGSKQALETVQRLLPVLCQDHGLTPDQVVAIANNN
GGKQALETVQRLLPVLCQDHGLTPDQVVAIASNIGGKQALETVQRLLPVLCQDHGLTLDQV
VAIASNGGKQALETVQRLLPVLCQDHGLTPNQVVAIASNSGGKQALETVQRLLPVLCQDHG
LTPNQVVAIASNGGKQALESIVAQLSRPDPALAALTNDHLVALACLG

FIG. 10

Gin-AvrΔ87

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSPDSMPAVGTPHTAAAPAECDEVQSGLRAADDPPPTV
RVAVTAARPPRAKPAPRRRAAQPSDASPAAQVDLRTLGYSQQQEKIKPKVRSTVAQHHE
ALVGHGFTHAHIVALSQHPAALGTVAVTYQDIIRALPEATHEDIVGVGKQWSGARALEALL
TEAGELRGPPLQLDTGQLLKIAKRGGVTAVEAVHAWRNALTGAPLNLTPDQVVAIASNIGG
KQALETVQRLLPVLCQDHGLTPDQVVAIASHGGGKQALETVQRLLPVLCQDHGLTPDQVV
AIASNIGGKQALETVQRLLPVLCQAHGLTPDQVVAIASNIGGKQALETVQRLLPVLCQDHGL
TPAQVVAIASNSGGKQALETVQRLLPVLCQDHGLTPDQVVAIASHDGGKQALETLQRLLPV
LCQDHGLTPDQVVAIANNNGGKQALETLQRLLPVLCQDHGLTPDQVVAIASHDGGKQALE
TVQRLLPVLCQDHGLTPDQVVAIASHDGGKQALETVQRLLPVLCQDHGLTPAQVVAIASHD
GGKQALETVQRLLPVLCQDHGLTPDQVVAIASNSGGKQALETVQRLLPVLCQDHGLTPDQ
VVAIASNGGKQALETVQRLLPVLCQDHGLTPDQVVAIASNGGKQALETVQRLLPVQRLLPV
LCQDHGLTQDQVVAIASHDGGKQALETVQRLLPVLCQDHGLTPDQVVAIASHDGGKQALE
TVQRLLPVLCQDHGLTPDQVVAIASNSGGKQALETVQRLLPVLCQDHGLTPDQVVAIASNS
GGKQALETVQRLLPVLCQDHGLTPDQVVAIASNNGGKQALETVQRLLPVLCQDHGLTPDQ
VVAIANNNGGKQALETVQRLLPVLCQDHGLTPAQVVAIASNIGGKQALETVQRLLPVLCQD
HGLTLDQVVAIASNGGSKQALETVQRLLPVLCQDHGLTPDQVVAIANNNGGKQALETVQR
LLPVLCQDHGLTPDQVVAIASNIGGKQALETVQRLLPVLCQDHGLTLDQVVAIASNGGKQA
LETVQRLLPVLCQDHGLTPNQVVAIASNSGGKQALETVQRLLPVLCQDHGLTPNQVVAIAS
NGGKQALESIVAQLSRPDPALAALTNDHLVALACLG

FIG. 11

Gin-AvrA120

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSTVRVAVTAARPPRAKPAPRRRAAQPSDASPAAQVDL
RTLGYSQQQQEKIKPKVRSTVAQHHEALVGHGFTHAHIVALSQHPAALGTVAVTYQDIIRA
LPEATHEDIVGVGKQWSGARALEALLTEAGELRGPPLQLDTGQLLKIAKRGGVTAVEAVHA
WRNALTGAPLNLTPDQVVAIASNIGGKQALETVQRLLPVLCQDHGLTPDQVVAIASHGGGK
QALETVQRLLPVLCQDHGLTPDQVVAIASNIGGKQALETVQRLLPVLCQAHGLTPDQVVAI
ASNIGGKQALETVQRLLPVLCQDHGLTPAQVVAIASNSGGKQALETVQRLLPVLCQDHGLT
PDQVVAIASHDGGKQALETLQRLLPVLCQDHGLTPDQVVAIANNNGGKQALETLQRLLPVL
CQDHGLTPDQVVAIASHDGGKQALETVQRLLPVLCQDHGLTPDQVVAIASHDGGKQALET
VQRLLPVLCQDHGLTPAQVVAIASHDGGKQALETVQRLLPVLCQDHGLTPDQVVAIASNSG
GKQALETVQRLLPVLCQDHGLTPDQVVAIASNGGKQALETVQRLLPVLCQDHGLTPDQVV
AIASNGGKQALETVQRLLPVQRLLPVLCQDHGLTQDQVVAIASHDGGKQALETVQRLLPVL
CQDHGLTPDQVVAIASHDGGKQALETVQRLLPVLCQDHGLTPDQVVAIASNSGGKQALET
VQRLLPVLCQDHGLTPDQVVAIASNSGGKQALETVQRLLPVLCQDHGLTPDQVVAIASNNG
GKQALETVQRLLPVLCQDHGLTPDQVVAIANNNGGKQALETVQRLLPVLCQDHGLTPAQV
VAIASNIGGKQALETVQRLLPVLCQDHGLTLDQVVAIASNGGSKQALETVQRLLPVLCQDH
GLTPDQVVAIANNNGGKQALETVQRLLPVLCQDHGLTPDQVVAIASNIGGKQALETVQRLL
PVLCQDHGLTLDQVVAIASNGGKQALETVQRLLPVLCQDHGLTPNQVVAIASNSGGKQALE
TVQRLLPVLCQDHGLTPNQVVAIASNGGKQALESIVAQLSRPDPALAALTNDHLVALACLG

FIG. 12

Gin-AvrA120*

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSTVRVAVTAARPPHAVAGPAAQVDLRTLGYSQQQQE
KIKPKVRSTVAQHHEALVGHGFTHAHIVALSQHPAALGTVAVTYQDIIRALPEATHEDIVGV
GKQWSGARALEALLTEAGELRGPPLQLDTGQLLKIAKRGGVTAVEAVHAWRNALTGAPLN
LTPDQVVAIASNIGGKQALETVQRLLPVLCQDHGLTPDQVVAIASHGGGKQALETVQRLLP
VLCQDHGLTPDQVVAIASNIGGKQALETVQRLLPVLCQAHGLTPDQVVAIASNIGGKQALE
TVQRLLPVLCQDHGLTPAQVVAIASNSGGKQALETVQRLLPVLCQDHGLTPDQVVAIASHD
GGKQALETLQRLLPVLCQDHGLTPDQVVAIANNNGGKQALETLQRLLPVLCQDHGLTPDQ
VVAIASHDGGKQALETVQRLLPVLCQDHGLTPDQVVAIASHDGGKQALETVQRLLPVLCQ
DHGLTPAQVVAIASHDGGKQALETVQRLLPVLCQDHGLTPDQVVAIASNSGGKQALETVQ
RLLPVLCQDHGLTPDQVVAIASNGGKQALETVQRLLPVLCQDHGLTPDQVVAIASNGGKQA
LETVQRLLPVQRLLPVLCQDHGLTQDQVVAIASHDGGKQALETVQRLLPVLCQDHGLTPDQ
VVAIASHDGGKQALETVQRLLPVLCQDHGLTPDQVVAIASNSGGKQALETVQRLLPVLCQD
HGLTPDQVVAIASNSGGKQALETVQRLLPVLCQDHGLTPDQVVAIASNNGGKQALETVQRL
LPVLCQDHGLTPDQVVAIANNNGGKQALETVQRLLPVLCQDHGLTPAQVVAIASNIGGKQA
LETVQRLLPVLCQDHGLTLDQVVAIASNGGSKQALETVQRLLPVLCQDHGLTPDQVVAIAN
NNGGKQALETVQRLLPVLCQDHGLTPDQVVAIASNIGGKQALETVQRLLPVLCQDHGLTLD
QVVAIASNGGKQALETVQRLLPVLCQDHGLTPNQVVAIASNSGGKQALETVQRLLPVLCQD
HGLTPNQVVAIASNGGKQALESIVAQLSRPDPALAALTNDHLVALACLG

FIG. 13

Gin-AvrΔ147

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSPASPAAQVDLRTLGYSQQQQEKIKPKVRSTVAQHHE
ALVGHGFTHAHIVALSQHPAALGTVAVTYQDIIRALPEATHEDIVGVGKQWSGARALEALL
TEAGELRGPPLQLDTGQLLKIAKRGGVTAVEAVHAWRNALTGAPLNLTPDQVVAIASNIGG
KQALETVQRLLPVLCQDHGLTPDQVVAIASHGGGKQALETVQRLLPVLCQDHGLTPDQVV
AIASNIGGKQALETVQRLLPVLCQAHGLTPDQVVAIASNIGGKQALETVQRLLPVLCQDHGL
TPAQVVAIASNSGGKQALETVQRLLPVLCQDHGLTPDQVVAIASHDGGKQALETLQRLLPV
LCQDHGLTPDQVVAIANNNGGKQALETLQRLLPVLCQDHGLTPDQVVAIASHDGGKQALE
TVQRLLPVLCQDHGLTPDQVVAIASHDGGKQALETVQRLLPVLCQDHGLTPAQVVAIASHD
GGKQALETVQRLLPVLCQDHGLTPDQVVAIASNSGGKQALETVQRLLPVLCQDHGLTPDQ
VVAIASNGGKQALETVQRLLPVLCQDHGLTPDQVVAIASNGGKQALETVQRLLPVQRLLPV
LCQDHGLTQDQVVAIASHDGGKQALETVQRLLPVLCQDHGLTPDQVVAIASHDGGKQALE
TVQRLLPVLCQDHGLTPDQVVAIASNSGGKQALETVQRLLPVLCQDHGLTPDQVVAIASNS
GGKQALETVQRLLPVLCQDHGLTPDQVVAIASNNGGKQALETVQRLLPVLCQDHGLTPDQ
VVAIANNNGGKQALETVQRLLPVLCQDHGLTPAQVVAIASNIGGKQALETVQRLLPVLCQD
HGLTLDQVVAIASNGGSKQALETVQRLLPVLCQDHGLTPDQVVAIANNNGGKQALETVQR
LLPVLCQDHGLTPDQVVAIASNIGGKQALETVQRLLPVLCQDHGLTLDQVVAIASNGGKQA
LETVQRLLPVLCQDHGLTPNQVVAIASNSGGKQALETVQRLLPVLCQDHGLTPNQVVAIAS
NGGKQALESIVAQLSRPDPALAALTNDHLVALACLG

FIG. 14

GinAvr15Δ128-synthetic protein

MLIGYVRVSTNDQNTDLQRNALVCAGCEQIFEDKLSGTRTDRPGLKRALKRLQKGDTLVV
WKLDRLGRSMKHLISLVGELRERGINFRSLTDSIDTSSPMGRFFFYVMGALAEMERELIIERT
MAGLAAARNKGRIGGRPRKSGSGSPALRPPRAKPAPRRAAQPSDASPAAQVDLRTLGYSQ
QQQEKIKPKVRSTVAQHHEALVGHGFTHAHIVALSQHPAALGTVAVTYQHIITALPEATHED
IVGVGKQWSGARALEALLTDAGELRGPPLQLDTGQLVKIAKRGGVTAMEAVHASRNALTG
APLNLTPDQVVAIASNIGGKQALETVQRLLPVLCQDHGLTPDQVVAIASNGGGKQALETVQ
RLLPVLCQDHGLTPDQVVAIASNIGGKQALETVQRLLPVLCQDHGLTPDQVVAIASNIGGKQ
ALETVQRLLPVLCQDHGLTPDQVVAIASNIGGKQALETVQRLLPVLCQDHGLTPDQVVAIAS
HDGGKQALETVQRLLPVLCQDHGLTPDQVVAIASHDGGKQALETVQRLLPVLCQDHGLTP
DQVVAIASHDGGKQALETVQRLLPVLCQDHGLTPDQVVAIASHDGGKQALETVQRLLPVL
CQDHGLTPDQVVAIASHDGGKQALETVQRLLPVLCQDHGLTPDQVVAIASNGGGKQALET
VQRLLPVLCQDHGLTPDQVVAIASHDGGKQALETVQRLLPVLCQDHGLTPDQVVAIASHDG
GKQALETVQRLLPVLCQDHGLTPDQVVAIASNIGGKQALETVQRLLPVLCQDHGLTPDQVV
AIASNIGGKQALESIVAQLSRPDPALAALTNDHLVALACLGPKKKRKV

FIG. 15

Gin-Avr15Δ128-synthetic DNA:

```
ATGCTGATTGGCTATGTAAGGGTATCAACAAATGACCAGAATACAGACCTGCAACGAA
ACGCTCTTGTTTGTGCAGGATGTGAACAAATATTTGAAGATAAATTAAGCGGAACAAGG
ACAGACCGACCGGGATTAAAACGCGCTTTAAAGCGCCTTCAAAAAGGTGACACACTGG
TTGTCTGGAAACTGGATCGCCTCGGGCGAAGCATGAAACATTTGATTTCTCTCGTAGGG
GAATTACGAGAGCGAGGGATTAATTTTCGCAGTCTTACTGACAGTATTGATACGTCATC
TCCAATGGGGCGTTTTTTCTTCTACGTTATGGGTGCCCTGGCTGAAATGGAACGAGAACT
AATTATCGAGCGAACGATGGCTGGACTTGCTGCCGCCAGAAATAAAGGCCGTATTGGAG
GTCGCCCGCGTAAATCGGGGTCTGGATCCCCCGCGCGGCCGCCGCGCGCCAAGCCGGCC
CCGCGACGGCGTGCTGCGCAACCCTCCGACGCTTCGCCGGCCGCGCAGGTGGATCTACG
CACGCTCGGCTACAGTCAGCAGCAGCAAGAGAAGATCAAACCGAAGGTGCGTTCGACA
GTGGCGCAGCACCACGAGGCACTGGTGGGCCATGGGTTTACACACGCGCACATCGTTGC
GCTCAGCCAACACCCGGCAGCGTTAGGGACCGTCGCTGTCACGTATCAGCACATAATCA
CGGCGTTGCCAGAGGCGACACACGAAGACATCGTTGGCGTCGGCAAACAGTGGTCCGG
CGCACGCGCCCTGGAGGCCTTGCTCACGGATGCGGGGGAGTTGAGAGGTCCGCCGTTAC
AGTTGGACACAGGCCAACTTGTGAAGATTGCAAAACGTGGCGGCGTGACCGCAATGGA
GGCAGTGCATGCATCGCGCAATGCACTGACGGGTGCCCCCCTGGAGCTGACTCCGGACC
AAGTGGTGGCTATCGCCAGCAACATTGGCGGCAAGCAAGCGCTCGAAACGGTGCAGCG
GCTGTTGCCGGTGCTGTGCCAGGACCATGGCCTGACTCCGGACCAAGTGGTGGCTATCG
CCAGCAACGGTGGCGGCAAGCAAGCGCTCGAAACGGTGCAGCGGCTGTTGCCGGTGCT
GTGCCAGGACCATGGCCTGACTCCGGACCAAGTGGTGGCTATCGCCAGCAACATTGGCG
GCAAGCAAGCGCTCGAAACGGTGCAGCGGCTGTTGCCGGTGCTGTGCCAGGACCATGG
CCTGACTCCGGACCAAGTGGTGGCTATCGCCAGCAACATTGGCGGCAAGCAAGCGCTCG
AAACGGTGCAGCGGCTGTTGCCGGTGCTGTGCCAGGACCATGGCCTGACTCCGGACCAA
GTGGTGGCTATCGCCAGCAACATTGGCGGCAAGCAAGCGCTCGAAACGGTGCAGCGGC
TGTTGCCGGTGCTGTGCCAGGACCATGGCCTGACTCCGGACCAAGTGGTGGCTATCGCC
AGCCACGATGGCGGCAAGCAAGCGCTCGAAACGGTGCAGCGGCTGTTGCCGGTGCTGT
GCCAGGACCATGGCCTGACTCCGGACCAAGTGGTGGCTATCGCCAGCCACGATGGCGG
CAAGCAAGCGCTCGAAACGGTGCAGCGGCTGTTGCCGGTGCTGTGCCAGGACCATGGC
CTGACTCCGGACCAAGTGGTGGCTATCGCCAGCCACGATGGCGGCAAGCAAGCGCTCG
AAACGGTGCAGCGGCTGTTGCCGGTGCTGTGCCAGGACCATGGCCTGACTCCGGACCAA
GTGGTGGCTATCGCCAGCCACGATGGCGGCAAGCAAGCGCTCGAAACGGTGCAGCGGC
TGTTGCCGGTGCTGTGCCAGGACCATGGCCTGACTCCGGACCAAGTGGTGGCTATCGCC
AGCCACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTGGCGG
CAAGCAAGCGCTCGAAACGGTGCAGCGGCTGTTGCCGGTGCTGTGCCAGGACCATGGC
CTGACTCCGGACCAAGTGGTGGCTATCGCCAGCCACGATGGCGGCAAGCAAGCGCTCG
AAACGGTGCAGCGGCTGTTGCCGGTGCTGTGCCAGGACCATGGCCTGACTCCGGACCAA
GTGGTGGCTATCGCCAGCCACGATGGCGGCAAGCAAGCGCTCGAAACGGTGCAGCGGC
TGTTGCCGGTGCTGTGCCAGGACCATGGCCTGACCCCGGACCAAGTGGTGGCTATCGCC
AGCAACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACATTGGCGG
CAAGCAAGCGCTCGAAAGCATTGTGGCCCAGCTGAGCCGGCCTGATCCGGCGTTGGCCG
CGTTGACCAACGACCACCTCGTCGCCTTGGCCTGCCTCGGCCCCAAGAAGAAGCGCAAG
GTGTAG
```

FIG. 16

GinAvr15Δ128-synthetic protein:

*MLIGYVRVSTNDQNTDLQRNALVCAGCEQIFEDKLSGTRTDRPGLKR*
*ALKRLQKGDTLVVWKLDRLGRSMKHLISLVGELRERGINFRSLTDSI*
*DTSSPMGRFFFYVMGALAEMERELIIERTMAGLAAARNKGRIGGRPR*
KSGSGSPALRPPRAKPAPRRRAAQPSDASPAAQVDLRTLGYSQQQE
KIKPKVRSTVAQHHEALVGHGFTHAHIVALSQHPAALGTVAVTYQHI
ITALPE
ATHEDIVGVGKQWSGARALEALLTDAGELRGPPLQ (-1)
LDTGQLVKIAKRGGVTAMEAVHASRNALTGAPLN (0)T
LTPDQVVAIASNIGGKQALETVQRLLPVLCQDHG     (1)A
LTPDQVVAIASNGGGKQALETVQRLLPVLCQDHG     (2)T
LTPDQVVAIASNIGGKQALETVQRLLPVLCQDHG     (3)A
LTPDQVVAIASNIGGKQALETVQRLLPVLCQDHG     (4)A
LTPDQVVAIASNIGGKQALETVQRLLPVLCQDHG     (5)A
LTPDQVVAIASHDGGKQALETVQRLLPVLCQDHG (6)C
LTPDQVVAIASHDGGKQALETVQRLLPVLCQDHG (7)C
LTPDQVVAIASHDGGKQALETVQRLLPVLCQDHG (8)C
LTPDQVVAIASHDGGKQALETVQRLLPVLCQDHG (9)C
LTPDQVVAIASHDGGKQALETVQRLLPVLCQDHG (10)C
LTPDQVVAIASNGGGKQALETVQRLLPVLCQDHG (11)T
LTPDQVVAIASHDGGKQALETVQRLLPVLCQDHG (12)C
LTPDQVVAIASHDGGKQALETVQRLLPVLCQDHG (13)C
LTPDQVVAIASNIGGKQALETVQRLLPVLCQDHG (14)A
LTPDQVVAIASNIGGKQALE             (15)A
SIVAQLSRPDPALAALTNDHLVALACLGPKKKRKV

Key:
Gin Recombinase (italics)
TALE N-terminal framework (double underline)
RVD (DNA binding domains) (emboldened)
TALE C-terminal framework (dotted underline)

FIG. 17

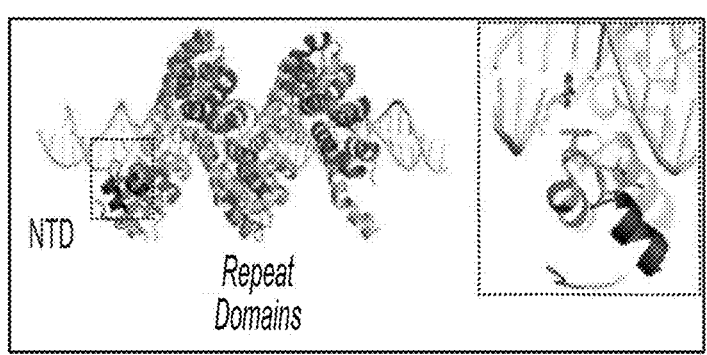
Δ152
VDLRTLGYSQQQQEKIKPKVRSTVAQHHEALVGHGFTHAHIVALSQHP
AALGTVAVTYQHIITALPEATHEDIVGVGKQWSGARALEALLTDAGELR
GPPLQLDTGQLVKIAKRGGVTAMEAVHASRNALTGAP... Repeat Domain
FIG. 18A
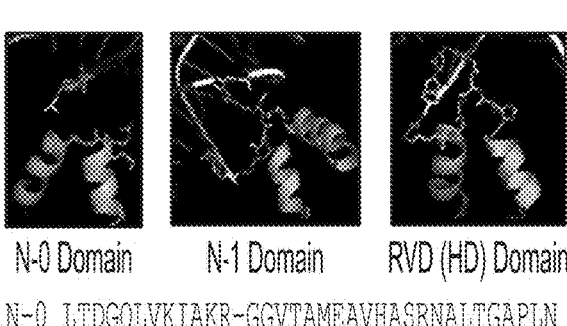
N-0 Domain        N-1 Domain        RVD (HD) Domain
N-0  LTDGQLVKIAKR-GGVTAMEAVHASRNALTGAPLN
N-1  -THEDIVGVGKQWSGARALEALLTDAGELRG----
RVD  LTPDQVVAIASXXGGKQALETVQRLLPVLCQDHG-
     ::* :.. .* *:*::        *
FIG. 18B
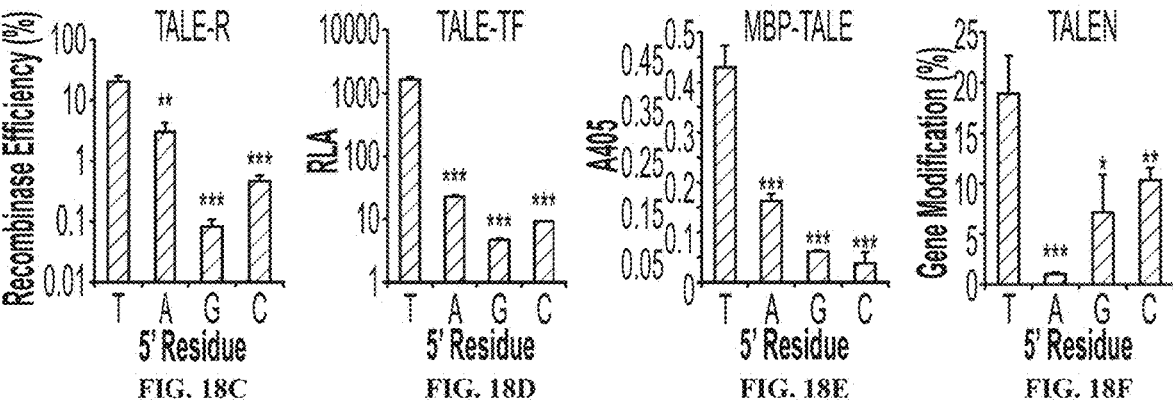
FIG. 18C          FIG. 18D          FIG. 18E          FIG. 18F

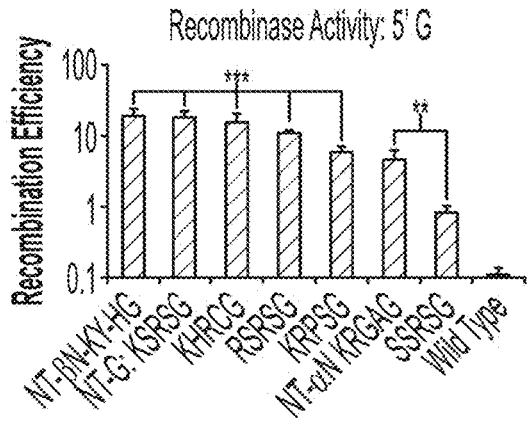
FIG. 19A
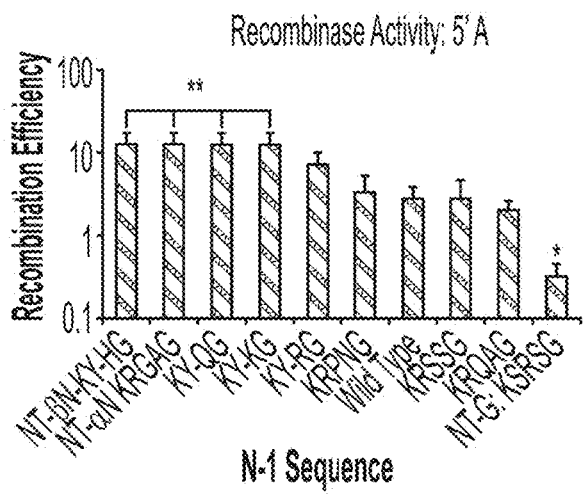
FIG. 19B
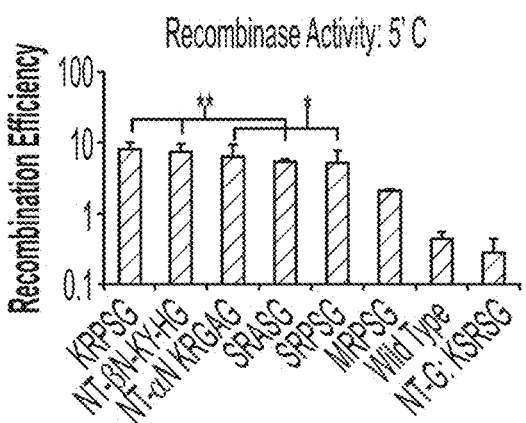
FIG. 19C
*Optimal Variants*
TALE NT-T    Asp225-IVGVKQWSGARAL-Glu239
TALE NT-G    Asp225-IVGVKSRSGARAL-Glu239
TALE NT-αN   Asp225-IVGVKRGAGARAL-Glu239
TALE NT-βN   Asp225-IVGVKY-HGARAL-Glu239
FIG. 19D
*Benchmark Recombinase Activity (% Max)*
|      | NT-T | NT-G | NT-αN | NT-βN |
|------|------|------|-------|-------|
| 5'T  | 100±30 | 0.8±0.3 | 9±4 | 73±31 |
| 5'G  | 0.9±0.4 | 96±33 | 18±9 | 107±42 |
| 5'A  | 13±6 | 3±1 | 90±39 | 91±36 |
| 5'C  | 2±1 | 3±1 | 46±26 | 89±41 |
FIG. 19E

5' X-ATAAACCCCCTCCAACCAGGC

3'

TALEN Gene Editing Efficiency

| TALEN Pair | NT-T | NT-G | NT-αN | NT-βN | dHax3 |
|------------|------|------|-------|-------|-------|
| T1/T2 | 18.9 ± 3.7 | 9.5 ± 2.7 | 14.5 ± 2.3 | 11.2 ± 0.3 | 22.1 ± 2.2 |
| G1/G2 | 7.1 ± 3.8 | 17.2 ± 2.8 | 14.4 ± 1.7 | 25.1 ± 3.2 | 8.25 ± 2.9 |
| A1/A2 | 1 ± 0.2 | 0.7 ± 0.4 | 9.1 ± 1.1 | 0.4 ± 0.2 | 1.2 ± 0.5 |
| C1/C2 | 10.4 ± 1.2 | 9.1 ± 0.4 | 21.1 ± 4.5 | 15.1 ± 2.3 | 11.3 ± 3.1 |

TALEN NTD Activity Enhancement vs. NT-T

| TALEN Pair | NT-T | NT-G | NT-αN | NT-βN | dHax3 |
|------------|------|------|-------|-------|-------|
| T1/T2 | 100 ± 19 | 50 ± 14 | 77 ± 12 | 59 ± 2 | 117 ± 12 |
| G1/G2 | 100 ± 51 | 242 ± 15 | 203 ± 23 | 354 ± 45 | 116 ± 41 |
| A1/A2 | 100 ± 20 | 70 ± 40 | 910 ± 110 | 40 ± 20 | 120 ± 50 |
| C1/C2 | 100 ± 12 | 88 ± 4 | 203 ± 43 | 145 ± 20 | 109 ± 30. |

N-terminus Alignment

```
TALE-R/TALE-MBP/TALE-TF   PRPPRAKPAPRRRAAQPSDASPAAQVDLRTLGYSQQQQEKIKPKVRSTVAQHHEALVGHG
        Goldy TALEN       -----------------------------VDLRTLGYSQQQQEKIKPKVRSTVAQHHEALVGHG
        NTD-dHax3         -----------------------------VDLRTLGYSQQQQEKIKPKVRSTVAQHHEALVGHG TALE-R/TALE-MBP/TALE-TF   FTHAHIVALSQHPAALGTVAVTYQHIITALPEATHEDIVGVGKXXXXXARALEALLTDAGE
        Goldy TALEN       FTHAHIVALSQHPAALGTVAVTYQHIITALPEATHEDIVGVGKXXXXXARALEALLTDAGE
        NTD-dHax3         FTHAHIVALSQHPAALGTVAVYQHIIAALPEATHEDIVGVGKXXSGARALEALLTDAGE TALE-R/TALE-MBP/TALE-TF   LRGPPLQLDTGQLVKIAKRGGVTAMEAVHASRNALTGAP
        Goldy TALEN       LRGPPLQLDTGQLVKIAKRGGVTAMEAVHASRNALTGAP
        NTD-dHax3         LRGPPLQLDTGQLKIAKRGGVTAVEAVHAPRNALTGAP
```

---------------------------RVD Domain-------------------------------

C-terminus Alignment

```
        TALE-TF           NDHLVALACLGGRPAMDAVKKGLPHAPELIRRVNRRIGERTSHRVADYAQVVKVLEFPQC
        Goldy TALEN       NDHLVALACLGGRPAMDAVKKGLPHAPELIRRVNRRIGERTSHRVA----------------
TALE-R/TALE-MBP           NDHLVALACL----------------------------------------------------

TALE-TF           HSHPAYAFDEAMTQFGMSGQ          VP64
        Goldy TALEN       ----------------------          FokI
TALE-R/TALE-MBP           ----------------------          Stop
```

FIG. 22

```
TALE-G      QVDLRTLGYSQQQQEKIKPKVRSTVAQHHEALVGHGFTHAHIVALSQHPAALGTVAVTYQ 60

Brg11       ---MAALGYSREQIRKLKQESLSGVAKYHAPLTRHGFTHTDICRISRRWQSLRMVAKNYP 57
            : ;*****;;* ,*;* ; * **;;* ,*, *****;,*  ;*;;  ;* ** ,*

TALE-G      HIITALPEATHEDIVGVGKSRSGARALEALLTDAGELRGPPLQLDTGQLVKIAKRGGVTA 120

Brg11       KLIAALPDLTRTHIVDIARGRSGDLALEALLPVATALAAAPLRLRASQIAIIAQCGERPA 117
            ;;*;***; *; ,**,;,; ; * *****, *  *  ,,**;* ;,*;, **; *  ,*

TALE-G      MEAVHASRNALTGAP 135

Brg11       ILALHRLRRKLTGAP 132
            ; *;* *, *****
```

| TALEN Pair | NTD | % Editing | Indels | TALEN Pair | NTD | % Editing | Indels |
|---|---|---|---|---|---|---|---|
| 1: T1/T2 | NT-T | 16.6% | | 12: A1/A2 | NT-G | 0.7% | |
| 2: T1/T2 | NT-G | 7.5% | | 13: A1/A2 | NT- βN | 0.4% | |
| 3: T1/T2 | NT-βN | 11.3% | | 14: A1/A2 | NT- αN | 9.1% | (3/30) |
| 4: T1/T2 | NT-αN | 12.9% | | 15: A1/A2 | NT-dHax3 | 1.2% | |
| 5: T1/T2 | NT-dHax3 | 20.1% | | 16: C1/C2 | NT-T | 8.6% | |
| 6: G1/G2 | NT-T | 4.4% | | 17: C1/C2 | NT-G | 8.9% | |
| 7: G1/G2 | NT-G | 15.2% | (9/30) | 18: C1/C2 | NT- βN | 13.4% | (9/30) |
| 8: G1/G2 | NT- αN | 4.8% | 3x Ave = 14.4 | 19: C1/C2 | NT- αN | 17.9% | (8/30) |
| 9: G1/G2 | NT- βN | 28.9% | (10/30) | 20: C1/C2 | NT-dHax3 | 9.1% | |
| 10: G1/G2 | NT-dHax3 | 6.2% | | | | | |
| 11: A1/A2 | NT-T | 1% | | | | | |

TALEN Pair 7 (9/30)

```
CCR5 (x20)  TGGAAATTCTTCCAGAATTGATACTGACTGTATGGAAAATGAGAGCTGCAGGTGTAATGAAGACCTTCTTTTTGAGATCTGGT
     -6 (x3)  TGGAAATTCTTCCATAATTGATATTGACTGTATGGA-------AGGCTGCGGGTGTAATGAATACCTTCTTTTTGAGATCTGGT
     -6       TGGAAATTCTTCCAGAATTGATACTGACTGTATGGAAAA-------CTGCAGGTGTAATGAAGACCTTCTTTTTGAGATCTGGT
     -6       TGGAAATTCTTCCAGAATTGATACTGACTGTATGGAAA-----AGCTGCAGGTGTAATGAAGACCTTCTTTTTGAGATCTGGT
     -7       TGGAAATTCTTCCAGAATTGATACTGACTGTATGGAA--------GCTGCAGGTGTAATGAAGACCTTCTTTTTGAGATCTGGT
    -10       TGGAAATTCTTCCAGAATTGATACTGACTGTAG----------AGCTGCAGGTGTAATGAAGACCTTCTTTTTGAGATCTGGT
    -11       TGGAAATTCTTCCAGAATTGATACTGACTGTAT----------GCTGCAGGTGTAATGAAGACCTTCTTTTTGAGATCTGGT
    -13       TGGAAATTCTTCCAGAATTGATACTGACTGT------------GCTGCAGGTGTAATGAAGACCTTCTTTTTGAGATCTGGT
```

TALEN pair 9 (10/30)
(CCR5 WT X 21)

```
            TGGAAATTCTTCCAGAATTGATACTGACTGTATGGAAAATGAGAGCTGCAGGTGTAATGAAGACCTTCTTTTTGAGATCTGGT
     -4      TGGAAATTCTTCCAGAATTGATACTGACTGTATGGAAA----GAGCTGCAGGTGTAATGAAGACCTTCTTTTTGAGATCTGGT
     -5      TGGAAATTCTTCCAGAATTGATACTGACTGTATGGAA-----GAGCTGCAGGTGTAATGAAGACCTTCTTTTTGAGATCTGGT
     -6      TGGAAATTCTTCCAGAATTGATACTGACTGTATGGA------GAGCTGCAGGTGTAATGAAGACCTTCTTTTTGAGATCTGGT
     -9      TGGAAATTCTTCCAGAATTGATACTGACT--------ATGAGAGCTGCAGGTGTAATGAAGACCTTCTTTTTGAGATCTGGT
    -10 (x2)  TGGAAATTCTTCCAGAATTGATACTGACTGTA----GAGCTGCAGGTGTAATGAAGACCTTCTTTTTGAGATCTGGT
    -11      TGGAAATTCTTCCAGAATTGATACTGAC---------TGAGAGCTGCAGGTGTAATGAAGACCTTCTTTTTGAGATCTGGT
    -11      TGGAAATTCTTCCAGAATTGATACTGACT-----------GAGAGCTGCAGGTGTAATGAAGACCTTCTTTTTGAGATCTGGT
    -11      TGGAAATTCTTCCAGAATTGATACTGACT----------GAGAGCTGCAGGTGTAATGAAGACCTTCTTTTTGAGATCTGGT
    -11      TGGAAATTCTTCCAGAATTGATACTGACT-----------AGGAGCTGCAGGTGTAATGAAGACCTTCTTTTTGAGATCTGGT
```

TALEN pair 14 (3/30)
(CCR5 WT X27)

```
            TGGAAATTCTTCCAGAATTGATACTGACTGTATGGAAAATGAGAGCTGCAGGTGTAATGAAGACCTTCTTTTTGAGATCTGGT
     -2      TGGAAATTCTTCCAGAATTGATACTGACT--ATGGAAAATGAGAGCTGCAGGTGTAATGAAGACCTTCTTTTTGAGATCTGGT
     -3      TGGAAATTCTTCCTCAATTGATACTGA---TATGGAAAATGAGAGCTGCAGGTGTAATGAAGACCTTCTTTTTGAGATCTGGT
     -9      TGGAAATTCTTCCAGAATTGATA---------TGGAAAATGAGAGCTGCAGGTGTAATGAAGACCTTCTTTTTGAGATCTGGT
```

TALEN Pair 18 (9/30)
(CCR5 WT X 28)

```
            TGGAAATTCTTCCAGAATTGATACTGACTGTATGGAAAATGAGAGCTGCAGGTGTAATGAAGACCTTCTTTTTGAGATCTGGT
     -4      TGGAAATTCTTCCAGAATTGATACTGACTGTATGA----TGAGAGCTGCAGGTGTAATGAAGACCTTCTTTTTGAGATCTGGT
     -4      TGGAAATTCTTCCAGAATTGATACTGACTGTATGG----TGAGAGCTGCAGGTGTAATGAAGACCTTCTTTTTGAGATCTGGT
     -5      TGGAAATTCTTCCAGAATTGATACTGACTGTA-----AATGAGAGCTGCAGGTGTAATGAAGACCTTCTTTTTGAGATCTGGT
     -5      TGGAAATTCTTCCAGAATTGATACTGACTGTATG-----TGAGAGCTGCAGGTGTAATGAAGACCTTCTTTTTGAGATCTGGT
     -9      TGGAAATTCTTCCAGAATTGATACTGA----------AATGAGAGCTGCAGGTGTAATGAAGACCTTCTTTTTGAGATCTGGT
     -9      TGGAAATTCTTCCAGAATTGATACTGACTGTATGGA---------CTGCAGGTGTAATGAAGACCTTCTTTTTGAGATCTGGT
    -10      TGGAAATTCTTCCAGAATTGATACTGACTG----------GAGAGCTGCAGGTGTAATGAAGACCTTCTTTTTGAGATCTGGT
    +3/-10   TGGAAATTCTTCCAGAATTGATACTGgta---------TGAGAGCTGCAGGTGTAATGAAGACCTTCTTTTTGAGATCTGGT
    -12      TGGAAATTCTTCCAGAATTGATACTGACTGT----------AGCTGCAGGTGTAATGAAGACCTTCTTTTTGAGATCTGGT
```

TALEN Pair 19 (8/30)
(CCR5 WT (x 23)

```
            TGGAAATTCTTCCAGAATTGATACTGACTGTATGGAAAATGAGAGCTGCAGGTGTAATGAAGACCTTCTTTTTGAGATCTGGT
     -7      TGGAAATTCTTCCAGAATTGATACTGACTGTATGGAAA-------CTGC-GGTGTAATGAAGACCTTCTTTTTGAGATCTGGT
     -7      TGGAAATTCTTCCAGAATTGATACTGACTGTA--------TGAGAGCTGCAGGTGTAATGAAGACCTTCTTTTTGAGATCTGGT
     -9      TGGAAATTCTTCCAGAATTAATACTGACT--------GAGAGCTGCAGGTGTAATGAAGACCTTCTTTTTGAGATCTGGT
    -10      TGGAAATTCTTCCAGAATTGATACTGACTG---------GAGAGCTGCAGGTGTAATGAAGACCTTCTTTTTGAGATCTGGT
    -11      TGGAAATTCTTCCAGAATTGATACTGACT----------GAGAGCTGCAGGTGTAATGAAGACCTTCTTTTTGAGATCTGGT
    -15      TGGAAATTCTTCCAGAATTGATACTGACTG-------------CTGCAGGTGTAATGAAGACCTTCTTTTTGAGATCTGGT
    -18      TGGAAATTCTTCCAGAATTGATACTGACTGT---------------ATGTGTAATGAAGACCTTCTTTTTGAGATCTGGT
    -44      TGGAAATTCTTCCAGAATTGATA--------------------------------CTTTTTGAGATCTGGT
```

FIG. 28

TALE-TF Architecture Comparison

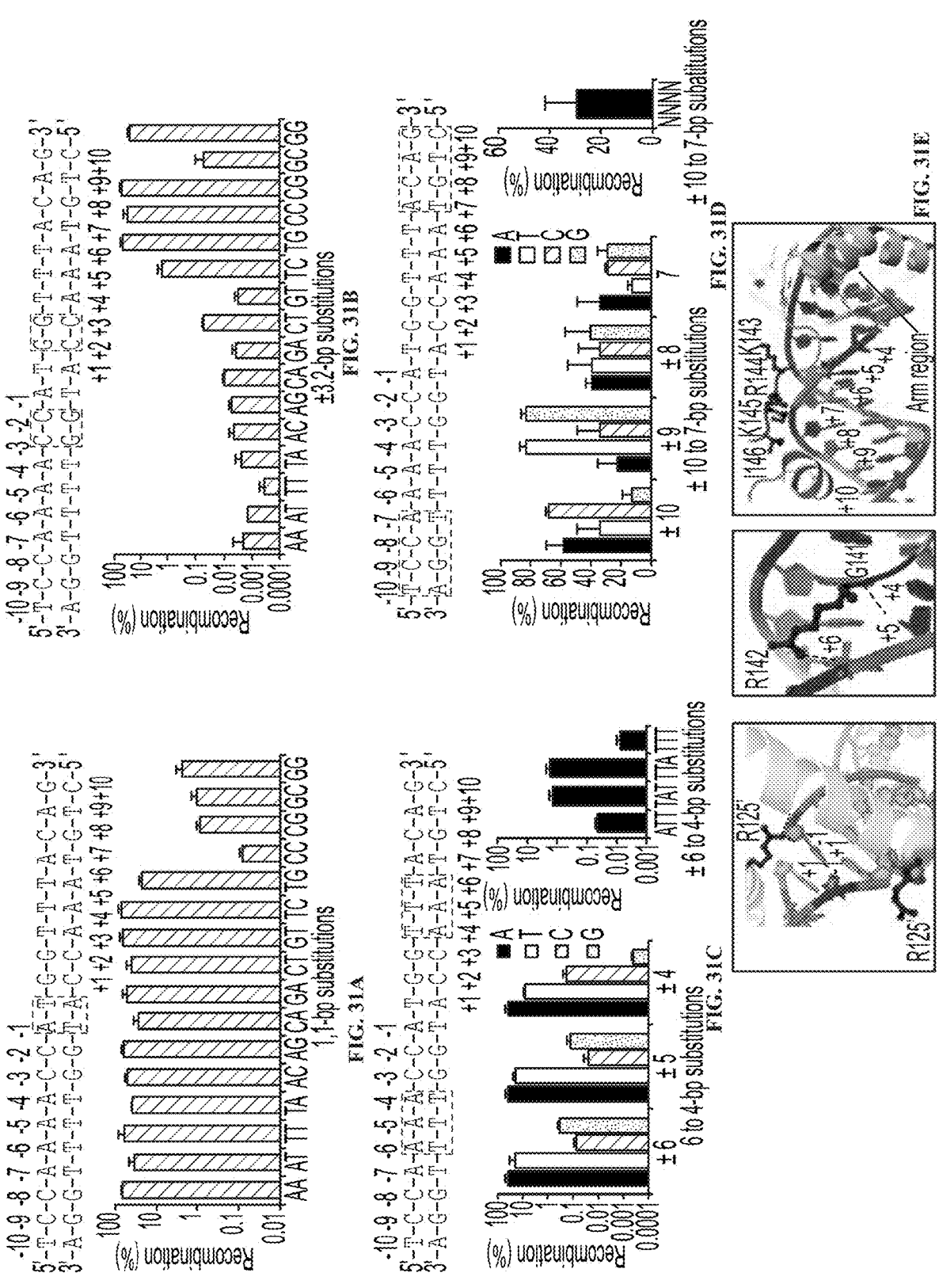

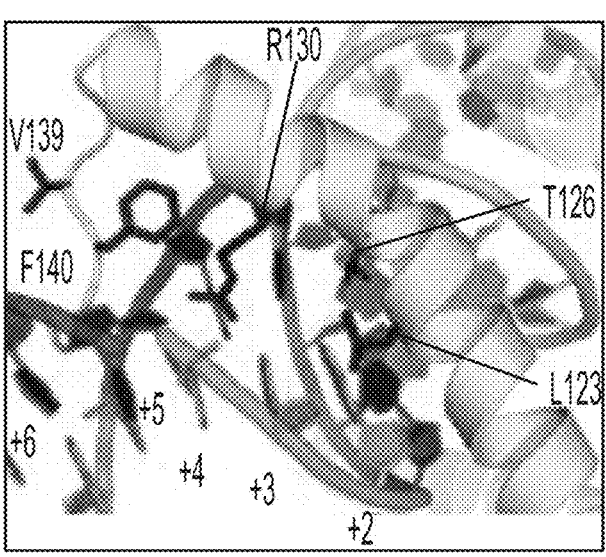

```
                                            33
γδ    MRLPGYARVSTSQQSLDIQVRALKDAGVKANRI
Gin   M-LIGYVRVSTNDQNTDLQRNALVCAG--CBQI
                                            66
γδ    FTDKASGSSCDRKGLDLLRMKVEEGDVILVKKL
Gin   FEDKLSGTRTDRPCLKRALKRLQKCDTLVVWKL
                                            99
γδ    DRLGRDTADMIQLIKEFDAQGVSIRFIDDGIST
Gin   DRLGRSMKHLISLVGELRERGINFRSLTDSIDT
                                            122
γδ    DGEMGKMVVTILSAVAQAERQRILERTNEGRQE
Gin   SSPMGRFFFHVMGALAEMERELIIERTMAGLAA
                        144              ↑  ↑  ↑
γδ    AMAKGVVFGRKR
Gin   ARNKGRIGGRPP
             ↑↑
```

FIG. 32B

5′-GGAGGCGTGTCCAAAAANNATNNTTTACAGCACGCCTCC-3′
3′-CACCCCTCCAGGTTTTTNNTANNAAATGACGTGCGGAGG-5′

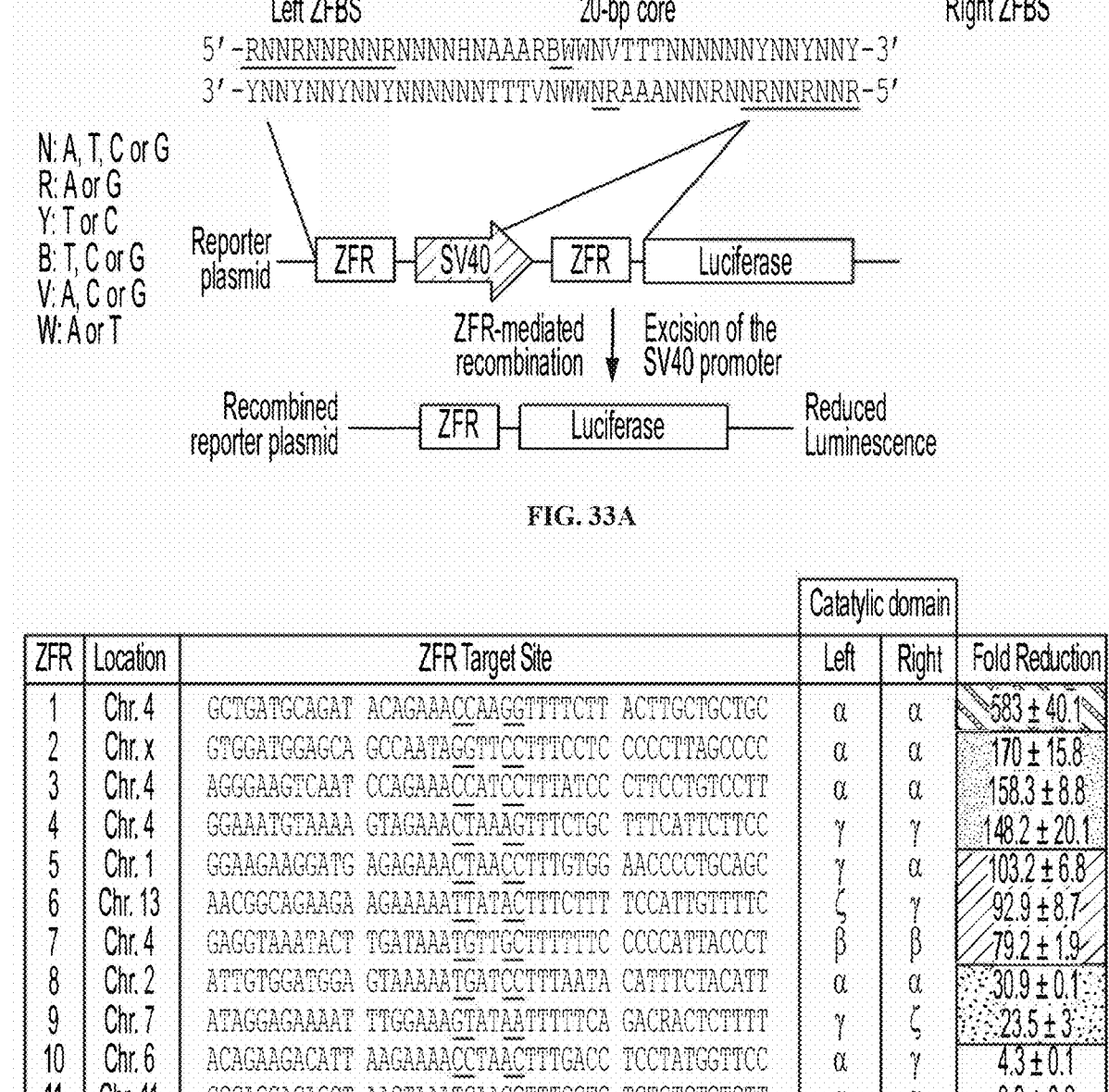

Left ZFBS          20-bp core          Right ZFBS

5'-RNNRNNRNNRNNNHNAAARBWWNVTTTNNNNNNYNNYNNY-3'
3'-YNNYNNYNNYNNNNNNTTTVNWWNRAAANNNRNNRNNRNNR-5'

| ZFR | Location | ZFR Target Site | Catalytic domain | | Fold Reduction |
|---|---|---|---|---|---|
| | | | Left | Right | |
| 1 | Chr. 4 | GCTGATGCAGAT ACAGAAACCAAGGTTTTCTT ACTTGCTGCTGC | α | α | 583 ± 40.1 |
| 2 | Chr. x | GTGGATGGAGCA GCCAATAGGTTCCTTTCCTC CCCCTTAGCCCC | α | α | 170 ± 15.8 |
| 3 | Chr. 4 | AGGGAAGTCAAT CCAGAAACCATCCTTTATCC CTTCCTGTCCTT | α | α | 158.3 ± 8.8 |
| 4 | Chr. 4 | GGAAATGTAAAA GTAGAAACTAAAGTTTCTGC TTTCATTCTTCC | γ | γ | 148.2 ± 20.1 |
| 5 | Chr. 1 | GGAAGAAGGATG AGAGAAACTAACCTTTGTGG AACCCCTGCAGC | γ | α | 103.2 ± 6.8 |
| 6 | Chr. 13 | AACGGCAGAAGA AGAAAAATTATACTTTCTTT TCCATTGTTTTC | ζ | γ | 92.9 ± 8.7 |
| 7 | Chr. 4 | GAGGTAAATACT TGATAAATGTTGCTTTTTTC CCCCATTACCCT | β | β | 79.2 ± 1.9 |
| 8 | Chr. 2 | ATTGTGGATGGA GTAAAAATGATCCTTTAATA CATTTCTACATT | α | α | 30.9 ± 0.1 |
| 9 | Chr. 7 | ATAGGAGAAAAT TTGGAAAGTATAATTTTTCA GACRACTCTTTT | γ | ζ | 23.5 ± 3 |
| 10 | Chr. 6 | ACAGAAGACATT AAGAAAACCTAACTTTGACC TCCTATGGTTCC | α | γ | 4.3 ± 0.1 |
| 11 | Chr. 11 | GGCAGGACAGCT AACTAAATGAAGGTTTGGTG TGTGTCTGTCTT | α | α | 3.9 ± 0.2 |
| 12 | Chr. 7 | AGGGATGAGGCC TCATAAAGTAAAGTTTTTTG TTTGTTTGTTTC | γ | γ | 3.7 ± 0.1 |
| 13 | Chr. 2 | ACAGTCAAAGTA TTTGAAAGTTAACTTTTTTC GTCAGCTCTTCC | γ | γ | 3.2 ± 0.3 |
| 14 | Chr. 2 | GAAATTGTGGAC AATTAAATTATCCTTTCTGG GCCCCTTATTTC | ζ | α | 3 ± 0.4 |
| 15 | Chr. 13 | GAAATTGgAAGG AAAAAAATTATCCTTATGG TGTAATACTTAT | ζ | α | 2.1 ± 0.2 |
| 16 | Chr. 11 | AAAACAGCTGGC TTTGAAAGGAAACTTTTAAC TACTATCCTGCC | α | γ | 1.1 ± 0.2 |
| 17 | Chr. 1 | ATAGTAAGTGCT CAATAAATGTTCGTTTATAT CATCATTGTGGC | α | α | 1.1 ± 0.1 |
| 18 | Chr. 7 | AAAGATGGAACA AACAAAATTAAGGTTTAGTA CATTATAATTCC | ζ | α | 0.9 ± 0.8 |
| GC4 | - | GCGGGAGGCGTG TCCAAAACCATGGTTTACAG CACGCCTCCGC | α | α | 107.6 ± 11.4 |

ZFR Target Site

| ZFR | 1 | 2 | 3 | 4 | 5 | 6 | 7 | 8 | 9 | GC4 |
|---|---|---|---|---|---|---|---|---|---|---|
| 1 | 100 | 1.4 | 1.8 | 0.8 | 1.8 | 1.3 | 1 | 1.6 | 1 | 0.4 |
| 2 | 0.5 | 100 | 1.9 | 0.5 | 0.6 | 0.8 | 0.7 | 0.4 | 0.6 | 0.3 |
| 3 | 5.7 | 5.3 | 100 | 5.8 | 4.8 | 5.9 | 5.6 | 5.1 | 5.9 | 4.2 |
| 4 | 3.1 | 2.2 | 2.6 | 100 | 1.3 | 1.2 | 4.7 | 2.9 | 1.9 | 2.5 |
| 5 | 3.1 | 2.9 | 3 | 2 | 100 | 1.3 | 1.7 | 2.7 | 2.6 | 2.8 |
| 6 | 5.7 | 5.6 | 4.6 | 4.9 | 3.9 | 100 | 4.9 | 8.6 | 4.5 | 2.1 |
| 7 | 2.1 | 1.5 | 3.5 | 3.8 | 3.7 | 2.9 | 100 | 2.3 | 2.5 | 5.9 |
| 8 | 12.6 | 9 | 9 | 8.5 | 3.7 | 6.2 | 8.7 | 100 | 6.7 | 5.8 |
| 9 | 7.2 | 8.6 | 7.4 | 3.5 | 2.2 | 4.7 | 5 | 7.7 | 100 | 9.5 |
| GC4 | 1.5 | 1.7 | 1.4 | 2 | 0.7 | 0.8 | 1.1 | 2.3 | 1.7 | 100 |

Low  | 0 | 20 | 40 | 60 | 80 | 100 | High

Recombination (%)

| Clone | Mutations | CC | GG | CG | GC | GT | TT |
|---|---|---|---|---|---|---|---|
| Parental | | 36 | 25 | 55 | 0.01 | 0.003 | 0.08 |
| *GC-1 | L127I, I136R, G137F | 44 | 78 | 57 | 20 | 0.09 | 0.06 |

| Clone | Mutations | CC | TT | GA | CA | GT | CT |
|---|---|---|---|---|---|---|---|
| Parental | | 36 | 0.002 | 0.008 | 0.004 | 0.003 | 0.086 |
| *GT-1 | I120L, T123V, L127T, I136R, G137W | 0.009 | 0.053 | 0.08 | 3.1 | 27 | 13.4 |
| GT-2 | L127M, I136R, G137C | 0.016 | 0.0003 | 0.092 | 0.207 | 39 | 6 |
| GT-3 | L127I | 0.0209 | 0.0009 | 0.41 | 0.77 | 39 | 13.5 |
| GT-4 | D12A*, I120Y, T123I, L127I, I136T, G137L | 0.0318 | 0.034 | - | - | 15 | - |
| GT-5 | I120M, T123V | 0.0068 | 0.013 | - | - | 6 | - |
| GT-6 | I120L, T123I, L127I, G137F | 0.0125 | 0.022 | - | - | 3 | - |

| Clone | Mutations | CC | TT | GA | CA | GT | CT |
|---|---|---|---|---|---|---|---|
| Parental | | 36 | 0.002 | 0.01 | 0.004 | 0.003 | 0.09 |
| *CA-1 | T123V, I136R, G137F | 0.018 | 0.003 | 1.2 | 13 | 23 | 14 |
| CA-2 | T123V | 0.02 | 0.06 | - | 11 | 27 | - |
| CA-3 | T123V, N132D | 0.02 | 0.6 | - | 8.2 | 11.2 | - |
| CA-4 | L52I*, L118S*, I120F, L127H, I136R, G137F | - | - | - | 0.87 | - | - |
| CA-5 | I120L, T123V, I136R, G137F | - | - | - | 0.43 | - | - |
| CA-6 | E117Q, L118C*, I120H, T123P, L127I | - | - | - | 0.5 | - | - |

| Clone | Mutations | TT | AC | CA | GT | AG | GC |
|---|---|---|---|---|---|---|---|
| Parental | | 0.002 | 0.005 | 0.004 | 0.003 | 0.008 | 0.01 |
| *AC-1 | E117L, L118S*, I120L, T123P, L127H, I136R, G137F | 0.09 | 1.7 | 0.05 | 6 | 1 | 0.008 |
| AC-2 | E117L, I120N, I136R, G137F | 0.0002 | 0.7 | - | 0.12 | - | 0.03 |
| AC-3 | R116Q*, E117L, L118S*, I120F, T123H, L127T, I136P, G127F | 0.0007 | 0.1 | 0.0005 | 0.0014 | 0.2 | - |
| AC-4 | E117Y, I120F, T123P, L127P, L127P, I136R, G137F | 0.0005 | 0.01 | 0.056 | 0.001 | 0.016 | - |

Low ◁0.1 1 10 100 High

Recombination (%)

CHIMERIC POLYPEPTIDES HAVING TARGETED BINDING SPECIFICITY

CROSS REFERENCE TO RELATED APPLICATION(S)

The subject patent application is a divisional of U.S. patent application Ser. No. 17/031,149 (filed Sep. 24, 2020; now pending), which is a divisional of U.S. patent application Ser. No. 15/878,043 (filed Jan. 23, 2018; now U.S. Pat. No. 10,829,766), which is a divisional of U.S. patent application Ser. No. 14/425,944 (filed Mar. 4, 2015; now U.S. Pat. No. 9,902,962), which is a § 371 U.S. national phase filing of PCT International Patent Application No. PCT/US2013/058100 (filed Sep. 4, 2013; now expired), which claims the benefit of priority to U.S. Provisional Patent Application No. 61/696,689 (filed Sep. 4, 2012; now expired), U.S. Provisional Patent Application No. 61/753,763 (filed Jan. 17, 2013; now expired), and U.S. Provisional Patent Application No. 61/818,364 (filed May 1, 2013; now expired). The disclosure of each of the aforementioned priority applications is incorporated herein by reference in its entirety and for all purposes.

STATEMENT OF GOVERNMENT SUPPORT

This invention was made with government support under grant numbers OD006990, GM065059 and CA174426 by the National Institutes of Health. The government has certain rights in the invention.

SEQUENCE LISTING

This application incorporates by reference a Sequence Listing in the form of a ST.26 XML file labeled "1544_2D3_Sequence_Listing.xml". The file is of 511 KB and was created on Oct. 10, 2022.

BACKGROUND OF THE INVENTION

Field of the Invention

The present invention relates generally to the field of biotechnology, and more specifically to chimeric recombinases that recognize specific DNA sequences.

Background Information

The ability of proteins to recognize DNA in a sequence-dependent manner is central to life, as a variety of protein domains have evolved to provide sequence-specific DNA recognition. DNA recognition by a select few of these domains is also the foundation for a wide variety of biotechnological applications. In particular, $C_2H_2$ zinc-finger proteins (ZFPs) were among the first DNA-binding proteins to be engineered to recognize user-defined DNA sequences and have been used with varying degrees of success for many applications, including transcriptional regulation, genome engineering and epigenetic modification. Modular assembly of ZFPs has facilitated these approaches. However, despite the advances and promise of ZFP technology, construction of specific, high-affinity ZFPs for certain sequences remains difficult and in select cases requires the use of time-consuming and labor-intensive selection systems not readily adopted by non-specialty laboratories.

Transcription activator-like effector (TALE) domains are a class of naturally occurring DNA-binding domains (DBDs) that represent a potential alternative to ZFP technology. TALEs, which are found in the plant pathogen *Xanthomonas*, contain a series of 33 to 35 amino acid repeats that function to selectively bind target DNA sequences. These repeats are identical with the exception of two adjacent repeat variable di-residues (RVDs) that confer DNA specificity by mediating binding to a single nucleotide. Arrays of over 30 repeats have been described that bind to DNA sites of similar numbers of base pairs (bps). Although there is inherent degeneracy in the binding of each RVD, recent reports have indicated that synthetic TALE proteins are specific enough to target single loci within the human genome.

The introduction of DNA double-strand breaks (DSBs) by chimeric nucleases, such as zinc-finger nucleases (ZFNs) can be used to knockout gene function or in the presence of exogenously added DNA drive cassette integration at the targeted loci. ZFNs have been extensively studied over the last decade and in some cases are approaching clinical use for gene therapy. Recently, a number of groups have explored the use of TALE DNA-binding domains fused to nucleases (TALENS) for targeted genome editing. Indeed, much of the work with ZFNs has been replicated with TALE nucleases, as TALENs may have advantages over ZFNs in regards to DNA-binding modularity. However, despite impressive research with ZFNs and TALENs, questions remain about their safety and specificity. In particular, off-target cleavage events remain difficult to detect, as the most likely result of an off-target DSB is the introduction of small insertions or deletions. Additionally, repair of DSBs relies on cell machinery that varies with cell type.

An alternate approach for achieving targeted genomic modifications is the use of site-specific recombinases (SSRs). SSRs, such as the tyrosine recombinases Cre and Flp, are valuable molecular biology tools that are routinely used to manipulate chromosome structure inside cells. Because these enzymes rely on a number of complex protein-protein and protein-DNA interactions to coordinate catalysis, SSRs exhibit remarkable target site specificity. To date, however, altering the specificity of many SSRs has proven difficult. Serine recombinases of the resolvase/invertase type provide a versatile alternative to tyrosine recombinases for genome engineering. In nature, these enzymes function as multi-domain protein complexes that coordinate recombination in a highly modular manner. However, mutants of several serine recombinases have been identified that do not require accessory factors for recombination. Additionally, numerous studies have shown that the native DBDs of serine recombinases can be replaced with custom-designed ZFPs to generate chimeric zinc-finger recombinases (ZFRs). In principle, ZFRs capable of recognizing an extended number of sequences could be generated, however, the lack of zinc-finger domains capable of recognizing all possible DNA triplets limits the potential modular targeting capacity of these enzymes.

ZFRs are composed of an activated catalytic domain derived from the resolvase/invertase family of serine recombinases and a zinc-finger DNA-binding domain that can be custom-designed to recognize almost any DNA sequence (FIG. 30A). ZFRs catalyze recombination between specific ZFR target sites that consist of two-inverted zinc-finger binding sites (ZFBS) flanking a central 20-bp core sequence recognized by the recombinase catalytic domain (FIG. 30B). In contrast to zinc-finger nucleases (ZFNs) and TAL effector nucleases (TALENs), ZFRs function autonomously and can excise and integrate transgenes in human and mouse cells without activating the cellular DNA damage response pathway. However, as with conventional site-specific recombinases, applications of ZFRs have been restricted by sequence requirements imposed by the recombinase catalytic domain, which dictate that ZFR target sites contain a 20-bp core derived from a native serine resolvase/invertase recombination site.

Site-specific DNA recombination systems such as Cre-loxP, FLP-FRT and ^C31-att have emerged as powerful tools for genetic engineering. The site-specific recombinases that promote these DNA rearrangements recognize short (30- to 40-bp) sequences and coordinate DNA cleavage, strand exchange and re-ligation by a mechanism that does not require DNA synthesis or a high-energy cofactor. This simplicity has allowed researchers to study gene function with extraordinary spatial and temporal sensitivity. However, the strict sequence requirements imposed by site-specific recombinases have limited their application to cells and organisms that contain artificially introduced recombination sites. In order to address this limitation, directed evolution has been used to alter the sequence specificity of several recombinases toward naturally occurring DNA sequences. Despite advances, the need for complex mutagenesis and selection strategies and the finding that re-engineered recombinase variants routinely exhibit relaxed substrate specificity have hindered the widespread adoption of this technology.

Accordingly, there is a need for a more generalized method of catalyzing targeted and site-specific recombination of the endogenous genome, particularly for gene therapy, as well as for enzymes that can catalyze such targeted and site-specific recombination. This is particularly useful for gene therapy, but would have many other applications in molecular biology, including in gene cloning and use in modification of industrial organisms and agricultural plants and animals.

SUMMARY OF THE INVENTION

Disclosed herein are targeted chimeric polypeptides, including compositions thereof, expression vectors, and methods of use thereof, for the generation of transgenic cells, tissues, plants, and animals. The compositions, vectors, and methods of the present invention are also useful in gene therapy techniques.

In one aspect, the invention provides a chimeric polypeptide. The polypeptide includes: a) a recombinase, nuclease or transcription factor, or fragment thereof; and b) a transcription activator-like effector (TALE) protein. In various embodiments, the TALE protein is truncated and includes a C-terminal or N-terminal truncation. In embodiments, the TALE protein is AvrXa7, Tal1c, and PthXo1. In embodiments, the TALE protein includes all or a portion an amino acid sequence as set forth in SEQ ID NO: 2. In some embodiments, the TALE protein is truncated between amino acid residues 27 and 268, 92 and 134, 120 and 129, 74 and 147, or 87 and 120 of SEQ ID NO: 2. In some embodiments, the TALE protein is truncated at amino acid residue 28, 74, 87, 92, 95, 120, 124, 128, 129, 147 and 150 of SEQ ID NO: 2.

In another aspect, the invention provides a method of generating a transcription activator-like effector (TALE) protein binding domain which specifically binds a desired nucleotide. The method includes a) randomizing the amino acid sequence of the TALE protein binding domain by mutating an amino acid residue within a variable di-residue (RVD), or within 1 to 2 amino acid residues N-terminal or C-terminal of the RVD; and b) selecting for the randomized TALE protein binding domain of (a), wherein the TALE protein binding domain specifically binds to the desired nucleotide.

In another aspect, the invention provides an isolated polypeptide comprising a *Xanthomonas* derived transcription activator-like effector (TALE) protein, the TALE protein having an N-terminal domain (NTD) comprising an amino acid sequence as set forth in SEQ ID NO: 3 (VGKQWSGARAL) having one or more mutations or deletions selected from: Q is Y, Qis S, Q is R, W is R, W is G, W is deleted, S is R, S is H, S is A, S is N, and S is T.

In another aspect, the invention provides an isolated polypeptide including a *Ralstonia* derived transcription activator-like effector (TALE) protein, the TALE protein having an N-terminal domain (NTD) including an amino acid sequence as set forth in SEQ ID NO: 8 (IVDIAR$_1$QR$_2$SGDLA) having one or more mutations or deletions selected from: R$_1$ is K, Q is Y, Q is S, Q is R, R$_2$ is W, R$_2$ is G, R$_2$ is deleted, S is R, S is H, Sis A, Sis N, and S is T.

In another embodiment, the invention provides a method of generating a transcription activator-like effector (TALE) protein N-terminal domain (NTD). The method includes: a) randomizing an amino acid sequence of the NTD by mutating or deleting one or more amino acid residues within the NTD, wherein the amino acid sequence is SEQ ID NO: 14 (VGKXXXGAR) or SEQ ID NO: 15 (VDIAXXXXGDLA); and b) selecting for the randomized TALE protein NTD of (a), wherein the TALE protein NTD specifically binds to a desired nucleotide or exhibits enhanced activity.

Also disclosed herein are chimeric proteins including a serine recombinase and one or more zinc finger binding domains, methods of generating ZFRs, compositions thereof, expression vectors, and methods of use thereof, for the generation of transgenic cells, tissues, plants, and animals. The compositions, vectors, and methods of the present invention are also useful in gene therapy techniques.

In one aspect, the invention provides a method of generating a plurality of zinc finger recombinase (ZFRs) proteins having catalytic specificity greater than the corresponding wild type recombinase. The method includes performing random mutagenesis on a recombinase catalytic domain at positions equivalent to Gin Ile120, Thr123, Leu127, Ile136 and Gly 137 or a combination thereof, mutating the DNA at positions 2 and 3 for each amino acid; fusing the recombinase catalytic domain with a plurality of zinc finger binding domains to form ZFRs, and enriching for ZFRs having catalytic specificity greater than the corresponding wild type recombinase. In embodiments the ZFRs have increased catalytic activity on DNA targets selected from GC, GT, CA, TT and AC. In one embodiment, the recombinase catalytic domain is mutagenized at Ile136 and/or Gly137.

In various aspects, the chimeric polypeptides described herein include a recombinase catalytic domain derived from or randomly mutagenized as disclosed herein from: a) Tn3, also known as EcoTn3; Hin, also known as StyHin; Gin, also known as MuGin; Sin; Beta; Pin; Min; Din; Cin; EcoTn21; SfaTn917; BmeTn5083; Bme53; Cpe; SauSK1; SauSK41; SauTn552; Ran; Aac; L1a; pMER05; Mlo92; Mlo90; Rrh; Pje; Req; PpsTn5501; Pae; Xan; ISXc5; Spy; RhizY4cG; SarpNL1; SsolSC1904a; SsolSC1904b; SsolSC1913; Aam606; MjaM0014; Pab; HpyIS607; MtulS_Y349; MtuRv2792c; MtuRv2979c; MtuRv3828c; MtuRv0921; MceRv0921; TnpX; TndX; WwK; lactococcal phage TP901-1 serine recombinase; *S. pyogenes* phage φ370.1 serine recombinase; *S. pyogenes* phage φFC1 serine recombinase; *Listeria* phage A118 serine recombinase; *S. coeli-*

*color* chromosome SC3C8.24 serine recombinase; *S. coeli-color* chromosome SC2E1.37 serine recombinase; *S. coelicolor* chromosome SCD78.04c serine recombinase; *S. coelicolor* chromosome SC8F4.15c serine recombinase; *S. coelicolor* chromosome SCD12A.23 serine recombinase; *S. coelicolor* chromosome SCH10.38c serine recombinase; *S. coelicolor* chromosome SCC88.14 serine recombinase; *Streptomyces* phage φC31 serine recombinase; *Streptomyces* phage R4 serine recombinase; *Bacillus* phage φ105 serine recombinase; *Bacillus* phage SPBc2 serine recombinase; *Bacillus* prophage SKIN serine recombinase; *S. aureus* ccrA serine recombinase; *S. aureus* ccrB serine recombinase; *M. tuberculosis* phage Bxb1 serine recombinase; *M. tuberculo-sis* prophage φRV1 serine recombinase; YBCK_ECOLI; Y4bA; Bja; Spn; Cac 1956; and Cac 1954; or b) muteins of a).

In yet another aspect, the invention provides an isolated nucleic acid molecule encoding the chimeric polypeptide described herein.

In yet another aspect, the invention provides an expression cassette including the nucleic acid molecule the chimeric polypeptide described herein.

In yet another aspect, the invention provides a vector including the expression cassette described herein.

In yet another aspect, the invention provides an isolated host cell containing the vector described herein.

In yet another aspect, the invention provides a method for site-specific integration into a DNA sequence. The method includes contacting the DNA sequence with a chimeric polypeptide of the present invention, wherein the chimeric polypeptide catalyzes site-specific integration.

In yet another aspect, the invention provides a method for gene therapy. The method includes administering to a subject a composition comprising a nucleic acid molecule encoding the chimeric polypeptide described herein, wherein upon expression of the nucleic acid molecule, a gene present in the genome of the subject is specifically removed or inactivated.

In yet another aspect, the invention provides a pharmaceutical composition. The composition includes the chimeric polypeptide described herein; and a pharmaceutically acceptable carrier. In another aspect, the composition includes a nucleic acid molecule encoding the chimeric polypeptide described herein; and a pharmaceutically acceptable carrier.

In yet another aspect, the invention provides a transgenic organism produced by recombination catalyzed by the chimeric polypeptide of the present invention.

In yet another aspect, the invention provides a method for gene therapy. The method includes administering to a subject a cell comprising a nucleic acid molecule having the DNA sequence generated by the method of site-specific integration described herein.

In another aspect, the invention provides an isolated nucleic acid molecule encoding the chimeric protein described herein.

In another aspect, the invention provides a method for site-specific recombination. The method includes: a) providing a DNA sequence comprising at least two binding sites for specifically interacting with the chimeric protein described herein; and b) reacting the DNA sequence with the chimeric protein, wherein the chimeric protein catalyzes a site-specific recombination event in which both strands of the DNA sequence are cleaved between the two sites specifically interacting with the chimeric protein.

BRIEF DESCRIPTION OF THE DRAWINGS

FIGS. 1A-1D are a series of graphical and diagrammatic representations regarding TALER fusion orientation and activity. (1A) Cartoon illustrating the split β-lactamase system used to evaluate TALER activity. (1B) Schematic showing the fusion orientation of each TALER and its corresponding target site (1-SEQ ID NO: 288; 2=SEQ ID NO: 289; 3=SEQ ID NO: 290). (1C) Activity of each designed TALER fusion against its intended DNA target. Recombination was normalized to background (vector only control). (1D) Gin-Avr activity against cognate (Avr-20G) and non-cognate (Avr-20T, Avr-20GG, PthXo1-20G) DNA targets. Error bars indicate standard deviation (s.d.) (n=3).

FIGS. 3A-3C are a series of graphical representations regarding TALER variants selected from incremental truncation library. (3A) Frequency of selected TALER truncation variants. After 3 rounds of selection, incrementally truncated Gin-AvrXa7 variants were isolated and DNA sequencing was used to determine truncation length. (3B) Activity of incrementally truncated TALER variants (between Δ92 and Δ134 in length) against the Avr-32G DNA target. For reference, the shortest (Δ145) and longest (Δ74) truncation variants, as well as Δ87 were included. (3C) Activity of Gin-AvrΔ74, Gin-AvrΔ128 and Gin-AvrΔ145 against a diverse panel of cognate and non-cognate DNA targets. Error bars indicate s.d. (n=3).

FIG. 7 is a diagrammatic representation of a comparison of native wild-type and synthetic RDV domains for the AvrXa7 target sequence (SEQ ID NOs: 16-18).

FIG. 8 is a diagrammatic representation of TALE and TALER amino acid sequences of AvrXa7 protein (SEQ ID NO: 19).

FIG. 9 is a diagrammatic representation of construct AvrXa7 DNA sequence (SEQ ID NO: 20).

FIG. 10. is a diagrammatic representation of construct Gin-AvrΔ74 amino acid sequence (SEQ ID NO: 21).

FIG. 11 is a diagrammatic representation of construct Gin-AvrΔ87 amino acid sequence (SEQ ID NO: 22).

FIG. 12 is a diagrammatic representation of construct Gin-AvrΔ120 amino acid sequence (SEQ ID NO: 23).

FIG. 13 is a diagrammatic representation of construct Gin-AvrΔ120* amino acid sequence (SEQ ID NO: 24).

FIG. 14 is a diagrammatic representation of construct Gin-AvrΔ147 amino acid sequence (SEQ ID NO: 25).

FIG. 15 is a diagrammatic representation of construct GinAvr15Δ128-synthetic protein amino acid sequence (SEQ ID NO: 26).

FIG. 16 is a diagrammatic representation of construct Gin-Avr15Δ128-synthetic protein DNA sequence (SEQ ID NO: 27).

FIG. 17 is a diagrammatic representation of construct GinAvr15Δ128-synthetic protein amino acid sequence (SEQ ID NO: 28).

FIGS. 18A-18F are a series of pictorial and graphical representations pertaining to the specificity of the TALE N-terminal domain. (18A) Illustration of a TALE (SEQ ID NO: 29) bound to its target DNA. (18B) Structural analysis suggests contact of the 5' T by W232 of the N−1 hairpin (N−0—SEQ ID NO: 30; N−1—SEQ ID NO: 31; and RVD—SEQ ID NO: 32). This hairpin shares significant sequence homology with RVD hairpins. (18C-18F) Analyses of NT-T (wt) NTD in the context of C) AvrXa7 TALE-R, D) AvrXa7 TALE-TF, E) AvrXa7 MBPTALE, and F) a CCR5 targeting TALEN. (*=p<0.05, =p<0.01, *=p<0.001 compared to 5'T).

FIGS. 19A-19E are a series of graphical and diagrammatic representations pertaining to recombinase variants. (19A-19C) Activities of recombinase selection variants against substrates with (19A) 5' G, (19B) 5' A, and (19C) 5' C. (19D) Alignment of optimized TALE NTDs SEQ ID NOs: 33-36), illustrating sequence differences in the N−1 hairpin. (19E) Comprehensive comparison of optimized NTD activities in the context of MBP-TALE AvrXa7. (*=p<0.05, =p<0.01, *=p<0.001, compared to wild type and 5'A/G/C).

FIG. 22 is a diagrammatic representation showing alignment of N- and C-terminal domains SEQ ID NOs: 48-53).

FIG. 28 is a diagrammatic representation showing alignment indel sequencing of selected TALEN experiments from FIG. 27 (SEQ ID NOs: 292-332 from top to bottom).

FIGS. 31A-31E are a series of graphical and diagrammatic representations of specificity of the Gin recombinase catalytic domain. (31A-31D) Recombination was measured on DNA targets that contained (31A, SEQ ID NO: 335) each possible two-base combination at the dinucleotide core, (31B, SEQ ID NO: 336) each possible two-base combination at positions 3 and 2, (31C, SEQ ID NO: 337) each possible single-base substitution at positions 6, 5, and 4, and (31D, SEQ ID NO: 338) each possible single-base substitution at positions 10, 9, 8, and 7. Substituted bases are boxed above each panel. Recombination was evaluated by split gene reassembly and measured as the ratio of carbenicillin-resistant to chloramphenicol-resistant transformants (Materials and Methods). Error bars indicate standard deviation (n=3). (31E) Interactions between the γδ resolvase dimer and DNA at (left) the dinucleotide core, (middle) positions 6, 5, and 4, and (right) positions 10, 9, 8, and 7 (PDB ID: 1GDT). Interacting residues are shown as purple sticks. Bases are colored as follows: A, yellow; T, blue; C, brown; and G, pink.

FIGS. 32A-32E are a series of graphical and diagrammatic representations of re-engineering Gin recombinase catalytic specificity. (32A) The canonical 20-bp core recognized by the Gin catalytic domain. Positions 3 and 2 are boxed (SEQ ID NO: 339). (32B) (Top) Structure of the γδ resolvase in complex with DNA (PDB ID: 1GDT). Arm region residues selected for mutagenesis are shown as purple sticks. (Bottom) Sequence alignment of the γδ resolvase (SEQ ID NO: 341) and Gin recombinase (SEQ ID NO: 342) catalytic domains. Conserved residues are shaded orange. Black arrows indicate arm region positions selected for mutagenesis. (32C) Schematic representation of the split gene reassembly selection system. Expression of active ZFR variants leads to restoration of the β-lactamase reading frame and host-cell resistance to ampicillin. Solid lines indicate the locations and identity of the ZFR target sites. Positions 3 and 2 are underlined (SEQ ID NO: 340). (32D) Selection of Gin mutants that recombine core sites containing GC, GT, CA, TT, and AC base combinations at positions 3 and 2. Asterisks indicate selection steps in which incubation time was decreased from 16 hr to 6 hr (Materials and Methods, Example 5). (32E) Recombination specificity of the selected catalytic domains (β, γ, δ, ε, and ζ, wild-type Gin indicated by a) for each possible two-base combination at positions 3 and 2. Intended DNA targets are underlined. Recombination was determined by split gene reassembly and performed in triplicate.

FIGS. 33A-33C are a series of graphical and diagrammatic representations illustrating the ability of ZFRs to recombine user-defined sequences in mammalian cells. (33A) Schematic representation of the luciferase reporter system used to evaluate ZFR activity in mammalian cells. ZFR target sites flank an SV40 promoter that drives luciferase expression. Solid lines denote the 44-bp consensus target sequence used to identify potential ZFR target sites. Underlined bases indicate zinc-finger targets and positions 3 and 2 (SEQ ID NO: 343). (33B) Fold-reduction of luciferase expression in HEK293T cells co-transfected with designed ZFR pairs and their cognate reporter plasmid. Fold-reduction was normalized to transfection with empty vector and reporter plasmid. The sequence identity and chromosomal location of each ZFR target site (SEQ ID NOs: 344-362 top to bottom) and the catalytic domain composition of each ZFR pair are shown. Underlined bases indicate positions 3 and 2. Standard errors were calculated from three independent experiments. ZFR amino acid sequences are provided in Table 2. (33C) Specificity of ZFR pairs. Fold-reduction of luciferase expression was measured for ZFR pairs 1 through 9 and GinC4 for each non-cognate reporter plasmid. Recombination was normalized to the fold-reduction of each ZFR pair with its cognate reporter plasmid. Assays were performed in triplicate.

FIG. 37 is a table showing core specificity of isolated catalytic domains. After 4 rounds of selection, the ability of selected catalytic domains to recombine core sequences with substitutions at positions 3 and 2 was evaluated. Assigned DNA targets are underlined. Recombinase mutations are shown. Asterisks indicate catalytic domains selected for further analysis. Wild-type base combination at positions 3 and 2 is CC. Recombination was determined by split gene reassembly (2) and performed in triplicate. Catalytic domains that recombine TT substitutions are described elsewhere (1).

FIGS. 38A-38B are a series of graphical representations of position specificity of selected catalytic domains. Recombination assays between the α, β, γ, δ and ζ catalytic domains and symmetrically substituted target sites. Recombination was measured on a library DNA targets that contained (38A (SEQ ID NO: 368))>4,000 random strong base (S: G or C) substitutions at positions 6, 5 and 4 and (38B (SEQ ID NO: 369))>10$^6$ (of a possible $4.29\times10^9$) unique base combinations at positions 10, 9, 8 and 7 (N: A, T, C or G). Recombination was measured by split gene reassembly (2) (n=3).

FIG. 39 is a series of graphical representations of ZFR homodimer activity. HEK293T cells were co-transfected with 150 ng ZFR-L or 150 ng ZFR-R with 2.5 ng of corresponding pGL3 ZFR reporter plasmid. Recombination was normalized to co-transfection with 150 ng ZFR-L and 150 ng ZFR-R with 2.5 ng pGL3 ZFR reporter plasmid.

DETAILED DESCRIPTION OF THE INVENTION

The present provides the first disclosure of a TALE recombinase (TALER). Using a library of incrementally truncated TALE domains, optimized TALER architecture that can be used to recombine DNA in bacterial and mammalian cells was identified. Any customized TALE repeat array can be inserted into the TALER architecture described herein, thus dramatically expanding the targeting capacity of engineered recombinases for applications in biotechnology and medicine.

Transcription activator-like effector (TALE) proteins can be designed to bind virtually any DNA sequence. General guidelines for design of TALE DNA-binding domains suggest that the 5'-most base of the DNA sequence bound by the TALE (the N$_0$ base) should be a thymine. The N$_0$ requirement was quantified by analysis of the activities of TALE transcription factors (TALE-TF), TALE recombinases (TALE-R) and TALE nucleases (TALENs) with each DNA base at this position. In the absence of a 5' T, decreases in TALE activity up to >1000-fold in TALE-TF activity, up to 100-fold in TALE-R activity and up to 10-fold reduction in TALEN activity compared with target sequences containing a 5' T was observed. To develop TALE architectures that recognize all possible No bases, structure-guided library design coupled with TALE-R activity selections were used to evolve novel TALE N-terminal domains to accommodate any NO base. A G-selective domain and broadly reactive domains were isolated and characterized. The engineered TALE domains selected in the TALE-R format demonstrated modularity and were active in TALE-TF and TALEN architectures. Evolved N-terminal domains provide effective and unconstrained TALE-based targeting of any DNA sequence as TALE binding proteins and designer enzymes.

Figure 35:
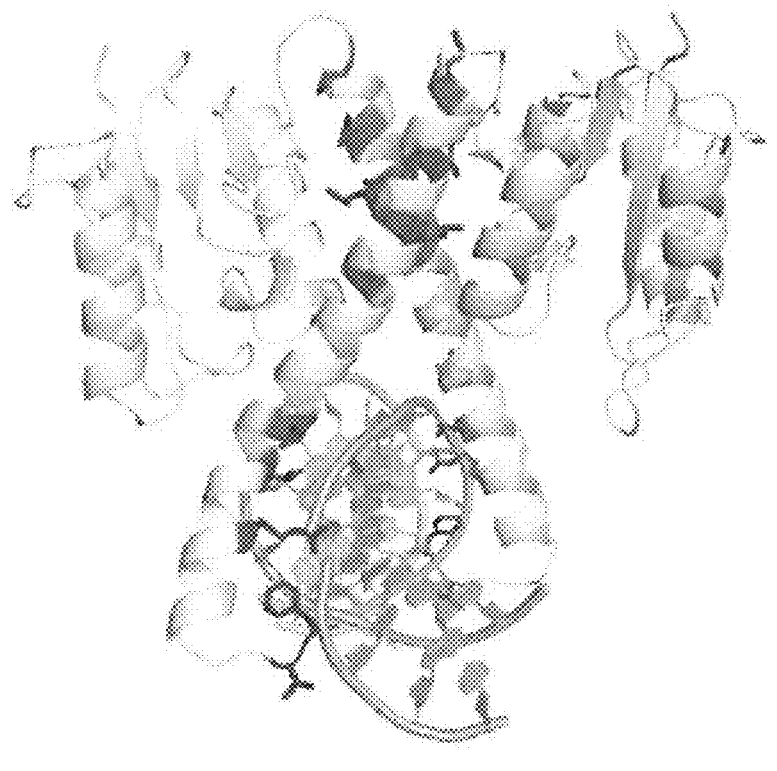
FIG. 35 is a diagrammatic representation of recombinase DNA-binding residues are located outside the dimer interface. The γδ resolvase in complex with target DNA. Catalytic domain dimer is colored cyan. DNA is colored grey. Arm region residues are shown as red sticks. Residues at the dimer interface are shown as purple sticks (PDB ID: 1GDT).

Additionally, in order to address sequence requirement limitations, a knowledge-base approach was described for re-engineering serine recombinase catalytic specificity. This strategy, which was based on the saturation mutagenesis of specificity-determining DNA-binding residues, was used to generate recombinase variants that showed a >10,000-fold shift in specificity. Importantly, this approach focused exclusively on amino acid residues located outside the recombinase dimer interface (FIG. 35). As a result, it was determined that re-engineered catalytic domains could associate to form ZFR heterodimers and that these designed ZFR pairs recombine pre-determined DNA sequences with exceptional specificity. Together, these results led us to hypothesize that an expanded catalog of specialized catalytic domains developed by this method could be used to generate ZFRs with custom specificity. Here, a combination of substrate specificity analysis and directed evolution is used to develop a diverse collection of Gin recombinase catalytic domains that are capable of recognizing an estimated $4 \times 10^8$ unique 20-bp core sequences. It is shown that ZFRs assembled from these re-engineered catalytic domains recombine user-defined sequences with high specificity and integrate DNA into targeted endogenous loci in human cells. These results demonstrate the potential of ZFR technology for a wide variety of applications, including genome engineering and gene therapy.

Before the present compositions and methods are described, it is to be understood that this invention is not limited to the particular compositions, methods, and experimental conditions described, as such devices, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the composition" or "the method" includes one or more compositions and methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

"Recombinases" are a family of enzymes that mediate site-specific recombination between specific DNA sequences recognized by the recombinase (Esposito, D., and Scocca, J. J., Nucleic Acids Research 25, 3605-3614 (1997);

Nunes-Duby, S. E., et al., Nucleic Acids Research 26, 391-406 (1998); Stark, W. M., et al., Trends in Genetics 8, 432-439 (1992)).

As used herein, the term "chimeric TALE recombinase" includes without limitation recombinases having a TALE domain derived from a naturally-occurring TALE protein or a synthetically derived TALE protein or domain with sequence-specific binding activity.

As used herein, the term "chimeric zinc finger recombinase" includes without limitation recombinases having a zinc finger binding domain derived from a naturally-occurring zinc finger DNA binding protein or a synthetically derived zinc finger binding protein or domain with sequence-specific binding activity.

As used herein, the term "zinc finger," "zinc finger nucleotide binding domain," or similar terminology refers both to naturally occurring and artificially produced zinc fingers. Such zinc fingers can have various framework structures, such as, but not limited to, C2H2, C4, H4, H3C, C3X, H3X, C2X2, and H2X2, where X is a zinc ligating amino acid. In these framework structures, as is conventional in the recitation of zinc finger structures, "C" represents a cysteine residue and "H" represents a histidine residue. Zinc fingers having the framework C2H2 include, but are not limited to, zinc fingers described, for example, in International Publication Number WO2008/006028 to Barbas et al., U.S. Pat. No. 7,101,972 to Barbas, U.S. Pat. No. 7,067,617 to Barbas et al., U.S. Pat. No. 6,790,941 to Barbas et al., U.S. Pat. No. 6,610,512 to Barbas, U.S. Pat. No. 6,242,568 to Barbas et al., U.S. Pat. No. 6,140,466 to Barbas et al., U.S. Pat. No. 6,140,081 to Barbas, United States Patent Application Publication No. 20060223757 by Barbas, United States Patent Application Publication No. 20060211846 by Barbas et al., United States Patent Application Publication No. 20060078880 by Barbas et al., United States Patent Application Publication No. 20050148075 by Barbas, United States Patent Application Publication No. 20050084885 by Barbas et al., United States Patent Application Publication No. 20040224385 by Barbas et al., United States Patent Application Publication No. 20030059767 by Barbas et al., and United States Patent Application Publication No. 20020165356 by Barbas et al., all of which are incorporated herein by this reference. Other zinc fingers are described in: U.S. Pat. No. 7,067,317 to Rebar et al.; U.S. Pat. No. 7,030,215 to Liu et al.; U.S. Pat. No. 7,026,462 to Rebar et al.; U.S. Pat. No. 7,013,219 to Case et al.; U.S. Pat. No. 6,979,539 to Cox III et al.; U.S. Pat. No. 6,933,113 to Case et al.; U.S. Pat. No. 6,824,978 to Cox III et al.; U.S. Pat. No. 6,794,136 to Eisenberg et al.; U.S. Pat. No. 6,785,613 to Eisenberg et al.; U.S. Pat. No. 6,777,185 to Case et al.; U.S. Pat. No. 6,706,470 to Choo et al.; U.S. Pat. No. 6,607,882 to Cox I M et al.; U.S. Pat. No. 6,599,692 to Case et al.; U.S. Pat. No. 6,534,261 to Cox I I et al.; U.S. Pat. No. 6,503,717 to Case et al.; U.S. Pat. No. 6,453,242 to Eisenberg et al.; United States Patent Application Publication No. 2006/0246588 to Rebar et al.; United States Patent Application Publication No. 2006/0246567 to Rebar et al.; United States Patent Application Publication No. 2006/0166263 to Case et al.; United States Patent Application Publication No. 2006/0078878 to Cox H I et at.; United States Patent Application Publication No. 2005/0257062 to Rebar et al.; United States Patent Application Publication No. 2005/0215502 to Cox III et al.; United States Patent Application Publication No. 2005/0130304 to Cox Ml et al.; United States Patent Application Publication No. 2004/0203064 to Case et al.; United States Patent Application Publication No. 2003/0166141 to Case et al.;

United States Patent Application Publication No. 2003/0134318 to Case et al.; United States Patent Application Publication No. 2003/0105593 to Eisenberg et al.; United States Patent Application Publication No. 2003/0087817 to Cox I M et al.; United States Patent Application Publication No. 2003/0021776 to Rebar et al.; and United States Patent Application Publication No. 2002/0081614 to Case et al., all of which are incorporated herein by this reference. For example, one alternative described in these patents and patent publications involves the use of so-called "D-able sites" and zinc finger modules or zinc finger DNA binding domains that can bind to such sites. A "D-able" site is a region of a target site that allows an appropriately designed zinc finger module or zinc finger DNA binding domain to bind to four bases rather than three of the target strand. Such a zinc finger module or zinc finger DNA binding domain binds to a triplet of three bases on one strand of a double-stranded DNA target segment (target strand) and a fourth base on the other, complementary, strand. Binding of a single zinc finger to a four base target segment imposes constraints both on the sequence of the target strand and on the amino acid sequence of the zinc finger.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al. Molecular Biology of the Gene, 4th Edition, 1987, Benjamin/Cummings, p. 224). In particular, such a conservative variant has a modified amino acid sequence, such that the change(s) do not substantially alter the protein's (the conservative variant's) structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or Ile), leucine (L or Leu), methionine (M or Met), valine (V or Val); and (6) phenylalanine (F or Phe), tyrosine (Y or Tyr), tryptophan (W or Trp); (see also, e.g., Creighton (1984) Proteins, W. H. Freeman and Company;

Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation.

As used herein, the term "expression vector" refers to a plasmid, virus, phagemid, or other vehicle known in the art that has been manipulated by insertion or incorporation of heterologous DNA, such as nucleic acid encoding the fusion proteins herein or expression cassettes provided herein. Such expression vectors typically contain a promoter sequence for efficient transcription of the inserted nucleic acid in a cell. The expression vector typically contains an origin of replication, a promoter, as well as specific genes that permit phenotypic selection of transformed cells.

As used herein, the term "host cells" refers to cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

As used herein, genetic therapy involves the transfer of heterologous DNA to the certain cells, target cells, of a mammal, particularly a human, with a disorder or conditions for which such therapy is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, or it may encode a product, such as a peptide or RNA that in some manner mediates, directly or indirectly, expression of a therapeutic product. Genetic therapy may also be used to deliver nucleic acid encoding a gene product that replaces a defective gene or supplements a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof. Genetic therapy may also involve delivery of an inhibitor or repressor or other modulator of gene expression.

As used herein, heterologous DNA is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease. Typically, DNA encoding a desired gene product is cloned into a plasmid vector and introduced by routine methods, such as calcium-phosphate mediated DNA uptake (see, (1981) Somat. Cell. Mol. Genet. 7:603-616) or microinjection, into producer cells, such as packaging cells. After amplification in producer cells, the vectors that contain the heterologous DNA are introduced into selected target cells.

As used herein, an expression or delivery vector refers to any plasmid or virus into which a foreign or heterologous DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors". Also included are vectors that allow cloning of cDNA (complementary DNA) from mRNAs produced using reverse transcriptase.

As used herein, a gene refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, the term "isolated" with reference to a nucleic acid molecule or polypeptide or other biomolecule means that the nucleic acid or polypeptide has been separated from the genetic environment from which the polypeptide or nucleic acid were obtained. It may also mean that the biomolecule has been altered from the natural state. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al. (1988) Gene 67:3140. The terms isolated and purified are sometimes used interchangeably.

Thus, by "isolated" is meant that the nucleic acid is free of the coding sequences of those genes that, in a naturally-occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

"Isolated" or "purified" as those terms are used to refer to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. Particularly for proteins, the procedures may include for example, but are not limited to, ammonium sulfate fractionation, gel filtration, ion exchange change chromatography, affinity chromatography, density gradient centrifugation, electrofocusing, chromatofocusing, and electrophoresis.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

As used herein, a promoter region of a gene includes the regulatory element or elements that typically lie 5' to a structural gene; multiple regulatory elements can be present, separated by intervening nucleotide sequences. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product. The promoter region may be a normal cellular promoter or, for example, an onco-promoter. An onco-promoter is generally a virus-derived promoter. Viral promoters to which zinc finger binding polypeptides may be targeted include, but are not limited to, retroviral long terminal repeats (LTRs), and Lentivirus promoters, such as promoters from human T-cell lymphotrophic virus (HTLV) 1 and 2 and human immunodeficiency virus (HIV) 1 or 2.

As used herein, the term "truncated" or similar terminology refers to a polypeptide derivative that contains less than the full amino acid sequence of a native protein, such as a ZFP, TALE or serine recombinase.

As used herein, a polypeptide "variant" or "derivative" refers to a polypeptide that is a mutagenized form of a polypeptide or one produced through recombination but that still retains a desired activity, such as the ability to bind to a ligand or a nucleic acid molecule or to modulate transcription.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier. Vectors include, but are not necessarily limited to, expression vectors.

As used herein with regard to nucleic acid molecules, including DNA fragments, the phrase "operatively linked" means the sequences or segments have been covalently joined, preferably by conventional phosphodiester bonds, into one strand of DNA, whether in single or double-stranded form such that operatively linked portions function as intended. The choice of vector to which transcription unit or a cassette provided herein is operatively linked depends directly, as is well known in the art, on the functional properties desired, e.g., vector replication and protein expression, and the host cell to be transformed, these being limitations inherent in the art of constructing recombinant DNA molecules.

As used herein, administration of a therapeutic composition can be effected by any means, and includes, but is not limited to, oral, subcutaneous, intravenous, intramuscular, intrasternal, infusion techniques, intraperitoneal administration and parenteral administration.

Methods of transforming cells are well known in the art. By "transformed" it is meant a heritable alteration in a cell resulting from the uptake of foreign DNA. Suitable methods include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14 (6): 6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCE package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

As such, the invention provides nucleic acid and amino acid sequences encoding chimeric polypeptides of the invention which are substantially homologous and encode polypeptides that retain equivalent biological activity.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.)

A first polynucleotide is "derived from" a second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Site-specific recombinases are powerful tools for genome engineering. Hyperactivated variants of the resolvase/invertase family of serine recombinases function without accessory factors, and thus can be re-targeted to sequences of interest by replacing native DNA-binding domains with engineered zinc-finger proteins (ZFPs).

The zinc finger recombinases described herein are chimeric enzymes composed of an activated catalytic domain derived from the resolvase/invertase family of serine recombinases and a custom-designed zinc-finger DNA-binding domain. The ZFRs assembled from engineered catalytic domains efficiently recombine user-defined DNA targets with high specificity and designed ZFRs integrate DNA into targeted endogenous loci in human cells.

In one aspect, the invention provides a method of generating a plurality of zinc finger recombinase (ZFRs) proteins having catalytic specificity greater than the corresponding wild type recombinase. The method includes performing random mutagenesis on a recombinase catalytic domain at positions equivalent to Gin Ile120, Thr123, Leu127, Ile136 and Gly 137 or a combination thereof with reference to a wild-type Gin catalytic domain, mutating the DNA at positions 2 and 3 for each amino acid; fusing the recombinase catalytic domain with a plurality of zinc finger binding domains to form ZFRs, and enriching for ZFRs having catalytic specificity greater than the corresponding wild type recombinase. In embodiments the ZFRs have increased catalytic activity on DNA targets selected from GC, GT, CA, TT and AC. In one embodiment, the recombinase catalytic domain is mutagenized at Ile136 and/or Gly 137.

As used herein, a wild-type Gin catalytic domain refers to a Gin catalytic domain including all or a portion of a polypeptide having the amino acid sequence set forth as SEQ ID NO: 56 as follows: MLIGYVRVSTNDQNTDLQR-NALVCAGCEQIFEDKLSGTRT-DRPGLKRALKRLQKGD TLVVWKLDRLGRSM-KHLISLVGELRERGINFRSLTDSIDTSSPMGRFFFYVM GALAE MERELIIERTMAGLAAARNKGRIGGRPPKLT-KAEWEQAGRLLAQGIPRKQVALIYDV ALSTLYKKHP In various embodiments, the chimeric polypeptides of the invention include a Gin catalytic domain, such as those generated by the method of the invention. Particular Gin catalytic domains include those set forth in Table 1.

TABLE 1

| | | Gin catalytic domains. |
|---|---|---|
| Var-iant | SEQ ID NO: | Sequence |
| Gin α | 57 | MLIGYVRVSTNDQNTDLQRNALVCAGCEQIFEDKLSGTRT DRPGLKRALKRLQKGDTLVVWKLDRLGRSMKHLISLVGEL RERGINFRSLTDSIDTSSPMGRFFFYVMGALAEMERELII ERTMAGLAAARNKGRIGGRPPKSG |
| Gin β | 58 | MLIGYVRVSTNDQNTDLQRNALVCAGCEQIFEDKLSGTRT DRPGLKRALKRLQKGDTLVVWKLDRLGRSMKHLISLVGEL RERGINFRSLTDSIDTSSPMGRFFFYVMGALAEMERELII ERTMAGIAAARNKGRRFGRPPKS |

TABLE 1-continued

Gin catalytic domains.
Gin catalytic domains.

| Var-iant | SEQ ID NO: | Sequence |
|---|---|---|
| Gin γ | 59 | MLIGYVRVSTNDQNTDLQRNALVCAGCEQIFEDKLSGTRT DRPGLKRALKRLQKGDTLVVWKLDRLGRSMKHLISLVGEL RERGINFRSLTDSIDTSSPMGRFFFYVMGALAEMERELIL ERVMAGIAAARNKGRRWGRPPKSG |
| Gin δ | 60 | MLIGYVRVSTNDQNTDLQRNALVCAGCEQIFEDKLSGTRT DRPGLKRALKRLQKGDTLVVWKLDRLGRSMKHLISLVGEL RERGINFRSLTDSIDTSSPMGRFFFYVMGALAEMERELII ERVMAGLAAARNKGRRFGRPPKSG |
| Gin ε | 61 | MLIGYVRVSTNDQNTDLQRNALVCAGCEQIFEDKLSGTRT DRPGLKRALKRLQKGDTLVVWKLDRLGRSMKHLISLVGEL RERGINFRSLTDSIDTSSPMGRFFFYVMGALAEMERLSIL ERPMAGHAAARNKGRRFGRPPKSG |

TABLE 1-continued

Gin catalytic domains.
Gin catalytic domains.

| Var-iant | SEQ ID NO: | Sequence |
|---|---|---|
| Gin ζ | 62 | MLIGYVRVSTNDQNTDLQRNALVCAGCEQIFEDKLSGTRT DRPGLKRALKRLQKGDTLVVWKLDRLGRSMKHLISLVGEL RERGINFRSLTDSIDTSSPMGRFFFYVMGALAEMERELII ERTSAGRAAAINKGRIMGRPRKSG |

Targeted arm region positions are double underlined.
Random substitutions are emboldened and underlined.
The hyperactivating H106Y mutation is underlined.

In various embodiments, the ZFRs generated by the method of the invention include a Gin catalytic domain operatively linked to a plurality of zinc finger binding domains. Exemplary ZFRs generated by the invention include those set forth in Table 2.

TABLE 2

ZFRs.
Amino acid sequences of exemplary ZFRs.

| ZFR-1 Left | SEQ ID NO: 63 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSTSGNLVRHQRTHTGEKPYKCPECG KSFSQSGDLRRHQRTHTGEKPYKCPECGKSFSTSGNLVRHQRTHTG EKPYKCPECGKSFSTSGELVRHQRTHTGKKTSGQAGQ |
|---|---|---|
| ZFR-1 Right | SEQ ID NO: 64 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSHRTTLTNHQRTHTGEKPYKCPECG KSFSQSGDLRRHQRTHTGEKPYKCPECGKSFSQSGDLRRHQRTHTG EKPYKCPECGKSFSQSGDLRRHQRTHTGKKTSGQAGQ |
| ZFR-2 Left | SEQ ID NO: 65 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSQSGDLRRHQRTHTGEKPYKCPECG KSFSQRAHLERHQRTHTGEKPYKCPECGKSFSTSGNLVRHQRTHTG EKPYKCPECGKSFSRSDELVRHQRTHTGKKTSGQAGQ |
| ZFR-2 Right | SEQ ID NO: 66 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSRSDKLVRHQRTHTGEKPYKCPECG KSFSRKDNLKNHQRTHTGEKPYKCPECGKSFSTSGELVRHQRTHTG EKPYKCPECGKSFSRSDKLVRHQRTHTGKKTSGQAGQ |
| ZFR-3 Left | SEQ ID NO: 67 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSTTGNLTVHQRTHTGEKPYKCPECG KSFSDPGALVRHQRTHTGEKPYKCPECGKSFSQSSNLVRHQRTHTG EKPYKCPECGKSFSRSDHLTNHQRTHTGKKTSGQAGQ |
| ZFR-3 Right | SEQ ID NO: 68 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELIIERTMAGLAAARNKGRIGG RPPKSGTGEKPYKCPECGKSFSRKDNLKNHQRTHTGEKPYKCPECG KSFSRSDHLTNHQRTHTGEKPYKCPECGKSFSDPGNLVRHQRTHTG EKPYKCPECGKSFSRKDNLKNHQRTHTGKKTSGQAGQ |
| ZFR-4 Left | SEQ ID NO: 69 | MLIGYVRVSTNDQNTDLQRNALVCAGCEQIFEDKLSGTRTDRPGLK RALKRLQKGDTLVVWKLDRLGRSMKHLISLVGELRERGINFRSLTD SIDTSSPMGRFFFYVMGALAEMERELILERVMAGIAAARNKGRRWG RPPKSGTGEKPYKCPECGKSFSQRANLRAHQRTHTGEKPYKCPECG KSFSQSSSLVRHQRTHTGEKPYKCPECGKSFSTTGNLTVHQRTHTG EKPYKCPECGKSFSQRAHLERHQRTHTGKKTSGQAGQ |

TABLE 2-continued

ZFRs.
Amino acid sequences of exemplary ZFRs.

ZFR-4 Right SEQ ID NO: 70　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELILERVMAGIAAARNKGRRWG
RPPKSGTGEKPYKCPECGKSFSQRANLRAHQRTHTGEKPYKCPECG
KSFSRRDELNVHQRTHTGEKPYKCPECGKSFSQLAHLRAHQRTHTG
EKPYKCPECGKSFSQRAHLERHQRTHTGKKTSGQAGQ ZFR-5 Left　SEQ ID NO: 71　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELILERVMAGIAAARNKGRRWG
RPPKSGTGEKPYKCPECGKSFSRRDELNVHQRTHTGEKPYKCPECG
KSFSRSDHLTNHQRTHTGEKPYKCPECGKSFSQLAHLRAHQRTHTG
EKPYKCPECGKSFSQRAHLERHQRTHTGKKTSGQAGQ ZFR-5 Right SEQ ID NO: 72　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELIIERTMAGLAAARNKGRIGG
RPPKSGTGEKPYKCPECGKSFSTSGSLVRHQRTHTGEKPYKCPECG
KSFSRSDKLVRHQRTHTGEKPYKCPECGKSFSQSGDLRRHQRTHTG
EKPYKCPECGKSFSTSGELVRHQRTHTGKKTSGQAGQ ZFR-6 Left　SEQ ID NO: 73　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELIIERTSAGRAAAINKGRIMG
RPPKSGTGEKPYKCPECGKSFSQLAHLRAHQRTHTGEKPYKCPECG
KSFSQLAHLRAHQRTHTGEKPYKCPECGKSFSDPGHLVRHQRTHTG
EKPYKCPECGKSFSDSGNLRVHQRTHTGKKTSGQAGQ ZFR-6 Right SEQ ID NO: 74　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELILERVMAGIAAARNKGRRWG
RPPKSGTGEKPYKCPECGKSFSQRAHLERHQRTHTGEKPYKCPECG
KSFSTTGNLTVHQRTHTGEKPYKCPECGKSFSDSGNLRVHQRTHTG
EKPYKCPECGKSFSQSSNLVRHQRTHTGKKTSGQAGQ ZFR-7 Left　SEQ ID NO: 75　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELIIERTMAGIAAARNKGRRFG
RPPKSGTGEKPYKCPECGKSFSTHLDLIRHQRTHTGEKPYKCPECG
KSFSTTGNLTVHQRTHTGEKPYKCPECGKSFSQSSSLVRHQRTHTG
EKPYKCPECGKSFSRSDNLVRHQRTHTGKKTSGQAGQ ZFR-7 Right SEQ ID NO: 76　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELIIERTMAGIAAARNKGRRFG
RPPKSGTGEKPYKCPECGKSFSRSDKLVRHQRTHTGEKPYKCPECG
KSFSRRDELNVHQRTHTGEKPYKCPECGKSFSQSSSLVRHQRTHTG
EKPYKCPECGKSFSRSDHLTNHQRTHTGKKTSGQAGQ ZFR-8 Left　SEQ ID NO: 77　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELIIERTMAGLAAARNKGRIGG
RPPKSGTGEKPYKCPECGKSFSQRAHLERHQRTHTGEKPYKCPECG
KSFSTSGNLVRHQRTHTGEKPYKCPECGKSFSRSDELVRHQRTHTG
EKPYKCPECGKSFSHKNALQNHQRTHTGKKTSGQAGQ ZFR-8 Right SEQ ID NO: 78　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELIIERTMAGLAAARNKGRIGG
RPPKSGTGEKPYKCPECGKSFSRRDELNVHQRTHTGEKPYKCPECG
KSFSQSSNLVRHQRTHTGEKPYKCPECGKSFSQSSSLVRHQRTHTG
EKPYKCPECGKSFSTTGNLTVHQRTHTGKKTSGQAGQ ZFR-9 Left　SEQ ID NO: 79　MLIGYVRVSTNDQNTDLQRNALVCAGCEQIFEDKLSGTRTDRPGLK
RALKRLQKGDTLVVWKLDRLGRSMKHLISLVGELRERGINFRSLTD
SIDTSSPMGRFFFYVMGALAEMERELILERVMAGIAAARNKGRRWG
RPPKSGTGEKPYKCPECGKSFSTTGNLTVHQRTHTGEKPYKCPECG
KSFSQSSNLVRHQRTHTGEKPYKCPECGKSFSQRAHLERHQRTHTG
EKPYKCPECGKSFSQKSSLIAHQRTHTGKKTSGQAGQ TABLE 2-continued ZFRs.
Amino acid sequences of exemplary ZFRs.

```
ZFR-9 Right SEQ ID NO: 80   MLIGYVRVSTNDQNTDLQRNALVCAGCEQIFEDKLSGTRTDRPGLK
                            RALKRLQKGDTLVVWKLDRLGRSMKHLISLVGELRERGINFRSLTD
                            SIDTSSPMGRFFFYVMGALAEMERELIIERTSAGRAAAINKGRIMG
                            RPRKSGTGEKPYKCPECGKSFSDPGALVRHQRTHTGEKPYKCPECG
                            KSFSQSSSLVRHQRTHTGEKPYKCPECGKSFSQLAHLRAHQRTHTG
                            EKPYKCPECGKSFSQRANLRAHQRTHTGKKTSGQAGQ
```

Arm region mutations are double underlined.
Specificity-determining α-helical zinc-finger residues are underlined.

While the Examples illustrate generation of ZFRs having a Gin catalytic domain, the methods may be applied to catalytic domains of a number of other recombinases. Such recombinases include: a) Tn3, also known as EcoTn3; Hin, also known as StyHin; MuGin; Sin; Beta; Pin; Min; Din; Cin; EcoTn21; SfaTn917; BmeTn5083; Bme53; Cpe; SauSK1; SauSK41; SauTn552; Ran; Aac; L1a; pMER05; Mlo92; Mlo90; Rrh; Pje; Req; PpsTn5501; Pae; Xan; ISXc5; Spy; RhizY4cG; SarpNL1; SsoISC1904a; SsoISC1904b; SsoISC1913; Aam606; MjaM0014; Pab; HpyIS607; MtuIS_Y349; MtuRv2792c; MtuRv2979c; MtuRv3828c; MtuRv0921; MceRv0921; TnpX; TndX; WwK; lactococcal phage TP901-1 serine recombinase; *S. pyogenes* phage $370.1 serine recombinase; *S. pyogenes* phage φFC1 serine recombinase; *Listeria* phage A118 serine recombinase; *S. coelicolor* chromosome SC3C8.24 serine recombinase; *S. coelicolor* chromosome SC2E1.37 serine recombinase; *S. coelicolor* chromosome SCD78.04c serine recombinase; *S. coelicolor* chromosome SC8F4.15c serine recombinase; *S. coelicolor* chromosome SCD12A.23 serine recombinase; *S. coelicolor* chromosome SCH10.38c serine recombinase; *S. coelicolor* chromosome SCC88.14 serine recombinase; *Streptomyces* phage φC31 serine recombinase; *Streptomyces* phage R4 serine recombinase; *Bacillus* phage φ105 serine recombinase; *Bacillus* phage SPBc2 serine recombinase; *Bacillus* prophage SKIN serine recombinase; *S. aureus* ccrA serine recombinase; *S. aureus* ccrB serine recombinase; *M. tuberculosis* phage Bxb1 serine recombinase; *M. tuberculosis* prophage ØRV1 serine recombinase; YBCK_ECOLI; Y4bA; Bja; Spn; Cac 1956; and Cac 1954; and b) muteins of a).

Imperfect modularity with particular domains, lack of high-affinity binding to all DNA triplets, and difficulty in construction has hindered the widespread adoption of ZFPs in unspecialized laboratories. The discovery of a novel type of DNA-binding domain in transcription activator-like effector (TALE) proteins from *Xanthomonas* provides an alternative to ZFPs. Described herein are chimeric TALE recombinases (TALERs): engineered fusions between a hyperactivated catalytic domain from the DNA invertase Gin and an optimized TALE architecture. A library of incrementally truncated TALE variants was identified to identify TALER fusions that modify DNA with efficiency and specificity comparable to zinc-finger recombinases in bacterial cells. Also shown in the Examples, TALERs recombine DNA in mammalian cells. The TALER architecture described herein provides a platform for insertion of customized TALE domains, thus significantly expanding the targeting capacity of engineered recombinases and their potential applications in biotechnology and medicine.

Transcription activator-like effector (TALE) proteins can be designed to bind virtually any DNA sequence. General guidelines for design of TALE DNA-binding domains suggest that the 5'-most base of the DNA sequence bound by the TALE (the No base) should be a thymine. We quantified the No requirement by analysis of the activities of TALE transcription factors (TALE-TF), TALE recombinases (TALE-R) and TALE nucleases (TALENs) with each DNA base at this position. In the absence of a 5' T, we observed decreases in TALE activity up to >1000-fold in TALE-TF activity, up to 100-fold in TALE-R activity and up to 10-fold reduction in TALEN activity compared with target sequences containing a 5' T. To develop TALE architectures that recognize all possible No bases, a structure-guided library design coupled with TALE-R activity selections was used to evolve novel TALE N-terminal domains to accommodate any No base. A G-selective domain and broadly reactive domains were isolated and characterized. The engineered TALE domains selected in the TALE-R format demonstrated modularity and were active in TALE-TF and TALEN architectures. Evolved N-terminal domains provide effective and unconstrained TALE-based targeting of any DNA sequence as TALE binding proteins and designer enzymes.

In one aspect, the invention provides a method of generating a transcription activator-like effector (TALE) protein binding domain which specifically binds a desired nucleotide. As shown in the Examples, the method includes a) randomizing the amino acid sequence of the TALE protein binding domain by mutating an amino acid residue within a variable di-residue (RVD), or within 1 to 2 amino acid residues N-terminal or C-terminal of the RVD; and b) selecting for the randomized TALE protein binding domain of (a), wherein the TALE protein binding domain specifically binds to the desired nucleotide.

Sequence-specific nucleases, recombinases, nucleases and transcription factors are provided herein. The sequence-specific polypeptides include customized TAL effector DNA binding domains. As such, in another aspect, the invention provides a chimeric polypeptide. The polypeptide includes: a) a recombinase, a transcription factor or nuclease; and b) a transcription activator-like effector (TALE) protein.

TALEs are proteins of plant pathogenic bacteria that are injected by the pathogen into the plant cell, where they travel to the nucleus and function as transcription factors to turn on specific plant genes. The primary amino acid sequence of a TALE dictates the nucleotide sequence to which it binds. Thus, target sites can be predicted for TALE, and TALE also can be engineered and generated for the purpose of binding to particular nucleotide sequences, as described herein.

Fused to the TALE-encoding nucleic acid sequences are sequences encoding a nuclease, transcription factor or recombinase, or a portion thereof. Many such proteins are known in art that may be used in the present invention.

In various embodiments, the chimeric polypeptide includes a catalytic domain of a recombinase. As discussed above, catalytic domains of a number of recombinases may be utilized. Such recombinases include: a) Tn3, also known as EcoTn3; Hin, also known as StyHin; Gin, also known as MuGin; Sin; Beta; Pin; Min; Din; Cin; EcoTn21; SfaTn917; BmeTn5083; Bme53; Cpe; SauSK1; SauSK41; SauTn552; Ran; Aac; L1a; pMER05; Mlo92; Mlo90; Rrh; Pje; Req; PpsTn5501; Pae; Xan; ISXc5; Spy; RhizY4cG; SarpNL1; SsolSC1904a; SsolSC1904b; SsoISC1913; Aam606; MjaM0014; Pab; HpyIS607; MtuIS_Y349; MtuRv2792c; MtuRv2979c; MtuRv3828c; MtuRv0921; MceRv0921; TnpX; TndX; WwK; lactococcal phage TP901-1 serine recombinase; *S. pyogenes* phage $370.1 serine recombinase; *S. pyogenes* phage øFC1 serine recombinase; *Listeria* phage A118 serine recombinase; *S. coelicolor* chromosome SC3C8.24 serine recombinase; *S. coelicolor* chromosome SC2E1.37 serine recombinase; *S. coelicolor* chromosome SCD78.04c serine recombinase; *S. coelicolor* chromosome SC8F4.15c serine recombinase; *S. coelicolor* chromosome SCD12A.23 serine recombinase; *S. coelicolor* chromosome SCH10.38c serine recombinase; *S. coelicolor* chromosome SCC88.14 serine recombinase; *Streptomyces* phage øC31 serine recombinase; *Streptomyces* phage R4 serine recombinase; *Bacillus* phage $105 serine recombinase; *Bacillus* phage SPBc2 serine recombinase; *Bacillus* prophage SKIN serine recombinase; *S. aureus* ccrA serine recombinase; *S. aureus* ccrB serine recombinase; *M. tuberculosis* phage Bxb1 serine recombinase; *M. tuberculosis* prophage øRV1 serine recombinase; YBCK_ECOLI; Y4bA; Bja; Spn; Cac 1956; and Cac 1954; and b) muteins of a). In preferred embodiments, a highly active Gin catalytic domain is utilized. Such a domain may be generated using the methods of the present invention as described herein.

As described herein, TALEs may include a number of imperfect repeats that determine the specificity with which they interact with DNA. Each repeat binds to a single base, depending on the particular di-amino acid sequence at residues 12 and 13 of the repeat. Thus, by engineering the repeats within a TALE, particular DNA sites can be targeted. Such engineered TALEs can be used, for example, as transcription factors targeted to particular DNA sequences.

As illustrated in the Examples, the chimeric proteins of the present invention are exemplified by the variants and portions thereof (e.g., RVDs and NTDs) as set forth in Table 3.

TABLE 3

| Variant | SEQ ID NO: | Sequence |
|---|---|---|
| TALEN (Goldy) NT-T T1 Protein Sequence | 81 | MRSPKKKRKVQVDLRTLGYSQQQQEKIKPKVRSTVAQHHEALVGHGFTH AHIVALSQHPAALGTVAVTYQHIITALPEATHEDIVGVGKQWSGARALE ALLTDAGELRGPPLQLDTGQLVKIAKRGGVTAMEAVHASRNALTGAPLN LTPDQVVAIASNGGGKQALETVQRLLPVLCQDHGLTPDQVVAIASHDGG KQALETVQRLLPVLCQDHGLTPDQVVAIASNIGGKQALETVQRLLPVLC QDHGLTPDQVVAIASNGGGKQALETVQRLLPVLCQDHGLTPDQVVAIAS NGGGKQALETVQRLLPVLCQDHGLTPDQVVAIASNIGGKQALETVQRLL PVLCQDHGLTPDQVVAIASHDGGKQALETVQRLLPVLCQDHGLTPDQVV AIASNIGGKQALETVQRLLPVLCQDHGLTPDQVVAIVSHDGGKQALETV QRLLPVLCQDHGLTPDQVVAIVSHDGGKQALETVQRLLPVLCQDHGLTP DQVVAIVSNGGGKQALETVQRLLPVLCQDHGLTPDQVVAIASNNGGKQA LETVQRLLPVLCQDHGLTPDQVVAIASHDGGKQALETVQRLLPVLCQDH GLTPDQVVAIASNIGGKQALETVQRLLPVLCQDHGLTPDQVVAIASNNG GKQALETVQRLLPVLCQDHGLTPDQVVAIASHDGGKQALESIVAQLSRP DPALAALTNDHLVALACLGGRPAMDAVKKGLPHAPELIRRVNRRIGERT SHRVAGSQLVKSELEEKKSELRHKLKYVPHEY1ELIEIARNSTQDRILE MKVMEFFMKVYGYRGKHLGGSRKPDGAIYTVGSPIDYGVIVDTKAYSGG YNLPIGQADEMQRYVEENQTRNKHINPNEWWKVYPSSVTEFKFLFVSGH FKGNYKAQLTRLNHITNCNGAVLSVEELLIGGEMIKAGTLTLEEVRRKF NNGEINF = N-Terminal Domain (NTD) -varied as shown below |

| TALEN RVD Sequences | | |
|---|---|---|
| G1 | 82 | NG-NN-HD-NG-HD-NI-NG-NG-NI-HD-NI-HD-HD-NG-NN-HD-NI targeting (TCTTCATTACACCTGCA; SEQ ID NO: 280) |
| G2 | 83 | HD-NI-NN-NG-HD-NI-NN-NG-NI-NG-HD-NI-NI-NG-NG targeting (CAGTCAGTATCAATT; SEQ ID NO: 281) |
| A1 | 84 | HD-HD-NG-NN-HD-NI-NN-HD-NG-HD-NG-HD-NI-NG-NG-NG-NG targeting (CCTGCAGCTCTCATTTT; SEQ ID NO: 282) |
| A2 | 85 | NI-NG-NG-HD-NG-NG-HD-HD-NI-NN-NI-NG-NG-NN-NI targeting (ATTCTTCCAGAATTGA; SEQ ID NO: 283) |
| C2 | 86 | HD-NI-NN-NI-NI-NG-NG-NN-NI-NG-NI-HD-NG-NN-NI-HD-NG targeting (CAGAATTGATACTGACT; SEQ ID NO: 284) |
| T1 | 87 | NG-HD-NI-NG-NG-NI-HD-NI-HD-HD-NG-NN-HD-NI-NN-HD targeting (TCATTACACCTGCAGC; SEQ ID NO: 285) |
| T2 | 88 | HD-NG-NG-HD-HD-NI-NN-NI-NI-NG-NG-NN-NI-NG-NI-HD-NG-NN targeting (CTTCCAGAATTGATACTG; SEQ ID NO: 286) |

TABLE 3-continued

| Variant | SEQ ID NO: | Sequence |
|---|---|---|
| | | N-Terminal Domains |
| NTD = dHax3-TALEN DNA Sequence | 89 | ATGAGATCTCCTAAGAAAAAGAGGAAGATGGTGGACTTGAGGACACTCG GTTATTCGCAACAGCAACAGGAGAAAATCAAGCCTAAGGTCAGGAGCAC CGTCGCGCAACACCACGAGGCGCTTGTGGGGCATGGCTTCACTCATGCG CATATTGTCGCGCTTTCACAGCACCCTGCGGCGCTTGGGACGGTGGCTG TCAAATACCAAGATATGATTGCGGCCCTGCCCGAAGCCACGCACGAGGC AATTGTAGGGGTCGGTAAACAGTGGTCGGGAGCGCGAGCACTTGAGGCG CTGCTGACTGTGGCGGGTGAGCTTAGGGGGCCTCCGCTCCAGCTCGACA CCGGGCAGCTGCTGAAGATCGCGAAGAGAGGGGGAGTAACAGCGGTAGA GGCAGTGCATGCATCGCGCAATGCACTGACGGGTGCCCCC |
| NTD = dHax3-TALEN | 90 | MRSPKKKRKMVDLRTLGYSQQQQEKIKPKVRSTVAQHHEALVGHGFTHA HIVALSQHPAALGTVAVKYQDMIAALPEATHEAIVGVGKQWSGARALEA LLTVAGELRGPPLQLDTGQLLKIAKRGGVTAVEAVHASRNALTGA P . . . repeat variable diresidues |
| NTD = NT-βN TALEN DNA Sequence | 91 | ATGAGATCTCCTAAGAAAAAGAGGAAGGTGCAGGTGGATCTACGCACGC TCGGCTACAGTCAGCAGCAGCAAGAGAAGATCAAACCGAAGGTGCGTTC GACAGTGGCGCAGCACCACGAGGCACTGGTGGGCCATGGGTTTACACAC GCGCACATCGTTGCGCTCAGCCAACACCCGGCAGCGTTAGGGACCGTCG CTGTCACGTATCAGCACATAATCACGGCGTTGCCAGAGGCGACACACGA AGACATCGTTGGCGTCGGCAAATATCATGGGGCACGCGCTCTGGAGGCC TTGCTCACGGATGCGGGGGAGTTGAGAGGTCCGCCGTTACAGTTGGACA CAGGCCAACTTGTGAAGATTGCAAAACGTGGCGGCGTGACCGCAATGGA GGCAGTGCATGCATCGCGCAATGCACTGACGGGTGCCCCC |
| NTD = NT-βN TALEN | 92 | MRSPKKKRKVQVDLRTLGYSQQQQEKIKPKVRSTVAQHHEALVGHGFTH AHIVALSQHPAALGTVAVTYQHIITALPEATHEDIVGVGKYHGARALEA LLTDAGELRGPPLQLDTGQLVKIAKRGGVTAMEAVHASRNALTGA P . . . repeat variable diresidues |
| NTD NT-G TALEN DNA Sequence | 93 | ATGAGATCTCCTAAGAAAAAGAGGAAGGTGCAGGTGGATCTACGCACGC TCGGCTACAGTCAGCAGCAGCAAGAGAAGATCAAACCGAAGGTGCGTTC GACAGTGGCGCAGCACCACGAGGCACTGGTGGGCCATGGGTTTACACAC GCGCACATCGTTGCGCTCAGCCAACACCCGGCAGCGTTAGGGACCGTCG CTGTCACGTATCAGCACATAATCACGGCGTTGCCAGAGGCGACACACGA AGACATCGTTGGCGTCGGCAAATCGCGGTCGGGGGCACGCGCTCTGGAG GCCTTGCTCACGGATGCGGGGGAGTTGAGAGGTCCGCCGTTACAGTTGG ACACAGGCCAACTTGTGAAGATTGCAAAACGTGGCGGCGTGACCGCAAT GGAGGCAGTGCATGCATCGCGCAATGCACTGACGGGTGCCCCC |
| NTD NT-G TALEN Protein Sequence | 94 | MRSPKKKRKVQVDLRTLGYSQQQQEKIKPKVRSTVAQHHEALVGHGFTH AHIVALSQHPAALGTVAVTYQHIITALPEATHEDIVGVGKSRSGARALE ALLTDAGELRGPPLQLDTGQLVKIAKRGGVTAMEAVHASRNALTGA P . . . repeat variable diresidues |
| NTD = NT-αN TALEN DNA Sequence | 95 | ATGAGATCTCCTAAGAAAAAGAGGAAGGTGCAGGTGGATCTACGCACGC TCGGCTACAGTCAGCAGCAGCAAGAGAAGATCAAACCGAAGGTGCGTTC GACAGTGGCGCAGCACCACGGGGCACTGGTGGGCCATGGGTTTACACAC GCGCACATCGTTGCGCTCAGCCAACACCCGGCAGCGTTAGGGACCGTCG CTGTCACGTATCAGCACATAATCACGGCGTTGCCAGAGGCGACACACGA AGACATCGTTGGCGTCGGCAAACGGGGGGCTGGTGCACGCGCTCTGGAG GCCTTGCTCACGGATGCGGGGGAGTTGAGAGGTCCGCCGTTACAGTTGG ACACAGGCCAACTTGTGAAGATTGCAAAACGTGGCGGCGTGACCGCAAT GGAGGCAGTGCATGCATCGCGCAATGCACTGACGGGTGCCCCC |
| NTD = NT-αN TALEN Protein | 96 | MRSPKKKRKVQVDLRTLGYSQQQQEKIKPKVRSTVAQHHGALVGHGFTH AHIVALSQHPAALGTVAVTYQHIITALPEATHEDIVGVGKRGAGARALE ALLTDAGELRGPPLQLDTGQLVKIAKRGGVTAMEAVHASRNALTGA P . . . repeat variable diresidues |
| NTD = NT-T T-1 TALEN DNA | 97 | ATGAGATCTCCTAAGAAAAAGAGGAAGGTGCAGGTGGATCTACGCACGC TCGGCTACAGTCAGCAGCAGCAAGAGAAGATCAAACCGAAGGTGCGTTC GACAGTGGCGCAGCACCACGAGGCACTGGTGGGCCATGGGTTTACACAC GCGCACATCGTTGCGCTCAGCCAACACCCGGCAGCGTTAGGGACCGTCG CTGTCACGTATCAGCACATAATCACGGCGTTGCCAGAGGCGACACACGA AGACATCGTTGGCGTCGGCAAACAGTGGTCCGGCGCACGCGCCCTGGAG GCCTTGCTCACGGATGCGGGGGAGTTGAGAGGTCCGCCGTTACAGTTGG ACACAGGCCAACTTGTGAAGATTGCAAAACGTGGCGGCGTGACCGCAAT GGAGGCAGTGCATGCATCGCGCAATGCACTGACGGGTGCCCCC |
| MBP-TALE Protein Sequence | 98 | MKIEEGKLVIWINGDKGYNGLAEVGKKFEKDTGIKVTVEHPDKLEEKFP QVAATGDGPDIIFWAHDRFGGYAQSGLLAEITPDKAFQDKLYPFTWDAV RYNGKLIAYPIAVEALSLIYNKDLLPNPPKTWEEIPALDKELKAKGKSA LMFNLQEPYFTWPLIAADGGYAFKYENGKYDIKDVGVDNAGAKAGLTFL VDLIKNKHMNADTDYSIAEAAFNKGETAMTINGPWAWSNIDTSKVNYGV |

TABLE 3-continued

| Variant | SEQ ID NO: | Sequence |
|---|---|---|
| | | TVLPTFKGQPSKPFVGVLSAGINAASPNKELAKEFLENYLLTDEGLEAV<br>NKDKPLGAVALKSYEEELAKDPRIAATMENAQKGEIMPNIPQMSAFWYA<br>VRTAVINAASGRQTVDEALKDAQTNSSSNNNNNNNNNNLGIEGRISEFG<br>SPARPPRAKPAPRRRSAQPSDASPAAQVDLRTLGYSQQQQEKIKPKVRS<br>TVAQHHEALVGHGFTHAHIVALSQHPAALGTVAVTYQHIITALPEATHE<br>DIVGVGK[XXX]GARALEALLTDAGELLRGPPLQLDTGQLVKIAKRGGV<br>TAMEAVHASRNALTGAPLNLTPDQVVAIASNIGGKQALETVQRLLPVLC<br>QDHGLTPDQVVAIASNGGGKQALETVQRLLPVLCQDHGLTPDQVVAIAS<br>NIGGKQALETVQRLLPVLCQDHGLTPDQVVAIASNIGGKQALETVQRLL<br>PVLCQDHGLTPDQVVAIASNIGGKQALETVQRLLPVLCQDHGLTPDQVV<br>AIASHDGGKQALETVQRLLPVLCQDHGLTPDQVVAIASHDGGKQALETV<br>QRLLPVLCQDHGLTPDQVVAIASHDGGKQALETVQRLLPVLCQDHGLTP<br>DQVVAIVSHDGGKQALETVQRLLPVLCQDHGLTPDQVVAIVSHDGGKQA<br>LETVQRLLPVLCQDHGLTPDQVVAIVSNGGGKQALETVQRLLPVLCQDH<br>GLTPDQVVAIASHDGGKQALETVQRLLPVLCQDHGLTPDQVVAIASHDG<br>GKQALETVQRLLPVLCQDHGLTPDQVVAIASNIGGKQALETVQRLLPVL<br>CQDHGLTPDQVVAIASNIGGKQALESIVAQLSRPDPALAALTNDHLVAL<br>ACLG<br>XXX: NT-T = QWS NT-G = SRS; NT-αN = RGA;<br>NT-βN = Y-H |
| TALE-R Protein<br>Sequence | 99 | MLIGYVRVSTNDQNTDLQRNALVCAGCEQIFEDKLSGTRTDRPGLKRAL<br>KRLQKGDTLVVWKLDRLGRSMKHLISLVGELRERGINFRSLTDSIDTSS<br>PMGRFFFYVMGALAEMERELIIERTMAGLAAARNKGRIGGRPPKSGSPR<br>PPRAKPAPRRRAAQPSDASPAAQVDLRTLGYSQQQQEKIKPKVRSTVAQ<br>HHEALVGHGFTHAHIVALSQHPAALGTVAVTYQHIITALPEATHEDIVG<br>VGK[XXX]GARALEALLTDAGELRGPPLQLDTGQLVKIAKRGGVTAMEA<br>VHASRNALTGAPLNLTPDQVVAIASNIGGKQALETVQRLLPVLCQDHGL<br>TPDQVVAIASNGGGKQALETVQRLLPVLCQDHGLTPDQVVAIASNIGGK<br>QALETVQRLLPVLCQDHGLTPDQVVAIASNIGGKQALETVQRLLPVLCQ<br>DHGLTPDQVVAIASNIGGKQALETVQRLLPVLCQDHGLTPDQVVAIASH<br>DGGKQALETVQRLLPVLCQDHGLTPDQVVAIASHDGGKQALETVQRLLP<br>VLCQDHGLTPDQVVAIASHDGGKQALETVQRLLPVLCQDHGLTPDQVVA<br>IVSHDGGKQALETVQRLLPVLCQDHGLTPDQVVAIVSHDGGKQALETVQ<br>RLLPVLCQDHGLTPDQVVAIVSNGGGKQALETVQRLLPVLCQDHGLTPD<br>QVVAIASHDGGKQALETVQRLLPVLCQDHGLTPDQVVAIASHDGGKQAL<br>ETVQRLLPVLCQDHGLTPDQVVAIASNIGGKQALETVQRLLPVLCQDHG<br>LTPDQVVAIASNIGGKQALESIVAQLSRPDPALAALTNDHLVALACLG<br>XXX: NT-T = QWS NT-G = SRS; NT-αN = RGA;<br>NT-βN = Y-H |
| Avr15 TALE-TF<br>Protein Sequence | 100 | MAQAASGSPRPPRAKPAPRRRAAQPSDASPAAQVDLRTLGYSQQQQEKI<br>KPKVRSTVAQHHEALVGHGFTHAHIVALSQHPAALGTVAVTYQHIITAL<br>PEATHEDIVGVGK[XXX]GARALEALLTDAGELRGPPLQLDTGQLVKIA<br>KRGGVTAMEAVHASRNALTGAPLNLTPDQVVAIASNIGGKQALETVQRL<br>LPVLCQDHGLTPDQVVAIASNGGGKQALETVQRLLPVLCQDHGLTPDQV<br>VAIASNIGGKQALETVQRLLPVLCQDHGLTPDQVVAIASNIGGKQALET<br>VQRLLPVLCQDHGLTPDQVVAIASNIGGKQALETVQRLLPVLCQDHGLT<br>PDQVVAIASHDGGKQALETVQRLLPVLCQDHGLTPDQVVAIASHDGGKQ<br>ALETVQRLLPVLCQDHGLTPDQVVAIASHDGGKQALETVQRLLPVLCQD<br>HGLTPDQVVAIVSHDGGKQALETVQRLLPVLCQDHGLTPDQVVAIVSHD<br>GGKQALETVQRLLPVLCQDHGLTPDQVVAIVSNGGGKQALETVQRLLPV<br>LCQDHGLTPDQVVAIASHDGGKQALETVQRLLPVLCQDHGLTPDQVVAI<br>ASHDGGKQALETVQRLLPVLCQDHGLTPDQVVAIASNIGGKQALETVQR<br>LLPVLCQDHGLTPDQVVAIASNIGGKQALESIVAQLSRPDPALAALTND<br>HLVALACLGGRPAMDAVKKGLPHAPELIRRVNRRIGERTSHRVADYAQV<br>VRVLEFFQCHSHPAYAFDEAMTQFGMSGQAGQASPKKKRKVGRADALDD<br>FDLDMLGSDALDDFDLDMLGSDALDDFDLDMLGSDALDDFDLDMLINYP<br>YDVPDYAS<br>XXX: NT-T = QWS NT-G = SRS; NT-αN = RGA;<br>NT-βN = Y-H |
| Avr15 RVD<br>Sequence (for<br>TALE-R, TALE-<br>TF, MBP-TALE) | 101 | NI-NG-NI-NI-NI-HD-HD-HD-HD-HD-NI-HD-HD-NI-NI<br>targeting (ATAAACCCCCTCCAA; SEQ ID NO: 287) |

In various embodiments, chimeric protein includes a TALE protein having a C-terminal or N-terminal truncation. For example, the TALE protein may include all or a portion of SEQ ID NO: 2. In embodiments, the TALE protein is truncated between amino acid residues 27 and 268, 92 and 134, 120 and 129, 74 and 147, or 87 and 120, such at amino acid residue 28, 74, 87, 92, 95, 120, 124, 128, 129, 147 and 150.

In another embodiment, a isolated polypeptide comprising a transcription activator-like effector (TALE) protein is provided in which the TALE protein has an N-terminal domain (NTD) comprising an amino acid sequence as set forth in SEQ ID NO: 3 (VGKQWSGARAL) having one or more mutations or deletions selected from: Q is Y, Q is S, Q is R, W is R, Wis G, W is deleted, S is R, S is H, Sis A, S is N, and Sis T.

In some embodiments, the NTD comprises an amino acid sequence selected from: VGKYRGARAL (SEQ ID NO: 4), VGKSRSGARAL (SEQ ID NO: 5), VGKYHGARAL (SEQ ID NO: 6), and VGKRGAGARAL (SEQ ID NO: 7).

In another embodiment, an isolated polypeptide comprising a transcription activator-like effector (TALE) protein is provided in which the TALE protein has an N-terminal domain (NTD) comprising an amino acid sequence as set forth in SEQ ID NO: 8 (IVDIAR$_1$QR$_2$SGDLA) having one or more mutations or deletions selected from: R$_1$ is K, Q is Y, Q is S, Q is R, R$_2$ is W, R$_2$ is G, R$_2$ is deleted, S is R, S is H, S is A, S is N, and S is T.

In some embodiments, the NTD comprises an amino acid sequence selected from:

```
                                (SEQ ID NO: 9)
        IVDIARQWSGDLA, (SEQ ID NO: 10)
        IVDIARYRGDLA, (SEQ ID NO: 11)
        IVDIARSRSGDLA, (SEQ ID NO: 12)
        IVDIARYHGDLA,
        and (SEQ ID NO: 13)
        IVDIARRGAGDLA.
```

In another embodiment, the TALE protein includes a modified No domain having an amino acid sequence set forth as follows: LTPDQLVKIAKRGGTAMEAVHASRNALTGAPLN (SEQ ID NO: 102). In various embodiments, the TALE protein includes a mutated variant in which KRGG (SEQ ID NO: 103) of SEQ ID NO: 102 is selected from LDYE (SEQ ID NO: 104), INLV (SEQ ID NO: 105), YSKK (SEQ ID NO: 106), NMAH (SEQ ID NO: 107), SPTN (SEQ ID NO: 108), SNTR (SEQ ID NO: 109), LTTT (SEQ ID NO: 110), VADL (SEQ ID NO: 111), MVLS (SEQ ID NO: 112), YNGR (SEQ ID NO: 113), RIPR (SEQ ID NO: 114), YSKI (SEQ ID NO: 115), LTQY (SEQ ID NO: 116), YLSK (SEQ ID NO: 117), LRPN (SEQ ID NO: 118), LFTN (SEQ ID NO: 119), LLTN (SEQ ID NO: 120), EEDK (SEQ ID NO: 121), VTAM (SEQ ID NO: 122), CPSR (SEQ ID NO: 123), LTRV (SEQ ID NO: 124), KGDL (SEQ ID NO: 125), QKAL (SEQ ID NO: 126), LYLL (SEQ ID NO: 127), WISV (SEQ ID NO: 128), GDQV (SEQ ID NO: 129) and CPSR (SEQ ID NO: 130).

In another embodiment, the TALE protein includes a modified N–1 domain having an amino acid sequence set forth as follows:

MRSPKKKRKVQVDLRTLGYSQQQQEKIKPKVRSTVA QHH EALVGHGFTHAHIVALSQHPAALGTVA- VTYQHIITALPEATHEDIVGVGXXXXXARA LEALLTDAGELRGPPLQLDTGQLVKI- AKRGGVTAMEAVHASRNALTGAP (SEQ ID NO: 131). In various embodiments, XXXXX of SEQ ID NO: 131 is KRPAG (SEQ ID NO: 132) or KRPSG (SEQ ID NO: 133). Additionally, the protein may include, a E40G mutation (with reference to SEQ ID NO: 131) that exhibits enhanced activity.

In another embodiment, the TALE protein includes a repeat domain having an amino acid sequence set forth as follows: LTPDVVAIS- NNGGKQALETVQRLLPVLCQDGH (SEQ ID NO: 134). In various embodiments, the TALE protein includes a mutated variant in which SNNG (SEQ ID NO: 135) of SEQ ID NO: 134 is selected from RGGG (SEQ ID NO: 136), RGGR (SEQ ID NO: 137), RGVR (SEQ ID NO: 138), KGGG (SEQ ID NO: 139), SGGG (SEQ ID NO: 140), GGRG (SEQ ID NO: 141), LGGS (SEQ ID NO: 142), MDNI (SEQ ID NO: 143), RVMA (SEQ ID NO: 144), LASV (SEQ ID NO: 145), VGTG (SEQ ID NO: 146) and QGGG (SEQ ID NO: 147).

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Chimeric Tale Recombinases

Experimental Summary

This study provides the first example of a TALE recombinase (TALER). Using a library of incrementally truncated TALE domains, an optimized TALER architecture was identified that can be used to recombine DNA in bacterial and mammalian cells. Any customized TALE repeat array can be inserted into the TALER architecture described herein, thus dramatically expanding the targeting capacity of engineered recombinases for applications in biotechnology and medicine.

The following Material and Methods were utilized in this Example.

Reagents.

All enzymes were purchased from New England BioLabs unless otherwise indicated. Primer sequences are provided in Table 4.

TABLE 4

Primers.

| Primers used in this study |
| :--: |
| Primers for pBLA substrate construction |

| AvrXa7 lac target F | SEQ ID NO: 148 | TTAATTAAGAGTCTAGAAATATAAACCCCCTC CAACCAGGTGCTAACTGTAAACCATGGTTTTG GATTAGCACCTGGTTGGAGGGGGTTTATAAGA TCTAGGAGGAATTTAAAATGAG |
| AvrXa7 lac target R | SEQ ID NO: 149 | ACTGACCTAGAGAAGCTTATATAAACCCCCTC CAACCAGGTGCTAATCCAAAACCATGGTTTAC AGTTAGCACCTGGTTGGAGGGGGTTTATACTG CAGTTATTTGTACAGTTCATC |

TABLE 4-continued

Primers.

| AvrXa7 N F | SEQ ID NO: 150 | TTAATTAAGAGTCTAGATTAGCACCTGGTTGG AGGGGGTTTATAAGGTTTTGGTACCAAATGTC TATAAACCCCCTCCAACCAGGTGCTAAAGATC TAGGAGGAATTTAAAATGAG |
|---|---|---|
| AvrXa7 N R | SEQ ID NO: 152 | ACTGACCTAGAGAAGCTTTTAGCACCTGGTTG GAGGGGGTTTATAGACATTTGGTACCAAAACC TTATAAACCCCCTCCAACCAGGTGCTAACTGC AGTTATTTGTACAGTTCATC |
| AvrXa7 N RC F | SEQ ID NO: 153 | TTAATTAAGAGTCTAGATTAGCACCTGGTTGG AGGGGGTTTATATCCAAAACCATGGTTTACAG TATAAACCCCCTCCAACCAGGTGCTAAAGATC TAGGAGGAATTTAAAATGAG |
| AvrXa7 N RC R | SEQ ID NO: 154 | ACTGACCTAGAGAAGCTTTTAGCACCTGGTTG GAGGGGGTTTATATCCAAAACCATGGTTTACA GTATAAACCCCCTCCAACCAGGTGCTAACTGC AGTTATTTGTACAGTTCATC |
| AvrXa7 N RC +3 F | SEQ ID NO: 155 | TTAATTAAGAGTCTAGATTAGCACCTGGTTGG AGGGGGTTTATAGCTTCCAAAACCATGGTTTA CAGGGTTATAAACCCCCTCCAACCAGGTGCTA AAGATCTAGGAGGAATTTAAAATGAG |
| AvrXa7 N RC +3 R | SEQ ID NO: 277 | ACTGACCTAGAGAAGCTTTTAGCACCTGGTTG GAGGGGGTTTATAACCCTGTAAACCATGGTTT TGGAAGCTATAAACCCCCTCCAACCAGGTGCT AACTGCAGTTATTTGTACAGTTCATC |
| AvrXa7 N RC +6 F | SEQ ID NO: 156 | TTAATTAAGAGTCTAGATTAGCACCTGGTTGG AGGGGGTTTATAGCTTCATCCAAAACCATGGT TTACAGGGTTCCTATAAACCCCCTCCAACCAG GTGCTAAAGATCTAGGAGGAATTTAAAATGAG |
| AvrXa7 N RC +6 R | SEQ ID NO: 157 | ACTGACCTAGAGAAGCTTTTAGCACCTGGTTG GAGGGGGTTTATAGCAACCCTGTAAACCATGG TTTTGGATGAAGCTATAAACCCCCTCCAACCA GGTGCTAACTGCAGTTATTTGTACAGTTCATC |
| AvrXa7 N RC +12 F | SEQ ID NO: 158 | TTAATTAAGAGTCTAGATTAGCACCTGGTTGG AGGGGGTTTATAGCTICAGCTICATCCAAAAC CATGGTTTACAGGGTTCCGGTTCCTATAAACC CCCTCCAACCAGGTGCTAAAGATCTAGGAGGA ATTTAAAATGAG |
| AvrXa7 N RC +12 R | SEQ ID NO: 278 | ACTGACCTAGAGAAGCTTTTAGCACCTGGTTG GAGGGGGTTTATAGCAACCGCAACCCTGTAAA CCATGGTTTTGGATGAAGCTGAAGCTATAAAC CCCCTCCAACCAGGTGCTAACTGCAGTTATTT GTACAGTTCATC |
| AvrXa7 N RC −3 F | SEQ ID NO: 160 | TTAATTAAGAGTCTAGATTAGCACCTGGTTGG AGGGGGTTTATAAAAACCATGGITTATATAAA CCCCCTCCAACCAGGTGCTAAAGATCTAGGAG GAATTTAAAATGAG |
| AvrXa7 N RC −3 R | SEQ ID NO: 161 | ACTGACCTAGAGAAGCTTTTAGCACCTGGTTG GAGGGGGTTTATATAAACCATGGTTTTTATAA ACCCCCTCCAACCAGGTGCTAACTGCAGTTAT TTGTACAGTTCATC |
| AvrXa7 N RC GG F | SEQ ID NO: 162 | TTAATTAAGAGTCTAGATTAGCACCTGGTTGG AGGGGGTTTATATCCAAAACCGGGGTTTACAG TATAAACCCCCTCCAACCAGGTGCTAAAGATC TAGGAGGAATTTAAAATGAG |
| AvrXa7 N RC GG R | SEQ ID NO: 163 | ACTGACCTAGAGAAGCTTTTAGCACCTGGTTG GAGGGGGTTTATACTGTAAACCCCGGTTTTGG ATATAAACCCCCTCCAACCAGGTGCTAACTGC AGTTATTTGTACAGTTCATC |
| AvrXa7 N 20t F | SEQ ID NO: 164 | TTAATTAAGAGTCTAGATTAGCACCTGGTTGG AGGGGGTTTATACGAAATATTATAAATTATCA TATAAACCCCCTCCAACCAGGTGCTAAAGATC TAGGAGGAATTTAAAATGAG |

TABLE 4-continued

| Primers. |
|---|

| AvrXa7 N RC 20t R | SEQ ID NO: 165 | ACTGACCTAGAGAAGCTTTTAGCACCTGGTTG<br>GAGGGGGTTTATATGATAATTTATAATATTTC<br>GTATAAACCCCCTCCAACCAGGTGCTAACTGC<br>AGTTATTTGTACAGTTCATC |
|---|---|---|
| AvrXa7 32 GG F | SEQ ID NO: 166 | TTAATTAAGAGTCTAGATTAGCACCTGGTTGG<br>AGGGGGGTTTATAGCTTCATCCAAAACCGGGGT<br>TTACAGGGTTCCTATAAACCCCCTCCAACCAG<br>GTGCTAAAGATCTAGGAGGAATTTAAAATGAG |
| AvrXa7 32 GG R | SEQ ID NO: 167 | ACTGACCTAGAGAAGCTTTTAGCACCTGGTTG<br>GAGGGGGTTTATAGCAACCCTGTAAACCGGGG<br>TTTTGGATGAAGCTATAAACCCCCTCCAACCA<br>GGTGCTAACTGCAGTTATTTGTACAGTTCATC |
| AvrXa7 32t F | SEQ ID NO: 168 | TTAATTAAGAGTCTAGATTAGCACCTGGTTGG<br>AGGGGGGTTTATAGCTTCACGAAATATTATAAA<br>TTATCAGGTTCCTATAAACCCCCTCCAACCAG<br>GTGCTAAAGATCTAGGAGGAATTTAAAATGAG |
| AvrXa7 32t R | SEQ ID NO: 169 | ACTGACCTAGAGAAGCTTTTAGCACCTGGTTG<br>GAGGGGGTTTATAGCAACCTGATAATTTATAA<br>TATTTCGTGAAGCTATAAACCCCCTCCAACCA<br>GGTGCTAACTGCAGTTATTTGTACAGTTCATC |

| Primers for pGL3Pro target site construction. |
|---|

| 5' pGL3 SV40<br>Avr.32G BglII | SEQ ID NO: 170 | TTAATTAAGAGAGATCTTTAGCACCTGGTTGG<br>AGGGGGGTTTATAGCTTCATCCAAAACCATGGT<br>TTACAGGGTTCCTATAAACCCCCTCCAACCAG<br>GTGCTAAGCGATCTGCATCTCAATTAGTCAGC |
|---|---|---|
| 3' pGL3 SV40<br>Avr.20G HindIII | SEQ ID NO: 171 | ACT GAC CTA GAG AAG CTT TTA GCA<br>CCT GGT TGG AGG GGG TTT<br>ATAGCAACC CTG TAA ACC ATG GTT<br>TTG GATGAAGCT ATA AAC CCC CTC<br>CAA CCA GGT GCT AAT TTG<br>CAA AAG CCT AGG CCT CCA AA |
| 5' pGL3 SV40<br>PH4.20G6Avr<br>BglII | SEQ ID NO: 172 | TTAATTAAGAGAGATCTGCGGGAGGCGTGTCC<br>AAAACCATGGTTTACAGGGTTCCTATAAACCC<br>CCTCCAACCAGGTGCTAAGCGATCTGCATCTC<br>AATTAGTCAGC |
| 3' pGL3 SV40<br>PH4.20G6Avr<br>HindIII | SEQ ID NO: 173 | ACT GAC CTA GAG AAG CTT TTA GCA<br>CCT GGT TGG AGG GGG TTT ATAGCAAC<br>CCTGTAAACCATGGTTTTGGACACGCCTCCCG<br>CTTTGCAAAAGCCTAGGCCTCCAAA |
| 5' pGL3 SV40<br>Avr.44G BglII | SEQ ID NO: 174 | TTAATTAAGAGAGATCTTTAGCACCTGGTTGG<br>AGGGGGGTTTATAGCTTCAGCTTCATCCAAAAC<br>CATGGTTTACAGGGTTCCGGTTCCTATAAACC<br>CCCTCCAACCAGGTGCTAAGCGATCTGCATCT<br>CAATTAGTCAGC |
| 3' pGL3 SV40<br>Avr.44G HindIII | SEQ ID NO: 175 | ACT GAC CTA GAG AAG CTT TTA GCA<br>CCT GGT TGG AGG GGG TTTATAGCAACC<br>GCAACCCTG TAA ACCATG GTT TTG<br>GATGAAGC TGAAGCT ATA AACCCCCTCC<br>AA CCA GGT GCT AAT TTG CAA AAG<br>CCT AGG CCT CCA AA |

| Primers for BamHI fusions |
|---|

| Gin N-term F | SEQ ID NO: 176 | AGTCAGTCGAGAGCTCATGGATCCCGGCTCTA<br>TGCTGATTGGCTATGTAAGG |
|---|---|---|
| Gin_N-term R | SEQ ID NO: 177 | ATGCTGATATCTAGACTATCCCGATTTAGGTG<br>GGCGACC |
| Gin_C-term F | SEQ ID NO: 178 | AGTCAGTCGAGAGCTCATGCTGATTGGCTATG<br>TAAGG |
| Gin C-term R | SEQ ID NO: 179 | TCTAGACTACGGATCCACCGATTTACGCGGGC |

TABLE 4-continued

Primers.

| Primers for designed truncations | | |
| --- | --- | --- |
| TalR + 28 Xba | SEQ ID NO: 180 | ATCGCGTATCTAGACTAGCCGAGGCAGGCCAA GGCGACG |
| TalR + 95 Xba AvrX | SEQ ID NO: 181 | ATCGCGTATCTAGACTAGCTCATCTCGAACTG CGTCATG |
| avr n 1 | SEQ ID NO: 182 | GTCGCCCGCGTAAATCGGGATCCACTGCAGAT CGGGGGGGGGGC |
| avr n 2 | SEQ ID NO: 183 | GTCGCCCGCGTAAATCGGGATCCCCCTCGCCT GCGTTCTCGGC |
| avr n 3 | SEQ ID NO: 184 | GTCGCCCGCGTAAATCGGGATCCGATTCGATG CCTGCCGTCGG |
| avr n 4 | SEQ ID NO: 185 | GTCGCCCGCGTAAATCGGGATCCACCGTGCGT GTCGCTGTCACTG |
| avr n 5 | SEQ ID NO: 186 | GTCGCCCGCGTAAATCGGGATCCGTGGATCTA CGCACGCTCGGC |
| avr n 6 | SEQ ID NO: 187 | GTCGCCCGCGTAAATCGGGATCCACACACGCG CACATCGTTGC |
| avr n 7 | SEQ ID NO: 188 | GTCGCCCGCGTAAATCGGGATCCCACGAAGAC ATCGTTGGCGTCG |
| avr n 8 | SEQ ID NO: 189 | GTCGCCCGCGTAAATCGGGATCCAGCGCTCTG GAGGCCTTGCTC |
| avr n 9 | SEQ ID NO: 190 | GTCGCCCGCGTAAATCGGGATCCTTGGACACA GGCCAACTTCTC |
| avr n 10 | SEQ ID NO: 191 | GTCGCCCGCGTAAATCGGGATCCAGCGGCGTG ACCGCAgTGGA |
| GinNTALPCRfusR | SEQ ID NO: 192 | GGATCCCGATTTACGCGGGC |
| Primers used for pcDNA cloning | | |
| Nhe-SD-Gin F | SEQ ID NO: 193 | ATCGTAGCAGCTAGCGCCACCATGCTGATTGG CTATGTAAG |
| GinGS R | SEQ ID NO: 194 | GGATCCAGACCCCGATTTACGCGGGC |

Plasmid construction.

In order to introduce a BamH1 restriction site either 5' or 3' to the Gin coding sequence, the Gin catalytic domain was PCR amplified with primers 5' Gin_N-term and 3' Gin_N-term or 5' Gin_C-term and 3' Gin_C-term, respectively. PCR products were ligated into the SacI and XbaI restriction sites of pBluescriptII (Fermentas) to generate pB-Bam-Gin and pB-Gin-Bam. To generate the C-terminal and N-terminal TALER fusions, the AvrXa7 gene (kindly provided by Dr. B. Yang, Iowa State University) was released from pWAvrXa7 with BamH1 and ligated into BamH1 sites of pB-Bam-Gin and pB-Gin-Bam (41) to establish pB-Avr-Bam-Gin and pB-Gin-Bam-Avr, respectively. Correct construction of each TALER was verified by sequence analysis (FIGS. 6-16).

To generate N-terminal truncations of AvrXa7, AvrXa7 was PCR amplified using the Expand High Fidelity PCR System (Roche) with 5' Avr-n-(1-10) and 3' Avr+28 or 3' Avr+95 primers with the following program: 1 cycle of 3 min at 94° C., 16 cycles of 1 min at 94° C., 1 min at 52° C., 6 min at 68° C.; and a final cycle of 1 hr at 68° C. The Gin catalytic domain was PCR amplified under standard PCR conditions with 5' Gin_C-term and 3' GinNTalPCRFus and fused to truncated AvrXa7 variants by overlap PCR using the PCR conditions described above. Purified Gin-Avr PCR products were mixed in an equimolar ratio and digested with SacI and XbaI.

To generate designer TALEs, we used a TALEN kit (Addgene) with the following modification: pTAL1 was modified to include truncations at Δ120, Δ128, or +28. To achieve this, AvrXa7Δ120 and AvrXa7Δ128 fragments were PCR amplified with 5' Avr n4 or Avr n128 and 3' TalR Xba+28 and ligated into the BamH1 restriction site of pTAL1 to generate pTALΔ120 and pTALΔ128. The plasmids pTALΔ120 and pTALΔ128 retained the Esp3I restriction sites for Golden Gate cloning. TALE arrays cloned into pTALΔ120 and pTALΔ128 were digested with BamH1 and XbaI for ligation into pB-Gin-Bam.

To generate mammalian TALER expression vectors, the Gin catalytic domain was PCR amplified from pB-Gin-Avr with 5' Nhe-SD-Gin F and 3' GinGS R and ligated into the NheI and BamHI restriction sites of pcDNA 3.1 (Invitrogen). Avr15 was digested from pTALΔ120 or pTALΔ128 with BamH1 and XbaI and ligated into pcDNA-Gin-Bam to generate pcDNA-Gin-Avr expression vectors.

The pBLA substrate plasmids were constructed as previously described.

To generate pGL3 reporter plasmids, the SV40 promoter was PCR amplified from pGL3-Promoter (Promega) with the recombination site-containing primers 5' pGL3 SV40 BglII and 3' pGL3 SV40 HindIII and ligated into the BglII and HindIII restriction sites of pGL3-Promoter.

Bacterial Recombination Assays.

Bacterial recombination assays were performed as previously described.

Incremental Truncation Library.

The incremental truncation library was generated using a modified protocol previously described. Briefly, in order to protect the Gin coding sequence from exonuclease digestion, a stuffer fragment with a SmaI restriction site was inserted into BamH1 to generate pB-Gin-SmaI-Bam-Avr. This plasmid was linearized with NheI and incubated with Exonuclease III for 2.5 min at 37° C. followed by heat inactivation at 75° C. for 25 min. pB-Gin-Bam-Avr was then incubated with Klenow Fragment (3' to 5' Exo) with 200 µM dNTPs and 5 µM [α]-S-dNTPs for 30 min at 37° C. followed by heat inactivation at 80° C. for 25 min. To generate the truncation library, pB-Gin-Bam-Avr was incubated with Exonuclease III for 2.5 min at 37° C. followed by heat inactivation and subsequent blunt-ending with Mung Bean Nuclease for 1 hr at 30° C. After digestion with SmaI, the blunt 3' end of the recombinase coding sequence was ligated to the blunt-ended library of TALE fragments. After transformation and purification, the plasmids were digested with SacI and XbaI to release Gin-ΔAvr.

Mammalian Reporter Assays.

HEK293T cells were seeded onto 96-well plates at a density of $4\times10^4$ cells per well and grown in a humidified 5% $CO_2$ atmosphere at 37° C. At 24 hr after seeding, cells were transfected with 150 ng pcDNA TALER expression vector, 2.5 ng pGL3 reporter plasmid, and 1 ng pRL-CMV for expression of *Renilla* luciferase using Lipofectamine 2000 (Invitrogen) according to the manufacturer's instructions. At 48 hr after transfection, cells were lysed with Passive Lysis Buffer (Promega) and luciferase expression was determined using the Dual-Luciferase® Reporter Assay System (Promega) according to the manufacturer's instructions. Luminescence was measured using a Veritas Microplate Luminometer (Turner Biosystems).

Results

TALER Architecture.

A quantitative system for the evaluation and directed evolution of recombinase activity has been described. In this system (FIG. 1A), a GFPuv transgene flanked by recombination sites is inserted into the gene encoding TEM-1 β-lactamase. This alteration disrupts β-lactamase expression and renders *Escherichia coli* cells that harbor this plasmid (pBLA) susceptible to ampicillin. Expression of an active recombinase from the substrate-containing plasmid, however, leads to recombination between target sites and restoration of the β-lactamase reading frame. This modification establishes host-cell resistance to ampicillin and enables isolation of active recombinase variants from the substrate-containing plasmid. By measuring the number of ampicillin-resistant transformants following plasmid purification and re-transformation, recombinase activity can be also directly assessed. Because the activity of a chimeric recombinase is dependent upon both the catalytic domain and the DBD, this split gene reassembly selection system can also be used to evaluate the effectiveness of individual DBDs. Thus, the system was adapted to determine an optimal TALER architecture.

Importantly, because the catalytic domain of the DNA invertase Gin and related serine recombinases have predefined catalytic specificities, TALER fusion proteins cannot be constructed using the design described for TALENs. Structural and functional studies with the γo resolvase and designed enzymes have indicated that the C-terminal E-helix mediates serine recombinase DNA recognition. In ZFRs, this helix binds DNA from the C to the N-terminus, 5' to 3'. Thus, because TALEs bind DNA in the 5' to 3' direction, it was anticipated that recombination could only occur when the TALE binding site is positioned on the opposite strand of the 20-bp core (FIG. 1B).

It was chosen to generate TALERs using AvrXa7, as this TALE protein has been previously used to generate TALE nucleases and transcription factors. Conveniently, BamHI restriction sites flank many TALEs, including AvrXa7 and multiple groups have used this restriction site to generate synthetic TALE fusions. Notably, this BamHI fragment leaves the N-terminus of the TALE intact but removes the native effector domain from the C-terminus. This strategy was adopted and generated a Gin-AvrXa7 fusion by BamH1 restriction digestion.

Gin-AvrXa7 was cloned into a pBLA selection vector containing recombination sites composed of a central 20-bp core sequence, which is recognized by the Gin catalytic domain, and two flanking 26-bp AvrXa7 binding sites. As anticipated, the Gin-AvrXa7 fusion was unable to recombine DNA when AvrXa7 binding sites were positioned adjacent to the 20-bp core (FIG. 1C). However, when AvrXa7 binding sites were positioned on the opposite strand of the 20-bp core, recombination was evident (FIG. 1C), indicating that recombination site orientation is a critical component for catalytic domain fusion to the TALE N-terminus. In order to further establish that N-terminal fusion is necessary for recombination, a C-terminal AvrXa7-Gin variant was constructed that contained a non-canonical fusion orientation predicted to constrain catalytic domain activity (FIG. 1B and Table 5). As expected, it was determined that this C-terminal AvrXa7 fusion demonstrated negligible activity in bacterial cells (FIG. 1C).

TABLE 5

| Variant | SEQ ID NO: | Sequence |
|---|---|---|
| Gin-Avr (#1)/ Avr20G | 195 | TTAGCACCTGGTTGGAGGGGGTTTATA TCCAAAACCATGGTTTACAGTATAAAC CCCCTCCAACCAGGTGCTAA |
| Gin-Avr (#2) | 196 | TTAGCACCTGGTTGGAGGGGGTTTATA AGGTTTTGGTACCAAATGTCTATAAAC CCCCTCCAACCAGGTGCTAA |
| Avr-Gin (#3) | 197 | TATAAACCCCCTCCAACCAGGTGCTAA CTGTAAACCATGGTTTTGGATTAGCAC CTGGTTGGAGGGGGTTTATA |
| Avr14G | 198 | TTAGCACCTGGTTGGAGGGGGTTTATA AAAACCATGGTTTATATAAACCCCCTC CAACCAGGTGCTAA |
| Avr26G | 199 | TTAGCACCTGGTTGGAGGGGGTTTATA GCTTCCAAAACCATGGTTTACAGGGTT ATAAACCCCCTCCAACCAGGTGCTAA |
| Avr32G | 200 | TTAGCACCTGGTTGGAGGGGGTTTATA GCTTCATCCAAAACCATGGTTTACAGG GTTCCTATAAACCCCCTCCAACCAGGT GCTAA |

TABLE 5-continued

| Variant | SEQ ID NO: | Sequence |
|---------|------------|----------|
| Avr44G | 201 | TTAGCACCTGGTTGGAGGGGGTTTATA GCTTCAGCTTCATCCAAAACCATGGTT TACAGGGTTCCGGTTCCTATAAACCCC CTCCAACCAGGTGCTAA |
| Avr20GG | 202 | TTAGCACCTGGTTGGAGGGGGTTTATA TCCAAAACCGGGGTTTACAGTATAAAC CCCCTCCAACCAGGTGCTAA |
| Avr20T | 203 | TTAGCACCTGGTTGGAGGGGGTTTATA CGAAATATTATAAATTATCATATAAAC CCCCTCCAACCAGGTGCTAA |
| Avr32GG | 204 | TTAGCACCTGGTTGGAGGGGGTTTATA GCTTCATCCAAAACCGGGGTTTACAGG GTTCCTATAAACCCCCTCCAACCAGGT GCTAA |
| Avr32T | 205 | TTAGCACCTGGTTGGAGGGGGTTTATA GCTTCACGAAATATTATAAATTATCAG GTTCCTATAAACCCCCTCCAACCAGGT GCTAA |
| Avr-G-ZF | 206 | GCGGGAGGCGTGTCCAAAACCATGGTT TACAGGGTTCCTATAAACCCCCTCCAA CCAGGTGCTAA |
| PthXo1-20G | 207 | GTGGTGTACAGTAGGGGGAGATGCATC CAAAACCATGGTTTACAGTGCATCTCC CCCTACTGTACACCAC |
| PthXho1-32G | 208 | GTGGTGTACAGTAGGGGGAGATGCAGC TGCTTCCAAAACCATGGTTTACAGGGT GGTTGCATCTCCCCCTACTGTACACCA C |

Designed Truncations.

Figure 2A:
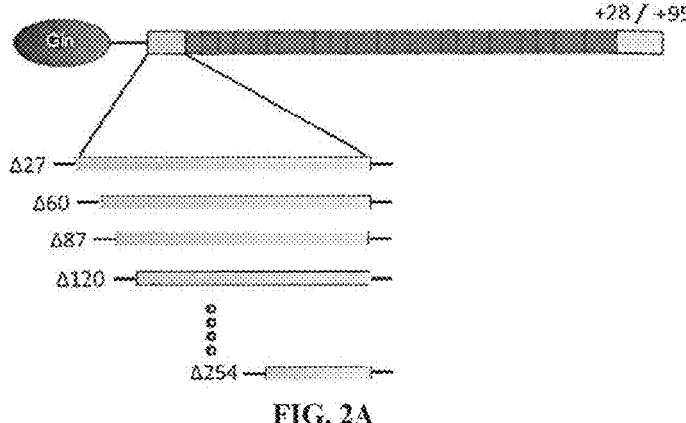
FIGS. 2A-2C are a series of graphical and diagrammatic representations regarding recombination profiles of selected TALER truncations. (2A) Schematic illustrating the design of the 20-member TALER truncation library. (2B) Activity of selected TALER variants against DNA targets containing core sequences of increasing length (14, 20, 26, 32 and 44-bp). (2C) Gin-AvrXa7Δ120 activity against a diverse panel of substrates containing non-cognate cores sequences or core sites of increasing length. Error bars indicate s.d. (n=3).

Although the Gin-AvrXa7 fusion described above catalyzed recombination, the activity of this variant was considerably lower than that of engineered ZFRs. Further, specificity analysis revealed that the Gin-AvrXa7 fusion was unable to faithfully discriminate between recognition sites containing non-cognate DBD sites and non-native 20-bp core sequences, indicating that recombination might not be Gin-mediated (FIG. 1D). Recent reports have shown that TALEN activity can be enhanced when the TALE portion of the fusion protein is truncated. Thus, in order to attempt to improve TALER activity, a series of N and C-terminal AvrXa7 truncations were generated (FIG. 2A).

Figure 2B:
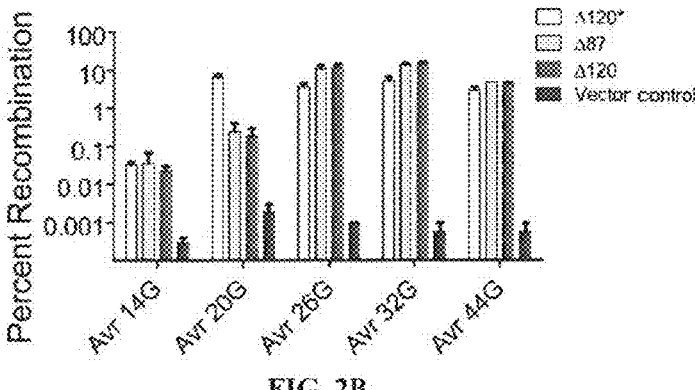
Figure 6:
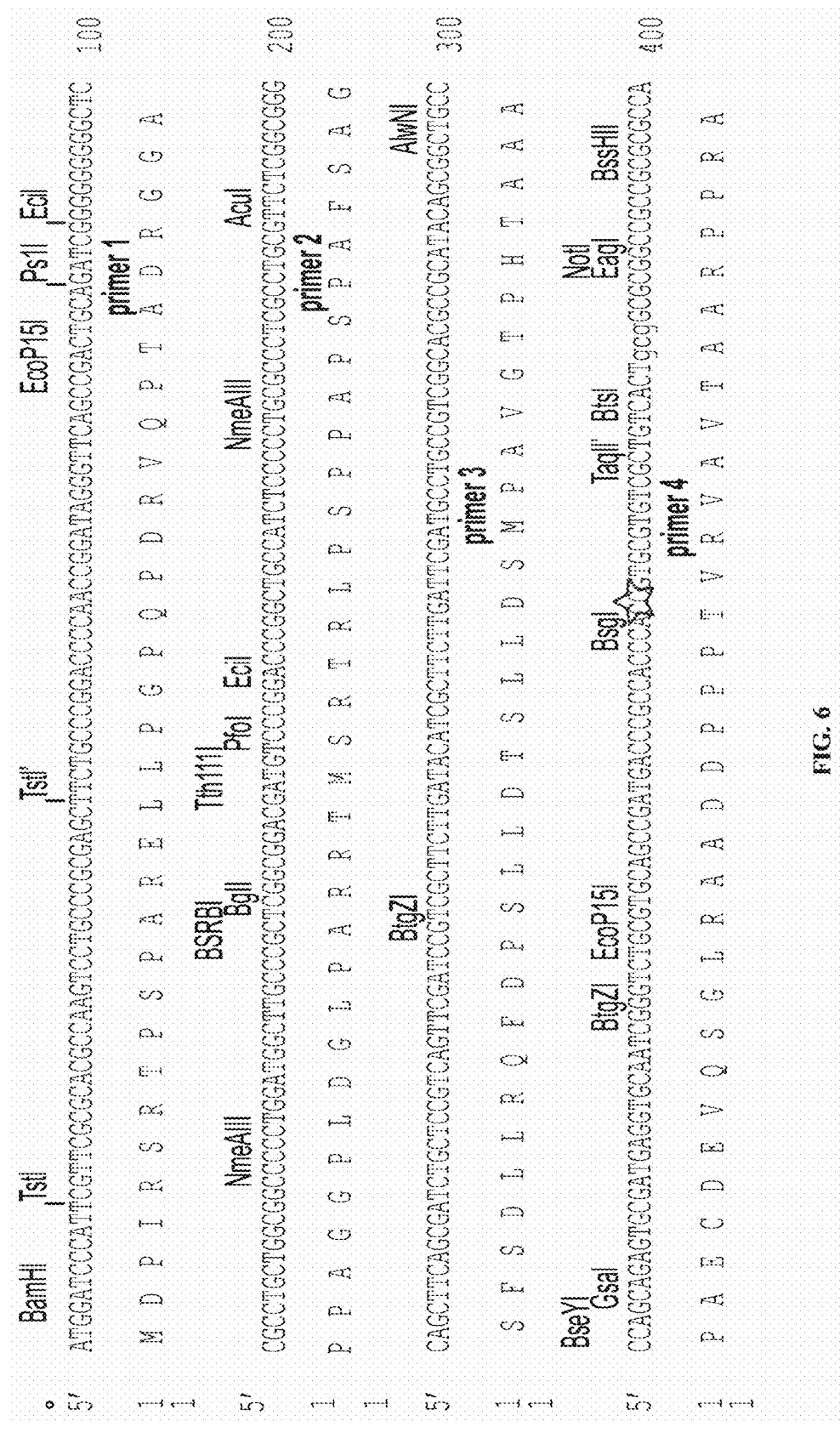
FIG. 6 is a diagrammatic representation of location of primers for N-terminal designed truncations of AvrXa7 (SEQ ID NO: 1 DNA sequence; SEQ ID NO: 2 amino acid sequence). Star denotes the location of Δ120 fusion point.

Ten N-terminal truncations were assembled at roughly equal intervals beginning at AvrXa7 Thr 27 (Δ27) and ending at AvrXa7 Gly 268 (Δ268) (FIG. 6). AvrXa7 Δ150, which has been reported as an N-terminal truncation variant for TALENs, was also generated. Two C-terminal AvrXa7 truncations were generated at positions 28 (+28) and 95 (+95). Both +28 and +95 have been reported as stable fusion points in TALENs. Each TALE truncation variant was fused to the Gin catalytic domain and this 20-member TALER library was cloned into a pBLA selection vector containing Avr-20G recognition sites. Following one round of selection in bacterial cells (Materials and Methods), individual ampicillin-resistant clones were sequences and it was found that all selected TALERs contained either one of two N-terminal truncations: Δ87 and Δ120. Each selected clone was also+28 on the C-terminus. With the exception of a single Δ120 clone with a spontaneous 12 amino acid deletion near the fusion point (Δ120*), the activity of these clones was quite low (FIG. 2B). In this assay, Gin-based ZFRs routinely show 20-40% recombination, however, the highest activity observed amongst the selected TALER fusions was ~7% recombination (Gin-AvrXa7Δ120*). Because the TALE DBD is three times larger than a ZF domain (not including the required flanking peptide sequence), we reasoned that the 20-bp spacer used for these TALER constructs might not be the optimal length for recombination.

Core Sequence Length.

Figure 2C:
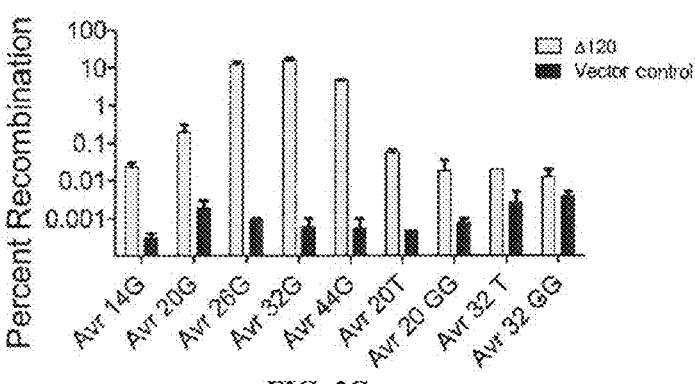

Next the effect core sequence length has on recombination was investigated by evaluating whether DNA targets containing 14 (Avr-14G), 26 (Avr-26G) and 32-bp (Avr-32G) core sites could be recombined by selected TALERs. In order to maintain the reading frame of the β-lactamase gene following recombinase-mediated reassembly, core half-sites were modified by ±3-bps (Table 1). The 20-member TALER library described above was subjected to one round of selection against each target site variant. Although identification of TALER variants capable of recombining the shortest target was not possible, Avr-14G (data not shown), two Gin-ΔAvrXa7 variants were identified (based on the N-terminal TALE truncations Δ87 and Δ120 and the C-terminal truncation+28) that recombined Avr-26G and Avr-32G. In particular, clonal analysis revealed that the selected TALERs (Gin-AvrXa7Δ87 and Gin-AvrXa7Δ120) recombined DNA with longer cores (e.g., 26 and 32-bps) at least 100-fold more efficiently than shorter cores (e.g., 14 and 20-bps) (FIG. 2B). Further, it was found that Gin-AvrXa7Δ120 recombined targets containing a cognate core sequence (Avr-26G and Avr-32G)>100-fold more efficiently than a non-cognate core (Avr-20T, Avr-20GG, Avr-32T and Avr-32GG) (FIG. 2C). Interestingly, the Gin-AvrXa7Δ120 fusion was not as active on 44-bp cores (Avr-44G) (recombination was ~3-fold lower than Avr-32G) (FIG. 2C), indicating that core lengths between 26 and 44-bp are likely optimal for recombination by Gin-AvrXa7Δ120 in E. coli.

Incremental Truncation Library.

Although Gin-AvrXa7Δ120 showed increased recombination in comparison to Gin-AvrXa7, it was suspected that Gin-AvrXa7Δ120 might not be an optimal TALE fusion architecture because: (i) ZFRs containing the Gin catalytic domain recombined DNA>2-fold more efficiently than Gin-AvrXa7Δ120 and (ii) Gin-AvrXa7Δ120 was not identified from a comprehensive library of TALE truncation variants. Thus, in order to identify better fusion architectures, a screen was devised based on the generation of a library of incrementally truncated TALE DBDs.

To achieve this, a protocol was adapted as previously described to enable fusion of an unmodified N-terminal domain (Gin) to a library of truncated C-terminal fragments (AvrXa7) (Materials and Methods). N-terminal AvrXa7 truncations that spanned the region between the AvrXa7 N-terminus (Met 1) and the first AvrXa7 repeat (Leu 298) were generated by exonuclease digestion and fused to an unmodified copy of the Gin catalytic domain (theoretical number of protein variants: ~300). Because previous results indicated that +28 is the optimal C-terminal truncation, we incorporated this architecture into the truncation library. TALERs were cloned into a pBLA selection vector containing Avr-32G target sites and transformed into E. coli (>1× 105 transformants). Sequence analysis confirmed an equal distribution of truncations spanning the region of interest (data not shown).

Following three rounds of selection, individual ampicillin-resistant clones were sequences and a number of unique truncation variants were identified (FIG. 3A). Consistent with the selections performed using the 20-member TALE truncation library, which suggested that the optimal N-terminal TALER fusion points were likely located in proximity to positions 87 and 120, all selected Gin-AvrXa7 variants were found to contain a truncation between positions 74 (Δ74) and 147 (Δ147). In particular, 26 of 73 (35.6%, p<. 001) clones contained truncations between positions 124 (Δ124) and 129 (Δ129). From this population, truncations at position 128 (Δ128) were among the most represented.

In order to systematically determine whether selected AvrXa7 domains increased TALER activity, we evaluated the performance of isolated Gin-AvrXa7 variants against DNA substrates containing Avr-32G target sites in *E. coli*. We focused our analysis on clones containing N-terminal deletions between AvrXa7 position 92 (Δ92) and 134 (Δ134). Consistent with sequence analysis, it was found that TALERs containing N-terminal truncations between Δ120 and Δ129 recombined DNA more efficiently than variants based on comparatively longer or shorter truncations, although the Δ92 fusion was also quite active (FIG. 3B). Three clones further characterized: Δ74 and Δ145 were chosen because they represented the boundaries of possible fusion points, and Δ128 was assayed because it was the most prevalent clone found in the selections. Five targets with spacer lengths from 14 to 44-bp were assayed along with three negative controls (Avr32T, Avr32GG, and PthXo1-32G). It was determined that Gin-Avr32GΔ74 and Gin-Avr32GΔ145 had modest activity on spacers longer than 20-bp, whereas Gin-Avr32GΔ128 recombined DNA with efficiencies comparable to the ZFR GinC4 (FIG. 3C). Furthermore, specificity analysis revealed that Gin-Avr32GΔ74, Gin-Avr32GΔ128, and Gin-Avr32GΔ145 could recombine substrates harboring cognate cores>100-fold more efficiently than non-cognate cores (Avr-32T, Avr-32GG and PthXo1-32G) (FIG. 3C). Together, these results suggest that TALE proteins containing N-terminal deletions between Δ120 and Δ129 represent an optimal truncation for fusion to a recombinase.

Incorporation of Synthetic TALE Repeat Arrays.

The studies described above used the native DBDs of the naturally occurring AvrXa7 TALE protein. In order to determine whether designed TALE repeat arrays can be incorporated into the selected Gin-ΔAvrXa7 frameworks, a series of synthetic TALE proteins (15 to 20 repeats in length) were generated designed to target the AvrXa7 binding site (FIG. 7). TALE proteins were constructed using a publicly available TALEN plasmid set (Addgene). The cloning plasmid was modified to include the +28 C-terminal truncation and either the Δ120 or Δ128 N-terminal truncation. Designed TALEs were fused to the Gin catalytic domain (denoted as Gin-Avr15Δ120 and Gin-Avr15Δ128) and cloned into a pBLA selection vector containing Avr-32G or Avr-32T target sites.

Figures 4A, 4B:
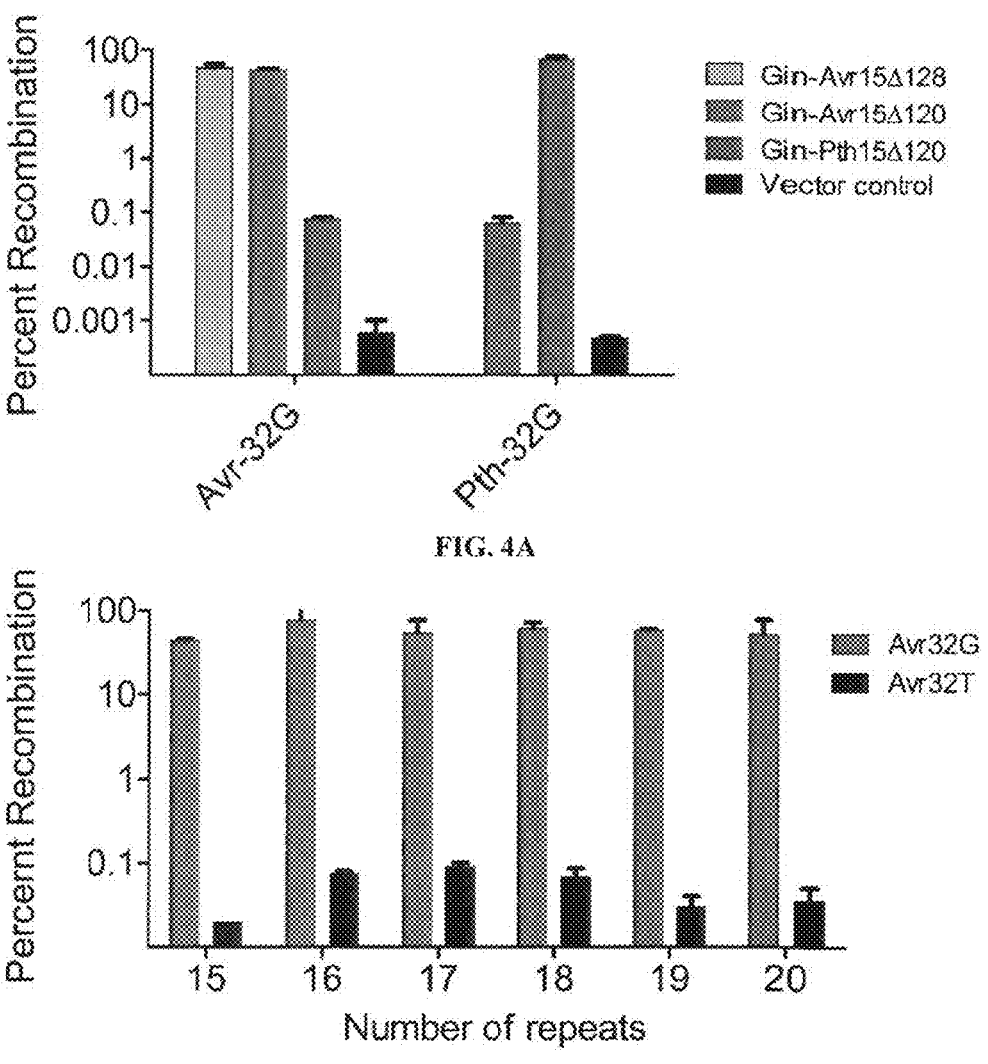
FIGS. 4A-4B are a series graphical representations regarding activity of synthetic TALERs. (4A) Activity of synthetic Gin-Avr15Δ128, Gin-Avr15Δ120 and Gin-Pht15Δ120 variants against the DNA targets Avr-32G or Pth-32G. (4B) Activity of synthetic TALERs with DBDs between 15 and 20 repeats in length based on Gin-AvrΔ120 against Avr-32G and Avr-32T. Error bars indicate s.d. (n=3).

Activity analysis in *E. coli* revealed that both Gin-Avr15Δ120 and Gin-Avr15Δ128 could be used to recombine DNA when fused to an active catalytic domain and that incorporation of synthetic repeats provided an increase in activity (FIG. 4A). Importantly, each TALER displayed stringent selectivity, recombining target sites that contained cognate cores>1,000-fold more efficiently than non-cognate cores (FIG. 4B). Surprisingly, TALERs based on the Δ120 truncation were also found to recombine DNA as effectively as TALEs based on the Δ128 architecture (FIG. 4A), indicating that designed TALEs may be less sensitive to N-terminal truncation than those containing the native AvrXa7 DBD.

To further demonstrate that the TALER architecture described herein can be reprogrammed to target any DNA sequence, a synthetic enzyme was created designed to target the sequence recognized by the naturally occurring TALE protein PthXo1 (Gin-Pth15Δ120). It was found that Gin-Pth154120 was highly active on its cognate substrate and that both Gin-Pth15Δ120 and Gin-Avr15Δ120 showed a >600 fold increase in recombination for targets with their cognate binding sites (FIG. 4A). The activity of a series of designed TALERs containing DBDs between 15 and 20 repeats in length was also assessed and found that each fusion catalyzed recombination with similarly high efficiency and specificity (FIG. 4B), demonstrating that chimeric recombinases that incorporate synthetic TALE repeat arrays can be used for site-specific recombination.

TALER Activity in Mammalian Cells.

It was also determined whether TALERs could modify DNA in mammalian cells. To achieve this, we used an episomal reporter assay that enables rapid assessment of recombinase activity in cell culture. In this assay, human embryonic kidney (HEK) 293T cells are co-transfected with a recombinase expression vector and a reporter plasmid (pGL3) that contains a luciferase gene under the control of a SV40 promoter flanked by recombination sites. Transient expression of the appropriate recombinase leads to excision of the SV40 promoter and reduced luciferase expression in cells. Recombinase activity is thus directly proportional to the fold-reduction in luciferase expression.

Figure 5A:
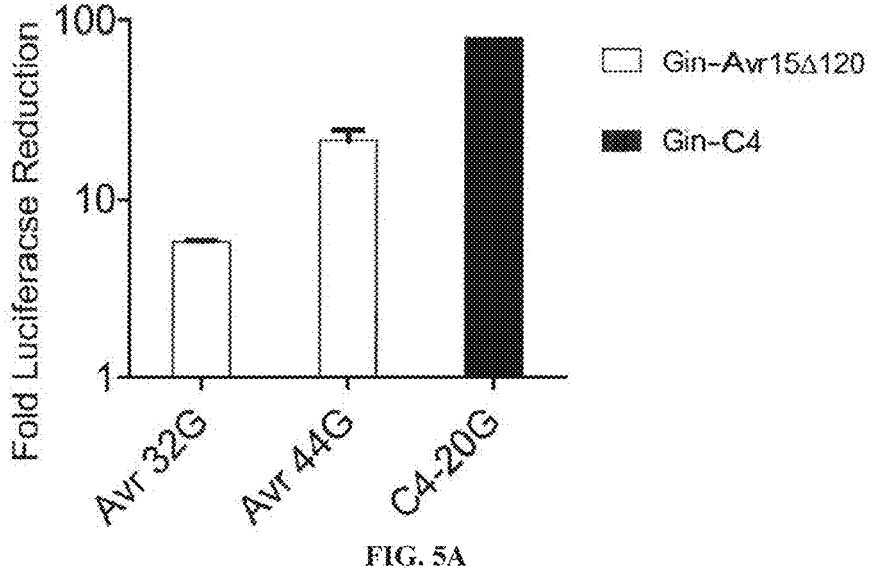
FIGS. 5A-5B are a series of graphical representations regarding TALER activity in mammalian cells. Fold-reduction of luciferase expression in HEK293T cells co-transfected with (5A) TALER or ZFR expression vectors (Gin-AvrΔ120 and GinC4) in the presence of reporter plasmid (Avr-32G, Avr-44G and C4-20G) or (5B) TALER and ZFR expression vector in combination (Gin-AvrΔ120+GinC4) with reporter plasmid (Avr-G-ZF). Error bars indicate s.d. (n=3).

Co-transfection of Gin-Avr15Δ120 with a reporter plasmid harboring Avr-44G recognition sites (pGL3-Avr-44G) led to a ~20-fold reduction in luciferase expression as compared to transfection of pGL3-Avr-44G alone (FIG. 5A). Despite the fact that Gin-Avr15Δ120 showed similar activity to the ZFR GinC4 in *E. coli*, we found that GinC4 reduced luciferase expression by >80-fold after co-transfection with its cognate target plasmid, pGL3-C4-20G (FIG. 5A). This discrepancy may be due to the comparatively shorter intervening DNA sequence between recombinase target sites in pGL3 than pBLA or differential expression between TALERs and ZFRs in mammalian cells. The underlying cause for this disparity, however, remains unclear. Finally, although 32-bp was determined to be the optimal core sequence length for TALERs in *E. coli*, it was determined that co-transfection of Gin-Avr15Δ120 with pGL3-Avr-32G led to only a 6-fold reduction in luciferase expression (FIG. 5A). The underlying cause behind this disparity also remains unclear.

Figure 5B:
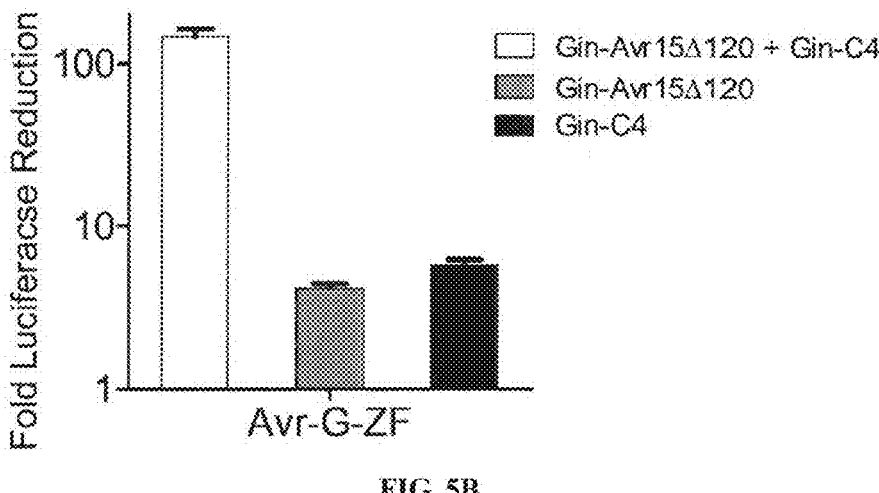

Next whether a ZFR (GinC4) and a TALER (Gin-Avr15Δ120) could form a compatible heterodimer in mammalian cells was investigated. To evaluate this possibility, a hybrid recombination site was generated in which the AvrXa7 binding site and the C4 zinc-finger binding site (GCG GGA GGC GTG; SEQ ID NO: 279) flank the core sequence recognized by the Gin catalytic domain (pGL3-Avr-G-ZF) (see Table 2). Surprisingly, co-transfection of pGL3-Avr-G-ZF with GinC4 and Gin-Avr15Δ120 led to a >140-fold reduction in luciferase expression as compared to pGL3-Avr-G-ZF (FIG. 5B), whereas transfection with either GinC4 or Gin-Avr15Δ120 with pGL3-Avr-G-ZF led to a negligible decrease in reporter gene expression. These results demonstrate that generating ZF-TALE heterodimers represents a potentially effective approach for improving the targeting capacity of chimeric recombinases.

Discussion

Unlike ZFPs, which contain a very minimal fusion architecture, TALE DBDs require native protein framework on either side of the DBD array to function. The so-called 0th and 1st repeats, which mediate binding of the thymidine residue at position 0 and are found in almost all known TALE recognition sites, represent such an N-terminal framework. A recent crystal structure provided a description of the binding of the position 0 thymine, yet there remains insufficient data to determine a minimal TALE architecture. Indeed, all studies to date have used an N-terminal truncation containing considerably more residues than those required to mediate binding at position 0. It remains uncertain what role this part of the protein has in enabling the proper DNA binding conformation or what might constitute a minimal TALE domain. Although initial attempts to generate functional TALE chimeras were based on fusion to full-length TALE proteins, more recent studies have focused on the identification of unique C-terminal truncations that improve effector domain function in the context of the $\Delta$150 N-terminal architecture. A previous report indicated that deletion of N-terminal residues 2-153 ($\Delta$150) of the AvrBs3 TALE removes the domain required for translocation of the TALE from its native bacteria to the target plant cell but does not compromise transcription factor activity.

Developing an active TALER, however, necessitated that unique N-terminal TALE variants be identified. A broad, systematic survey was initially conducted of N-terminal TALEs with the C-terminal truncations +28 and +95 and found that only two domains (487 with +28 and $\Delta$120 with +28) demonstrated sufficiently high activity for further analysis. A secondary analysis based on incremental truncation of the AvrXa7 N-terminus led to the identification of a broad cluster of truncation variants centered between AvrXa7 position 74 ($\Delta$74) and position 145 ($\Delta$145). Of the clones recovered in this experiment, 38% contained truncations between positions $\Delta$119 and $\Delta$128, and a survey of data obtained on TALERs with fusions in this region showed high activity. In particular, it was determined that TALERs based on N-terminal truncations from this region ($\Delta$128 and $\Delta$120) could be used to recombine DNA in bacteria and mammalian cells. The clustering of truncation variants between $\Delta$119 and $\Delta$128 may also be indicative of the intrinsic stability of this region.

ZFRs typically catalyze recombination between target sites 44 to 50-bp in length. Each target site contains a central 20-bp core sequence, which is recognized by the recombinase catalytic domain, and two adjacent ZFP binding sites. The fusion orientation of TALERs, however, necessitates that TALE binding sites are on the opposite strand relative to the central core sequence. This unique geometry led us to investigate the minimum core sequence requirements for recombination. Because of the length of TALE DBDs (TALE repeats are 3 to 4 times longer than ZFPs) and the extended N-terminal linker between the catalytic domain and the TALE domain, we reasoned that longer core sequences (32 or 44-bp) would be necessary for recombination. Indeed, with the exception of a TALE variant harboring a spontaneous deletion ($\Delta$120*), most N-terminal truncation variants identified in this study demonstrated optimal performance against 32-bp cores. These results are consistent with those reported with TALENs, which unlike ZFNs require significantly longer spacer sequences (e.g. TALENs: 17 to 20-bp, ZFNs: 5 to 6-bp) to efficiently cleave DNA. In support of these observations, it was found that selection for unique N-terminal truncation variants against a short core sequence (14-bp) did not yield any clones.

Gin-AvrXa7$\Delta$128 was identified as an optimal TALE fusion, but subsequent studies using synthetic TALE proteins generated using a publicly available TALE assembly kit indicated that $\Delta$128 and $\Delta$120-based TALERs showed similar activity in *E. coli*. These designed TALEs were based on a chimeric protein derived from the closely related and naturally occurring Tal1c and PthXo1 TALE proteins. Although TALEs share high homology, they are not identical. While polymorphisms in RVD repeats outside of residues 12 and 13 have been shown to have no affect on TALE fusion activities, to our knowledge no systematic evaluation of differences in TALE framework outside the DBDs has been reported. As demonstrated by the analysis of the incremental truncation library, minor amino acid alterations can significantly influence the activity of a particular fusion. Thus, some of the discrepancy in activity we observed between Gin-AvrXa7$\Delta$120 and the synthetic Gin-Avrl5$\Delta$120 may be attributable to the sequence variations between AvrXa7 framework and the TALE framework architecture used previously.

The four RVDs (NI: A, HD: C, NG: T, and NN: G) favored for construction of synthetic TALEs are the most prevalent in nature; however, it remains to be determined whether these repeats represent the most specific RVD modules. For the 26-repeat AvrXa7 TALE, a synthetic version targeting the same sequence would have 16 changes in RVD composition (FIG. 7). It was hypothesized that because they are more commonly found in nature, the four RVDs selected for synthetic use might have a higher affinity for their cognate bases than other RVDs. If this were the case, it would be reasonable to assume that a TALE created with the synthetic RVD repeats could have higher DNA-binding affinity than a TALE using the native domains. Although the issue of RVD affinity was not directly addressed, it was determined that that TALERs containing synthetic repeat arrays were more active than constructs, which contained the native AvrXa7 DBD. TALERs with synthetic DBDs showed approximately two-fold higher activities than constructs containing the native repeats, despite containing significantly fewer DBDs. Additionally, the gain in activity observed with the synthetic arrays was not correlated with any increase in off-target recombination.

Several studies have shown that TALEs can tolerate some mismatches in their target sequence. These findings are unsurprising, as RVDs that are positively associated with particular bases have been shown to tolerate non-cognate bases in nature. The cooperative specificity afforded by TALERs could be used to circumvent potential limitations, however. Because the catalytic domain contributes specificity to recombination, it is envisioned that designer TALERs capable of selectively modifying highly homologous genomic sequences could be generated as well. Indeed, it has been recently demonstrated that recombinase catalytic specificity can be effectively reprogrammed to target unnatural core sites.

Example 2

Selection of Novel $0^{th}$ Residue Specificity

A new class of Tal-based DNA binding proteins was engineered. TAL (transcription activator-like) effectors constitute a novel class of DNA-binding proteins with predictable specificity. Tal effectors are employed by Gram-negative plant-pathogenic bacteria of the genus *Xanthomonas* which translocate a cocktail of different effector proteins via a type III secretion system (T3SS) into plant cells where they serve as virulence determinants. DNA-binding specificity of TALs is determined by a central domain of tandem repeats. Each repeat confers recognition of one base pair (bp) in the DNA. Rearrangement of repeat modules allows design of proteins with desired DNA-binding specificities with certain important limitations. For example, the most constraining feature of targeting a DNA sequence with a Tal domain is the requirement that the Tal DNA site start with the base T and sometimes C. Targeting a binding site starting with a G or A base has not been possible at the −1 position. Tal-recombinase activity selections were used to select for Tal DNA binding domains that lack this restriction by targeting mutations to the −1 and $0^{th}$ RVD regions. The practical consequences of this discovery are vast since now every DNA sequence can be targeted with new Tal domains facilitating new unrestricted approaches to TAL transcription factors to turn transcription on/up or off/down, to target TAL nucleases to knock out gene function or to direct homologous recombination or to target our own TAL recombinases or other TAL enzymes.

For G specificity at the (−1) position, the amino acids QWSG (SEQ ID NO: 209) were first randomized using an NNK codon strategy within the (−1) domain of the GinAvr15Δ128-synthetic protein. Following 3 rounds of tal recombinase activity selection of the resulting library, novel tal binding domains with the selected sequences RSNG (SEQ ID NO: 210) and SRSG (SEQ ID NO: 211) in the targeted region were selected. These were then shown to bind G at the 0th position of the target sequence over the parental T recognized by the starting clone. The selection was repeated randomizing the KQW region shown below in red that overlaps with the QWSG (SEQ ID NO: 212) selected initially. Now clones with selected SSR, SRA, SRC, and KRC sequences were selected. All selected Tal binding domains were assayed in binding studies to defined oligos bearing the G substitution and shown to now preferentially bind the sequence G-ATAAACCCCTCCAA (SEQ ID NO: 213). Note that the Tal recombinase activity selection was performed using this same sequence. The starting Tal binding protein the GinAvr15Δ128 binds T-ATAAACCCCTCCAA (SEQ ID NO: 214). Subsequence testing of Tal nucleases bearing the selected mutations verify the G specify of these sequences allowing for this novel class of Tals to be developed for the first time. Selected sequences are portable to Tals derived from other species.

TABLE 6

| Selections | |
| --- | --- |
| SEQ ID NO: 215 | ATHEDIVGVGKQWSGARALEALLTDAGELR GPPLQ (−1 domain) |
| SEQ ID NO: 216 | ATHEDIVGVGKQWSGARALEALLTDAGELR GPPLQ (randomized AA in bold) |
| SEQ ID NO: 217 | KQWSG-starting clone sequence |
| SEQ ID NO: 218 | K*RSNG*-selected to bind G |
| SEQ ID NO: 219 | K*SRSG*-selected to bind G |
| SEQ ID NO: 220 | ATHEDIVGVGKKQWSGARALEALLTDAGELR GPPLQ |
| SEQ ID NO: 221 | KQWSG- WT SSR-selected to bind G SRA-selected to bind G SRC-selected to bind G KRC-selected to bind G |

Selections were also performed using this same library to target A. In this study, sequences PRG, PTR, and PKD were selected. All selected Tal binding domains were assayed in binding studies to defined oligos bearing the A substitution and shown to now preferentially bind the sequence A-ATAAACCCCTCCAA (SEQ ID NO: 222). Note that the Tal recombinase activity selection was performed using this same sequence. The starting Tal binding protein the GinAvr15Δ128 binds T-ATAAACCCCTCCAA (SEQ ID NO: 223). Subsequence testing of Tal nucleases bearing the selected mutations verify the A specify of these sequences allowing for this novel class of Tals to be developed for the first time. Subsequent refinements in binding activities can be achieved by random mutagenesis of the N-terminal domain or target mutagenesis of the KRGG (SEQ ID NO: 224) sequence within the 0th domain and reselection in the recombinase system.

Example 3

Selections

For context dependent RVD selections and selections of RVDs with new specificities, libraries were created that randomize the HD sequence emboldened below. LTPDQVVAIASHDGGKQALETVQRLLPVLCQDHG (prototype RVD sequence; SEQ ID NO: 225)

Typically the library allows all amino acids at these two positions, though libraries limited to N, D, H, K, and Q amino acids are often successful substitutes for the H residue. Alternatively larger libraries that randomized the SHDG (SEQ ID NO: 226) and ASHDGG (SEQ ID NO: 227) regions allow for the selection of unique RVD specificities with context dependent characteristics.

Tal recombinase activity selections then rapidly allow for the selection of new specificities within the targeted RVD domain. The resulting RVDs can be highly modular or context dependent in their sequence recognition and can be then used to create Tal nucleases and transcription factors.

Utility of this technology includes unrestricted approaches to TAL transcription factors to turn transcription on/up or off/down, to target TAL nucleases to knock out gene function or to direct homologous recombination or to target our own TAL recombinases or other TAL enzymes for use as tools and therapeutics.

Advantages and the practical consequences of this discovery are vast since now every DNA sequence can be targeted with our new Tal domains and their specificities can be readily optimized.

Example 4

Directed Evolution of Tale N-Terminal Domain to Accommodate 5' Bases Other than Thymine Transcription activator-like effector (TALE) proteins can be designed to bind virtually any DNA sequence of interest. The DNA binding sites for natural TALE transcription factors (TALE-TFs) that target plant avirulence genes have a 5' thymidine. Synthetic TALE-TFs also have this requirement. Recent structural data indicate that there is an interaction between the N-terminal domain (NTD) and a 5' T of the target sequence. A survey of the recent TALE nuclease (TALEN) literature yielded conflicting data regarding the importance of the first base of the target sequence, the No residue. Additionally, there have been no studies regarding the impact of the No base on the activities of TALE recombinases (TALE-Rs). Here, the impact of the No base is quantified in the binding regions of TALE-Rs, TALE-TFs, TALE DNA-binding domains expressed as fusions with maltose binding protein (MBP-TALEs) and TALENs. Each of these TALE platforms have distinct N- and C-terminal architectures, but all demonstrated highest activity when the No residue was a thymidine. To simplify the rules for constructing effective TALEs in these platforms, and allow precision genome engineering applications at any arbitrary DNA sequence, we devised a structure-guided activity selection using our recently developed TALE-R system. Novel NTD sequences were identified that provided highly active and selective TALE-R activity on TALE binding sites with 5' G, and additional domain sequences were selected that permitted general targeting of any 5' $N_0$ residue. These domains were imported into TALE-TF, MBP-TALE and TALEN architectures and consistently exhibited greater activity than did the wild-type NTD on target sequences with non-T 5' residues. The novel NTDs are compatible with the golden gate TALEN assembly protocol and now make possible the efficient construction of TALE transcription factors, recombinases, nucleases and DNA-binding proteins that recognize any DNA sequence allowing for precise and unconstrained positioning of TALE-based proteins on DNA without regard to the 5' T rule that limits most natural TALE proteins.

The following Material and Methods were utilized in this Example.

Oligonucleotides.

Primers and other oligonucleotides (Table 4 below) were ordered from Integrated DNA Technologies (San Diego, CA).

TABLE 7

Primers.

| Primer | SEQ ID NO: | Sequence |
|---|---|---|
| KXXG Lib Rev | 228 | TCTCAACTCCCCCGCCTCCGTGAGCAAGGCCT CCAGAGCGCGTGCCCCMNNMNNTTTGCCGACG CCAACGATGTCTTCGTG |
| KXXXX Lib Rev | 229 | TCT CAA CTC CCC CGC CTC CGT GAG CAA GGC CTC CAG AGC GCG TGC MNN MNN MNN MNN TTT GCC GAC GCC AAC GAT GTC TTC GTG |
| XXXSG Lib Rev | 230 | CCCGCCTCCGTGAGCAAGGCCTCCAGGGCGCG TGCGCCGGAMNNMNNMNNMNNGCCGACGCCAACGA TGTCTTCGTGTGTCGC |
| KRGG Lib Rev | 231 | GGC ACC CGT CAG TGC ATT GCG CCA TGC ATG CAC TGC CTC CAC TGC GGT CAC MNN MNN MNN MNN TGC AAT CTT GAG AAG TTG GCC TGT GTC |
| Goldy TALEN fwd | 232 | AGAGAGAGAAGAAAATGAGATCTCCTAAGAAA AAGAGGAAGGTGCAGGTGGATCTACGCACGCT CGGCTAC |
| NTD-dHax3 Fwd | 233 | AGGAAGAAGAGAAGCATGAGATCTCCTAAGAA AAAGAGGAAGGTGATGGTGGACTTGAGGACAC TCGGTTA |
| NTD-dHax3 Rev | 234 | AAGAGAAGAAGAAGAAGCATTGCGCCATGCAT GCACTGCCTCTA |
| pTal127 Not1 fwd | 235 | CCC GCC ACC CAC CGT GC |
| N-Term Sph1 | 236 | TGC TCT ATG CAT GCA CTG CCT CC |
| pTAL127-SFI Fwd | 237 | AGA GAA GAG AAG AGA AGG CGC CCG CGG CCC AGG CGG CCT CGG GAT CCC CTC GGC CTC CGC GCG CCA AG |

TABLE 7-continued

Primers.

| pTAL127-SFI +95 Rev | 238 | AGA GAG AGA GAG AGA GTC TAG AGG CCG GCC TGG CCG CTC ATC CCG AAC TGC GTC ATG GCC TCA TC |
|---|---|---|
| pTAL127 Xba +28 Rev | 239 | GCC CCA GAT CCT GGT ACG CTC TAG AGG |
| Avr 5' A biotin hairpin | 240 | 5'BiosgATC TTA GCA CCT GGT TGG AGG GGG TTT ATTGG GTT TTC CCAAT AAA CCC CCT CCA ACC AGG TGC TAA GAT |
| Avr 5'T biotin hairpin | 241 | 5'Biosg/ATC TTA GCA CCT GGT TGG AGG GGG TTT ATAGG GTT TTC CCTAT AAA CCC CCT CCA ACC AGG TGC TAA GAT |
| Avr 5'G biotin hairpin | 242 | 5'BiosgATC TTA GCA CCT GGT TGG AGG GGG TTT ATCGG GTT TTC CCGAT AAA CCC CCT CCA ACC AGG TGC TAA GAT |
| Avr 5'C biotin hairpin | 243 | 5'BiosgATC TTA GCA CCT GGT TGG AGG GGG TTT ATGGG GTT TTC CCCAT AAA CCC CCT CCA ACC AGG TGC TAA GAT |
| CCR5-inner fwd | 244 | TTAAAAGCCAGGACGGTCAC |
| CCR5-inner rev | 245 | TGTAGGGAGCCCAGAAGAGA |
| CCR5-outer fwd | 246 | ACAGTTTGCATTCATGGAGGGC |
| CCR5-outer rev | 247 | CCGAGCGAGCAAGCTCAGTT |
| CCR5-indel fwd | 248 | CGCGGATCCCCGCCCAGTGGGACTTTG |
| CCR5-indel rev2 | 249 | CCGGAATTCACCTGTTAGAGCTACTGC |
| pGL3 NTD stuffer fwd | 250 | AGA GAG AGA GAG AGG CGG CCG CCC TAC CAG GGA TTT CAG TCG ATG TAC ACG TTC |
| pGL3 NTD stuffer rev | 251 | AAG AAG AAG AAG GAA GAG AAG TAG GCC TGT CAT CGT CGG GAA GAC CTG CGA CAC CTG C |
| pgl3 5X Avr Xho1 | 252 | ACTGCTATCCGAGTATAAACCCCCTCCAACCA GGTATAAACCCCCTCCAACCAGGTATAAACCC CCTCCAACCAGGTATAAACCCCCTCCAACCAG GTATAAACCCCCTCCAACCAGGATCTGCGATC TAAGTAAGCT |
| AvrXa7 32G A F | 253 | TTAATTAAGAGTCTAGAttagcacctggttgg aggggtttatTgcttcaTCCAAAACCATGGT TTACAGggttccAATAAACCCCCTCCAACCAG GTGCTAAAGATCTAGGAGGAATTTAAAATGAG |
| AvrXa7 32G A R | 254 | ACTGACCTAGAGAAGCTTTTAGCACCTGGTTG GAGGGGGTTTATTgcaaccCTGTAAACCATGG TTTTGGAtgaagcAATAAACCCCCTCCAACCA GGTGCTAACTGCAGTTATTTGTACAGTTCATC |
| AvrXa7 32G G F | 255 | TTAATTAAGAGTCTAGAttagcacctggttgg aggggtttatCgcttcaTCCAAAACCATGGT TTACAGggttccGATAAACCCCCTCCAACCAG GTGCTAAAGATCTAGGAGGAATTTAAAATGAG |

53 54

TABLE 7-continued

Primers.

```
AvrXa7 32G   256   ACTGACCTAGAGAAGCTTTTAGCACCTGGTTG
G R                GAGGGGGTTTATCgcaaccCTGTAAACCATGG
                   TTTTGGAtgaagcGATAAACCCCCTCCAACCA
                   GGTGCTAACTGCAGTTATTTGTACAGTTCATC AvrXa7 32G   257   TTAATTAAGAGTCTAGAttagcacctggttgg
C F                aggggggtttatGgcttcaTCCAAAACCATGGT
                   TTACAGgggttccCATAAACCCCCTCCAACCAG
                   GTGCTAAAGATCTAGGAGGAATTTAAAATGAG AvrXa7 32G   258   ACTGACCTAGAGAAGCTTTTAGCACCTGGTTG
C R                GAGGGGGTTTATGgcaaccCTGTAAACCATGG
                   TTTTGGAtgaagcCATAAACCCCCTCCAACCA
                   GGTGCTAACTGCAGTTATTTGTACAGTTCATC
```

Luciferase, Vector = pg13 basic, XhoI/SphI

Forward
target
containing:              SEQ ID NO:

```
5x Avr15     259   actgctatctcgagcTATAAACCCCCTCCAAC
n-1c xhoF:         CAGGcTATAAACCCCCTCCAACCAGGcTATAA
                   ACCCCCTCCAACCAGGcTATAAACCCCCTCCA
                   ACCAGGcTATAAACCCCCTCCAACCAGGATCT
                   GCGATCTAAGTAAGCT 5x Avr15     260   actgctatctcgagcAATAAACCCCCTCCAAC
0 = A              CAGGcAATAAACCCCCTCCAACCAGGcAATAA
n-1c               ACCCCCTCCAACCAGGcAATAAACCCCCTCCA
                   ACCAGGcAATAAACCCCCTCCAACCAGGATCT
                   GCGATCTAAGTAAGCT 5x Avr15     261   actgctatctcgagcCATAAACCCCCTCCAAC
0 = C              CAGGcCATAAACCCCCTCCAACCAGGcCATAA
n-1c               ACCCCCTCCAACCAGGcCATAAACCCCCTCCA
                   ACCAGGcCATAAACCCCCTCCAACCAGGATCT
                   GCGATCTAAGTAAGCT 5x Avr15     262   actgctatctcgagcGATAAACCCCCTCCAAC
0 = G              CAGGcGATAAACCCCCTCCAACCAGGcGATAA
n-1c               ACCCCCTCCAACCAGGcGATAAACCCCCTCCA
                   ACCAGGcGATAAACCCCCTCCAACCAGGATCT
                   GCGATCTAAGTAAGCT Luciferase   263   TCAGAAACAGCTCTTCTTCAAATCT
Reverse
Primer:
```

Generation of TALE-R NTD Evolution Plasmids.

The TALE-R system previously reported was adapted for this study. Briefly, pBCS (containing chloramphenicol and carbenicillin resistance genes) was digested with HindIII/SpeI. The stuffer (Avr X, where X is the NO base), containing twin recombinase sites, was digested with HindIII/XbaI and ligated into the vector to create a split beta-lactamase gene. pBCS AvrX was then digested with BamH1/SacI, and Gin127-N-stuffer-Avr15 was digested with BamH1/SacI and ligated into the vector to create Gin127-N-stuffer-Avr15-X. The stuffer was digested with Not1/Stu1 for evolutions at the N–1 TALE hairpin and Not1/Sph1 for evolutions at the N₀ TALE hairpin.

Generation of TALE NTD Evolution Libraries.

Primer ptal 127 Not1 fwd and reverse primers KXXG lib rev or KXXXX lib rev were used to generate N-terminal variants at the N₋₁ TALE hairpin and were subsequently digested with Not1/Stu1 then ligated into digested Gin127-AvrX. Forward primer ptal127 Not1 fwd and reverse primer KRGG Lib Rev were used to PCR amplify a library with mutations in the No TALE hairpin. This was subsequently digested with Not1/Sph1 and ligated into Not1/Sph1-digested Gin127-AvrX.

TALE-R NTD Evolution Assay.

Round 1 ligations were ethanol precipitated and transformed into electrocompetent Top10 F' cells then recovered in SOC for 1 h. The cells were grown overnight in 100 ml Super Broth (SB) media containing 100 mg/ml chloramphenicol. DNA was isolated via standard procedures. The resulting plasmid DNA (Rd 1 input) was transformed into electrocompetent Top10F' cells; cells were grown overnight in 100 ml of SB containing 100 mg/ml carbenicillin and 100 mg/ml chloramphenicol. Plasmid DNA was isolated via standard procedures. Round 1 output was digested with Not1/XbaI and ligated into the Gin127-AvrX vector with complementary sticky ends. This protocol was repeated three to four times when a consensus sequence was observed and clones were characterized.

Measurement of N-Terminal TALEN Activity.

Four TALEN pairs containing each possible base were generated using the golden gate protocol. Fusion A and B plasmids were directly ligated via second golden gate reaction into the Goldy TALEN (N Δ152/C+63) framework. The NTD was modified by digesting the pCAG vector with BglII/NsiI and ligating with PCR amplified NTD digested with BglII/NsiI. TALEN pairs (50-75 ng each TALEN/well) were transfected into HeLa cells in wells of 96-well plates at a density of 1.5×10⁴ cells/well. After transfection, cells were placed in a 37° C. incubator for 24 h, then were moved to 30° C. for 2 days and then moved to 37° C. for 24 h. Genomic DNA was isolated according to a published protocol, and DNA mutation rates were quantified with the Cell Surveyor assay and by sequencing. For Cell assays, genomic DNA was amplified by nested PCR, first with primers CCR5 outer fwd/CCR5 outer rev and then with CCR5 inner fwd/CCR5 inner rev. For sequencing of indels, the second PCR was performed with CCR5 indel fwd/CCR5 indel rev. Fragments were then digested with BamH1/EcoR1 and ligated into pUC19 with complementary digestion.

TALE-TFs and Luciferase Assay.

Variant NTDs from the recombinase selection were PCR amplified with primers ptal127 SFI fwd and N-Term Sph1. The PCR product was amplified and digested with Not1/Stu1 and ligated into pTAL127-SFI Avr15, which contains twin SFI-1 digestion sites facilitating transfer of the N-terminal-modified TALE from pTAL127-SFI Avr15 into pcDNA 3.0 VP64. Corresponding TALE binding sites were cloned into the pGL3 Basic vector (Promega) upstream of the luciferase gene. For each assay, 100 ng of pcDNA was co-transfected with 5 ng of pGL3 vector and 1 ng of pRL Renilla luciferase control vector into HEK293t cells in a well of a 96-well plate using Lipofectimine 2000 (Life Technology) according to manufacturer's specifications. After 48 h, cells were washed, lysed and luciferase activity assessed with the Dual-Luciferase® reporter system (Promega) on a Veritas Microplate luminometer (Turner Biosystems). Transfections were done in triplicate and results averaged.

Mbp-Tale Assay.

Affinity assays of MBP-TALE binding to biotinylated oligonucleotides were performed using a protocol previously described. Briefly, AvrXa7 TALE domains were expressed from pMAL MBP-AvrXa7 plasmid in XL1-Blue cells and purified on amylose resin. Biotinylated oligonucleotides containing the target AvrXa7 target site with modified residues were used to determine TALE-binding activity in sandwich enzyme-linked immunosorbent assay format. Antibodies targeting the MBP substituent were used for assay development.

Results

Preliminary Analysis of the 5' T Rule.

A recent crystal structure of a TALE protein bound to PthXo7 DNA sequence revealed a unique interaction between W232 in the N−1 hairpin with a thymidine at the 5' end of the contacted region of the DNA substrate (the No base). This study provided a structural basis for the previously established 5' T rule reported when the TALE code was first deciphered (FIGS. 18A and 18B). There are conflicting data regarding the importance of the first base of the target sequence of TALENs. The requirement for a 5' T in the target DNA was initially assesses in the context of TALE-Rs using four split beta lactamase TALE recombinase selection vectors containing four AvrXa7 binding sites with all possible 5' residues flanking a Gin32G core (FIG. 18C). Recognition of the $N_0$ residue by TALE-TFs was then evaluated using four luciferase reporter vectors containing a pentamer AvrXa7 promoter region with recognition sites containing each possible 5' residue (FIG. 18D). With bases other than a 5' T, we observed decreases in activity up to >100-fold in TALE-Rs and 1000-fold in TALE-TFs relative to the sequence with a 5' T (FIGS. 18C and 18D). These reductions were observed despite variations in the C-terminal architectures of these chimeras that reportedly remove the 5' T bias, especially in the presence of a greatly shortened C-terminal domain (CTD). Enzyme-linked immunosorbent assay also indicated decreased affinity of MBP-TALE DNA-binding proteins toward target oligonucleotides with non-T 5' residues (FIG. 18E). Finally, examination of the activity of designed TALENs with wild-type NTDs on targets with non-T 5' nucleotides showed up to 10-fold decrease in activity versus those with a 5' T (FIG. 18F). The results indicate that a 5' T is an important design parameter for maximally effective TALE domains in the context of recombinases, transcription factors, nucleases and simple DNA-binding proteins.

Evolution of the TALE NTD to Accommodate Non-T 5' Residues.

Figure 23:
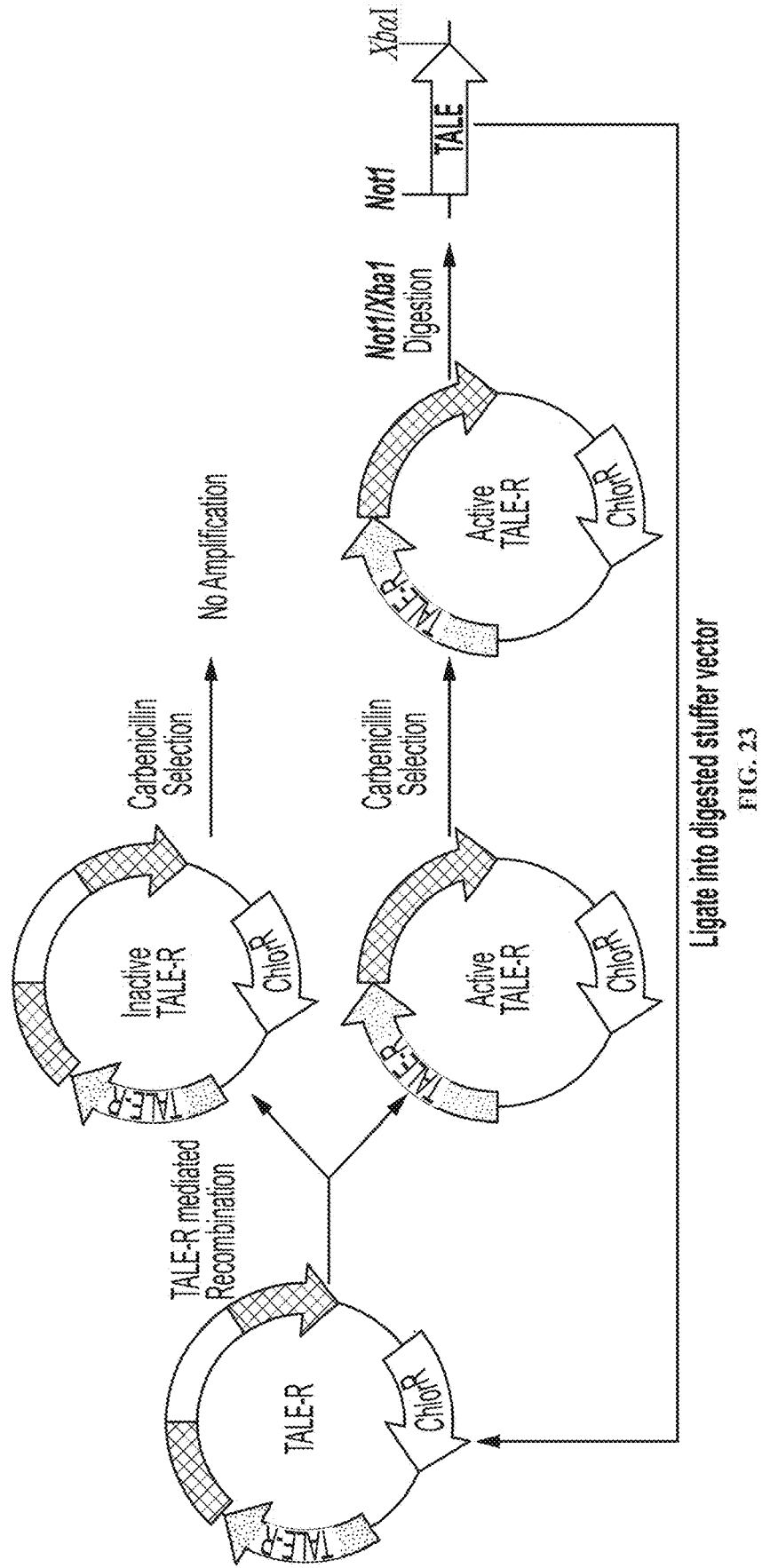
FIG. 23 is a schematic representation illustrating TALE-Recombinase selection protocol. A library of NTD was cloned into Avr15 TALE-R using NotI/StuI restriction enzymes and complementary ligation. Active TALE-R's result in more frequent recombination events that can be selected and amplified with antibiotics (carbenecillin). The resulting output plasmid was the digested NotI/Xba1 and ligated into the TALE-R backbone vector for further selection and amplification.
Figures 24, 25:
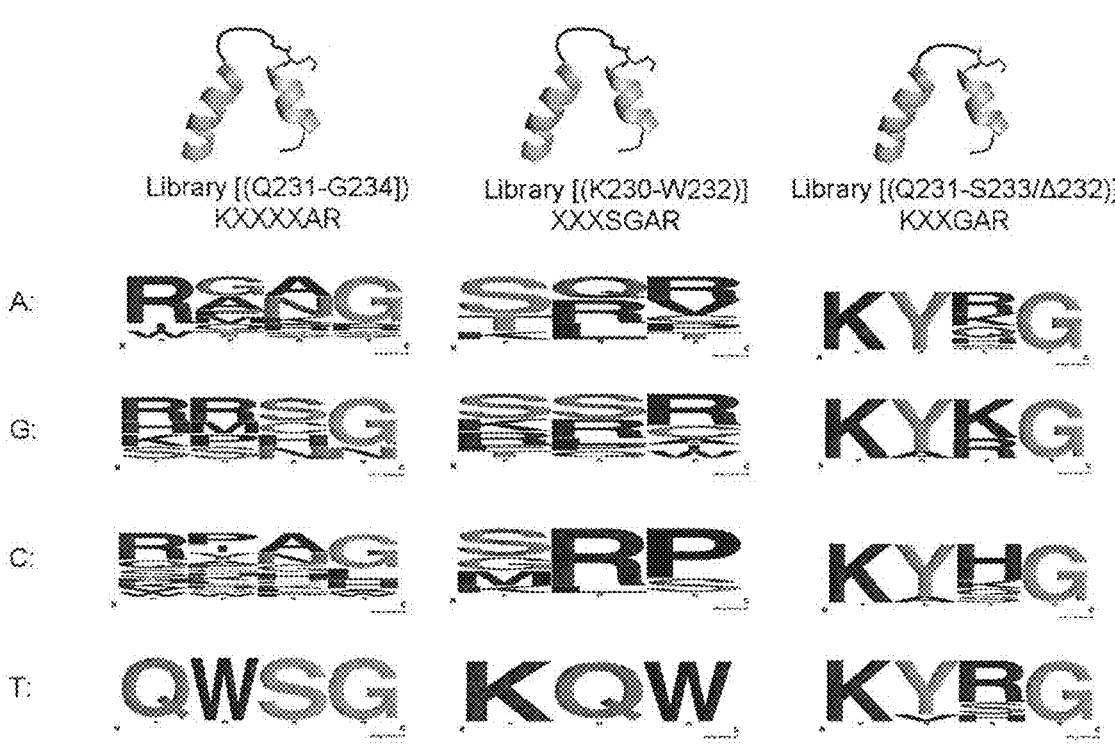
FIG. 24 is a diagrammatic representation of a summary of variant populations discovered from library selections (Library XXXSGAR (SEQ ID NO: 39) and Library KXXGAR (SEQ ID NO: 291)).
FIG. 25 is a diagrammatic representation showing alignment of NT-G (SEQ ID NO: 54) with NTD-Brg11 (SEQ ID NO: 55), a *Ralstonia* TALE domain. Alignment indicates Brg11 could exhibit specificity for 5' G bases.

To create a more flexible system for DNA recognition, it was hypothesized that the recently developed TALE-R selection system could be utilized to evolve the NTD of the TALE to remove the 5' T constraint (FIG. 23). Libraries were generated with residues K230 through G234 randomized, and TALE-Rs with activity against each possible 5' base were isolated after several rounds of selection (FIGS. 19A-19C). The most active selected clones exhibited strong conservation of K230 and G234; the former may contact the DNA phosphate backbone, and the latter may influence hairpin loop formation (FIG. 24). In the case of library K230-W232, K230S was frequently observed but had much lower activity than K230R or K230 variants in nearly all variants assayed individually. One clone (NT-G) of several observed with a W232 to R232 mutation demonstrated a significant shift of selectivity from 5' T to 5' G; the sequence resembles that of the NTD of a recently described *Ralstonia* TALE protein in this region. The *Ralstonia* NTD, in the context of plant transcription factor reporter gene regulation, has been reported to prefer a 5' G in its substrate (see FIG. 25 for a protein alignment). Residue R232 may contact the G base specifically, as indicated by the stringency of NT-G for 5' G. The preference of NT-G for a 5' G was comparable with the specificity of the wild-type domain for 5' T. NTD variants specific for 5' A or 5' C were not able to be derived, but a permissive NTD, NT-aN, was obtained that resembles the K265-G268 No hairpin that accepts substrates with any 5' residue and maintains high activity. It was hypothesized that this variant makes enhanced non-specific contacts with the DNA phosphate backbone compared with the wild-type NTD, enhancing the overall binding of the TALE-DNA complex without contacting a specific 5' residue. It was hypothesized that a shortened hairpin structure would allow selection of variants with specificity for 5' A or 5' C residues. A library with randomization at Q231-W232 and with residue 233 deleted was designed to shorten the putative DNA-binding loop. Recombinase selection revealed a highly conserved Q231Y mutation that had high activity in a number of clones (FIG. 19D). In particular, NT-BN demonstrated improved activity on substrates with 5' A, C and G but diminished activity on 5' T substrates compared with TALEs with the wild-type NTD (FIG. 19E).

Applications of Evolved TALE NTDs.

Figure 20A:
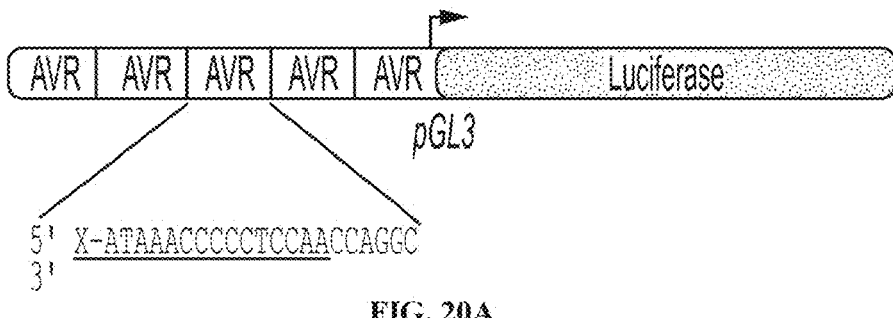
FIGS. 20A-20B are a series of diagrammatic and graphical representations of analysis of selected NTDs in the context of TALE-TFs. (20A) Illustration of 5×Avr promoter region (SEQ ID NO: 37) on the luciferase reporter plasmid used for transcription activation experiments. (20B) Relative luciferase activation of substrates with indicated 5' residues by TALE-TFs with NT-T, NT-G, NT-áN, and NT-âN domains. (*=p<0.05, =p<0.01, *=p<0.001, compared to NT-T and respective 5'A/G/C/T).
Figure 20B:
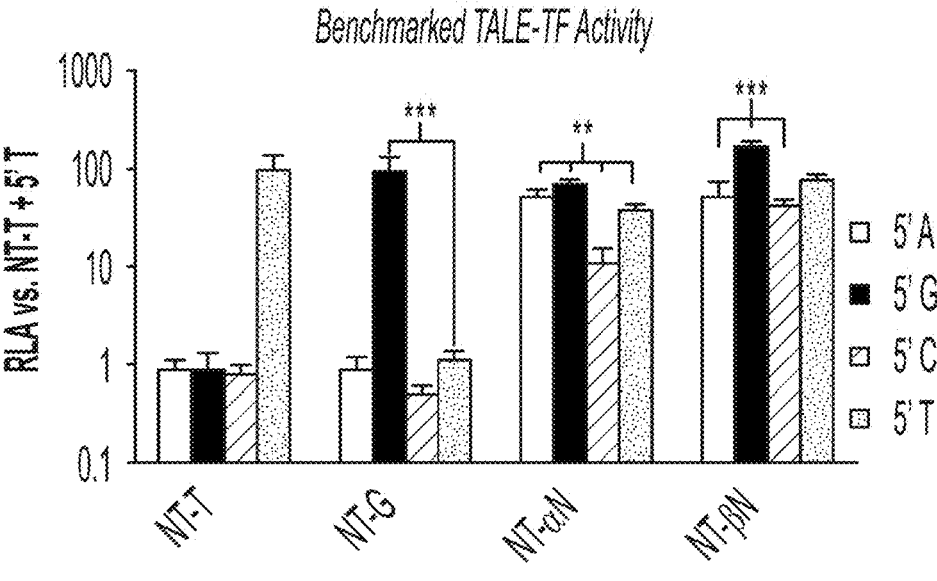
Figures 26, 27:
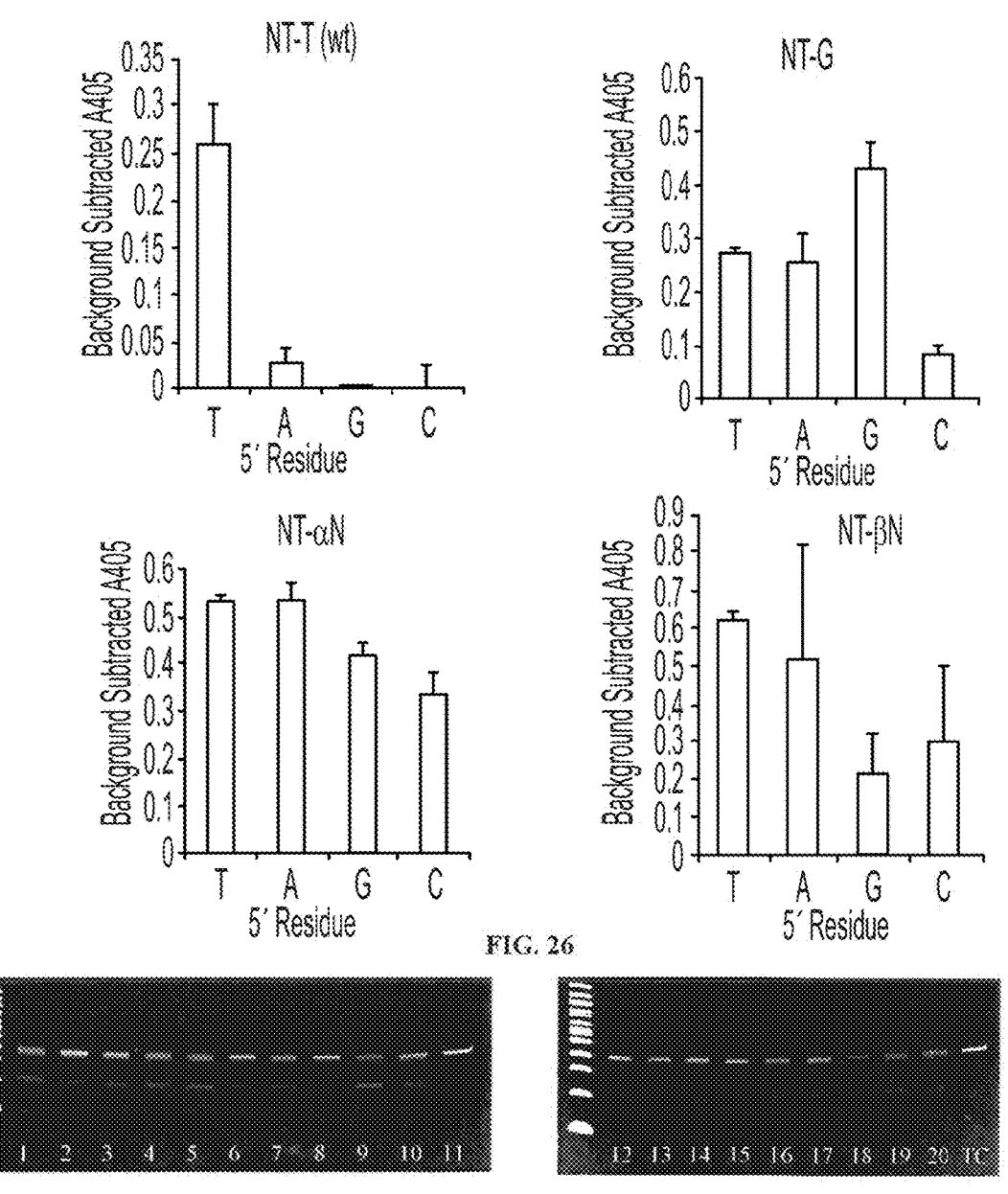
FIG. 26 is a series of graphical representations of relative binding affinity of MBP-TALE proteins to target 5' A/G/C/T Avr15 hairpin oligonucleotides as assayed by ELISA. Protein concentrations were ~75 nM and plates were developed for 120 minutes.
FIG. 27 is a series of pictorial and graphical representations of a cell assay of PCR amplified CCR5 after TALEN editing with % indels and indel populations shown on the right.

To assess the portability of the evolved NTDs in designer TALE fusion protein applications, optimized NTDs were incorporated into TALE-TFs, MBP-TALEs and TALENs. TALE-TFs with NT-G, NT-αN and NT-βN domains demonstrated 400-1500-fold increases in transcriptional activation of a luciferase target gene bearing operator sites without a 5' T residue when compared with the TALE-TF with the NT-T domain. The NT-G-based TF retained the 5' G selectivity as observed in the TALE-R selection system. The activities of NT-αN- and NT-βN-based TFs against all 5' nucleotides tracked the relative activity observed in the recombinase format (FIGS. 20A and 20B). MBP-TALEs also exhibited greater relative binding affinity for target oligonucleotides with sites that did not have a 5' T than did the wild-type MBP-TALE (FIG. 26), providing further evidence that the selected domains enhanced recognition of or tolerance for non-thymine 5' bases.

Figures 21A, 21B, 21C:
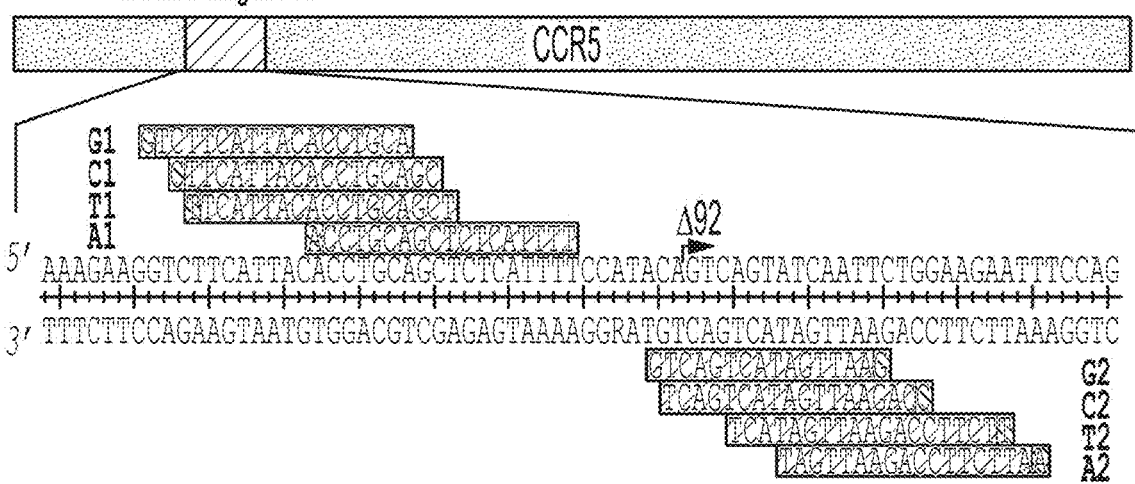
FIGS. 21A-21C are a series of diagrammatic and graphical representations of design and activity of TALEN pairs with wild-type and evolved NTD's with varying 5' bases. (21A) The CCR5 gene (SEQ ID NOs: 38-39) expanded to highlight the target site (SEQ ID NOs: 40-47) for induction of the H32 mutation. (21B) Gene editing efficiency of the wild type (NT-T) TALEN, TALENs with domains optimized for non-T 5' residues, and dHax3 NTD. (21C) Fold enhancement of the TALEN pairs with optimized NTD vs. TALENs with 5' T specificity. The activity of each NTD is shown on each TALEN pair substrate.

Four of the optimized NTDs were then imported into the Goldy TALEN framework. For these experiments, four substrates were constructed within the context of the Δ32 locus of the CCR5 gene (FIG. 21A). Each substrate contained a different 5' residue. Experiments included TALENs with wild-type (NT-T) and dHax3 NTDs (dHax3 is commonly used NTD variant isolated from *Xanthomonas campestris*) with specificity for 5' T, to benchmark gene editing activity. The substrate TALEN pairs were designed to retain as much RVD homology (50-90%) as possible to determine the activity enhancing contributions of the variant NTDs (FIG. 21A).

Activities of the TALENs were analyzed both by sequencing and by using the Cell assay. The selected domains exhibited increases in gene editing activity between 2- and 9-fold for the non-T 5' residues when compared with activities of the TALEN containing the wild-type domain (FIGS. 21A-21C, and FIG. 27). Activity was highest on TALEN pair T1/T2 with wild-type or dHax3 NTD. The TALEN pair substrate G1/G2 was processed most effectively by TALENs with NT-αN, NT-βN and NT-G, with 2.0-3.5-fold enhancement versus NT-T. NT-αN had activity 9- and 2-fold higher than the wild-type NT-T on TALEN pairs Δ1/Δ2 and C1/C2, respectively. Although the impact of a mismatch at the 5' residue is more modest in TALENs than in TALE-TF and TALE-R frameworks, the optimized NTDs greatly improved TALEN activity when used in gene editing experiments.

Discussion

Most, but not all, previous studies have suggested that a thymidine is required as the 5'-most residue in design of optimal TALE DNA-binding domains. The analyses described here indicate that a thymidine is optimal, and in some cases critical, for building functional TALE fusion proteins. This requirement therefore imposes limitations on the sequences that can be effectively targeted with TALE transcription factor, nuclease and recombinase chimeras. Although this requirement theoretically imposes minor limitations on the use of TALENs for inducing gene knockout, given their broad spacer region tolerance, NTD's that can accommodate any 5' residue would further simplify the rules for effective TALE construction and greatly enhance applications requiring precise TALE placement for genome engineering and interrogation (e.g. precise cleavage of DNA at a defined base pair using TALENs, seamless gene insertion and exchange via TALE-Recombinases, displacement of natural DNA-binding proteins from specific endogenous DNA sequences to interrogate their functional role, the development of orthogonal transcription factors for pathway engineering, the synergistic activation of natural and synthetic genes wherein transcription factor placement is key and many other applications). Other uses in DNA-based nanotechnology include decorating DNA nanostructures/origami with specific DNA-binding proteins. Here, targeting to specific sites is constrained based on DNA folding/structure and thus being able to bind any site is critical. Elaboration of these structures and devices with DNA-binding proteins could be a fascinating approach to expanding function. Indeed, it is not difficult to imagine many applications for DNA binding proteins and their fusions when all targeting constraints are removed. Encouraged by these potential applications, we aimed to develop NTDs that enable targeting of sites initiated at any base.

The recently developed TALE-R system was used to evolve the NTD of the TALE to remove the 5'-T constraint. In three rounds of selection, an NTD was obtained with specificity for a 5' G. Numerous selections were performed in attempts to obtain variants that recognized either 5' A or 5' C. The G230-K234 hairpin was inverted, the K230-G234/ins232 hairpin extended, modification of the K265-G268 No hairpin attempted, and random mutagenesis libraries evaluated. None of these strategies yielded NTDs with affinity for target sequences with 5' A or 5' C, although we did identify an NTD, NT-βN, with a deletion that recognized substrates with both 5' A and 5' C residues with acceptable affinity. The strong selection preference exhibited by the NTDs NT-T and NT-G and the importance of W232 in NT-T and R232 in NT-G are likely due to specific interactions of these amino acids with the 5' terminal residue of the DNA recognition sequence. It was recently reported that the *Ralstonia solanacearum* TALE stringently requires a 5' G, and a sequence alignment with NT-G shows what appears to be a comparable N–1 hairpin containing an arginine at the position analogous to 232 in NT-G (FIG. 25). Owing to the high structural homology between the NTDs Brg11 and NT-T, it may be possible to modify the preference of the *Ralstonia* TALE NTD to thymine by a simple arginine to tryptophan mutation or to eliminate specificity by grafting NT-αN or NT-βN domains into this related protein. It is also interesting to note that arginine-guanine interactions are common in evolved zinc finger domains.

The variant NTDs selected were successfully imported into TALE-TFs, MBP-TALEs and TALENs and generally conferred the activity and specificity expected based on data from the recombinase evolution system. TALE-TFs with optimized NTDs enhanced TALE activation between 400- and 1500-fold relative to the activity of NT-T against AvrXa7 promoter sites with non-T 5' residues. When incorporated into TALENs, our NTD with non-T selectivity enhanced activity 2-9-fold relative to that of the NT-T domain on substrates with 5' A, C or G. The increases in TALEN gene editing generally correlated with increases in activity observed in TALE-R and TALE-TF constructs. The specificity and high activity of NT-G was maintained, as evidenced by the lower activity in assays with TALEN pairs A1/A2, C1/C2, and T1/T2, and the generally high activity of NT-αN and NT-βN was also imparted into the TALEN Δ152/+63 architecture.

Figure 29:
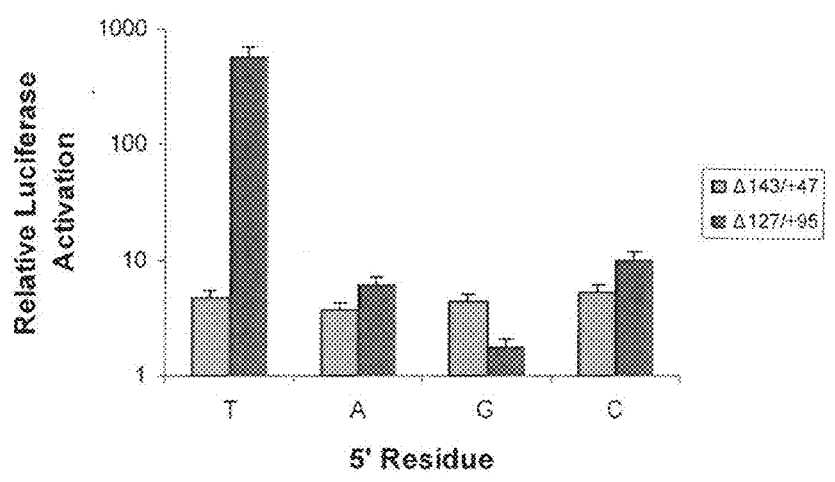
FIG. 29 is a graphical representation of a comparison of the activity of two separate Goldy TALE-Transcription factor architectures, each targeting identical 5×AvrXa7 promoters varying only in the 5' residue.
Figure 30A:
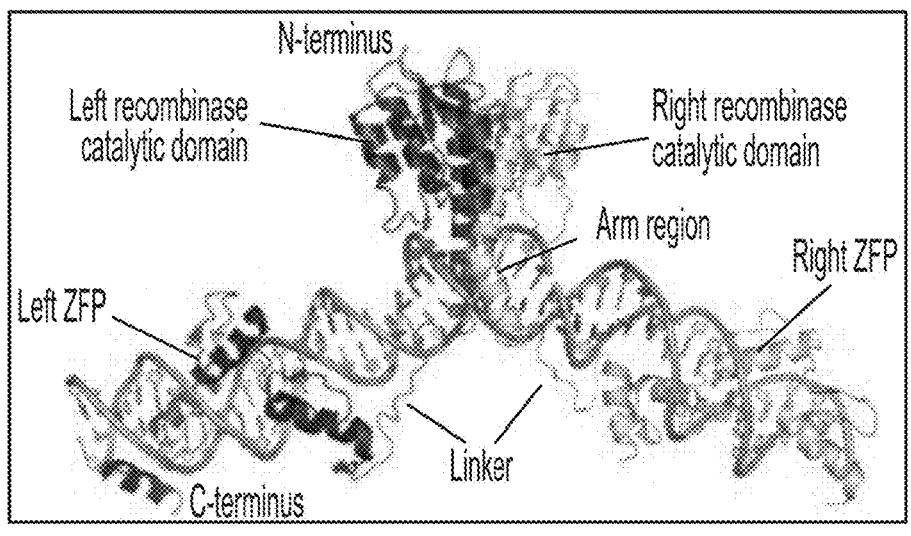
FIGS. 30A-30B are a series of diagrammatic representations relating to the structure of the zinc-finger recombinase dimer bound to DNA. (30A) Each zinc-finger recombinase (ZFR) monomer (blue or orange) consists of an activated serine recombinase catalytic domain linked to a custom-designed zinc-finger DNA-binding domain. Model was generated from crystal structures of the γδ resolvase and Aart zinc-finger protein (PDB IDs: 1GDT and 2I13, respectively). (30B) Cartoon of the ZFR dimer bound to DNA (SEQ ID NOs: 333-334). ZFR target sites consist of two-inverted zinc-finger binding sites (ZFBS) flanking a central 20-bp core sequence recognized by the ZFR catalytic domain. Zinc-finger proteins (ZFPs) can be designed to recognize 'left' or 'right' half-sites (blue and orange boxes, respectively). Abbreviations are as follows: N indicates A, T, C, or G; R indicates G or A; and Y indicates C or T.
Figure 30B:
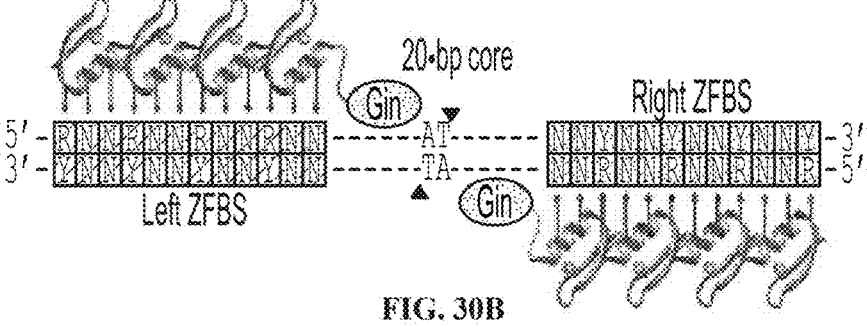

It was recently reported that alternatively truncated TALEs with synthetic TALE RVD domains do not require a 5' T in the DNA substrate. The reported 4143, +47 truncation was constructed as a Goldy TALE-TF and substantially lower activity on the AvrXa7 substrate was observed than for the Δ127, +95 truncation, which has been most commonly used by others and which is the truncation set used in our study (FIG. 29). Thus, the difference in reported outcomes could be due to the truncated architectures used.

In summary, the importance of a 5' thymidine in the DNA substrate for binding and activity of designed TALEs was determined in the context of TALE-R, TALE-TF, MBP-TALEs and TALEN chimeras. Targeted mutagenesis and TALE-R selection were applied to engineer TALE NTDs that recognize bases other than thymine as the 5' most base of the substrate DNA. The engineered TALE domains developed here demonstrated modularity and were highly active in TALE-TF and TALEN architectures. These novel NTDs expand by ~15-fold the number of sites that can be targeted by current TALE-Rs, which have strict geometric requirements on their binding sites and which are highly sensitive to the identity of the $N_0$ base. Furthermore, they now allow for the precise placement of TALE DBDs and TALE-TFs at any DNA sequence to facilitate gene regulation, displacement of endogenous DNA-binding proteins and synthetic biology applications where precise binding might be key. Although TALENs based on the native NTD show varying degrees of tolerance of No base substitutions, the data indicate that the novel NTDs reported here also facilitate higher efficiency gene editing with any No base as compared with natural NTD-based TALENs.

Example 5

Chimeric Zinc Finger Recombinases

The following materials and method were utilized.

The split gene reassembly vector (pBLA) was derived from pBluescriptII SK (–) (Stratagene) and modified to contain a chloramphenicol resistance gene and an interrupted TEM-1 p lactamase gene under the control of a lac promoter. ZFR target sites were introduced as previously described. Briefly, GFPuv (Clontech) was PCR amplified with the primers GFP-ZFR-XbaI-Fwd and GFP—ZFR-HindIII-Rev and cloned into the SpeI and HindIII restriction sites of pBLA to generate pBLA-ZFR substrates. All primer sequences are provided in Table 8.

TABLE 8

| | | |
|---|---|---|
| Primer Sequences. | | |
| Primer | SEQ ID NO: | Sequence |
| GFP-ZFR-20G-XbaI-Fwd | 264 | TTAATTAAGAGTCTAGAGGAGGCGTGTCCA AAACCATGGTTTACAGCACGCCTCCAGATC TAGGAGGAATTTAAAATGAG |

TABLE 8-continued

Primer Sequences.

| Primer | SEQ ID NO: | Sequence |
|---|---|---|
| GFP-ZFR-20G-HindIII-Rev | 265 | ACTGACCTAGAGAAGCTTGGAGGCGTGCTG TAAACCATGGTTTTGGAC<u>ACGCCTCCCTGC</u> <u>AGTTATTTGTACAGTTCATC</u> |
| SV40-ZFR-1-BglII-Fwd | 266 | TTAATTAAGAGAGATCTGCTGATGCAGATA CAGAAACCAAGGTTTTCTTACTTGCTGCTG CGGATCTGCATCTCAATTAGTCAGC |
| CMV-PstI-ZFR-1 Rev | 267 | CACCACCACGGATCCGCAGCAGCAAGTAAG AAAACCTTGGTTTCTGTATCTGCATCAGCA ATTTCGATAAGCCAGTAAGCAG |
| 5' Gin-HBS-Koz | 268 | CACCACCACGCGCGCAAGCTTAGATCTGGC CCAGGCGGCCACCATGCTGATTGGCTATGT AAGGG |
| 3' Gin-AgeI-Rev | 269 | CACCACCACACCGGTTCCCGATTTAGGTGG GCGAC |
| ZFR-Target-1-Fwd | 270 | GTTCCTGCCAGGATCCACTAG |
| ZFR-Target-1-Rev | 271 | GCATGTGTCCAGATGCATAGG |
| ZFR-Target-2-Fwd | 272 | CACCTTCTCCCAGGATAAGG |
| ZFR-Target-2-Rev | 273 | GTTGGCCTGTATTCCTCTGG |
| ZFR-Target-3-Fwd | 274 | AATGAAGTTCCCTTGGCACTTC |
| ZFR-Target-3-Rev | 275 | CTGAAGGGTTTTAAGTGCAGAAG |
| CMV-Mid Prim-1 | 276 | TGACGTCAATGACGGTAAATGG |

ZFR targets are underlined.

To generate luciferase reporter plasmids, the SV40 promoter was PCR amplified from pGL3-Prm (Promega) with the primers SV40-ZFR-BglIII-Fwd and SV40-ZFR-HindIII-Rev. PCR products were digested with BglII and HindIII and ligated into the same restriction sites of pGL3-Prm to generate pGL3-ZFR-1, 2, 3 . . . 18. The pBPS-ZFR donor plasmid was constructed as previously described with the following exception: the ZFR-1, 2 and 3 recombination sites were encoded by primers 3' CMV-PstI-ZFR-1, 2 or 3-Rev. Correct construction of each plasmid was verified by sequence analysis.

Recombination Assays.

ZFRs were assembled by PCR as previously described. PCR products were digested with SacI and XbaI and ligated into the same restrictions sites of pBLA. Ligations were transformed by electroporation into *Escherichia coli* TOP10F' (Invitrogen). After 1 hr recovery in SOC medium, cells were incubated with 5 mL SB medium with 30 ˆg mL$^{-1}$ chloramphenicol and cultured at 37° C. At 16 hr, cells were harvested; plasmid DNA was isolated by Mini-prep (Invitrogen) and 200 ng pBLA was used to transform *E. coli* TOP10F'. After 1 hr recovery in SOC, cells were plated on solid LB media with 30 ˆg mL$^{-1}$ chloramphenicol or 30 ˆg mL$^{-1}$ chloramphenicol and 100  g mL$^{-1}$ carbenicillin, an ampicillin analogue. Recombination was determined as the number of colonies on LB media containing chloramphenicol and carbenicillin divided by the number of colonies on LB media containing chloramphenicol. Colony number was determined by automated counting using the GelDoc XR Imaging System (Bio-Rad).

Selections.

The ZFR library was constructed by overlap extension PCR as previously described. Mutations were introduced at positions 120, 123, 127, 136 and 137 with the degenerate codon NNK (N: A, T, C or G and K: G or T), which encodes all 20 amino acids. PCR products were digested with SacI and XbaI and ligated into the same restriction sites of pBLA. Ligations were ethanol precipitated and used to transform *E. coli* TOP1OF'. Library size was routinely determined to be ~5×10$^7$. After 1 hr recovery in SOC medium, cells were incubated in 100 mL SB medium with 30 ˆg mL$^{-1}$ chloramphenicol at 37° C. At 16 hr, 30 mL of cells were harvested; plasmid DNA was isolated by Mini-prep and 3 ˆg plasmid DNA was used to transform *E. coli* TOP10F'. After 1 hr recovery in SOC, cells were incubated with 100 mL SB medium with 30 ˆg mL$^{-1}$ chloramphenicol and 100 ˆg mL$^{-1}$ carbenicillin at 37° C. At 16 hr, cells were harvested and plasmid DNA was isolated by Maxi-prep (Invitrogen). Enriched ZFRs were isolated by SacI and XbaI digestion and ligated into fresh pBLA for further selection. After 4 rounds of selection, sequence analysis was performed on individual carbenicillin-resistant clones. Recombination assays were performed as described above.

ZFR Construction.

Recombinase catalytic domains were PCR amplified from their respective pBLA selection vector with the primers 5' Gin-HBS-Koz and 3' Gin-AgeI-Rev. PCR products were digested with HindIII and AgeI and ligated into the same restriction sites of pBH to generate the SuperZiF-compitable subcloning plasmids: pBH-Gin-a, P, y, 5, s or Z. Zinc-fingers were assembled by SuperZiF and ligated into the AgeI and SpeI restriction sites of pBH-Gin-a, P, y, 5, s or Z to generate pBH-ZFR-L/R-1, 2, 3.18 (L: left ZFR; R: right ZFR). ZFR genes were released from pBH by SfiI digestion and ligated into pcDNA 3.1 (Invitrogen) to generate pcDNA-ZFR-L/R-1, 2, 3.18. Correct construction of each ZFR was verified by sequence analysis (Table 9).

TABLE 9

Catalytic domain substitutions and intended DNA targets.

| Catalytic domain | Target | Positions | | | | |
|---|---|---|---|---|---|---|
|  |  | 120 | 123 | 127 | 136 | 137 |
| A | CC[a] | Ile | Thr | Leu | Ile | Gly |
| B | GC | Ile | Thr | Leu | Arg | Phe |
| Γ | GT | Leu | Val | Ile | Arg | Trp |
| Δ | CA | Ile | Val | Leu | Arg | Phe |
| ε[b] | AC | Leu | Pro | His | Arg | Phe |
| ζ[c] | TT | Ile | Thr | Arg | Ile | Phe |

[a]Indicates wild-type DNA target.
[b]The ε catalytic domain also contains the substitutions E117L and L118S.
[c]The ζ catalytic domain also contains the substitutions M124S, R131I and P141R.

Luciferase Assays.

Human embryonic kidney (HEK) 293 and 293T cells (ATCC) were maintained in DMEM containing 10% (vol/vol) FBS and 1% (vol/vol) Antibiotic-Antimycotic (Anti-Anti; Gibco). HEK293 cells were seeded onto 96-well plates at a density of 4×10$^4$ cells per well and established in a humidified 5% CO$_2$ atmosphere at 37° C. At 24 hr after seeding, cells were transfected with 150 ng pcDNA-ZFR-L 1-18, 150 ng pcDNA-ZFR-R 1-18, 2.5 ng pGL3-ZFR-1, 2, 3, or 18 and 1 ng pRL-CMV using Lipofectamine 2000 (Invitrogen) according to the manufacturer's instructions. At 48 hr after transfection, cells were lysed with Passive Lysis Buffer (Promega) and luciferase expression was determined with the Dual-Luciferase® Reporter Assay System (Promega) using a Veritas Microplate Luminometer (Turner Biosystems).

Integration Assays.

HEK293 cells were seeded onto 6-well plates at a density of $5\times10^5$ cells per well and maintained in serum-containing media in a humidified 5% $CO_2$ atmosphere at 37° C. At 24 hr after seeding, cells were transfected with 1 ˆg pcDNA-ZFR-L-1, 2 or 3 and 1 ˆg pcDNA-ZFR-R-1, 2 or 3 and 200 ng pBPS-ZFR-1, 2 or 3 using Lipofectamine 2000 according to the manufacturer's instructions. At 48 hr after transfection, cells were split onto 6-well plates at a density of $5\times10^4$ cells per well and maintained in serum-containing media with 2 ˆg mL" puromycin. Cells were harvested upon reaching 100% confluence and genomic DNA was isolated with the Quick Extract DNA Extraction Solution (Epicentre). ZFR targets were PCR amplified with the following primer combinations: ZFR-Target-1, 2 or 3-Fwd and ZFR-Target-1, 2 or 3-Rev (Unmodified target); ZFR-Target-1, 2 or 3-Fwd and CMV-Mid-Prim-1 (Forward integration); and CMV-Mid-Prim-1 and ZFR-Target-1, 2 or 3-Rev (Reverse integration) using the Expand High Fidelity Taq System (Roche). For clonal analysis, at 2 days post-transfection $1\times10^5$ cells were split onto a 100 mm dish and maintained in serum-containing media with 2 ˆg mL$^{-1}$ puromycin. Individual colonies were isolated with 10 mm×10 mm open-ended cloning cylinders with sterile silicone grease (Millipore) and expanded in culture. Cells were harvested upon reaching 100% confluence and genomic DNA was isolated and used as template for PCR, as described above. For colony counting assays, at 2 days post-transfection cells were split into 6-well plates at a density of $1\times10^4$ cells per well and maintained in serum-containing media with or without 2 ˆg mL$^{-1}$ puromycin. At 16 days, cells were stained with a 0.2% crystal violet solution and integration efficiency was determined by counting the number of colonies formed in puromycin-containing media divided by the number of colonies formed in the absence of puromycin. Colony number was determined by automated counting using the GelDoc XR Imaging System (Bio-Rad).

Results

Specificity Profile of the Gin Recombinase.

In order to re-engineer serine recombinase catalytic specificity, a detailed understanding was developed of the factors underlying substrate recognition by this family of enzymes. To accomplish this, the ability of an activated mutant of the catalytic domain of the DNA invertase Gin to recombine a comprehensive set of symmetrically substituted target sites was evaluated. The Gin catalytic domain recombines a pseudo-symmetric 20-bp core that consists of two 10-bp half-site regions. This collection of recombination sites therefore contained each possible single-base substitution at positions 10, 9, 8, 7, 6, 5, and 4 and each possible two-base combination at positions 3 and 2 and in the dinucleotide core. Recombination was determined by split gene reassembly, a previously described method that links recombinase activity to antibiotic resistance.

In general, it was found that Gin tolerates (i) 12 of the 16 possible two-base combinations at the dinucleotide core (AA, AT, AC, AG, TA, TT, TC, TG, CA, CT, GA, GT); (ii) 4 of the 16 possible two-base combinations at positions 3 and 2 (CC, CG, GG and TG); (iii) a single A to T substitution at positions 6, 5, or 4; and (iv) all 12 possible single-base substitutions at positions 10, 9, 8, and 7 (FIGS. 31A-31D). Further, it was found that Gin could recombine a target site library containing at least $10^6$ (of a possible $4.29\times10^9$) unique base combinations at positions 10, 9, 8, and 7 (FIG. 31D).

These findings are consistent with observations made from crystal structures of the yS resolvase, which indicate that (i) the interactions made by the recombinase dimer across the dinucleotide core are asymmetric and predominately non-specific; (ii) the interactions between an evolutionarily conserved Gly-Arg motif in the recombinase arm region and the DNA minor groove imposes a requirement for adenine or thymine at positions 6, 5, and 4; and (iii) there are no sequence-specific interactions between the arm region and the minor groove at positions 10, 9, 8, or 7 (FIG. 31E). These results are also consistent with studies that focused on determining the DNA-binding properties of the closely related Hin recombinase.

Re-Engineering Gin Recombinase Catalytic Specificity.

Based on the finding that Gin tolerates conservative substitutions at positions 3 and 2 (i.e., CC, CG, GG, and TG), whether Gin catalytic specificity could be re-engineered to specifically recognize core sequences containing each of the 12 base combinations not tolerated by the native enzyme (FIG. 32A) was investigated. In order to identify the specific amino acid residues involved in DNA recognition by Gin, the crystal structures of two related serine recombinases, the y6 resolvase and Sin recombinase, in complex with their respective DNA targets were examined. Based on these models, five residues were identified that contact DNA at positions 3 and 2: Leu 123, Thr 126, Arg 130, Val 139, and Phe 140 (numbered according to the y5 resolvase) (FIG. 32B). Random mutagenesis was performed on the equivalent residues in the Gin catalytic domain (Ile 120, Thr 123, Leu 127, Ile 136, and Gly 137) by overlap extension PCR and constructed a library of ZFR mutants by fusing these catalytic domain variants to an unmodified copy of the 'H1' ZFP. The theoretical size of this library was $3.3\times10^7$ variants.

Figures 32C, 32D, 32E:
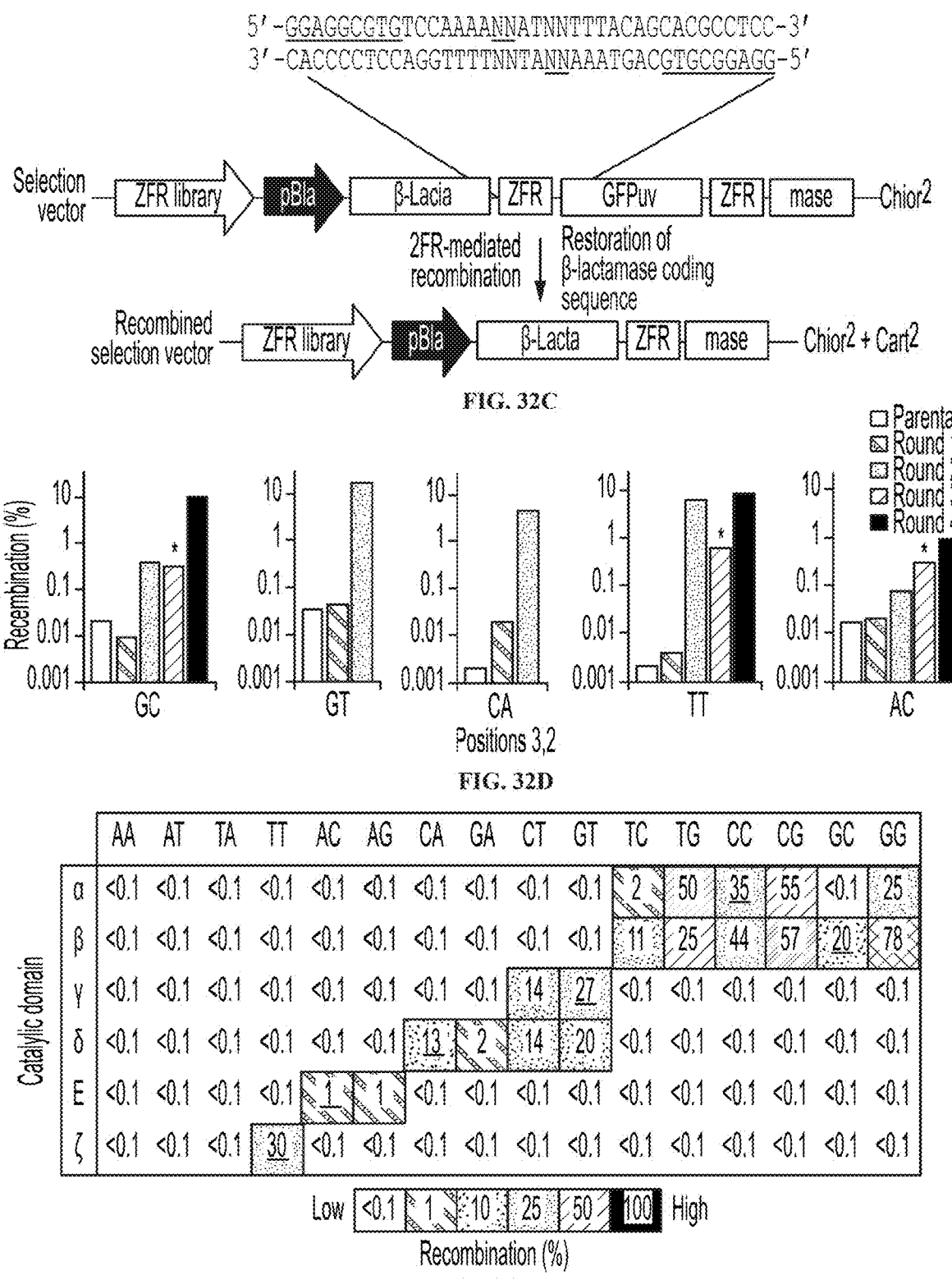

The ZFR library was cloned into substrate plasmids containing one of the five base combinations not tolerated by the native enzyme (GC, GT, CA, AC, or TT) and enriched for active ZFRs by split gene reassembly (FIG. 32C). After 4 rounds of selection, it was found that the activity of each ZFR population increased>1,000-fold on DNA targets containing GC, GT, CA, and TT substitutions and >100-fold on a DNA target containing AC substitutions (FIG. 32D).

Figure 36:
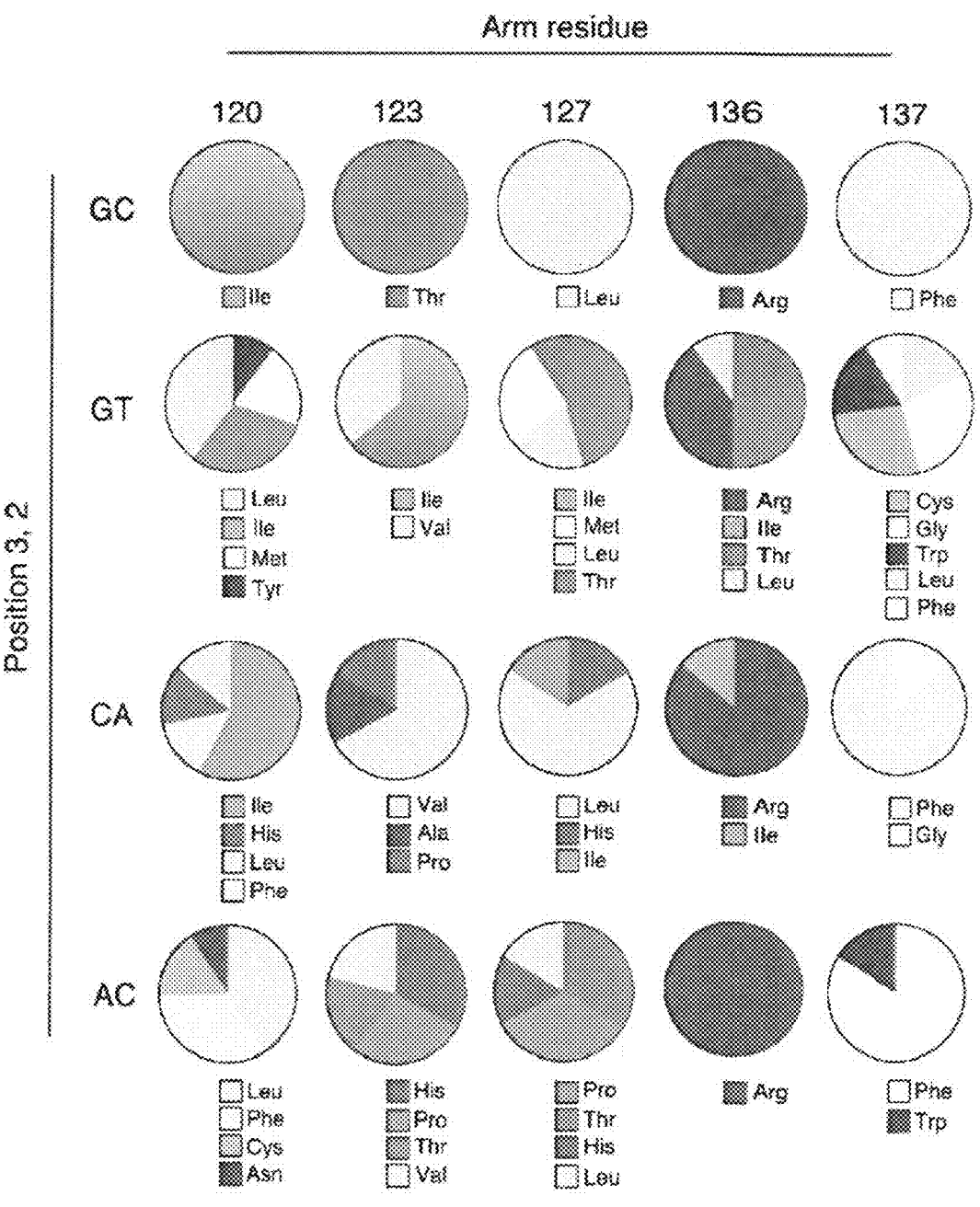
FIG. 36 is a diagrammatic representation of sequence analysis of selected recombinases. Pie charts showing the percentage of amino acid substitutions at each targeted arm position. After the 4th round of selection, >20 clones were sequenced from each library. Sequence analysis of clones that recombine TT are described elsewhere (1).
Figure 40:
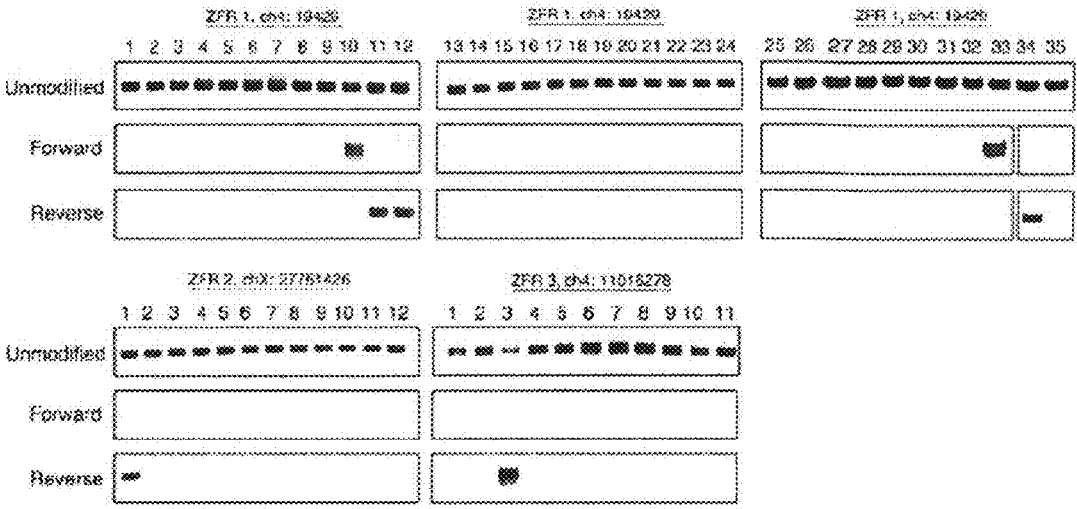
FIG. 40 is a series of pictorial representations depicting clonal analysis of ZFR-modified cells. PCR primer combinations amplified either unmodified genomic target or integrated plasmid in the forward or reverse orientation.

Individual recombinase variants were sequenced from each population and found that a high level of amino acid diversity was present at positions 120, 123, and 127 and that >80% of selected clones contained Arg at position 136 and Trp or Phe at position 137 (FIG. 36). These results suggest that positions 136 and 137 play critical roles in the recognition of unnatural core sequences. The ability of each selected enzyme to recombine its target DNA was evaluated and it was found that nearly all recombinases showed activity (>10% recombination) and displayed a >1,000-fold shift in specificity toward their intended core sequence (FIG. 37). As with the parental Gin, it was found that several recombinases tolerated conservative substitutions at positions 3 and 2 (i.e., cross-reactivity against GT and CT or AC and AG), indicating that a single re-engineered catalytic domain could be used to target multiple core sites (FIG. 37).

In order to further investigate recombinase specificity, the recombination profiles were determined of five Gin variants (hereafter designated Gin p, y, 6, e and Z) shown to recognize nine of the 12 possible two-base combinations not tolerated by the parental enzyme (GC, TC, GT, CT, GA, CA, AG, AC, and TT) (Table 1). Gin p, 6, and e recombined their intended core sequences with activity and specificity comparable to that of the parental enzyme (hereafter referred to as Gin a) and that Gin y and Z were able to recombine their intended core sequences with specificity exceeding that of Gin a (FIG. 32E). Each recombinase displayed>1,000-fold preference for adenine or thymine at positions 6, 5, and 4 and showed no base preference at positions 10, 9, 8, and 7 (FIGS. 38A and 38B). These results indicate that mutagenesis of the DNA-binding arm did not compromise recombinase specificity. It was not possible to select for Gin variants capable of tolerating AA, AT, or TA substitutions at positions 3 and 2. One possibility for this result is that DNA targets containing>4 consecutive A-T bps might exhibit bent DNA conformations that interfere with recombinase binding and/or catalysis.

Engineering ZFRs to Recombine User-Defined Sequences

Whether ZFRs composed of the re-engineered catalytic domains could recombine pre-determined sequences was investigated. To test this possibility, the human genome (GRCh37 primary reference assembly) was searched for potential ZFR target sites using a 44-bp consensus recombination site predicted to occur approximately once every 400,000 bp of random DNA (FIG. 4A). This ZFR consensus target site, which was derived from the core sequence profiles of the selected Gin variants, includes approximately $7 \times 10^8$ (of a possible $1.0955 \times 10^{12}$) unique 20-bp core combinations predicted to be tolerated by the 21 possible catalytic domain combinations and a conservative selection of modular zinc finger domains that excludes 5'-CNN-3' and 5'-TNN-3' triplets within each ZFBS. Using ZFP specificity as the primary determinant for selection, 18 possible ZFR target sites across 8 human chromosomes (Chr. 1, 2, 4, 6, 7, 11, 13 and X) at non-protein coding loci were identified. On average, each 20-bp core showed ~46% sequence identity to the core sequence recognized by the native Gin catalytic domain (FIG. 33B). Each corresponding ZFR was constructed by modular assembly (see Materials and Methods).

To determine whether each ZFR pair could recombine its intended DNA target, a transient reporter assay was developed that correlates ZFR-mediated recombination to reduced luciferase expression (FIGS. 33A and 39). To accomplish this, ZFR target sites were introduced upstream and downstream an SV40 promoter that drives expression of a luciferase reporter gene. Human embryonic kidney (HEK) 293T cells were co-transfected with expression vectors for each ZFR pair and its corresponding reporter plasmid. Luciferase expression was measured 48 hr after transfection. Of the 18 ZFR pairs analyzed, 38% (7 of 18) reduced luciferase expression by >75-fold and 22% (4 of 18) decreased luciferase expression by >140-fold (FIG. 33B). In comparison, GinC4, a positive ZFR control designed to target the core sequence recognized by the native Gin catalytic domain, reduced luciferase expression by 107 fold. Overall, it was found that 50% (9 of 18) of the evaluated ZFR pairs decreased luciferase expression by at least 20-fold. Importantly, virtually every catalytic domain that displayed significant activity in bacterial cells (>20% recombination) was successfully used to recombine at least one naturally occurring sequence in mammalian cells.

In order to evaluate ZFR specificity, separately HEK293T cells were co-transfected with expression plasmids for the nine most active ZFRs with each non-cognate reporter plasmid. Each ZFR pair demonstrated high specificity for its intended DNA target and 77% (7 of 9) of the evaluated ZFRs showed an overall recombination specificity nearly identical to that of the positive control GinC4 (FIG. 4C). To establish that reduced luciferase expression is the product of the intended ZFR heterodimer and not the byproduct of recombination-competent ZFR homodimers, the contribution of each ZFR monomer to recombination was measured. Co-transfection of the ZFR 1 'left' monomer with its corresponding reporter plasmid led to a modest reduction in luciferase expression (total contribution to recombination: ~22%), but the vast majority of individual ZFR monomers (16 of 18) did not significantly contribute to recombination (<10% recombination), and many (7 of 18) showed no activity (FIG. 39). Taken together, these studies indicate that ZFRs can be engineered to recombine user-defined sequences with high specificity.

Engineered ZFRs Mediate Targeted Integration into the Human Genome.

Figure 34A:
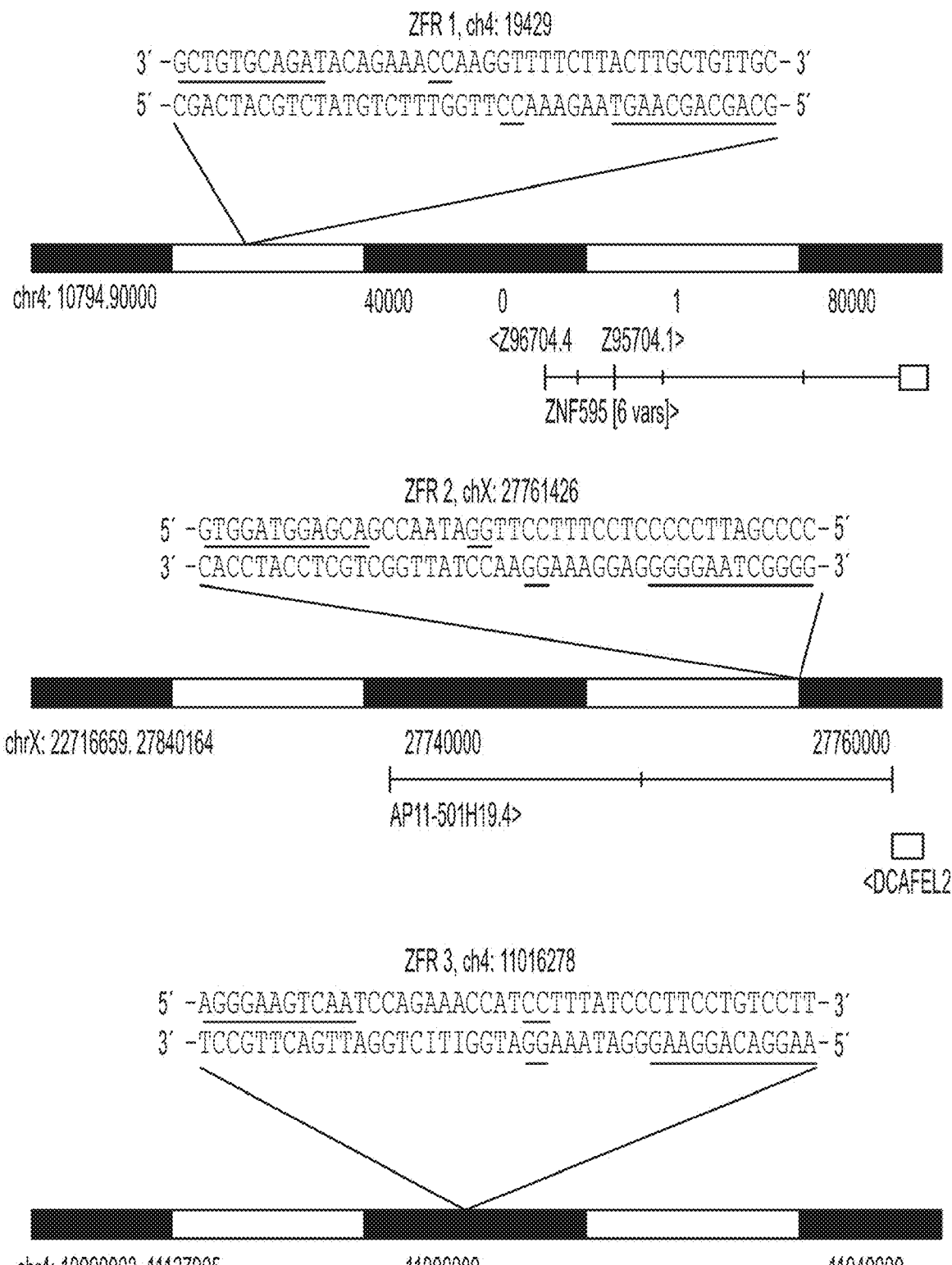
FIGS. 34A-34D are a series of graphical and diagrammatic representations illustrating ZFRs ability to target integration into the human genome. (34A) Schematic representation of the donor plasmid (top) and the genomic loci targeted by ZFRs 1 (SEQ ID NO: 363), 2 (SEQ ID NO: 364), and 3 (SEQ ID NO: 365). Open boxes indicate neighboring exons. Arrows indicate transcript direction. The sequence and location of each ZFR target are shown. Underlined bases indicate zinc-finger targets and positions 3 and 2. (34B) Efficiency of ZFR-mediated integration. Data were normalized to data from cells transfected with donor plasmid only. Error bars indicate standard deviation (n=3). (34C) PCR analysis of ZFR-mediated integration. PCR primer combinations amplified (top) unmodified locus or integrated plasmid in (middle) the forward or (bottom) the reverse orientation. (34D) Representative chromatograms of PCR-amplified integrated donor for ZFRs 1 (SEQ ID NO: 366) and 3 (SEQ ID NO: 367). Arrows indicate sequencing primer orientation. Shaded boxes denote genomic target sequences.
Figure 34B:
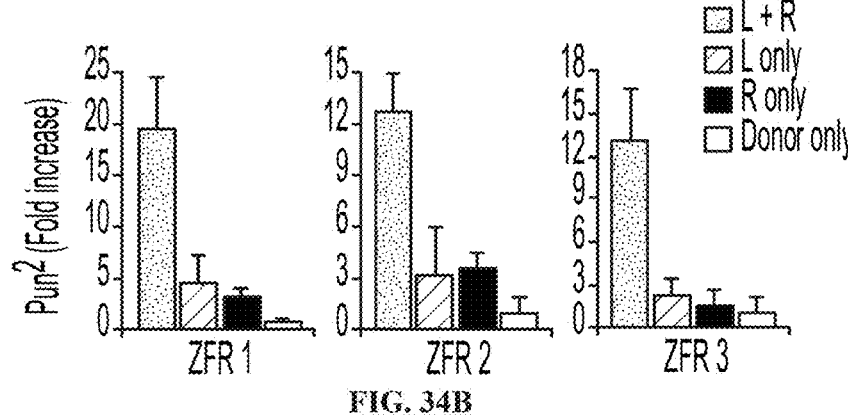
Figure 34C:
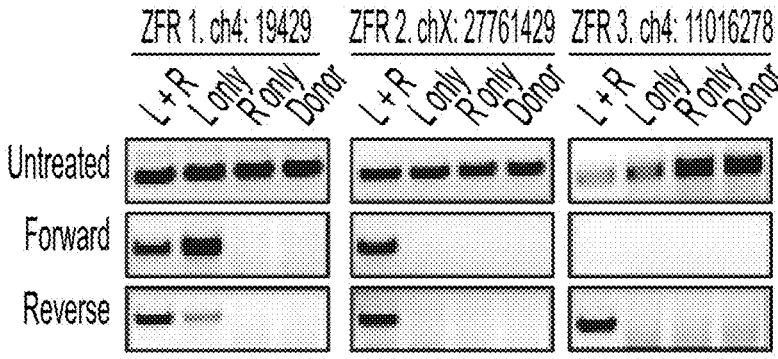
Figure 34D:
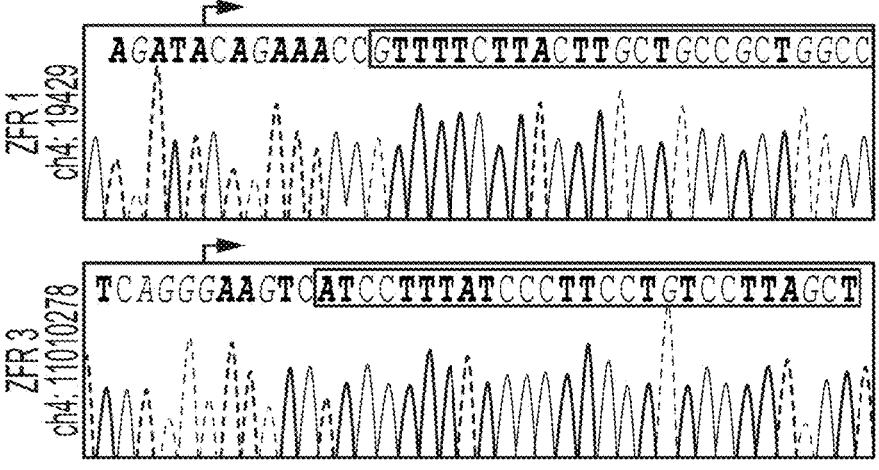

Whether ZFRs could integrate DNA into endogenous loci in human cells was evaluated next. To accomplish this, HEK293 cells were co-transfected with ZFR expression vectors and a corresponding DNA donor plasmid that contained a specific ZFR target site and a puromycin-resistance gene under the control of an SV40 promoter. For this analysis, ZFR pairs 1, 2, and 3, were used which were designed to target non-protein coding loci on human chromosomes 4, X, and 4, respectively (FIG. 34A). At 2 days post-transfection, cells were incubated with puromycin-containing media and measured integration efficiency by determining the number of puromycin-resistant (puro$^R$) colonies. It was found that (i) co-transfection of the donor plasmid and the corresponding ZFR pair led to a >12-fold increase in puro$^R$ colonies in comparison to transfection with donor plasmid only and that (ii) co-transfection with both ZFRs led to a 6- to 9 fold increase in puro$^R$ colonies in comparison to transfection with individual ZFR monomers (FIG. 34B). In order to evaluate whether ZFR pairs correctly targeted integration, genomic DNA was isolated from puro$^R$ populations and amplified each targeted locus by PCR. The PCR products corresponding to integration in the forward and/or reverse orientations were observed at each locus targeted by these ZFR pairs (FIG. 34C). Next, to determine the overall specificity of ZFR-mediated integration, genomic DNA was isolated from clonal cell populations and evaluated plasmid insertion by PCR. This analysis revealed targeting efficiencies of 8.3% (1 of 12 clones), 14.2% (5 of 35 clones), and 9.1% (1 of 11 clones) for ZFR pairs 1, 2, and 3, respectively. Sequence analysis of each PCR product confirmed ZFR-mediated integration (FIG. 34D). Taken together, these results indicate that ZFRs can be designed to accurately integrate DNA into endogenous loci.

Finally, it is noted that the ZFR-1 'left' monomer was found to target integration into the ZFR-1 locus (FIG. 34C). This result, which is consistent with the luciferase reporter studies described above (FIG. 39) indicates that recombination-competent ZFR homodimers have the capacity to mediate off-target integration. Future development of an optimized heterodimeric ZFR architecture and a comprehensive evaluation of off-target integration should lead to the design of ZFRs that demonstrate greater targeting efficiency.

It is herein shown that ZFRs can be designed to recombine user-defined sequences with high specificity and that ZFRs can integrate DNA into pre-determined endogenous loci in human cells. By combining substrate specificity analysis and directed evolution, virtually all sequence requirements imposed by the ZFR catalytic domain were eliminated. Using the archive of 45 pre-selected zinc-finger modules, it is estimated that ZFRs can be designed to recognize>1×10$^{22}$ unique 44-bp DNA sequences, which corresponds to approximately one potential ZFR target site for every 4,000 [5] bp of random sequence. Construction of customized zinc-finger domains by selection would further extend targeting. The re-engineered catalytic domains described herein will be compatible with recently described TAL effector recombinases. This work demonstrates the feasibility of generating ZFRs with custom specificity and illustrates the potential utility of ZFRs for a wide range of applications, including genome engineering, synthetic biology, and gene therapy.

Although the invention has been described with reference to the above example, it will be understood that modifications and variations are encompassed within the spirit and scope of the invention. Accordingly, the invention is limited only by the following claims.

---

What is claimed is:

1. A polypeptide comprising a *Ralstonia* derived transcription activator-like effector (TALE) protein, the TALE protein having an N-terminal domain (NTD) comprising an amino acid sequence as set forth in SEQ ID NO: 8 (IVDIAR1QR2SGDLA) having one or more mutations or deletions selected from: R1 is K, Q is Y, Q is S, Q is R, R2 is W, R2 is G, R2 is deleted, S is R, Sis H, Sis A, S is N, and Sis T.

2. The polypeptide of claim 1, wherein the NTD comprises an amino acid sequence selected from: IVDIAR-QWSGDLA (SEQ ID NO: 9), IVDIARYRGDLA (SEQ ID NO: 10), IVDIARSRSGDLA (SEQ ID NO: 11), IVDI-ARYHGDLA (SEQ ID NO: 12), and IVDIARRGAGDLA (SEQ ID NO: 13).

3. The polypeptide of claim 1, wherein the TALE protein further comprises a synthetic repeat variable di-residues (RVD) domain.

4. The polypeptide of claim 1, wherein the TALE protein comprises a C-terminal or N-terminal truncation relative to a wildtype *Ralstonia* TALE protein from which the TALE protein was derived.

5. The polypeptide of claim 1, further comprising a recombinase domain or a nuclease domain.

6. The polypeptide of claim 5, wherein the recombinase domain is selected from the group consisting of Gin, Hin, Tn3, Sin, Beta, Pin, Min, Din, Cin, muteins of Gin, muteins of Hin, muteins of Tn3, muteins of Sin, muteins of Beta, muteins of Pin, muteins of Min, muteins of Din, and muteins of Cin.

7. A nucleic acid molecule encoding the polypeptide of claim 1.

8. An expression cassette comprising the nucleic acid molecule of claim 7.

9. A vector comprising the expression cassette of claim 8.

10. A host cell transformed or transfected with the vector of claim 9.

*     *     *     *     *

```
                         SEQUENCE LISTING

Sequence total quantity: 369
SEQ ID NO: 1               moltype = DNA   length = 864
FEATURE                    Location/Qualifiers
misc_feature               1..864
                           note = Synthetic construct
source                     1..864
                           mol_type = other DNA
                           organism = synthetic construct
SEQUENCE: 1
atggatccca ttcgttcgcg cacgccaagt cctgcccgcg agcttctgcc cggaccccaa   60
ccggataggg ttcagccgac tgcagatcgg gggggggctc cgcctgctgg cggccccctg  120
gatggcttgc ccgctcggcg gacgatgtcc cggacccggc tgccatctcc ccctgcgccc  180
tcgcctgcgt tctcggcggg cagcttcagc gatctgctcc gtcagttcga tccgtcgctt  240
cttgatacat cgcttcttga ttcgatgcct gccgtcggca cgccgcatac agcggctgcc  300
ccagcagagt gcgatgaggt gcaatcgggt ctgcgtgcag ccgatgaccc gccacccacc  360
gtgcgtgtcg ctgtcactgc ggcgcggccg ccgcgcgcca agccggcccc gcgacggcgt  420
gcggcgcaac cctccgacgc ttcgccggcc gcgcaggtgg atctacgcac gctcggctac  480
agtcagcagc agcaagagaa gatcaaaccg aaggtgcgtt cgacagtggc gcagcaccac  540
gaggcactgg tgggccatgg gtttacacac gcgcacatcg ttgcgctcag ccaacacccg  600
gcagcgttag ggaccgttgc tgtcacgtat caggacataa tcagggcgtt gccagaggcg  660
acacacgaag acatcgttgg cgtcggcaaa cagtggtccg gcgcacgcgc tctggaggcc  720
ttgctcacgg aggcggggga gttgagaggt ccgccgttac agttggacac aggccaactt  780
ctcaagattg caaaacgtgg cggcgtgacc gcagtggagg cagtgcatgc atggcgcaat  840
gcactgacgg gtgcccccct gaac                                         864

SEQ ID NO: 2               moltype = AA   length = 288
FEATURE                    Location/Qualifiers
REGION                     1..288
                           note = Synthetic construct
source                     1..288
                           mol_type = protein
                           organism = synthetic construct
SEQUENCE: 2
MDPIRSRTPS PARELLPGPQ PDRVQPTADR GGAPPAGGPL DGLPARRTMS RTRLPSPPAP   60
SPAFSAGSFS DLLRQFDPSL LDTSLLDSMP AVGTPHTAAA PAECDEVQSG LRAADDPPPT  120
VRVAVTAARP PRAKPAPRRR AAQPSDASPA AQVDLRTLGY SQQQQEKIKP KVRSTVAQHH  180
EALVGHGFTH AHIVALSQHP AALGTVAVTY QDIIRALPEA THEDIVGVGK QWSGARALEA  240
LLTEAGELRG PPLQLDTGQL LKIAKRGGVT AVEAVHAWRN ALTGAPLN                288

SEQ ID NO: 3               moltype = AA   length = 11
FEATURE                    Location/Qualifiers
REGION                     1..11
                           note = Synthetic construct
VAR_SEQ                    4
                           note = X is Y, S or R
VAR_SEQ                    5
                           note = X is R or G
VAR_SEQ                    6
                           note = X is R, H, A, N or T
source                     1..11
                           mol_type = protein
                           organism = synthetic construct
SEQUENCE: 3
VGKXXXGARA L                                                         11

SEQ ID NO: 4               moltype = AA   length = 10
FEATURE                    Location/Qualifiers
REGION                     1..10
                           note = Synthetic construct
source                     1..10
                           mol_type = protein
                           organism = synthetic construct
SEQUENCE: 4
VGKYRGARAL                                                           10

SEQ ID NO: 5               moltype = AA   length = 11
```

-continued

```
FEATURE            Location/Qualifiers
REGION             1..11
                   note = Synthetic construct
source             1..11
                   mol_type = protein
                   organism = synthetic construct
SEQUENCE: 5
VGKSRSGARA L                                                          11

SEQ ID NO: 6       moltype = AA  length = 10
FEATURE            Location/Qualifiers
REGION             1..10
                   note = Synthetic construct
source             1..10
                   mol_type = protein
                   organism = synthetic construct
SEQUENCE: 6
VGKYHGARAL                                                            10

SEQ ID NO: 7       moltype = AA  length = 11
FEATURE            Location/Qualifiers
REGION             1..11
                   note = Synthetic construct
source             1..11
                   mol_type = protein
                   organism = synthetic construct
SEQUENCE: 7
VGKRGAGARA L                                                         11

SEQ ID NO: 8       moltype = AA  length = 13
FEATURE            Location/Qualifiers
REGION             1..13
                   note = Synthetic construct
SITE               7
                   note = MISC_FEATURE - Xaa is Y, S or R
SITE               8
                   note = MISC_FEATURE - Xaa is W or G
SITE               9
                   note = MISC_FEATURE - Xaa is R, H, A, N or T
source             1..13
                   mol_type = protein
                   organism = synthetic construct
SEQUENCE: 8
IVDIAKXXXG DLA                                                       13

SEQ ID NO: 9       moltype = AA  length = 13
FEATURE            Location/Qualifiers
REGION             1..13
                   note = Synthetic construct
source             1..13
                   mol_type = protein
                   organism = synthetic construct
SEQUENCE: 9
IVDIARQWSG DLA                                                       13

SEQ ID NO: 10      moltype = AA  length = 12
FEATURE            Location/Qualifiers
REGION             1..12
                   note = Synthetic construct
source             1..12
                   mol_type = protein
                   organism = synthetic construct
SEQUENCE: 10
IVDIARYRGD LA                                                        12

SEQ ID NO: 11      moltype = AA  length = 13
FEATURE            Location/Qualifiers
REGION             1..13
                   note = Synthetic construct
source             1..13
                   mol_type = protein
                   organism = synthetic construct
SEQUENCE: 11
IVDIARSRSG DLA                                                       13

SEQ ID NO: 12      moltype = AA  length = 12
FEATURE            Location/Qualifiers
REGION             1..12
                   note = Synthetic construct
```

-continued

```
source                    1..12
                          mol_type = protein
                          organism = synthetic construct
SEQUENCE: 12
IVDIARYHGD LA                                                             12

SEQ ID NO: 13             moltype = AA  length = 13
FEATURE                   Location/Qualifiers
REGION                    1..13
                          note = Synthetic construct
source                    1..13
                          mol_type = protein
                          organism = synthetic construct
SEQUENCE: 13
IVDIARRGAG DLA                                                            13

SEQ ID NO: 14             moltype = AA  length = 9
FEATURE                   Location/Qualifiers
REGION                    1..9
                          note = Synthetic construct
VAR_SEQ                   4..6
                          note = X can be any naturally occurring amino acid
source                    1..9
                          mol_type = protein
                          organism = synthetic construct
SEQUENCE: 14
VGKXXXGAR                                                                 9

SEQ ID NO: 15             moltype = AA  length = 12
FEATURE                   Location/Qualifiers
REGION                    1..12
                          note = Synthetic construct
VAR_SEQ                   5..8
                          note = Xaa can be any naturally occurring amino acid
source                    1..12
                          mol_type = protein
                          organism = synthetic construct
SEQUENCE: 15
VDIAXXXXGD LA                                                             12

SEQ ID NO: 16             moltype = AA  length = 48
FEATURE                   Location/Qualifiers
REGION                    1..48
                          note = Synthetic construct
source                    1..48
                          mol_type = protein
                          organism = synthetic construct
SEQUENCE: 16
NIHGNININS HDNNHDHDHD NSNNHDHDNS NSNNNNNING NNNINNSN                      48

SEQ ID NO: 17             moltype = DNA  length = 26
FEATURE                   Location/Qualifiers
misc_feature              1..26
                          note = Synthetic construct
source                    1..26
                          mol_type = other DNA
                          organism = synthetic construct
SEQUENCE: 17
ataaacccccc tccaaccagg tgctaa                                            26

SEQ ID NO: 18             moltype = AA  length = 52
FEATURE                   Location/Qualifiers
REGION                    1..52
                          note = Synthetic construct
source                    1..52
                          mol_type = protein
                          organism = synthetic construct
SEQUENCE: 18
NINGNININI HDHDHDHDHD NGHDHDNINI HDHDNINNNN NGNNHDNGNI NI                 52

SEQ ID NO: 19             moltype = AA  length = 1446
FEATURE                   Location/Qualifiers
REGION                    1..1446
                          note = Synthetic construct
source                    1..1446
                          mol_type = protein
                          organism = synthetic construct
SEQUENCE: 19
MDPIRSRTPS PARELLPGPQ PDRVQPTADR GGAPPAGGPL DGLPARRTMS RTRLPSPPAP  60
```

```
SPAFSAGSFS DLLRQFDPSL LDTSLLDSMP AVGTPHTAAA PAECDEVQSG LRAADDPPPT  120
VRVAVTAARP PRAKPAPRRR AAQPSDASPA AQVDLRTLGY SQQQQEKIKP KVRSTVAQHH  180
EALVGHGFTH AHIVALSQHP AALGTVAVTY QDIIRALPEA THEDIVGVGK QWSGARALEA  240
LLTEAGELRG PPLQLDTGQL LKIAKRGGVT AVEAVHAWRN ALTGAPLNLT PDQVVAIASN  300
IGGKQALETV QRLLPVLCQD HGLTPDQVVA IASHGGKQA LETVQRLLPV LCQDHGLTPD  360
QVVAIASNIG GKQALETVQR LLPVLCQAHG LTPDQVVAIA SNIGGKQALE TVQRLLPVLC  420
QDHGLTPAQV VAIASNSGGK QALETVQRLL PVLCQDHGLT PDQVVAIASH DGGKQALETL  480
QRLLPVLCQD HGLTPDQVVA IANNNGGKQA LETLQRLLPV LCQDHGLTPD QVVAIASHDG  540
GKQALETVQR LLPVLCQDHG LTPDQVVAIA SHDGGKQALE TVQRLLPVLC QDHGLTPAQV  600
VAIASHDGGK QALETVQRLL PVLCQDHGLT PDQVVAIASN SGGKQALETV QRLLPVLCQD  660
HGLTPDQVVA IASNGGKQAL ETVQRLLPVL CQDHGLTPDQ VVAIASNGGK QALETVQRLL  720
PVQRLLPVLC QDHGLTQDQV VAIASHDGGK QALETVQRLL PVLCQDHGLT PDQVVAIASH  780
DGGKQALETV QRLLPVLCQD HGLTPDQVVA IASNSGGKQA LETVQRLLPV LCQDHGLTPD  840
QVVAIASNSG GKQALETVQR LLPVLCQDHG LTPDQVVAIA SNNGGKQALE TVQRLLPVLC  900
QDHGLTPDQV VAIANNNGGK QALETVQRLL PVLCQDHGLT PAQVVAIASN IGGKQALETV  960
QRLLPVLCQD HGLTLDQVVA IASNGGSKQA LETVQRLLPV LCQDHGLTPD QVVAIANNNG 1020
GKQALETVQR LLPVLCQDHG LTPDQVVAIA SNIGGKQALE TVQRLLPVLC QDHGLTLDQV 1080
VAIASNGGKQ ALETVQRLLP VLCQDHGLTP NQVVAIASNS GGKQALETVQ RLLPVLCQDH 1140
GLTPNQVVAI ASNGGKQALE SIVAQLSRPD PALAALTNDH LVALACLGGR PALDAVKKGL 1200
PHAPELIRRI NRRIPERTSH RVPDLAHVVR VLGFFQSHSH PAQAFDDAMT QFEMSRHGLV 1260
QLFRRVGVTE FEARYGTLPP ASQRWDRILQ ASGMKRAKPS PTSAQTPDQA SLHAFADSLE 1320
RDLDAPSPMH EGDQTRASSR KRSRSDRAVT GPSTQQSFEV RVPEQQDALH LPLSWRVKRP 1380
RTRIGGGLPD PGTPIAADLA ASSTVMWEQD AAPFAGAADD FPAFNEEELA WLMELLPQSG 1440
SVGGTI                                                             1446

SEQ ID NO: 20            moltype = DNA   length = 4341
FEATURE                  Location/Qualifiers
misc_feature             1..4341
                         note = Synthetic construct
source                   1..4341
                         mol_type = other DNA
                         organism = synthetic construct
SEQUENCE: 20
atggatccca ttcgttcgcg cacgccaagt cctgcccgcg agcttctgcc cggaccccaa   60
ccggataggg ttcagccgac tgcagatcgg ggggggctc cgcctgctgg cggcccctg   120
gatggcttgc ccgctcggcg gacgatgtcc cggacccggc tgccatctcc ccctgcgccc  180
tcgcctgcgt tctcggcggg cagcttcagc gatctgctcc gtcagttcga tccgtcgctt  240
cttgatacat cgcttcttga ttcgatgcct gccgtcggca cgccgcatac agcggctgcc  300
ccagcagagt gcgatgaggt gcaatcgggt ctgcgtgcag ccgatgaccc gccaacccac  360
gtgcgtgtcg ctgtcactgc ggcgcggccg ccgcgcgcca agccggcccc gcgacggcgt  420
gcggcgcaac cctccgacgc ttcgccggcc gcgcaggtgg atctacgcac gctcggctac  480
agtcagcagc agcaagagaa gatcaaaccg aaggtgcgtt cgacagtggc gcagcaccac  540
gaggcactgg tgggccatgg gtttacacac gcgcacatcg ttgcgctcag ccaacaccac  600
gcagcgttag ggaccgttgc tgtcacgtat caggacataa tcaggcgtt gccagaggca  660
acacacgaag acatcgttgg cgtcggcaaa cagtggtccg gcgcacgcgc tctggaggcc  720
ttgctcacgg aggcggggga gttgagaggt ccgccgttac agttggacac aggccaactt  780
ctcaagattg caaaacgtgg cggcgtgacc gcagtggagg cagtgcatgc atggcgcaat  840
gcactgacgg gtgcccccct gaacctgacc ccggaccaag tggtggccat cgccagcaat  900
attggcggca agcaggcgct ggagacggta cagcggctgt tgccggtgct gtgccaggac  960
catggcctga ccccggacca ggtcgtggcc atcgccagcc atggcggcgg caagcaggcg 1020
ctggacgagg tgcagcggct gttgccggtg ctgtgccagg accatggcct gaccccggac 1080
caggtggtgg ccatcgccag caatattggc ggcaagcagg cgctagagac ggtgcagcgg 1140
ctgttgccgg tgctgtgcca ggcccatggc ctgaccccgg accaggtcgt ggccatcgcc 1200
agcaatattg cggcaagca ggcgctggag acggtgcagc ggctgttgcc ggtgctgtgc 1260
caggaccatg gcctgacccc ggcccaggtg gtggccatcg ccagcaatag tggcggcaag 1320
caggcgctgg agacggtgca gcggctgttg ccggtgctgt gccaggacca tggcctgacc 1380
ccggaccaag tcgtggccat cgccagccac gatggcggca gcaggcgct ggagacgctg 1440
cagcggctgt tgccggtgct gtgccaggac catggcctga ccccggacca ggtcgtggcc 1500
atcgccaaca ataacggcgg caagcaggcg ctggagacgg tgcagcggca gttgccggtg 1560
ctgtgccagg accatggcct gacccccggac caagtggtgg ccatcgccag ccacgatggc 1620
ggcaagcagg cgctggagac ggtgcagcgg ctgttgccgg tgctgtgcca ggaccatggc 1680
ctgaccccgg accaggtggt ggccatcgcc agccacgatg gcggcaagca ggcgctggag 1740
acggtgcagc ggctgttgcc ggtgctgtgc caggaccatg gcctgacccc ggcccaagtg 1800
gtggccatcg ccagccacga tggcggcaag caggcgctgg agacggtgca gcggctgttg 1860
ccggtgctgt gccaggacca tggcctgacc cggaccagg tggtggccat cgccagcaat 1920
agcggcggca gcaggcgct ggagacggta cagcggctgt tgccggtgct gtgccaggac 1980
catggactga ccccggacca ggtcgtggcc atcgccagca tggcggcaa gcaggcgctg 2040
gagacggtac agcggctgtt gccggtgctg tgccaggacc atggcctgac cccggaccag 2100
gtcgtggcca tcgccagcaa tggcggcaag caggcgctga gacggtgca gcggctgttg 2160
ccggtacagc ggctgttgcc ggtgctgtgc caggaccatg gcctgaccca ggaccaggtg 2220
gtggccatcg ccagccacga tggcggcaag caggcgctgg agacggtgca gcggctgttg 2280
ccggtgctgt gccaggacca tggcctgacc cggaccaag tggtggccat cgccagccac 2340
gatggcggca acaggcgct ggagacggtg cagcggctgt tgccggtgct gtgccaggac 2400
catggcctga ccccggacca ggtggtggcc atcgccagca tagtggcggc aagcaggcgc 2460
tggagacgtg cagcggct gttgccggtg ctgtgccagg accatggcct gaccccggac 2520
caagtggtgg ccatcgccag caatagtggc ggcaagcagg cgctggagac ggtgcagcgg 2580
ctgttgccgg tgctgtgcca ggaccatggc ctgaccccgg accaggtggt ggccatcgcc 2640
agcaataacg gcggcaagca ggcgctggag acggtgcagc ggctgttgcc ggtgctgtgc 2700
caggaccatg gcctgacccc ggaccaggtc gtggccatcg ccaacaataa cggcggcaag 2760
```

```
caggcgctgg agacggtgca gcggctgttg ccggtgctgt gccaggacca tggcctgacc   2820
ccggcgcagg tggtggccat cgccagcaat attggcggca agcaggcgct ggagacggtg   2880
cagcggctgt tgccggtgct gtgccaggac catggcctga ccctggacca ggtggtggcc   2940
attgccagca atggcggcag caaacaggcg ctagagacgg tgcagcggct gttgccggtg   3000
ctgtgccagg accatggcct gaccccgcag caagtggtgg ccatcgccaa caataacgcg   3060
ggcaagcagg cgctggagac ggtgcagcgg ctgttgccgg tgctgtgcca ggaccatggc   3120
ctgaccccgg accaggtcgt ggccatcgcc agcaatattg cggcaagca ggcgctggag   3180
acggtgcagc ggctgttgcc ggtgctgtgc caggaccatg gcctgaccct ggaccaggtg   3240
gtggccatcg ccagcaatgg cggcaagcag gcgctggaga cggtgcagcg gctgttgccg   3300
gtgctgtgcc aggaccatgg cctgaccccg aaccaggtgg tggccatcgc cagcaatagt   3360
ggcggcaagc aggcgctgga cacggtgcag cggctgttgc cggtgctgtg ccaggaccat   3420
ggcctgaccc cgaaccaggt ggtggccatc gccagcaatg gcggcaagca ggcgctggag   3480
agcattgttg cccagttatc tcgccctgat ccggcgttgg ccgcgttgac caacgaccac   3540
ctcgtcgcct tggcctgcct cggcggacgt cctgccctgg atgcagtgaa aaagggattg   3600
ccgcacgcgc cggaattgat cagaagaatc aatcgccgca ttcccgaacg cacgtcccat   3660
cgcgttcccg acctcgcgca cgtggttcgc gtgcttggtt ttttccagag ccactcccac   3720
ccagcgcaag cattcgatga cgccatgacg cagttcgaga tgagcaggca cggcttggta   3780
cagctctttc gcagagtggg cgtcaccgaa ttcgaagccc gctacggaac gctcccccca   3840
gcctcgcagc gttgggaccg tatcctccag gcatcaggga tgaaaagggc caaaccgtcc   3900
cctacttcag ctcaaacacc ggatcaggcg tctttgcatg cattcgccga ttcgctggag   3960
cgtgaccttg atgcgcccag cccaatgcac gagggagatc agacgcgggc aagcagccgt   4020
aaacggtccc gatcggatcg tgctgtcacc ggccctcca cacagcaatc tttcgaggtg   4080
cgcgttcccg aacagcaaga tgcgctgcat ttgcccctca gctggagggt aaaacgcccg   4140
cgtaccagga tcgggggcgg cctcccggat cctggtacgc ccatcgctgc cgacctggca   4200
gcgtccagca ccgtgatgtg ggaacaagat gcggccccct tcgcagggc agcggatgat   4260
ttcccggcat tcaacgaaga ggagctcgca tggttgatgg agctattgcc tcagtcaggc   4320
tcagtcggag ggacgatctg a                                             4341
```

SEQ ID NO: 21              moltype = AA   length = 1263
FEATURE                    Location/Qualifiers
REGION                     1..1263
                           note = Synthetic construct
source                     1..1263
                           mol_type = protein
                           organism = synthetic construct
SEQUENCE: 21
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII   120
ERTMAGLAAA RNKGRIGGRP RKSGSGSPRQ FDPSLLDTSL LDSMPAVGTP HTAAAPAECD   180
EVQSGLRAAD DPPPTVRVAV TAARPPRAKP APRRRAAQPS DASPAAQVDL RTLGYSQQQQ   240
EKIKPKVRST VAQHHEALVG HGFTHAHIVA LSQHPAALGT VAVTYQDIIR ALPEATHEDI   300
VGVGKQWSGA RALEALLTEA GELRGPPLQL DTGQLLKIAK RGGVTAVEAV HAWRNALTGA   360
PLNLTPDQVV AIASNIGGKQ ALETVQRLLP VLCQDHGLTP DQVVAIASHG GKQALETVQ   420
RLLPVLCQDH GLTPDQVVAI ASNIGGKQAL ETVQRLLPVL CQAHGLTPDQ VVAIASNIGG   480
KQALETVQRL LPVLCQDHGL TPAQVVAIAS NSGGKQALET VQRLLPVLCQ DHGLTPDQVV   540
AIASHDGGKQ ALETLQRLLP VLCQDHGLTP DQVVAIANNN GGKQALETLQ RLLPVLCQDH   600
GLTPDQVVAI ASHDGGKQAL ETVQRLLPVL CQDHGLTPDQ VVAIASHDGG KQALETVQRL   660
LPVLCQDHGL TPAQVVAIAS HDGGKQALET VQRLLPVLCQ DHGLTPDQVV AIASNSGGKQ   720
ALETVQRLLP VLCQDHGLTP DQVVAIASNG GKQALETVQR LLPVLCQDHG LTPDQVVAIA   780
SNGGKQALET VQRLLPVQRL LPVLCQDHGL TQDQVVAIAS HDGGKQALET VQRLLPVLCQ   840
DHGLTPDQVV AIASHDGGKQ ALETVQRLLP VLCQDHGLTP DQVVAIASNS GGKQALETVQ   900
RLLPVLCQDH GLTPDQVVAI ASNSGGKQAL ETVQRLLPVL CQDHGLTPDQ VVAIASNNGG   960
KQALETVQRL LPVLCQDHGL TPDQVVAIAN NNGGKQALET VQRLLPVLCQ DHGLTPAQVV   1020
AIASNIGGKQ ALETVQRLLP VLCQDHGLTL DQVVAIASNG GSKQALETVQ RLLPVLCQDH   1080
GLTPDQVVAI ANNNGGKQAL ETVQRLLPVL CQDHGLTPDQ VVAIASNIGG KQALETVQRL   1140
LPVLCQDHGL TLDQVVAIAS NGGKQALETV QRLLPVLCQD HGLTPNQVVA IASNSGGKQA   1200
LETVQRLLPV LCQDHGLTPN QVVAIASNGG KQALESIVAQ LSRPDPALAA LTNDHLVALA   1260
CLG                                                                1263

SEQ ID NO: 22              moltype = AA   length = 1250
FEATURE                    Location/Qualifiers
REGION                     1..1250
                           note = Synthetic construct
source                     1..1250
                           mol_type = protein
                           organism = synthetic construct
SEQUENCE: 22
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII   120
ERTMAGLAAA RNKGRIGGRP RKSGSGSPDS MPAVGTPHTA AAPAECDEVQ SGLRAADDPP   180
PTVRVAVTAA RPPRAKPAPR RRAAQPSDAS PAAQVDLRTL GYSQQQQEKI KPKVRSTVAQ   240
HHEALVGHGF THAHIVALSQ HPAALGTVAV TYQDIIRALP EATHEDIVGV GKQWSGARAL   300
EALLTEAGEL RGPPLQLDTG QLLKIAKRGG VTAVEAVHAW RNALTGAPLN LTPDQVVAIA   360
SNIGGKQALE TVQRLLPVLC QDHGLTPDQV VAIASHGGGK QALETVQRLL PVLCQDHGLT   420
PDQVVAIASN IGGKQALETV QRLLPVLCQA HGLTPDQVVA IASNIGGKQA LETVQRLLPV   480
LCQDHGLTPA QVVAIASNSG GKQALETVQR LLPVLCQDHG LTPDQVVAIA SHDGGKQALE   540
TLQRLLPVLC QDHGLTPDQV VAIANNNGGK QALETLQRLL PVLCQDHGLT PDQVVAIASH   600
DGGKQALETV QRLLPVLCQD HGLTPDQVVA IASHDGGKQA LETVQRLLPV LCQDHGLTPA   660
QVVAIASHDG GKQALETVQR LLPVLCQDHG LTPDQVVAIA SNSGGKQALE TVQRLLPVLC   720
```

```
QDHGLTPDQV VAIASNGGKQ ALETVQRLLP VLCQDHGLTP DQVVAIASNG GKQALETVQR   780
LLPVQRLLPV LCQDHGLTQD QVVAIASHDG GKQALETVQR LLPVLCQDHG LTPDQVVAIA   840
SHDGGKQALE TVQRLLPVLC QDHGLTPDQV VAIASNSGGK QALETVQRLL PVLCQDHGLT   900
PDQVVAIASN SGGKQALETV QRLLPVLCQD HGLTPDQVVA IASNNGGKQA LETVQRLLPV   960
LCQDHGLTPD QVVAIANNNG GKQALETVQR LLPVLCQDHG LTPAQVVAIA SNIGGKQALE  1020
TVQRLLPVLC QDHGLTLDQV VAIASNGGS KQALETVQRLL PVLCQDHGLT PDQVVAIANN  1080
NGGKQALETV QRLLPVLCQD HGLTPDQVVA IASNIGGKQA LETVQRLLPV LCQDHGLTLD  1140
QVVAIASNGG KQALETVQRL LPVLCQDHGL TPNQVVAIAS NSGGKQALET VQRLLPVLCQ  1200
DHGLTPNQVV AIASNGGKQA LESIVAQLSR PDPALAALTN DHLVALACLG            1250

SEQ ID NO: 23            moltype = AA  length = 1216
FEATURE                  Location/Qualifiers
REGION                   1..1216
                         note = Synthetic construct
source                   1..1216
                         mol_type = protein
                         organism = synthetic construct
SEQUENCE: 23
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP RKSGSGSTVR VAVTAARPPR AKPAPRRRAA QPSDASPAAQ  180
VDLRTLGYSQ QQQEKIKPKV RSTVAQHHEA LVGHGFTHAH IVALSQHPAA LTVAVTYQD   240
IIRALPEATH EDIVGVGKQW SGARALEALL TEAGELRGPP LQLDTGQLLK IAKRGGVTAV  300
EAVHAWRNAL TGAPLNLTPD QVVAIASNIG GKQALETVQR LLPVLCQDHG LTPDQVVAIA  360
SHGGGKQALE TVQRLLPVLC QDHGLTPDQV VAIASNIGGK QALETVQRLL PVLCQAHGLT  420
PDQVVAIASN IGGKQALETV QRLLPVLCQD HGLTPAQVVA IASNGGKQA LETVQRLLPV   480
LCQDHGLTPD QVVAIASHDG GKQALETLQR LLPVLCQDHG LTPDQVVAIA NNNGGKQALE  540
TLQRLLPVLC QDHGLTPDQV VAIASHDGGK QALETVQRLL PVLCQDHGLT PDQVVAIASH  600
DGGKQALETV QRLLPVLCQD HGLTPAQVVA IASHDGGKQA LETVQRLLPV LCQDHGLTPD  660
QVVAIASNSG GKQALETVQR LLPVLCQDHG LTPDQVVAIA SNGGKQALET VQRLLPVLCQ  720
DHGLTPDQVV AIASNGGKQA LETVQRLLPV QRLLPVLCQD HGLTQDQVVA IASHDGGKQA  780
LETVQRLLPV LCQDHGLTPD QVVAIASHDG GKQALETVQR LLPVLCQDHG LTPDQVVAIA  840
SNSGGKQALE TVQRLLPVLC QDHGLTPDQV VAIASNSGGK QALETVQRLL PVLCQDHGLT  900
PDQVVAIASN NGGKQALETV QRLLPVLCQD HGLTPDQVVA IANNNGGKQA LETVQRLLPV  960
LCQDHGLTPA QVVAIASNIG GKQALETVQR LLPVLCQDHG LTLDQVVAIA SNGGSKQALE 1020
TVQRLLPVLC QDHGLTPDQV VAIANNNGGK QALETVQRLL PVLCQDHGLT PDQVVAIASN 1080
IGGKQALETV QRLLPVLCQD HGLTLDQVVA IASNGGKQAL ETVQRLLPVL CQDHGLTPNQ 1140
VVAIASNSGG KQALETVQRL LPVLCQDHGL TPNQVVAIAS NGGKQALESI VAQLSRPDPA 1200
LAALTNDHLV ALACLG                                                1216

SEQ ID NO: 24            moltype = AA  length = 1204
FEATURE                  Location/Qualifiers
REGION                   1..1204
                         note = Synthetic construct
source                   1..1204
                         mol_type = protein
                         organism = synthetic construct
SEQUENCE: 24
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP RKSGSGSTVR VAVTAARPPH AVAGPAAQVD LRTLGYSQQQ  180
QEKIKPKVRS TVAQHHEALV GHGFTHAHIV ALSQHPAALG TVAVTYQDII RALPEATHED  240
IVGVGKQWSG ARALEALLTE AGELRGPPLQ LDTGQLLKIA KRGGVTAVEA VHAWRNALTG  300
APLNLTPDQV VAIASNIGGK QALETVQRLL PVLCQDHGLT PDQVVAIASH GGGKQALETV  360
QRLLPVLCQD HGLTPDQVVA IASNIGGKQA LETVQRLLPV LCQAHGLTPD QVVAIASNIG  420
GKQALETVQR LLPVLCQDHG LTPAQVVAIA SNSGGKQALE TVQRLLPVLC QDHGLTPDQV  480
VAIASHDGGK QALETLQRLL PVLCQDHGLT PDQVVAIANN NGGKQALETL QRLLPVLCQD  540
HGLTPDQVVA IASHDGGKQA LETVQRLLPV LCQDHGLTPD QVVAIASHDG GKQALETVQR  600
LLPVLCQDHG LTPAQVVAIA SHDGGKQALE TVQRLLPVLC QDHGLTPDQV VAIASNSGGK  660
QALETVQRLL PVLCQDHGLT PDQVVAIASN GGKQALETVQ RLLPVLCQDH GLTPDQVVAI  720
ASNGGKQALE TVQRLLPVQR LLPVLCQDHG LTQDQVVAIA SHDGGKQALE TVQRLLPVLC  780
QDHGLTPDQV VAIASHDGGK QALETVQRLL PVLCQDHGLT PDQVVAIASN SGGKQALETV  840
QRLLPVLCQD HGLTPDQVVA IASNSGGKQA LETVQRLLPV LCQDHGLTPD QVVAIASNNG  900
GKQALETVQR LLPVLCQDHG LTPDQVVAIA NNNGGKQALE TVQRLLPVLC QDHGLTPAQV  960
VAIASNIGGK QALETVQRLL PVLCQDHGLT LDQVVAIASN GGSKQALETV QRLLPVLCQD 1020
HGLTPDQVVA IANNNGGKQA LETVQRLLPV LCQDHGLTPD QVVAIASNIG GKQALETVQR 1080
LLPVLCQDHG LTLDQVVAIA SNGGKQALET VQRLLPVLCQ DHGLTPNQVV AIASNSGGKQ 1140
ALETVQRLLP VLCQDHGLTP NQVVAIASNG GKQALESIVA QLSRPDPALA ALTNDHLVAL 1200
ACLG                                                            1204

SEQ ID NO: 25            moltype = AA  length = 1190
FEATURE                  Location/Qualifiers
REGION                   1..1190
                         note = Synthetic construct
source                   1..1190
                         mol_type = protein
                         organism = synthetic construct
SEQUENCE: 25
MLIGYVRVST NDQNTDLQRN ALVCAGCEQI FEDKLSGTRT DRPGLKRALK RLQKGDTLVV   60
```

```
WKLDRLGRSM KHLISLVGEL RERGINFRSL TDSIDTSSPM GRFFFYVMGA LAEMERELII    120
ERTMAGLAAA RNKGRIGGRP RKSGSGSPAS PAAQVDLRTL GYSQQQQEKI KPKVRSTVAQ    180
HHEALVGHGF THAHIVALSQ HPAALGTVAV TYQDIIRALP EATHEDIVGV GKQWSGARAL    240
EALLTEAGEL RGPPLQLDTG QLLKIAKRGG VTAVEAVHAW RNALTGAPLN LTPDQVVAIA    300
SNIGGKQALE TVQRLLPVLC QDHGLTPDQV VAIASHGGK QALETVQRLL PVLCQDHGLT    360
PDQVVAIASN IGGKQALETV QRLLPVLCQA HGLTPDQVVA IASNIGGKQA LETVQRLLPV    420
LCQDHGLTPA QVVAIASNSG GKQALETVQR LLPVLCQDHG LTPDQVVAIA SHDGGKQALE    480
TLQRLLPVLC QDHGLTPDQV VAIANNNGGK QALETLQRLL PVLCQDHGLT PDQVVAIASH    540
DGGKQALETV QRLLPVLCQD HGLTPDQVVA IASHDGGKQA LETVQRLLPV LCQDHGLTPA    600
QVVAIASHDG GKQALETVQR LLPVLCQDHG LTPDQVVAIA SNSGGKQALE TVQRLLPVLC    660
QDHGLTPDQV VAIASNGGKQ ALETVQRLLP VLCQDHGLTP DQVVAIASNG GKQALETVQR    720
LLPVQRLLPV LCQDHGLTQD QVVAIASHDG GKQALETVQR LLPVLCQDHG LTPDQVVAIA    780
SHDGGKQALE TVQRLLPVLC QDHGLTPDQV VAIASNSGGK QALETVQRLL PVLCQDHGLT    840
PDQVVAIASN SGGKQALETV QRLLPVLCQD HGLTPDQVVA IASNNGGKQA LETVQRLLPV    900
LCQDHGLTPD QVVAIANNNG GKQALETVQR LLPVLCQDHG LTPAQVVAIA SNIGGKQALE    960
TVQRLLPVLC QDHGLTLDQV VAIASNGGSK QALETVQRLL PVLCQDHGLT PDQVVAIANN   1020
NGGKQALETV QRLLPVLCQD HGLTPDQVVA IASNIGGKQA LETVQRLLPV LCQDHGLTLD   1080
QVVAIASNGG KQALETVQRL LPVLCQDHGL TPNQVVAIAS NSGGKQALET VQRLLPVLCQ   1140
DHGLTPNQVV AIASNGGKQA LESIVAQLSR PDPALAALTN DHLVALACLG              1190

SEQ ID NO: 26              moltype = AA  length = 841
FEATURE                    Location/Qualifiers
REGION                     1..841
                           note = Synthetic construct
source                     1..841
                           mol_type = protein
                           organism = synthetic construct
SEQUENCE: 26
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII    120
ERTMAGLAAA RNKGRIGGRP RKSGSGSPAL RPPRAKPAPR RRAAQPSDAS PAAQVDLRTL    180
GYSQQQQEKI KPKVRSTVAQ HHEALVGHGF THAHIVALSQ HPAALGTVAV TYQHIITALP    240
EATHEDIVGV GKQWSGARAL EALLTDAGEL RGPPLQLDTG QLVKIAKRGG VTAMEAVHAS    300
RNALTGAPLN LTPDQVVAIA SNIGGKQALE TVQRLLPVLC QDHGLTPDQV VAIASNGGGK    360
QALETVQRLL PVLCQDHGLT PDQVVAIASN IGGKQALETV QRLLPVLCQD HGLTPDQVVA    420
IASNIGGKQA LETVQRLLPV LCQDHGLTPD QVVAIASNIG GKQALETVQR LLPVLCQDHG    480
LTPDQVVAIA SHDGGKQALE TVQRLLPVLC QDHGLTPDQV VAIASHDGGK QALETVQRLL    540
PVLCQDHGLT PDQVVAIASH DGGKQALETV QRLLPVLCQD HGLTPDQVVA IASHDGGKQA    600
LETVQRLLPV LCQDHGLTPD QVVAIASHDG GKQALETVQR LLPVLCQDHG LTPDQVVAIA    660
SNGGGKQALE TVQRLLPVLC QDHGLTPDQV VAIASHDGGK QALETVQRLL PVLCQDHGLT    720
PDQVVAIASH DGGKQALETV QRLLPVLCQD HGLTPDQVVA IASNIGGKQA LETVQRLLPV    780
LCQDHGLTPD QVVAIASNIG GKQALESIVA QLSRPDPALA ALTNDHLVAL ACLGPKKKRK    840
V                                                                    841

SEQ ID NO: 27              moltype = DNA  length = 2523
FEATURE                    Location/Qualifiers
misc_feature               1..2523
                           note = Synthetic construct
source                     1..2523
                           mol_type = other DNA
                           organism = synthetic construct
SEQUENCE: 27
atgctgattg gctatgtaag ggtatcaaca aatgaccaga atacagacct gcaacgaaac     60
gctcttgttt gtgcaggatg tgaacaaata tttgaagata aattaagcgg aacaaggaca    120
gaccgaccgg gattaaaacg cgctttaaag cgccttcaaa aaggtgacac actggttgtc    180
tggaaactgg atcgcctcgg cgcaagcatg aaacatttga tttctctcgt aggggaatta    240
cgagagcgag ggattaattt tcgcagtctt actgacagta ttgatacgtc atctccaatg    300
gggcgttttt tcttctacgt tatgggtgcc ctggctgaaa tggaacgaga actaattatc    360
gagcgaacga tggctggact tgctgccgcc agaaataaag gccgtattgg aggtcgcccc    420
cgtaaatcgg ggtctggatc ccccgccgcg ccgccgcgcg ccaagccggc cccgcgacgg    480
cgtgctcgc aaccctccga cgcttcgccg gccgcgcagg tggatctacg cacgctcggc     540
tacagtcagc agcagcaaga gaagatcaaa ccgaaggtgc gttcgacagt ggcgcagcac    600
cacgaggcac tggtgggcca tgggtttaca cacgcgcaca tcgttgcgct cagccaacac    660
ccggcagcgt tagggaccgt cgctgtcacg tatcagcaac taatcacggc gttgccagag    720
gcgacacacg aagacatcgt tggcgtcggc aaacagtggt ccggcgcacg cgccctggag    780
gccttgctca cggatgcggg ggagttgaga ggtccgccgt tacagttgga cacaggccaa    840
cttgtgaaga ttgcaaaacg tggcggcgtg accgcaatgg aggcagtgca tgcatcgcgc    900
aatgcactga cgggtgcccc cctggagctg actccggacc aagtggtggc tatcgccagc    960
aacattggcg gcaagcaagc gctcgaaacg gtgcagcggc tgttgccggt gctgtgcage   1020
gaccatggcc tgactccgga ccaagtggtg gctatcgcca gcaacggtgg cggcaagcaa   1080
gcgctcgaaa cggtgcagcg gctgttgccg gtgctgtgcc aggaccatgg cctgactccg   1140
gaccaagtgg tggctatcgc cagcaacatt ggcggcaagc aagcgctcga aacggtgcag   1200
cggctgttgc cggtgctgtg ccaggaccat ggcctgactc ggaccaagt ggtggctatc    1260
gccagcaaca ttggcggcaa gcaagcgctc gaaacggtgc aggcggtgtt gccggtgctg   1320
tgccaggacc atggcctgac tccggaccaa gtggtggcta tcgccagcaa cattggcggc   1380
aagcaagcgc tcgaaacggt gcagcggctg ttgccggtgc tgtgccagga ccatggcctg   1440
actccggacc aagtggtggc tatcgccagc acgatggcg gcaagcaagc gctcgaaacg    1500
gtgcagcggc tgttgccggt gctgtgccag gaccatggcc tgactccgga ccaagtggtg   1560
gctatcgcca ccacgatgg cggcaagcaa gcgctcgaaa cggtgcagcg gctgttgccg    1620
```

```
gtgctgtgcc aggaccatgg cctgactccg gaccaagtgg tggctatcgc cagccacgat   1680
ggcggcaagc aagcgctcga aacggtgcag cggctgttgc cggtgctgtg ccaggaccat   1740
ggcctgactc cggaccaagt ggtggctatc gccagccacg atggcggcaa gcaagcgctc   1800
gaaacggtgc agcggctgtt gccggtgctg tgccaggacc atggcctgac tccgaccaa    1860
gtggtggcta tcgccagcca cgatggcggc aagcaagcgc tcgaaacggc tgttgccgg   1920
ttgccggtgc tgtgccagga ccatggcctg accccggacc aagtggtggc tatcgccagc   1980
aacggtggcg gcaagcaagc gctcgaaacg gtgcagcggc tgttgccggt gctgtgccag   2040
gaccatggcc tgactccgga ccaagtggtg ctatcgcca gccacgatgg cggcaagcaa   2100
gcgctcgaaa cggtgcagcg gctgttgccg gtgctgtgcc aggaccatgg cctgactccg   2160
gaccaagtgg tggctatcgc cagccacgat ggcggcaagc aagcgctcga aacggtgcag   2220
cggctgttgc cggtgctgtg ccaggaccat ggcctgaccc cggaccaagt ggtggctatc   2280
gccagcaaca ttggcggcaa gcaagcgctc gaaacggtgc agcggctgtt gccggtgctg   2340
tgccaggacc atggcctgac cccggaccaa gtggtggcta tcgccagcaa cattggcggc   2400
aagcgacgc tcgaaagcat tgtggcccag ctgagccggc tgatccggc gttggccgcg   2460
ttgaccaacg accacctcgt cgccttggcc tgcctcggcc caagaagaa gcgcaaggtg   2520
tag                                                                 2523
```

```
SEQ ID NO: 28                moltype = AA  length = 841
FEATURE                      Location/Qualifiers
REGION                       1..841
                             note = Synthetic construct
source                       1..841
                             mol_type = protein
                             organism = synthetic construct
SEQUENCE: 28
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII   120
ERTMAGLAAA RNKGRIGGRP RKSGSGSPAL RPPRAKPAPR RRAAQPSDAS PAAQVDLRTL   180
GYSQQQQEKI KPKVRSTVAQ HHEALVGHGF THAHIVALSQ HPAALGTVAV TYQHIITALP   240
EATHEDIVGV GKQWSGARAL EALLTDAGEL RGPPLQLDTG QLVKIAKRGG VTAMEAVHAS   300
RNALTGAPLN LTPDQVVAIA SNIGGKQALE TVQRLLPVLC QDHGLTPDQV VAIASNGGGK   360
QALETVQRLL PVLCQDHGLT PDQVVAIASN IGGKQALETV QRLLPVLCQD HGLTPDQVVA   420
IASNIGGKQA LETVQRLLPV LCQDHGLTPD QVVAIASNIG GKQALETVQR LLPVLCQDHG   480
LTPDQVVAIA SHDGGKQALE TVQRLLPVLC QDHGLTPDQV VAIASHDGGK QALETVQRLL   540
PVLCQDHGLT PDQVVAIASH DGGKQALETV QRLLPVLCQD HGLTPDQVVA IASHDGGKQA   600
LETVQRLLPV LCQDHGLTPD QVVAIASHDG GKQALETVQR LLPVLCQDHG LTPDQVVAIA   660
SNGGGKQALE TVQRLLPVLC QDHGLTPDQV VAIASHDGGK QALETVQRLL PVLCQDHGLT   720
PDQVVAIASH DGGKQALETV QRLLPVLCQD HGLTPDQVVA IASNIGGKQA LETVQRLLPV   780
LCQDHGLTPD QVVAIASNIG GKQALESIVA QLSRPDPALA ALTNDHLVAL ACLGPKKKRK   840
V                                                                   841
```

```
SEQ ID NO: 29                moltype = AA  length = 134
FEATURE                      Location/Qualifiers
REGION                       1..134
                             note = Synthetic construct
source                       1..134
                             mol_type = protein
                             organism = synthetic construct
SEQUENCE: 29
VDLRTLGYSQ QQQEKIKPKV RSTVAQHHEA LVGHGFTHAH IVALSQHPAA LGTVAVTYQH   60
IITALPEATH EDIVGVGKQW SGARALEALL TDAGELRGPP LQLDTGQLVK IAKRGGVTAM   120
EAVHASRNAL TGAP                                                     134
```

```
SEQ ID NO: 30                moltype = AA  length = 34
FEATURE                      Location/Qualifiers
REGION                       1..34
                             note = Synthetic construct
source                       1..34
                             mol_type = protein
                             organism = synthetic construct
SEQUENCE: 30
LTDGQLVKIA KRGGVTAMEA VHASRNALTG APLN                               34
```

```
SEQ ID NO: 31                moltype = AA  length = 30
FEATURE                      Location/Qualifiers
REGION                       1..30
                             note = Synthetic construct
source                       1..30
                             mol_type = protein
                             organism = synthetic construct
SEQUENCE: 31
THEDIVGVGK QWSGARALEA LLTDAGELRG                                    30
```

```
SEQ ID NO: 32                moltype = AA  length = 34
FEATURE                      Location/Qualifiers
REGION                       1..34
                             note = Synthetic construct
VAR_SEQ                      12..13
                             note = X can be any naturally occurring amino acid
```

-continued

```
source                  1..34
                        mol_type = protein
                        organism = synthetic construct
SEQUENCE: 32
LTPDQVVAIA SXXGGKQALE TVQRLLPVLC QDHG                        34

SEQ ID NO: 33           moltype = AA   length = 15
FEATURE                 Location/Qualifiers
REGION                  1..15
                        note = Synthetic construct
source                  1..15
                        mol_type = protein
                        organism = synthetic construct
SEQUENCE: 33
DIVGVKQWSG ARALE                                             15

SEQ ID NO: 34           moltype = AA   length = 15
FEATURE                 Location/Qualifiers
REGION                  1..15
                        note = Synthetic construct
source                  1..15
                        mol_type = protein
                        organism = synthetic construct
SEQUENCE: 34
DIVGVKSRSG ARALE                                             15

SEQ ID NO: 35           moltype = AA   length = 15
FEATURE                 Location/Qualifiers
REGION                  1..15
                        note = Synthetic construct
source                  1..15
                        mol_type = protein
                        organism = synthetic construct
SEQUENCE: 35
DIVGVKRGAG ARALE                                             15

SEQ ID NO: 36           moltype = AA   length = 14
FEATURE                 Location/Qualifiers
REGION                  1..14
                        note = Synthetic construct
source                  1..14
                        mol_type = protein
                        organism = synthetic construct
SEQUENCE: 36
DIVGVKYHGA RALE                                              14

SEQ ID NO: 37           moltype = DNA   length = 21
FEATURE                 Location/Qualifiers
misc_feature            1..21
                        note = Synthetic construct
source                  1..21
                        mol_type = other DNA
                        organism = synthetic construct
SEQUENCE: 37
ataaaccccc tccaaccagg c                                      21

SEQ ID NO: 38           moltype = DNA   length = 71
FEATURE                 Location/Qualifiers
misc_feature            1..71
                        note = Synthetic construct
source                  1..71
                        mol_type = other DNA
                        organism = synthetic construct
SEQUENCE: 38
aagaaggtct tcattacacc tgcagctctc attttccata cagtcagtat caattctgga  60
agaatttcca g                                                71

SEQ ID NO: 39           moltype = AA   length = 7
FEATURE                 Location/Qualifiers
REGION                  1..7
                        note = Synthetic construct
VAR_SEQ                 1..3
                        note = X can be any naturally occurring amino acid
source                  1..7
                        mol_type = protein
                        organism = synthetic construct
SEQUENCE: 39
XXXSGAR                                                      7
```

-continued

```
SEQ ID NO: 40          moltype = DNA   length = 18
FEATURE                Location/Qualifiers
misc_feature           1..18
                       note = Synthetic construct
source                 1..18
                       mol_type = other DNA
                       organism = synthetic construct SEQUENCE: 40
gtcttcatta cacctgca                                              18

SEQ ID NO: 41          moltype = DNA   length = 18
FEATURE                Location/Qualifiers
misc_feature           1..18
                       note = Synthetic construct
source                 1..18
                       mol_type = other DNA
                       organism = synthetic construct SEQUENCE: 41
cttcattaca cctgcagc                                              18

SEQ ID NO: 42          moltype = DNA   length = 18
FEATURE                Location/Qualifiers
misc_feature           1..18
                       note = Synthetic construct
source                 1..18
                       mol_type = other DNA
                       organism = synthetic construct SEQUENCE: 42
ttcattacac ctgcagct                                              18

SEQ ID NO: 43          moltype = DNA   length = 18
FEATURE                Location/Qualifiers
misc_feature           1..18
                       note = Synthetic construct
source                 1..18
                       mol_type = other DNA
                       organism = synthetic construct SEQUENCE: 43
acctgcagct ctcatttt                                              18

SEQ ID NO: 44          moltype = DNA   length = 16
FEATURE                Location/Qualifiers
misc_feature           1..16
                       note = Synthetic construct
source                 1..16
                       mol_type = other DNA
                       organism = synthetic construct SEQUENCE: 44
gtcagtcata gttaag                                                16

SEQ ID NO: 45          moltype = DNA   length = 18
FEATURE                Location/Qualifiers
misc_feature           1..18
                       note = Synthetic construct
source                 1..18
                       mol_type = other DNA
                       organism = synthetic construct SEQUENCE: 45
tcagtcatag ttaagacc                                              18

SEQ ID NO: 46          moltype = DNA   length = 19
FEATURE                Location/Qualifiers
misc_feature           1..19
                       note = Synthetic construct
source                 1..19
                       mol_type = other DNA
                       organism = synthetic construct SEQUENCE: 46
tcatagttaa gaccttctt                                             19

SEQ ID NO: 47          moltype = DNA   length = 17
FEATURE                Location/Qualifiers
misc_feature           1..17
                       note = Synthetic construct
source                 1..17
                       mol_type = other DNA
                       organism = synthetic construct SEQUENCE: 47
agttaagacc ttcttaa                                               17
```

-continued

```
SEQ ID NO: 48              moltype = AA   length = 159
FEATURE                    Location/Qualifiers
REGION                     1..159
                           note = Synthetic construct
VAR_SEQ                    104..107
                           note = X can be any naturally occurring amino acid
source                     1..159
                           mol_type = protein
                           organism = synthetic construct
SEQUENCE: 48
PRPPRAKPAP RRRAAQPSDA SPAAQVDLRT LGYSQQQEK IKPKVRSTVA QHHEALVGHG   60
FTHAHIVALS QHPAALGTVA VTYQHIITAL PEATHEDIVG VGKXXXXARA LEALLTDAGE  120
LRGPPLQLDT GQLVKIAKRG GVTAMEAVHA SRNALTGAP                        159

SEQ ID NO: 49              moltype = AA   length = 134
FEATURE                    Location/Qualifiers
REGION                     1..134
                           note = Synthetic construct
VAR_SEQ                    79..82
                           note = X can be any naturally occurring amino acid
source                     1..134
                           mol_type = protein
                           organism = synthetic construct
SEQUENCE: 49
VDLRTLGYSQ QQQEKIKPKV RSTVAQHHEA LVGHGFTHAH IVALSQHPAA LGTVAVTYQH   60
IITALPEATH EDIVGVGKXX XXARALEALL TDAGELRGPP LQLDTGQLVK IAKRGGVTAM  120
EAVHASRNAL TGAP                                                   134

SEQ ID NO: 50              moltype = AA   length = 134
FEATURE                    Location/Qualifiers
REGION                     1..134
                           note = Synthetic construct
source                     1..134
                           mol_type = protein
                           organism = synthetic construct
SEQUENCE: 50
VDLRTLGYSQ QQQEKIKPKV RSTVAQHHEA LVGHGFTHAH IVALSQHPAA LGTVAVKYQD   60
MIAALPEATH EAIVGVGKQW SGARALEALL TVAGELRGPP LQLDTGQLLK IAKRGGVTAV  120
EAVHAWRNAL TGAP                                                   134

SEQ ID NO: 51              moltype = AA   length = 80
FEATURE                    Location/Qualifiers
REGION                     1..80
                           note = Synthetic construct
source                     1..80
                           mol_type = protein
                           organism = synthetic construct
SEQUENCE: 51
NDHLVALACL GGRPAMDAVK KGLPHAPELI RRVNRRIGER TSHRVADYAQ VVRVLEFFQC   60
HSHPAYAFDE AMTQFGMSGQ                                              80

SEQ ID NO: 52              moltype = AA   length = 46
FEATURE                    Location/Qualifiers
REGION                     1..46
                           note = Synthetic construct
source                     1..46
                           mol_type = protein
                           organism = synthetic construct
SEQUENCE: 52
NDHLVALACL GGRPAMDAVK KGLPHAPELI RRVNRRIGER TSHRVA                 46

SEQ ID NO: 53              moltype = AA   length = 10
FEATURE                    Location/Qualifiers
REGION                     1..10
                           note = Synthetic construct
source                     1..10
                           mol_type = protein
                           organism = synthetic construct
SEQUENCE: 53
NDHLVALACL                                                         10

SEQ ID NO: 54              moltype = AA   length = 135
FEATURE                    Location/Qualifiers
REGION                     1..135
                           note = Synthetic construct
source                     1..135
                           mol_type = protein
                           organism = synthetic construct
```

-continued

```
SEQUENCE: 54
QVDLRTLGYS QQQQEKIKPK VRSTVAQHHE ALVGHGFTHA HIVALSQHPA ALGTVAVTYQ    60
HIITALPEAT HEDIVGVGKS RSGARALEAL LTDAGELRGP PLQLDTGQLV KIAKRGGVTA   120
MEAVHASRNA LTGAP                                                     135

SEQ ID NO: 55              moltype = AA   length = 132
FEATURE                    Location/Qualifiers
REGION                     1..132
                           note = Synthetic construct
source                     1..132
                           mol_type = protein
                           organism = synthetic construct
SEQUENCE: 55
MAALGYSREQ IRKLKQESLS GVAKYHAPLT RHGFTHTDIC RISRRWQSLR MVAKNYPKLI    60
AALPDLTRTH IVDIARQRSG DLALEALLPV ATALAAAPLR LRASQIAIIA QCGERPAILA   120
LHRLRRKLTG AP                                                       132

SEQ ID NO: 56              moltype = AA   length = 180
FEATURE                    Location/Qualifiers
REGION                     1..180
                           note = Synthetic construct
source                     1..180
                           mol_type = protein
                           organism = synthetic construct
SEQUENCE: 56
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII   120
ERTMAGLAAA RNKGRIGGRP PKLTKAEWEQ AGRLLAQGIP RKQVALIYDV ALSTLYKKHP   180

SEQ ID NO: 57              moltype = AA   length = 144
FEATURE                    Location/Qualifiers
REGION                     1..144
                           note = Synthetic construct
source                     1..144
                           mol_type = protein
                           organism = synthetic construct
SEQUENCE: 57
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII   120
ERTMAGLAAA RNKGRIGGRP PKSG                                          144

SEQ ID NO: 58              moltype = AA   length = 143
FEATURE                    Location/Qualifiers
REGION                     1..143
                           note = Synthetic construct
source                     1..143
                           mol_type = protein
                           organism = synthetic construct
SEQUENCE: 58
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII   120
ERTMAGIAAA RNKGRRFGRP PKS                                           143

SEQ ID NO: 59              moltype = AA   length = 144
FEATURE                    Location/Qualifiers
REGION                     1..144
                           note = Synthetic construct
source                     1..144
                           mol_type = protein
                           organism = synthetic construct
SEQUENCE: 59
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELIL   120
ERVMAGIAAA RNKGRRWGRP PKSG                                          144

SEQ ID NO: 60              moltype = AA   length = 144
FEATURE                    Location/Qualifiers
REGION                     1..144
                           note = Synthetic construct
source                     1..144
                           mol_type = protein
                           organism = synthetic construct
SEQUENCE: 60
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII   120
ERVMAGLAAA RNKGRRFGRP PKSG                                          144

SEQ ID NO: 61              moltype = AA   length = 144
FEATURE                    Location/Qualifiers
```

-continued

```
REGION                   1..144
                         note = Synthetic construct
source                   1..144
                         mol_type = protein
                         organism = synthetic construct
SEQUENCE: 61
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERLSIL  120
ERPMAGHAAA RNKGRRFGRP PKSG                                         144

SEQ ID NO: 62            moltype = AA  length = 144
FEATURE                  Location/Qualifiers
REGION                   1..144
                         note = Synthetic construct
source                   1..144
                         mol_type = protein
                         organism = synthetic construct
SEQUENCE: 62
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTSAGRAAA INKGRIMGRP RKSG                                         144

SEQ ID NO: 63            moltype = AA  length = 267
FEATURE                  Location/Qualifiers
REGION                   1..267
                         note = Synthetic construct
source                   1..267
                         mol_type = protein
                         organism = synthetic construct
SEQUENCE: 63
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP PKSGTGEKPY KCPECGKSFS TSGNLVRHQR THTGEKPYKC  180
PECGKSFSQS GDLRRHQRTH TGEKPYKCPE CGKSFSTSGN LVRHQRTHTG EKPYKCPECG  240
KSFSTSGELV RHQRTHTGKK TSGQAGQ                                      267

SEQ ID NO: 64            moltype = AA  length = 267
FEATURE                  Location/Qualifiers
REGION                   1..267
                         note = Synthetic construct
source                   1..267
                         mol_type = protein
                         organism = synthetic construct
SEQUENCE: 64
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP PKSGTGEKPY KCPECGKSFS HRTTLTNHQR THTGEKPYKC  180
PECGKSFSQS GDLRRHQRTH TGEKPYKCPE CGKSFSQSGD LRRHQRTHTG EKPYKCPECG  240
KSFSQSGDLR RHQRTHTGKK TSGQAGQ                                      267

SEQ ID NO: 65            moltype = AA  length = 267
FEATURE                  Location/Qualifiers
REGION                   1..267
                         note = Synthetic construct
source                   1..267
                         mol_type = protein
                         organism = synthetic construct
SEQUENCE: 65
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP PKSGTGEKPY KCPECGKSFS QSGDLRRHQR THTGEKPYKC  180
PECGKSFSQR AHLERHQRTH TGEKPYKCPE CGKSFSTSGN LVRHQRTHTG EKPYKCPECG  240
KSFSRSDELV RHQRTHTGKK TSGQAGQ                                      267

SEQ ID NO: 66            moltype = AA  length = 267
FEATURE                  Location/Qualifiers
REGION                   1..267
                         note = Synthetic construct
source                   1..267
                         mol_type = protein
                         organism = synthetic construct
SEQUENCE: 66
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP PKSGTGEKPY KCPECGKSFS RSDKLVRHQR THTGEKPYKC  180
PECGKSFSRK DNLKNHQRTH TGEKPYKCPE CGKSFSTSGE LVRHQRTHTG EKPYKCPECG  240
KSFSRSDKLV RHQRTHTGKK TSGQAGQ                                      267

SEQ ID NO: 67            moltype = AA  length = 267
```

-continued

```
FEATURE               Location/Qualifiers
REGION                1..267
                      note = Synthetic construct
source                1..267
                      mol_type = protein
                      organism = synthetic construct
SEQUENCE: 67
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP PKSGTGEKPY KCPECGKSFS TTGNLTVHQR THTGEKPYKC  180
PECGKSFSDP GALVRHQRTH TGEKPYKCPE CGKSFSQSSN LVRHQRTHTG EKPYKCPECG  240
KSFSRSDHLT NHQRTHTGKK TSGQAGQ                                      267

SEQ ID NO: 68         moltype = AA  length = 267
FEATURE               Location/Qualifiers
REGION                1..267
                      note = Synthetic construct
source                1..267
                      mol_type = protein
                      organism = synthetic construct
SEQUENCE: 68
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP PKSGTGEKPY KCPECGKSFS RKDNLKNHQR THTGEKPYKC  180
PECGKSFSRS DHLTNHQRTH TGEKPYKCPE CGKSFSDPGN LVRHQRTHTG EKPYKCPECG  240
KSFSRKDNLK NHQRTHTGKK TSGQAGQ                                      267

SEQ ID NO: 69         moltype = AA  length = 267
FEATURE               Location/Qualifiers
REGION                1..267
                      note = Synthetic construct
source                1..267
                      mol_type = protein
                      organism = synthetic construct
SEQUENCE: 69
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELIL  120
ERVMAGIAAA RNKGRRWGRP PKSGTGEKPY KCPECGKSFS QRANLRAHQR THTGEKPYKC  180
PECGKSFSQS SSLVRHQRTH TGEKPYKCPE CGKSFSTTGN LTVHQRTHTG EKPYKCPECG  240
KSFSQRAHLE RHQRTHTGKK TSGQAGQ                                      267

SEQ ID NO: 70         moltype = AA  length = 267
FEATURE               Location/Qualifiers
REGION                1..267
                      note = Synthetic construct
source                1..267
                      mol_type = protein
                      organism = synthetic construct
SEQUENCE: 70
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELIL  120
ERVMAGIAAA RNKGRRWGRP PKSGTGEKPY KCPECGKSFS QRANLRAHQR THTGEKPYKC  180
PECGKSFSRR DELNVHQRTH TGEKPYKCPE CGKSFSQLAH LRAHQRTHTG EKPYKCPECG  240
KSFSQRAHLE RHQRTHTGKK TSGQAGQ                                      267

SEQ ID NO: 71         moltype = AA  length = 267
FEATURE               Location/Qualifiers
REGION                1..267
                      note = Synthetic construct
source                1..267
                      mol_type = protein
                      organism = synthetic construct
SEQUENCE: 71
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELIL  120
ERVMAGIAAA RNKGRRWGRP PKSGTGEKPY KCPECGKSFS RRDELNVHQR THTGEKPYKC  180
PECGKSFSRS DHLTNHQRTH TGEKPYKCPE CGKSFSQLAH LRAHQRTHTG EKPYKCPECG  240
KSFSQRAHLE RHQRTHTGKK TSGQAGQ                                      267

SEQ ID NO: 72         moltype = AA  length = 267
FEATURE               Location/Qualifiers
REGION                1..267
                      note = Synthetic construct
source                1..267
                      mol_type = protein
                      organism = synthetic construct
SEQUENCE: 72
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
```

```
ERTMAGLAAA RNKGRIGGRP PKSGTGEKPY KCPECGKSFS TSGSLVRHQR THTGEKPYKC    180
PECGKSFSRS DKLVRHQRTH TGEKPYKCPE CGKSFSQSGD LRRHQRTHTG EKPYKCPECG    240
KSFSTSGELV RHQRTHTGKK TSGQAGQ                                        267

SEQ ID NO: 73              moltype = AA   length = 267
FEATURE                    Location/Qualifiers
REGION                     1..267
                           note = Synthetic construct
source                     1..267
                           mol_type = protein
                           organism = synthetic construct
SEQUENCE: 73
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII    120
ERTSAGRAAA INKGRIMGRP RKSGTGEKPY KCPECGKSFS QLAHLRAHQR THTGEKPYKC    180
PECGKSFSQL AHLRAHQRTH TGEKPYKCPE CGKSFSDPGH LVRHQRTHTG EKPYKCPECG    240
KSFSDSGNLR VHQRTHTGKK TSGQAGQ                                        267

SEQ ID NO: 74              moltype = AA   length = 267
FEATURE                    Location/Qualifiers
REGION                     1..267
                           note = Synthetic construct
source                     1..267
                           mol_type = protein
                           organism = synthetic construct
SEQUENCE: 74
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELIL    120
ERVMAGIAAA RNKGRRWGRP PKSGTGEKPY KCPECGKSFS QRAHLERHQR THTGEKPYKC    180
PECGKSFSTT GNLTVHQRTH TGEKPYKCPE CGKSFSDSGN LRVHQRTHTG EKPYKCPECG    240
KSFSQSSNLV RHQRTHTGKK TSGQAGQ                                        267

SEQ ID NO: 75              moltype = AA   length = 267
FEATURE                    Location/Qualifiers
REGION                     1..267
                           note = Synthetic construct
source                     1..267
                           mol_type = protein
                           organism = synthetic construct
SEQUENCE: 75
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII    120
ERTMAGIAAA RNKGRRFGRP PKSGTGEKPY KCPECGKSFS THLDLIRHQR THTGEKPYKC    180
PECGKSFSTT GNLTVHQRTH TGEKPYKCPE CGKSFSQSSS LVRHQRTHTG EKPYKCPECG    240
KSFSRSDNLV RHQRTHTGKK TSGQAGQ                                        267

SEQ ID NO: 76              moltype = AA   length = 267
FEATURE                    Location/Qualifiers
REGION                     1..267
                           note = Synthetic construct
source                     1..267
                           mol_type = protein
                           organism = synthetic construct
SEQUENCE: 76
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII    120
ERTMAGIAAA RNKGRRFGRP PKSGTGEKPY KCPECGKSFS RSDKLVRHQR THTGEKPYKC    180
PECGKSFSRR DELNVHQRTH TGEKPYKCPE CGKSFSQSSS LVRHQRTHTG EKPYKCPECG    240
KSFSRSDHLT NHQRTHTGKK TSGQAGQ                                        267

SEQ ID NO: 77              moltype = AA   length = 267
FEATURE                    Location/Qualifiers
REGION                     1..267
                           note = Synthetic construct
source                     1..267
                           mol_type = protein
                           organism = synthetic construct
SEQUENCE: 77
MLIGYVRVST NDQNTDLQRN ALVCAGCEQI FEDKLSGTRT DRPGLKRALK RLQKGDTLVV    60
WKLDRLGRSM KHLISLVGEL RERGINFRSL TDSIDTSSPM GRFFFYVMGA LAEMERELII    120
ERTMAGLAAA RNKGRIGGRP PKSGTGEKPY KCPECGKSFS QRAHLERHQR THTGEKPYKC    180
PECGKSFSTS GNLVRHQRTH TGEKPYKCPE CGKSFSRSDE LVRHQRTHTG EKPYKCPECG    240
KSFSHKNALQ NHQRTHTGKK TSGQAGQ                                        267

SEQ ID NO: 78              moltype = AA   length = 267
FEATURE                    Location/Qualifiers
REGION                     1..267
                           note = Synthetic construct
source                     1..267
```

-continued

```
                            mol_type = protein
                            organism = synthetic construct
SEQUENCE: 78
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP PKSGTGEKPY KCPECGKSFS RRDELNVHQR THTGEKPYKC  180
PECGKSFSQS SNLVRHQRTH TGEKPYKCPE CGKSFSQSSS LVRHQRTHTG EKPYKCPECG  240
KSFSTTGNLT VHQRTHTGKK TSGQAGQ                                      267

SEQ ID NO: 79            moltype = AA   length = 267
FEATURE                  Location/Qualifiers
REGION                   1..267
                         note = Synthetic construct
source                   1..267
                         mol_type = protein
                         organism = synthetic construct
SEQUENCE: 79
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELIL  120
ERVMAGIAAA RNKGRRWGRP PKSGTGEKPY KCPECGKSFS TTGNLTVHQR THTGEKPYKC  180
PECGKSFSQS SNLVRHQRTH TGEKPYKCPE CGKSFSQRAH LERHQRTHTG EKPYKCPECG  240
KSFSQKSSLI AHQRTHTGKK TSGQAGQ                                      267

SEQ ID NO: 80            moltype = AA   length = 267
FEATURE                  Location/Qualifiers
REGION                   1..267
                         note = Synthetic construct
source                   1..267
                         mol_type = protein
                         organism = synthetic construct
SEQUENCE: 80
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTSAGRAAA INKGRIMGRP RKSGTGEKPY KCPECGKSFS DPGALVRHQR THTGEKPYKC  180
PECGKSFSQS SSLVRHQRTH TGEKPYKCPE CGKSFSQLAH LRAHQRTHTG EKPYKCPECG  240
KSFSQRANLR AHQRTHTGKK TSGQAGQ                                      267

SEQ ID NO: 81            moltype = AA   length = 938
FEATURE                  Location/Qualifiers
REGION                   1..938
                         note = Synthetic construct
source                   1..938
                         mol_type = protein
                         organism = synthetic construct
SEQUENCE: 81
MRSPKKKRKV QVDLRTLGYS QQQQEKIKPK VRSTVAQHHE ALVGHGFTHA HIVALSQHPA   60
ALGTVAVTYQ HIITALPEAT HEDIVGVGKQ WSGARALEAL LTDAGELRGP PLQLDTGQLV  120
KIAKRGGVTA MEAVHASRNA LTGAPLNLTP DQVVAIASNG GGKQALETVQ RLLPVLCQDH  180
GLTPDQVVAI ASHDGGKQAL ETVQRLLPVL CQDHGLTPDQ VVAIASNIGG KQALETVQRL  240
LPVLCQDHGL TPDQVVAIAS NGGGKQALET VQRLLPVLCQ DHGLTPDQVV AIASNGGGKQ  300
ALETVQRLLP VLCQDHGLTP DQVVAIASNI GGKQALETVQ RLLPVLCQDH GLTPDQVVAI  360
ASHDGGKQAL ETVQRLLPVL CQDHGLTPDQ VVAIASNIGG KQALETVQRL LPVLCQDHGL  420
TPDQVVAIVS HDGGKQALET VQRLLPVLCQ DHGLTPDQVV AIVSHDGGKQ ALETVQRLLP  480
VLCQDHGLTP DQVVAIVSNG GGKQALETVQ RLLPVLCQDH GLTPDQVVAI ASNNGGKQAL  540
ETVQRLLPVL CQDHGLTPDQ VVAIASHDGG KQALETVQRL LPVLCQDHGL TPDQVVAIAS  600
NIGGKQALET VQRLLPVLCQ DHGLTPDQVV AIASNNGGKQ ALETVQRLLP VLCQDHGLTP  660
DQVVAIASHD GGKQALESIV AQLSRPDPAL AALTNDHLVA LACLGGRPAM DAVKKGLPHA  720
PELIRRVNRR IGERTSHRVA GSQLVKSELE EKKSELRHKL KYVPHEYIEL IEIARNSTQD  780
RILEMKVMEF FMKVYGYRGK HLGGSRKPDG AIYTVGSPID YGVIVDTKAY SGGYNLPIGQ  840
ADEMQRYVEE NQTRNKHINP NEWWKVYPSS VTEFKFLFVS GHFKGNYKAQ LTRLNHITNC  900
NGAVLSVEEL LIGGEMIKAG TLTLEEVRRK FNNGEINF                          938

SEQ ID NO: 82            moltype = AA   length = 34
FEATURE                  Location/Qualifiers
REGION                   1..34
                         note = Synthetic construct
source                   1..34
                         mol_type = protein
                         organism = synthetic construct
SEQUENCE: 82
NGNNHDNGHD NINGNGNIHD NIHDHDNGNN HDNI                               34

SEQ ID NO: 83            moltype = AA   length = 30
FEATURE                  Location/Qualifiers
REGION                   1..30
                         note = Synthetic construct
source                   1..30
                         mol_type = protein
                         organism = synthetic construct
```

```
SEQUENCE: 83
HDNINNNGHD NINNNGNING HDNININGNG                                          30

SEQ ID NO: 84          moltype = AA  length = 34
FEATURE                Location/Qualifiers
REGION                 1..34
                       note = Synthetic construct
source                 1..34
                       mol_type = protein
                       organism = synthetic construct
SEQUENCE: 84
HDHDNGNNHD NINNHDNGHD NGHDNINGNG NGNG                                     34

SEQ ID NO: 85          moltype = AA  length = 30
FEATURE                Location/Qualifiers
REGION                 1..30
                       note = Synthetic construct
source                 1..30
                       mol_type = protein
                       organism = synthetic construct
SEQUENCE: 85
NINGNGHDNG NGHDHDNINN NINGNGNNNI                                          30

SEQ ID NO: 86          moltype = AA  length = 34
FEATURE                Location/Qualifiers
REGION                 1..34
                       note = Synthetic construct
source                 1..34
                       mol_type = protein
                       organism = synthetic construct
SEQUENCE: 86
HDNINNNINI NGNGNNNING NIHDNGNNNI HDNG                                     34

SEQ ID NO: 87          moltype = AA  length = 32
FEATURE                Location/Qualifiers
REGION                 1..32
                       note = Synthetic construct
source                 1..32
                       mol_type = protein
                       organism = synthetic construct
SEQUENCE: 87
NGHDNINGNG NIHDNIHDHD NGNNHDNINN HD                                       32

SEQ ID NO: 88          moltype = AA  length = 36
FEATURE                Location/Qualifiers
REGION                 1..36
                       note = Synthetic construct
source                 1..36
                       mol_type = protein
                       organism = synthetic construct
SEQUENCE: 88
HDNGNGHDHD NINNNINING NGNNNINGNI HDNGNN                                   36

SEQ ID NO: 89          moltype = DNA  length = 432
FEATURE                Location/Qualifiers
misc_feature           1..432
                       note = Synthetic construct
source                 1..432
                       mol_type = other DNA
                       organism = synthetic construct
SEQUENCE: 89
atgagatctc ctaagaaaaa gaggaagatg gtggacttga ggacactcgg ttattcgcaa   60
cagcaacagg agaaaatcaa gcctaaggtc aggagcaccg tcgcgcaaca ccacgaggcg  120
cttgtggggc atggcttcac tcatgcgcat attgtcgcgc tttcacagca ccctgcgcg   180
cttgggacgg tggctgtcaa ataccaagat atgattgcgg ccctgcccga agccacgcac  240
gaggcaattg taggggtcgg taaacagtgg tcgggagcgc gagcacttga ggcgctgctg  300
actgtggcgg gtgagcttag ggggcctccg ctccagctcg acaccgggca gctgctgaag  360
atcgcgaaga gaggggggagt aacagcggta gaggcagtgc atgcatcgcg caatgcactg  420
acgggtgccc cc                                                        432

SEQ ID NO: 90          moltype = AA  length = 144
FEATURE                Location/Qualifiers
REGION                 1..144
                       note = Synthetic construct
source                 1..144
                       mol_type = protein
                       organism = synthetic construct
SEQUENCE: 90
MRSPKKKRKM VDLRTLGYSQ QQQEKIKPKV RSTVAQHHEA LVGHGFTHAH IVALSQHPAA  60
```

```
LGTVAVKYQD MIAALPEATH EAIVGVGKQW SGARALEALL TVAGELRGPP LQLDTGQLLK   120
IAKRGGVTAV EAVHASRNAL TGAP                                          144

SEQ ID NO: 91            moltype = DNA   length = 432
FEATURE                  Location/Qualifiers
misc_feature             1..432
                         note = Synthetic construct
source                   1..432
                         mol_type = other DNA
                         organism = synthetic construct
SEQUENCE: 91
atgagatctc ctaagaaaaa gaggaaggtg caggtggatc tacgcacgct cggctacagt   60
cagcagcagc aagagaagat caaaccgaag gtgcgttcga cagtggcgca gcaccacgag   120
gcactggtgg gccatgggtt tacacacgcg cacatcgttg cgctcagcca acacccggca   180
gcgttaggga ccgtcgctgt cacgtatcag cacataatca cggcgttgcc agaggcgaca   240
cacgaagaca tcgttggcgt cggcaaatat catgggcac gcgctctgga ggccttgctc   300
acggatgcgg gggagttgag aggtccgccg ttacagttgg acacaggcca acttgtgaag   360
attgcaaaac gtggcggcgt gaccgcaatg gaggcagtgc atgcatcgcg caatgcactg   420
acgggtgccc cc                                                      432

SEQ ID NO: 92            moltype = AA   length = 144
FEATURE                  Location/Qualifiers
REGION                   1..144
                         note = Synthetic construct
source                   1..144
                         mol_type = protein
                         organism = synthetic construct
SEQUENCE: 92
MRSPKKKRKV QVDLRTLGYS QQQQEKIKPK VRSTVAQHHE ALVGHGFTHA HIVALSQHPA   60
ALGTVAVTYQ HIITALPEAT HEDIVGVGKY HGARALEALL TDAGELRGPP LQLDTGQLVK   120
IAKRGGVTAM EAVHASRNAL TGAP                                          144

SEQ ID NO: 93            moltype = DNA   length = 435
FEATURE                  Location/Qualifiers
misc_feature             1..435
                         note = Synthetic construct
source                   1..435
                         mol_type = other DNA
                         organism = synthetic construct
SEQUENCE: 93
atgagatctc ctaagaaaaa gaggaaggtg caggtggatc tacgcacgct cggctacagt   60
cagcagcagc aagagaagat caaaccgaag gtgcgttcga cagtggcgca gcaccacgag   120
gcactggtgg gccatgggtt tacacacgcg cacatcgttg cgctcagcca acacccggca   180
gcgttaggga ccgtcgctgt cacgtatcag cacataatca cggcgttgcc agaggcgaca   240
cacgaagaca tcgttggcgt cggcaaatcg cggtcggggg cacgcgctct ggaggccttg   300
ctcacggatg cggggggagtt gagaggtccg ccgttacagt tggacacagg ccaacttgtg   360
aagattgcaa aacgtggcgg cgtgaccgca atggaggcag tgcatgcatc gcgcaatgca   420
ctgacgggtg ccccc                                                   435

SEQ ID NO: 94            moltype = AA   length = 145
FEATURE                  Location/Qualifiers
REGION                   1..145
                         note = Synthetic construct
source                   1..145
                         mol_type = protein
                         organism = synthetic construct
SEQUENCE: 94
MRSPKKKRKV QVDLRTLGYS QQQQEKIKPK VRSTVAQHHE ALVGHGFTHA HIVALSQHPA   60
ALGTVAVTYQ HIITALPEAT HEDIVGVGKS RSGARALEAL LTDAGELRGP PLQLDTGQLV   120
KIAKRGGVTA MEAVHASRNA LTGAP                                         145

SEQ ID NO: 95            moltype = DNA   length = 435
FEATURE                  Location/Qualifiers
misc_feature             1..435
                         note = Synthetic construct
source                   1..435
                         mol_type = other DNA
                         organism = synthetic construct
SEQUENCE: 95
atgagatctc ctaagaaaaa gaggaaggtg caggtggatc tacgcacgct cggctacagt   60
cagcagcagc aagagaagat caaaccgaag gtgcgttcga cagtggcgca gcaccacggg   120
gcactggtgg gccatgggtt tacacacgcg cacatcgttg cgctcagcca acacccggca   180
gcgttaggga ccgtcgctgt cacgtatcag cacataatca cggcgttgcc agaggcgaca   240
cacgaagaca tcgttggcgt cggcaaacgg ggggctggtg cacgcgctct ggaggccttg   300
ctcacggatg cggggggagtt gagaggtccg ccgttacagt tggacacagg ccaacttgtg   360
aagattgcaa aacgtggcgg cgtgaccgca atggaggcag tgcatgcatc gcgcaatgca   420
ctgacgggtg ccccc                                                   435

SEQ ID NO: 96            moltype = AA   length = 145
```

-continued

```
FEATURE             Location/Qualifiers
REGION              1..145
                    note = Synthetic construct
source              1..145
                    mol_type = protein
                    organism = synthetic construct
SEQUENCE: 96
MRSPKKKRKV QVDLRTLGYS QQQQEKIKPK VRSTVAQHHG ALVGHGFTHA HIVALSQHPA   60
ALGTVAVTYQ HIITALPEAT HEDIVGVGKR GAGARALEAL LTDAGELRGP PLQLDTGQLV  120
KIAKRGGVTA MEAVHASRNA LTGAP                                        145

SEQ ID NO: 97       moltype = DNA   length = 435
FEATURE             Location/Qualifiers
misc_feature        1..435
                    note = Synthetic construct
source              1..435
                    mol_type = other DNA
                    organism = synthetic construct
SEQUENCE: 97
atgagatctc ctaagaaaaa gaggaaggtg caggtggatc tacgcacgct cggctacagt   60
cagcagcagc aagagaagat caaaccgaag gtgcgttcga cagtggcgca gcaccacgag  120
gcactggtgg gccatgggtt tacacacgcg cacatcgttg cgctcagcca acacccggca  180
gcgttaggga ccgtcgctgt cacgtatcag cacataatca cggcgttgcc agaggcgaca  240
cacgaagaca tcgttggcgt cggcaaacag tggtccggcg cacgcgccct ggaggccttg  300
ctcacggatg cgggggagtt gagaggtccg ccgttacagt tggacacagg ccaacttgtg  360
aagattgcaa aacgtggcgg cgtgaccgca atggaggcag tgcatgcatc gcgcaatgca  420
ctgacgggtg ccccc                                                  435

SEQ ID NO: 98       moltype = AA   length = 1080
FEATURE             Location/Qualifiers
REGION              1..1080
                    note = Synthetic construct
VAR_SEQ             498
                    note = X is Q, S, R or Y
VAR_SEQ             499
                    note = X is W, R or G
VAR_SEQ             500
                    note = X is S, A or H
source              1..1080
                    mol_type = protein
                    organism = synthetic construct
SEQUENCE: 98
MKIEEGKLVI WINGDKGYNG LAEVGKKFEK DTGIKVTVEH PDKLEEKFPQ VAATGDGPDI   60
IFWAHDRFGG YAQSGLLAEI TPDKAFQDKL YPFTWDAVRY NGKLIAYPIA VEALSLIYNK  120
DLLPNPPKTW EEIPALDKEL KAKGKSALMF NLQEPYFTWP LIAADGGYAF KYENGKYDIK  180
DVGVDNAGAK AGLTFLVDLI KNKHMNADTD YSIAEAAFNK GETAMTINGP WAWSNIDTSK  240
VNYGVTVLPT FKGQPSKPFV GVLSAGINAA SPNKELAKEF LENYLLTDEG LEAVNKDKPL  300
GAVALKSYEE ELAKDPRIAA TMENAQKGEI MPNIPQMSAF WYAVRTAVIN AASGRQTVDE  360
ALKDAQTNSS SNNNNNNNNN NLGIEGRISE FGSPARPPRA KPAPRRRSAQ PSDASPAAQV  420
DLRTLGYSQQ QQEKIKPKVR STVAQHHEAL VGHGFTHAHI VALSQHPAAL GTVAVTYQHI  480
ITALPEATHE DIVGVGKXXX GARALEALLT DAGELLRGPP LQLDTGQLVK IAKRGGVTAM  540
EAVHASRNAL TGAPLNLTPD QVVAIASNIG GKQALETVQR LLPVLCQDHG LTPDQVVAIA  600
SNGGGKQALE TVQRLLPVLC QDHGLTPDQV VAIASNIGGK QALETVQRLL PVLCQDHGLT  660
PDQVVAIASN IGGKQALETV QRLLPVLCQD HGLTPDQVVA IASNIGGKQA LETVQRLLPV  720
LCQDHGLTPD QVVAIASHDG KQALETVQR LLPVLCQDHG LTPDQVVAIA SHDGGKQALE  780
TVQRLLPVLC QDHGLTPDQV VAIASHDGGK QALETVQRLL PVLCQDHGLT PDQVVAIVSH  840
DGGKQALETV QRLLPVLCQD HGLTPDQVVA IVSHDGGKQA LETVQRLLPV LCQDHGLTPD  900
QVVAIVSNGG KQALETVQR LLPVLCQDHG LTPDQVVAIA SHDGGKQALE TVQRLLPVLC  960
QDHGLTPDQV VAIASHDGGK QALETVQRLL PVLCQDHGLT PDQVVAIASN IGGKQALETV 1020
QRLLPVLCQD HGLTPDQVVA IASNIGGKQA LESIVAQLSR PDPALAALTN DHLVALACLG 1080

SEQ ID NO: 99       moltype = AA   length = 830
FEATURE             Location/Qualifiers
REGION              1..830
                    note = Synthetic construct
VAR_SEQ             249
                    note = X is Q, S, R or Y
VAR_SEQ             250
                    note = X is W, R or G
VAR_SEQ             251
                    note = X is S, A or H
source              1..830
                    mol_type = protein
                    organism = synthetic construct
SEQUENCE: 99
MLIGYVRVST NDQNTDLQRN ALVCAGCEQI FEDKLSGTRT DRPGLKRALK RLQKGDTLVV   60
WKLDRLGRSM KHLISLVGEL RERGINFRSL TDSIDTSSPM GRFFFYVMGA LAEMERELII  120
ERTMAGLAAA RNKGRIGGRP PKSGSPRPPR AKPAPRRRAA QPSDASPAAQ VDLRTLGYSQ  180
QQQEKIKPKV RSTVAQHHEA LVGHGFTHAH IVALSQHPAA LGTVAVTYQH IITALPEATH  240
```

-continued

```
EDIVGVGKXX XGARALEALL TDAGELRGPP LQLDTGQLVK IAKRGGVTAM EAVHASRNAL     300
TGAPLNLTPD QVVAIASNIG GKQALETVQR LLPVLCQDHG LTPDQVVAIA SNGGGKQALE     360
TVQRLLPVLC QDHGLTPDQV VAIASNIGGK QALETVQRLL PVLCQDHGLT PDQVVAIASN     420
IGGKQALETV QRLLPVLCQD HGLTPDQVVA IASNIGGKQA LETVQRLLPV LCQDHGLTPD     480
QVVAIASHDG GKQALETVQR LLPVLCQDHG LTPDQVVAIA SHDGGKQALE TVQRLLPVLC     540
QDHGLTPDQV VAIASHDGGK QALETVQRLL PVLCQDHGLT PDQVVAIVSH DGGKQALETV     600
QRLLPVLCQD HGLTPDQVVA IVSHDGGKQA LETVQRLLPV LCQDHGLTPD QVVAIVSNGG     660
GKQALETVQR LLPVLCQDHG LTPDQVVAIA SHDGGKQALE TVQRLLPVLC QDHGLTPDQV     720
VAIASHDGGK QALETVQRLL PVLCQDHGLT PDQVVAIASN IGGKQALETV QRLLPVLCQD     780
HGLTPDQVVA IASNIGGKQA LESIVAQLSR PDPALAALTN DHLVALACLG               830

SEQ ID NO: 100          moltype = AA   length = 839
FEATURE                 Location/Qualifiers
REGION                  1..839
                        note = Synthetic construct
VAR_SEQ                 112
                        note = X is Q, S, R or Y
VAR_SEQ                 113
                        note = X is W or R
VAR_SEQ                 114
                        note = X is S, A or H
source                  1..839
                        mol_type = protein
                        organism = synthetic construct

SEQUENCE: 100

MAQAASGSPR PPRAKPAPRR RAAQPSDASP AAQVDLRTLG YSQQQQEKIK PKVRSTVAQH      60
HEALVGHGFT HAHIVALSQH PAALGTVAVT YQHIITALPE ATHEDIVGVG KXXXGARALE     120
ALLTDAGELR GPPLQLDTGQ LVKIAKRGGV TAMEAVHASR NALTGAPLNL TPDQVVAIAS     180
NIGGKQALET VQRLLPVLCQ DHGLTPDQVV AIASNGGGKQ ALETVQRLLP VLCQDHGLTP     240
DQVVAIASNI GGKQALETVQ RLLPVLCQDH GLTPDQVVAI ASNIGGKQAL ETVQRLLPVL     300
CQDHGLTPDQ VVAIASNIGG KQALETVQRL LPVLCQDHGL TPDQVVAIAS HDGGKQALET     360
VQRLLPVLCQ DHGLTPDQVV AIASHDGGKQ ALETVQRLLP VLCQDHGLTP DQVVAIASHD     420
GGKQALETVQ RLLPVLCQDH GLTPDQVVAI VSHDGGKQAL ETVQRLLPVL CQDHGLTPDQ     480
VVAIVSHDGG KQALETVQRL LPVLCQDHGL TPDQVVAIVS NGGGKQALET VQRLLPVLCQ     540
DHGLTPDQVV AIASHDGGKQ ALETVQRLLP VLCQDHGLTP DQVVAIASHD GGKQALETVQ     600
RLLPVLCQDH GLTPDQVVAI ASNIGGKQAL ETVQRLLPVL CQDHGLTPDQ VVAIASNIGG     660
KQALESIVAQ LSRPDPALAA LTNDHLVALA CLGGRPAMDA VKKGLPHAPE LIRRVNRRIG     720
ERTSHRVADY AQVVRVLEFF QCHSHPAYAF DEAMTQFGMS GQAGQASPKK KRKVGRADAL     780
DDFDLDMLGS DALDDFDLDM LGSDALDDFD LDMLGSDALD DFDLDMLINY PYDVPDYAS      839

SEQ ID NO: 101          moltype = AA   length = 30
FEATURE                 Location/Qualifiers
REGION                  1..30
                        note = Synthetic construct
source                  1..30
                        mol_type = protein
                        organism = synthetic construct
SEQUENCE: 101
NINGNININI HDHDHDHDHD NIHDHDNINI                                        30

SEQ ID NO: 102          moltype = AA   length = 33
FEATURE                 Location/Qualifiers
REGION                  1..33
                        note = Synthetic construct
source                  1..33
                        mol_type = protein
                        organism = synthetic construct
SEQUENCE: 102
LTPDQLVKIA KRGGTAMEAV HASRNALTGA PLN                                    33

SEQ ID NO: 103          moltype = AA   length = 4
FEATURE                 Location/Qualifiers
REGION                  1..4
                        note = Synthetic construct
source                  1..4
                        mol_type = protein
                        organism = synthetic construct
SEQUENCE: 103
KRGG                                                                     4

SEQ ID NO: 104          moltype = AA   length = 4
FEATURE                 Location/Qualifiers
REGION                  1..4
                        note = Synthetic construct
source                  1..4
                        mol_type = protein
                        organism = synthetic construct
SEQUENCE: 104
LDYE                                                                     4
```

-continued

```
SEQ ID NO: 105          moltype = AA  length = 4
FEATURE                 Location/Qualifiers
REGION                  1..4
                        note = Synthetic construct
source                  1..4
                        mol_type = protein
                        organism = synthetic construct
SEQUENCE: 105
INLV                                                                  4

SEQ ID NO: 106          moltype = AA  length = 4
FEATURE                 Location/Qualifiers
REGION                  1..4
                        note = Synthetic construct
source                  1..4
                        mol_type = protein
                        organism = synthetic construct
SEQUENCE: 106
YSKK                                                                  4

SEQ ID NO: 107          moltype = AA  length = 4
FEATURE                 Location/Qualifiers
REGION                  1..4
                        note = Synthetic construct
source                  1..4
                        mol_type = protein
                        organism = synthetic construct
SEQUENCE: 107
NMAH                                                                  4

SEQ ID NO: 108          moltype = AA  length = 4
FEATURE                 Location/Qualifiers
REGION                  1..4
                        note = Synthetic construct
source                  1..4
                        mol_type = protein
                        organism = synthetic construct
SEQUENCE: 108
SPTN                                                                  4

SEQ ID NO: 109          moltype = AA  length = 4
FEATURE                 Location/Qualifiers
REGION                  1..4
                        note = Synthetic construct
source                  1..4
                        mol_type = protein
                        organism = synthetic construct
SEQUENCE: 109
SNTR                                                                  4

SEQ ID NO: 110          moltype = AA  length = 4
FEATURE                 Location/Qualifiers
REGION                  1..4
                        note = Synthetic construct
source                  1..4
                        mol_type = protein
                        organism = synthetic construct
SEQUENCE: 110
LTTT                                                                  4

SEQ ID NO: 111          moltype = AA  length = 4
FEATURE                 Location/Qualifiers
REGION                  1..4
                        note = Synthetic construct
source                  1..4
                        mol_type = protein
                        organism = synthetic construct
SEQUENCE: 111
VADL                                                                  4

SEQ ID NO: 112          moltype = AA  length = 4
FEATURE                 Location/Qualifiers
REGION                  1..4
                        note = Synthetic construct
source                  1..4
                        mol_type = protein
                        organism = synthetic construct
SEQUENCE: 112
```

-continued

```
MVLS                                                            4

SEQ ID NO: 113           moltype = AA  length = 4
FEATURE                  Location/Qualifiers
REGION                   1..4
                         note = Synthetic construct
source                   1..4
                         mol_type = protein
                         organism = synthetic construct
SEQUENCE: 113
YNGR                                                           4

SEQ ID NO: 114           moltype = AA  length = 4
FEATURE                  Location/Qualifiers
REGION                   1..4
                         note = Synthetic construct
source                   1..4
                         mol_type = protein
                         organism = synthetic construct
SEQUENCE: 114
RIPR                                                           4

SEQ ID NO: 115           moltype = AA  length = 4
FEATURE                  Location/Qualifiers
REGION                   1..4
                         note = Synthetic construct
source                   1..4
                         mol_type = protein
                         organism = synthetic construct
SEQUENCE: 115
YSKI                                                           4

SEQ ID NO: 116           moltype = AA  length = 4
FEATURE                  Location/Qualifiers
REGION                   1..4
                         note = Synthetic construct
source                   1..4
                         mol_type = protein
                         organism = synthetic construct
SEQUENCE: 116
LTQY                                                           4

SEQ ID NO: 117           moltype = AA  length = 4
FEATURE                  Location/Qualifiers
REGION                   1..4
                         note = Synthetic construct
source                   1..4
                         mol_type = protein
                         organism = synthetic construct
SEQUENCE: 117
YLSK                                                           4

SEQ ID NO: 118           moltype = AA  length = 4
FEATURE                  Location/Qualifiers
REGION                   1..4
                         note = Synthetic construct
source                   1..4
                         mol_type = protein
                         organism = synthetic construct
SEQUENCE: 118
LRPN                                                           4

SEQ ID NO: 119           moltype = AA  length = 4
FEATURE                  Location/Qualifiers
REGION                   1..4
                         note = Synthetic construct
source                   1..4
                         mol_type = protein
                         organism = synthetic construct
SEQUENCE: 119
LFTN                                                           4

SEQ ID NO: 120           moltype = AA  length = 4
FEATURE                  Location/Qualifiers
REGION                   1..4
                         note = Synthetic construct
source                   1..4
                         mol_type = protein
                         organism = synthetic construct
```

-continued

```
SEQUENCE: 120
LLTN                                                                                   4

SEQ ID NO: 121          moltype = AA   length = 4
FEATURE                 Location/Qualifiers
REGION                  1..4
                        note = Synthetic construct
source                  1..4
                        mol_type = protein
                        organism = synthetic construct
SEQUENCE: 121
EEDK                                                                                   4

SEQ ID NO: 122          moltype = AA   length = 4
FEATURE                 Location/Qualifiers
REGION                  1..4
                        note = Synthetic construct
source                  1..4
                        mol_type = protein
                        organism = synthetic construct
SEQUENCE: 122
VTAM                                                                                   4

SEQ ID NO: 123          moltype = AA   length = 4
FEATURE                 Location/Qualifiers
REGION                  1..4
                        note = Synthetic construct
source                  1..4
                        mol_type = protein
                        organism = synthetic construct
SEQUENCE: 123
CPSR                                                                                   4

SEQ ID NO: 124          moltype = AA   length = 4
FEATURE                 Location/Qualifiers
REGION                  1..4
                        note = Synthetic construct
source                  1..4
                        mol_type = protein
                        organism = synthetic construct
SEQUENCE: 124
LTRV                                                                                   4

SEQ ID NO: 125          moltype = AA   length = 4
FEATURE                 Location/Qualifiers
REGION                  1..4
                        note = Synthetic construct
source                  1..4
                        mol_type = protein
                        organism = synthetic construct
SEQUENCE: 125
KGDL                                                                                   4

SEQ ID NO: 126          moltype = AA   length = 4
FEATURE                 Location/Qualifiers
REGION                  1..4
                        note = Synthetic construct
source                  1..4
                        mol_type = protein
                        organism = synthetic construct
SEQUENCE: 126
QKAL                                                                                   4

SEQ ID NO: 127          moltype = AA   length = 4
FEATURE                 Location/Qualifiers
REGION                  1..4
                        note = Synthetic construct
source                  1..4
                        mol_type = protein
                        organism = synthetic construct
SEQUENCE: 127
LYLL                                                                                   4

SEQ ID NO: 128          moltype = AA   length = 4
FEATURE                 Location/Qualifiers
REGION                  1..4
                        note = Synthetic construct
source                  1..4
                        mol_type = protein
```

-continued

```
                            organism = synthetic construct
SEQUENCE: 128
WISV                                                                  4

SEQ ID NO: 129           moltype = AA  length = 4
FEATURE                  Location/Qualifiers
REGION                   1..4
                         note = Synthetic construct
source                   1..4
                         mol_type = protein
                         organism = synthetic construct
SEQUENCE: 129
GDQV                                                                  4

SEQ ID NO: 130           moltype = AA  length = 4
FEATURE                  Location/Qualifiers
REGION                   1..4
                         note = Synthetic construct
source                   1..4
                         mol_type = protein
                         organism = synthetic construct
SEQUENCE: 130
CPSR                                                                  4

SEQ ID NO: 131           moltype = AA  length = 145
FEATURE                  Location/Qualifiers
REGION                   1..145
                         note = Synthetic construct
VAR_SEQ                  89..93
                         note = X can be any naturally occurring amino acid
source                   1..145
                         mol_type = protein
                         organism = synthetic construct
SEQUENCE: 131
MRSPKKKRKV QVDLRTLGYS QQQQEKIKPK VRSTVAQHHE ALVGHGFTHA HIVALSQHPA  60
ALGTVAVTYQ HIITALPEAT HEDIVGVGXX XXXARALEAL LTDAGELRGP PLQLDTGQLV  120
KIAKRGGVTA MEAVHASRNA LTGAP                                        145

SEQ ID NO: 132           moltype = AA  length = 5
FEATURE                  Location/Qualifiers
REGION                   1..5
                         note = Synthetic construct
source                   1..5
                         mol_type = protein
                         organism = synthetic construct
SEQUENCE: 132
KRPAG                                                                 5

SEQ ID NO: 133           moltype = AA  length = 5
FEATURE                  Location/Qualifiers
REGION                   1..5
                         note = Synthetic construct
source                   1..5
                         mol_type = protein
                         organism = synthetic construct
SEQUENCE: 133
KRPSG                                                                 5

SEQ ID NO: 134           moltype = AA  length = 32
FEATURE                  Location/Qualifiers
REGION                   1..32
                         note = Synthetic construct
source                   1..32
                         mol_type = protein
                         organism = synthetic construct
SEQUENCE: 134
LTPDVVAISN NGGKQALETV QRLLPVLCQD GH                                  32

SEQ ID NO: 135           moltype = AA  length = 4
FEATURE                  Location/Qualifiers
REGION                   1..4
                         note = Synthetic construct
source                   1..4
                         mol_type = protein
                         organism = synthetic construct
SEQUENCE: 135
SNNG                                                                  4

SEQ ID NO: 136           moltype = AA  length = 4
```

-continued

```
FEATURE              Location/Qualifiers
REGION               1..4
                     note = Synthetic construct
source               1..4
                     mol_type = protein
                     organism = synthetic construct
SEQUENCE: 136
RGGG                                                                 4

SEQ ID NO: 137       moltype = AA   length = 4
FEATURE              Location/Qualifiers
REGION               1..4
                     note = Synthetic construct
source               1..4
                     mol_type = protein
                     organism = synthetic construct
SEQUENCE: 137
RGGR                                                                 4

SEQ ID NO: 138       moltype = AA   length = 4
FEATURE              Location/Qualifiers
REGION               1..4
                     note = Synthetic construct
source               1..4
                     mol_type = protein
                     organism = synthetic construct
SEQUENCE: 138
RGVR                                                                 4

SEQ ID NO: 139       moltype = AA   length = 4
FEATURE              Location/Qualifiers
REGION               1..4
                     note = Synthetic construct
source               1..4
                     mol_type = protein
                     organism = synthetic construct
SEQUENCE: 139
KGGG                                                                 4

SEQ ID NO: 140       moltype = AA   length = 4
FEATURE              Location/Qualifiers
REGION               1..4
                     note = Synthetic construct
source               1..4
                     mol_type = protein
                     organism = synthetic construct
SEQUENCE: 140
SGGG                                                                 4

SEQ ID NO: 141       moltype = AA   length = 4
FEATURE              Location/Qualifiers
REGION               1..4
                     note = Synthetic construct
source               1..4
                     mol_type = protein
                     organism = synthetic construct
SEQUENCE: 141
GGRG                                                                 4

SEQ ID NO: 142       moltype = AA   length = 4
FEATURE              Location/Qualifiers
REGION               1..4
                     note = Synthetic construct
source               1..4
                     mol_type = protein
                     organism = synthetic construct
SEQUENCE: 142
LGGS                                                                 4

SEQ ID NO: 143       moltype = AA   length = 4
FEATURE              Location/Qualifiers
REGION               1..4
                     note = Synthetic construct
source               1..4
                     mol_type = protein
                     organism = synthetic construct
SEQUENCE: 143
MDNI                                                                 4
```

-continued

```
SEQ ID NO: 144          moltype = AA   length = 4
FEATURE                 Location/Qualifiers
REGION                  1..4
                        note = Synthetic construct
source                  1..4
                        mol_type = protein
                        organism = synthetic construct
SEQUENCE: 144
RVMA                                                                   4

SEQ ID NO: 145          moltype = AA   length = 4
FEATURE                 Location/Qualifiers
REGION                  1..4
                        note = Synthetic construct
source                  1..4
                        mol_type = protein
                        organism = synthetic construct
SEQUENCE: 145
LASV                                                                   4

SEQ ID NO: 146          moltype = AA   length = 4
FEATURE                 Location/Qualifiers
REGION                  1..4
                        note = Synthetic construct
source                  1..4
                        mol_type = protein
                        organism = synthetic construct
SEQUENCE: 146
VGTG                                                                   4

SEQ ID NO: 147          moltype = AA   length = 4
FEATURE                 Location/Qualifiers
REGION                  1..4
                        note = Synthetic construct
source                  1..4
                        mol_type = protein
                        organism = synthetic construct
SEQUENCE: 147
QGGG                                                                   4

SEQ ID NO: 148          moltype = DNA   length = 118
FEATURE                 Location/Qualifiers
misc_feature            1..118
                        note = Primer
source                  1..118
                        mol_type = other DNA
                        organism = synthetic construct
SEQUENCE: 148
ttaattaaga gtctagaaat ataaaccccc tccaaccagg tgctaactgt aaaccatggt   60
tttggattag cacctggttg gaggggtttt ataagatcta ggaggaattt aaaatgag    118

SEQ ID NO: 149          moltype = DNA   length = 117
FEATURE                 Location/Qualifiers
misc_feature            1..117
                        note = Primer
source                  1..117
                        mol_type = other DNA
                        organism = synthetic construct
SEQUENCE: 149
actgacctag agaagcttat ataaaccccc tccaaccagg tgctaatcca aaaccatggt   60
ttacagttag cacctggttg gaggggtttt atactgcagt tatttgtaca gttcatc     117

SEQ ID NO: 150          moltype = DNA   length = 116
FEATURE                 Location/Qualifiers
misc_feature            1..116
                        note = Primer
source                  1..116
                        mol_type = other DNA
                        organism = synthetic construct
SEQUENCE: 150
ttaattaaga gtctagatta gcacctggtt ggaggggggtt tataaggttt tggtaccaaa   60
tgtctataaa cccctccaa ccaggtgcta aagatctagg aggaatttaa aatgag        116

SEQ ID NO: 151          moltype = DNA   length = 116
FEATURE                 Location/Qualifiers
misc_feature            1..116
                        note = Primer
source                  1..116
                        mol_type = other DNA
```

```
                            organism = synthetic construct
SEQUENCE: 151
ttaattaaga gtctagatta gcacctggtt ggaggggggtt tataaggttt tggtaccaaa  60
tgtctataaa cccctccaa ccaggtgcta aagatctagg aggaatttaa aatgag        116

SEQ ID NO: 152            moltype = DNA  length = 116
FEATURE                  Location/Qualifiers
misc_feature             1..116
                         note = Primer
source                   1..116
                         mol_type = other DNA
                         organism = synthetic construct
SEQUENCE: 152
actgacctag agaagctttt agcacctggt tggagggggt ttatagacat ttggtaccaa  60
aaccttataa acccctcca accaggtgct aactgcagtt atttgtacag ttcatc        116

SEQ ID NO: 153            moltype = DNA  length = 116
FEATURE                  Location/Qualifiers
misc_feature             1..116
                         note = Primer
source                   1..116
                         mol_type = other DNA
                         organism = synthetic construct
SEQUENCE: 153
ttaattaaga gtctagatta gcacctggtt ggagggggt tatatccaaa accatggttt   60
acagtataaa cccctccaa ccaggtgcta aagatctagg aggaatttaa aatgag        116

SEQ ID NO: 154            moltype = DNA  length = 116
FEATURE                  Location/Qualifiers
misc_feature             1..116
                         note = Primer
source                   1..116
                         mol_type = other DNA
                         organism = synthetic construct
SEQUENCE: 154
actgacctag agaagctttt agcacctggt tggagggggt ttatatccaa aaccatggtt   60
tacagtataa acccctcca accaggtgct aactgcagtt atttgtacag ttcatc        116

SEQ ID NO: 155            moltype = DNA  length = 122
FEATURE                  Location/Qualifiers
misc_feature             1..122
                         note = Primer
source                   1..122
                         mol_type = other DNA
                         organism = synthetic construct
SEQUENCE: 155
ttaattaaga gtctagatta gcacctggtt ggagggggt tatagcttcc aaaaccatgg   60
tttacagggt tataaacccc ctccaaccag gtgctaaaga tctaggagga atttaaaatg  120
ag                                                                  122

SEQ ID NO: 156            moltype = DNA  length = 128
FEATURE                  Location/Qualifiers
misc_feature             1..128
                         note = Primer
source                   1..128
                         mol_type = other DNA
                         organism = synthetic construct
SEQUENCE: 156
ttaattaaga gtctagatta gcacctggtt ggagggggt tatagcttca tccaaaacca   60
tggtttacag ggttcctata aacccctcc aaccaggtgc taaagatcta ggaggaattt  120
aaaatgag                                                            128

SEQ ID NO: 157            moltype = DNA  length = 128
FEATURE                  Location/Qualifiers
misc_feature             1..128
                         note = Primer
source                   1..128
                         mol_type = other DNA
                         organism = synthetic construct
SEQUENCE: 157
actgacctag agaagctttt agcacctggt tggagggggt ttatagcaac cctgtaaacc   60
atggttttgg atgaagctat aaacccctc caaccaggtg ctaactgcag ttatttgtac  120
agttcatc                                                            128

SEQ ID NO: 158            moltype = DNA  length = 140
FEATURE                  Location/Qualifiers
misc_feature             1..140
                         note = Primer
source                   1..140
```

```
                         mol_type = other DNA
                         organism = synthetic construct
SEQUENCE: 158
ttaattaaga gtctagatta gcacctggtt ggaggggggtt tatagcttca gcttcatcca   60
aaaccatggt ttacagggtt ccggttccta taaacccct ccaaccaggt gctaaagatc   120
taggaggaat ttaaaatgag                                               140

SEQ ID NO: 159          moltype = DNA   length = 140
FEATURE                 Location/Qualifiers
misc_feature            1..140
                        note = Primer
source                  1..140
                        mol_type = other DNA
                        organism = synthetic construct
SEQUENCE: 159
ttaattaaga gtctagatta gcacctggtt ggaggggggtt tatagcttca gcttcatcca   60
aaaccatggt ttacagggtt ccggttccta taaacccct ccaaccaggt gctaaagatc   120
taggaggaat ttaaaatgag                                               140

SEQ ID NO: 160          moltype = DNA   length = 110
FEATURE                 Location/Qualifiers
misc_feature            1..110
                        note = Primer
source                  1..110
                        mol_type = other DNA
                        organism = synthetic construct
SEQUENCE: 160
ttaattaaga gtctagatta gcacctggtt ggaggggggtt tataaaaacc atggtttata   60
taaacccct ccaaccaggt gctaaagatc taggaggaat ttaaaatgag               110

SEQ ID NO: 161          moltype = DNA   length = 110
FEATURE                 Location/Qualifiers
misc_feature            1..110
                        note = Primer
source                  1..110
                        mol_type = other DNA
                        organism = synthetic construct
SEQUENCE: 161
actgacctag agaagctttt agcacctggt tggaggggt ttatataaac catggtttt    60
ataaaccccc tccaaccagg tgctaactgc agttatttgt acagttcatc              110

SEQ ID NO: 162          moltype = DNA   length = 116
FEATURE                 Location/Qualifiers
misc_feature            1..116
                        note = Primer
source                  1..116
                        mol_type = other DNA
                        organism = synthetic construct
SEQUENCE: 162
ttaattaaga gtctagatta gcacctggtt ggaggggggtt tatatccaaa accggggtttt   60
acagtataaa cccctccaa ccaggtgcta aagatctagg aggaatttaa aatgag        116

SEQ ID NO: 163          moltype = DNA   length = 116
FEATURE                 Location/Qualifiers
misc_feature            1..116
                        note = Primer
source                  1..116
                        mol_type = other DNA
                        organism = synthetic construct
SEQUENCE: 163
actgacctag agaagctttt agcacctggt tggaggggt ttatactgta aaccccggtt    60
ttggatataa acccctcca accaggtgct aactgcagtt atttgtacag ttcatc        116

SEQ ID NO: 164          moltype = DNA   length = 116
FEATURE                 Location/Qualifiers
misc_feature            1..116
                        note = Primer
source                  1..116
                        mol_type = other DNA
                        organism = synthetic construct
SEQUENCE: 164
ttaattaaga gtctagatta gcacctggtt ggaggggggtt tatacgaaat attataaatt   60
atcatataaa cccctccaa ccaggtgcta aagatctagg aggaatttaa aatgag        116

SEQ ID NO: 165          moltype = DNA   length = 116
FEATURE                 Location/Qualifiers
misc_feature            1..116
                        note = Primer
source                  1..116
```

-continued

```
                          mol_type = other DNA
                          organism = synthetic construct
SEQUENCE: 165
actgacctag agaagctttt agcacctggt tggagggggt ttatatgata atttataata   60
tttcgtataa accccctcca accaggtgct aactgcagtt atttgtacag ttcatc       116

SEQ ID NO: 166           moltype = DNA   length = 128
FEATURE                  Location/Qualifiers
misc_feature             1..128
                         note = Primer
source                   1..128
                         mol_type = other DNA
                         organism = synthetic construct
SEQUENCE: 166
ttaattaaga gtctagatta gcacctggtt ggaggggggt tatagcttca tccaaaaccg   60
gggtttacag ggttcctata aacccctcc aaccaggtgc taaagatcta ggaggaattt   120
aaaatgag                                                            128

SEQ ID NO: 167           moltype = DNA   length = 128
FEATURE                  Location/Qualifiers
misc_feature             1..128
                         note = Primer
source                   1..128
                         mol_type = other DNA
                         organism = synthetic construct
SEQUENCE: 167
actgacctag agaagctttt agcacctggt tggagggggt ttatagcaac cctgtaaacc   60
ggggttttgg atgaagctat aaaccccctc caaccaggtg ctaactgcag ttatttgtac   120
agttcatc                                                            128

SEQ ID NO: 168           moltype = DNA   length = 128
FEATURE                  Location/Qualifiers
misc_feature             1..128
                         note = Primer
source                   1..128
                         mol_type = other DNA
                         organism = synthetic construct
SEQUENCE: 168
ttaattaaga gtctagatta gcacctggtt ggaggggggt tatagcttca cgaaatatta   60
taaattatca ggttcctata aacccctcc aaccaggtgc taaagatcta ggaggaattt   120
aaaatgag                                                            128

SEQ ID NO: 169           moltype = DNA   length = 128
FEATURE                  Location/Qualifiers
misc_feature             1..128
                         note = Primer
source                   1..128
                         mol_type = other DNA
                         organism = synthetic construct
SEQUENCE: 169
actgacctag agaagctttt agcacctggt tggagggggt ttatagcaac ctgataattt   60
ataatatttc gtgaagctat aaacccctc caaccaggtg ctaactgcag ttatttgtac   120
agttcatc                                                            128

SEQ ID NO: 170           moltype = DNA   length = 128
FEATURE                  Location/Qualifiers
misc_feature             1..128
                         note = Primer
source                   1..128
                         mol_type = other DNA
                         organism = synthetic construct
SEQUENCE: 170
ttaattaaga gagatcttta gcacctggtt ggaggggggt tatagcttca tccaaaacca   60
tggtttacag ggttcctata aacccctcc aaccaggtgc taagcgatct gcatctcaat   120
tagtcagc                                                            128

SEQ ID NO: 171           moltype = DNA   length = 128
FEATURE                  Location/Qualifiers
misc_feature             1..128
                         note = Primer
source                   1..128
                         mol_type = other DNA
                         organism = synthetic construct
SEQUENCE: 171
actgacctag agaagctttt agcacctggt tggagggggt ttatagcaac cctgtaaacc   60
atggttttgg atgaagctat aaacccccte caaccaggtg ctaatttgca aaagcctagg   120
cctccaaa                                                            128

SEQ ID NO: 172           moltype = DNA   length = 107
```

-continued

```
FEATURE                 Location/Qualifiers
misc_feature            1..107
                        note = Primer
source                  1..107
                        mol_type = other DNA
                        organism = synthetic construct
SEQUENCE: 172
ttaattaaga gagatctgcg ggaggcgtgt ccaaaaccat ggtttacagg gttcctataa   60
accccctcca accaggtgct aagcgatctg catctcaatt agtcagc                 107

SEQ ID NO: 173          moltype = DNA   length = 107
FEATURE                 Location/Qualifiers
misc_feature            1..107
                        note = Primer
source                  1..107
                        mol_type = other DNA
                        organism = synthetic construct
SEQUENCE: 173
actgacctag agaagctttt agcacctggt tggagggggt ttatagcaac cctgtaaacc   60
atggtttttgg acacgcctcc cgctttgcaa aagcctaggc ctccaaa                107

SEQ ID NO: 174          moltype = DNA   length = 140
FEATURE                 Location/Qualifiers
misc_feature            1..140
                        note = Primer
source                  1..140
                        mol_type = other DNA
                        organism = synthetic construct
SEQUENCE: 174
ttaattaaga gagatctttta gcacctggtt ggagggggtt tatagcttca gcttcatcca   60
aaaccatggt ttacagggtt ccggttccta taaaccccct ccaaccaggt gctaagcgat  120
ctgcatctca attagtcagc                                               140

SEQ ID NO: 175          moltype = DNA   length = 140
FEATURE                 Location/Qualifiers
misc_feature            1..140
                        note = Primer
source                  1..140
                        mol_type = other DNA
                        organism = synthetic construct
SEQUENCE: 175
actgacctag agaagctttt agcacctggt tggaggggggt ttatagcaac cgcaaccctg   60
taaaccatgg ttttggatga agctgaagct ataaaccccc tccaaccagg tgctaatttg  120
caaaagccta ggcctccaaa                                               140

SEQ ID NO: 176          moltype = DNA   length = 52
FEATURE                 Location/Qualifiers
misc_feature            1..52
                        note = Primer
source                  1..52
                        mol_type = other DNA
                        organism = synthetic construct
SEQUENCE: 176
agtcagtcga gagctcatgg atcccggctc tatgctgatt ggctatgtaa gg            52

SEQ ID NO: 177          moltype = DNA   length = 39
FEATURE                 Location/Qualifiers
misc_feature            1..39
                        note = Primer
source                  1..39
                        mol_type = other DNA
                        organism = synthetic construct
SEQUENCE: 177
atgctgatat ctagactatc ccgatttagg tgggcgacc                           39

SEQ ID NO: 178          moltype = DNA   length = 37
FEATURE                 Location/Qualifiers
misc_feature            1..37
                        note = Primer
source                  1..37
                        mol_type = other DNA
                        organism = synthetic construct
SEQUENCE: 178
agtcagtcga gagctcatgc tgattggcta tgtaagg                             37

SEQ ID NO: 179          moltype = DNA   length = 32
FEATURE                 Location/Qualifiers
misc_feature            1..32
                        note = Primer
```

-continued

```
source                   1..32
                         mol_type = other DNA
                         organism = synthetic construct
SEQUENCE: 179
tctagactac ggatccaccg atttacgcgg gc                                    32

SEQ ID NO: 180           moltype = DNA   length = 39
FEATURE                  Location/Qualifiers
misc_feature             1..39
                         note = Primer
source                   1..39
                         mol_type = other DNA
                         organism = synthetic construct
SEQUENCE: 180
atcgcgtatc tagactagcc gaggcaggcc aaggcgacg                             39

SEQ ID NO: 181           moltype = DNA   length = 39
FEATURE                  Location/Qualifiers
misc_feature             1..39
                         note = Primer
source                   1..39
                         mol_type = other DNA
                         organism = synthetic construct
SEQUENCE: 181
atcgcgtatc tagactagct catctcgaac tgcgtcatg                             39

SEQ ID NO: 182           moltype = DNA   length = 43
FEATURE                  Location/Qualifiers
misc_feature             1..43
                         note = Primer
source                   1..43
                         mol_type = other DNA
                         organism = synthetic construct
SEQUENCE: 182
gtcgcccgcg taaatcggga tccactgcag atcggggggg ggc                       43

SEQ ID NO: 183           moltype = DNA   length = 43
FEATURE                  Location/Qualifiers
misc_feature             1..43
                         note = Primer
source                   1..43
                         mol_type = other DNA
                         organism = synthetic construct
SEQUENCE: 183
gtcgcccgcg taaatcggga tccccctcgc ctgcgttctc ggc                       43

SEQ ID NO: 184           moltype = DNA   length = 43
FEATURE                  Location/Qualifiers
misc_feature             1..43
                         note = Primer
source                   1..43
                         mol_type = other DNA
                         organism = synthetic construct
SEQUENCE: 184
gtcgcccgcg taaatcggga tccgattcga tgcctgccgt cgg                       43

SEQ ID NO: 185           moltype = DNA   length = 45
FEATURE                  Location/Qualifiers
misc_feature             1..45
                         note = Primer
source                   1..45
                         mol_type = other DNA
                         organism = synthetic construct
SEQUENCE: 185
gtcgcccgcg taaatcggga tccaccgtgc gtgtcgctgt cactg                     45

SEQ ID NO: 186           moltype = DNA   length = 44
FEATURE                  Location/Qualifiers
misc_feature             1..44
                         note = Primer
source                   1..44
                         mol_type = other DNA
                         organism = synthetic construct
SEQUENCE: 186
gtcgcccgcg taaatcggga tccgtggatc tacgcacgct cggc                      44

SEQ ID NO: 187           moltype = DNA   length = 43
FEATURE                  Location/Qualifiers
misc_feature             1..43
```

-continued

```
                              note = Primer
source                        1..43
                              mol_type = other DNA
                              organism = synthetic construct
SEQUENCE: 187
gtcgcccgcg taaatcggga tccacacacg cgcacatcgt tgc              43

SEQ ID NO: 188        moltype = DNA   length = 45
FEATURE               Location/Qualifiers
misc_feature          1..45
                      note = Primer
source                1..45
                      mol_type = other DNA
                      organism = synthetic construct
SEQUENCE: 188
gtcgcccgcg taaatcggga tcccacgaag acatcgttgg cgtcg            45

SEQ ID NO: 189        moltype = DNA   length = 44
FEATURE               Location/Qualifiers
misc_feature          1..44
                      note = Primer
source                1..44
                      mol_type = other DNA
                      organism = synthetic construct
SEQUENCE: 189
gtcgcccgcg taaatcggga tccagcgctc tggaggcctt gctc             44

SEQ ID NO: 190        moltype = DNA   length = 44
FEATURE               Location/Qualifiers
misc_feature          1..44
                      note = Primer
source                1..44
                      mol_type = other DNA
                      organism = synthetic construct
SEQUENCE: 190
gtcgcccgcg taaatcggga tccttggaca caggccaact tctc             44

SEQ ID NO: 191        moltype = DNA   length = 43
FEATURE               Location/Qualifiers
misc_feature          1..43
                      note = Primer
source                1..43
                      mol_type = other DNA
                      organism = synthetic construct
SEQUENCE: 191
gtcgcccgcg taaatcggga tccagcggcg tgaccgcagt gga              43

SEQ ID NO: 192        moltype = DNA   length = 20
FEATURE               Location/Qualifiers
misc_feature          1..20
                      note = Primer
source                1..20
                      mol_type = other DNA
                      organism = synthetic construct
SEQUENCE: 192
ggatcccgat ttacgcgggc                                        20

SEQ ID NO: 193        moltype = DNA   length = 41
FEATURE               Location/Qualifiers
misc_feature          1..41
                      note = Primer
source                1..41
                      mol_type = other DNA
                      organism = synthetic construct
SEQUENCE: 193
atcgtagcag ctagcgccac catgctgatt ggctatgtaa g                41

SEQ ID NO: 194        moltype = DNA   length = 26
FEATURE               Location/Qualifiers
misc_feature          1..26
                      note = Primer
source                1..26
                      mol_type = other DNA
                      organism = synthetic construct
SEQUENCE: 194
ggatccagac cccgatttac gcgggc                                 26

SEQ ID NO: 195        moltype = DNA   length = 74
FEATURE               Location/Qualifiers
```

-continued

```
misc_feature            1..74
                        note = Synthetic construct
source                  1..74
                        mol_type = other DNA
                        organism = synthetic construct
SEQUENCE: 195
ttagcacctg gttggagggg gtttatatcc aaaaccatgg tttacagtat aaaccccctc    60
caaccaggtg ctaa                                                       74

SEQ ID NO: 196          moltype = DNA   length = 74
FEATURE                 Location/Qualifiers
misc_feature            1..74
                        note = Synthetic construct
source                  1..74
                        mol_type = other DNA
                        organism = synthetic construct
SEQUENCE: 196
ttagcacctg gttggagggg gtttataagg ttttggtacc aaatgtctat aaaccccctc    60
caaccaggtg ctaa                                                       74

SEQ ID NO: 197          moltype = DNA   length = 74
FEATURE                 Location/Qualifiers
misc_feature            1..74
                        note = Synthetic construct
source                  1..74
                        mol_type = other DNA
                        organism = synthetic construct
SEQUENCE: 197
tataaacccc ctccaaccag gtgctaactg taaaccatgg ttttggatta gcacctggtt    60
ggaggggtt tata                                                        74

SEQ ID NO: 198          moltype = DNA   length = 68
FEATURE                 Location/Qualifiers
misc_feature            1..68
                        note = Synthetic construct
source                  1..68
                        mol_type = other DNA
                        organism = synthetic construct
SEQUENCE: 198
ttagcacctg gttggagggg gtttataaaa accatggttt atataaaccc cctccaacca    60
ggtgctaa                                                              68

SEQ ID NO: 199          moltype = DNA   length = 80
FEATURE                 Location/Qualifiers
misc_feature            1..80
                        note = Synthetic construct
source                  1..80
                        mol_type = other DNA
                        organism = synthetic construct
SEQUENCE: 199
ttagcacctg gttggagggg gtttatagct tccaaaacca tggtttacag ggttataaac    60
cccctccaac caggtgctaa                                                 80

SEQ ID NO: 200          moltype = DNA   length = 86
FEATURE                 Location/Qualifiers
misc_feature            1..86
                        note = Synthetic construct
source                  1..86
                        mol_type = other DNA
                        organism = synthetic construct
SEQUENCE: 200
ttagcacctg gttggagggg gtttatagct tcatccaaaa ccatggttta cagggttcct    60
ataaccccc tccaaccagg tgctaa                                           86

SEQ ID NO: 201          moltype = DNA   length = 98
FEATURE                 Location/Qualifiers
misc_feature            1..98
                        note = Synthetic construct
source                  1..98
                        mol_type = other DNA
                        organism = synthetic construct
SEQUENCE: 201
ttagcacctg gttggagggg gtttatagct tcagcttcat ccaaaaccat ggtttacagg    60
gttccggttc ctataaaccc cctccaacca ggtgctaa                             98

SEQ ID NO: 202          moltype = DNA   length = 74
FEATURE                 Location/Qualifiers
misc_feature            1..74
                        note = Synthetic construct
```

```
source                     1..74
                           mol_type = other DNA
                           organism = synthetic construct
SEQUENCE: 202
ttagcacctg gttggagggg gtttatatcc aaaaccgggg tttacagtat aaaccccctc   60
caaccaggtg ctaa                                                      74

SEQ ID NO: 203             moltype = DNA   length = 74
FEATURE                    Location/Qualifiers
misc_feature               1..74
                           note = Synthetic construct
source                     1..74
                           mol_type = other DNA
                           organism = synthetic construct
SEQUENCE: 203
ttagcacctg gttggagggg gtttatacga aatattataa attatcatat aaaccccctc   60
caaccaggtg ctaa                                                      74

SEQ ID NO: 204             moltype = DNA   length = 86
FEATURE                    Location/Qualifiers
misc_feature               1..86
                           note = Synthetic construct
source                     1..86
                           mol_type = other DNA
                           organism = synthetic construct
SEQUENCE: 204
ttagcacctg gttggagggg gtttatagct tcatccaaaa ccggggttta cagggttcct   60
ataaaccccc tccaaccagg tgctaa                                         86

SEQ ID NO: 205             moltype = DNA   length = 86
FEATURE                    Location/Qualifiers
misc_feature               1..86
                           note = Synthetic construct
source                     1..86
                           mol_type = other DNA
                           organism = synthetic construct
SEQUENCE: 205
ttagcacctg gttggagggg gtttatagct tcacgaaata ttataaatta tcaggttcct   60
ataaaccccc tccaaccagg tgctaa                                         86

SEQ ID NO: 206             moltype = DNA   length = 65
FEATURE                    Location/Qualifiers
misc_feature               1..65
                           note = Synthetic construct
source                     1..65
                           mol_type = other DNA
                           organism = synthetic construct
SEQUENCE: 206
gcgggaggcg tgtccaaaac catggtttac agggttccta taaacccct ccaaccaggt   60
gctaa                                                                65

SEQ ID NO: 207             moltype = DNA   length = 70
FEATURE                    Location/Qualifiers
misc_feature               1..70
                           note = Synthetic construct
source                     1..70
                           mol_type = other DNA
                           organism = synthetic construct
SEQUENCE: 207
gtggtgtaca gtaggggag atgcatccaa aaccatggtt tacagtgcat ctcccccta    60
tgtacaccac                                                           70

SEQ ID NO: 208             moltype = DNA   length = 82
FEATURE                    Location/Qualifiers
misc_feature               1..82
                           note = Synthetic construct
source                     1..82
                           mol_type = other DNA
                           organism = synthetic construct
SEQUENCE: 208
gtggtgtaca gtaggggag atgcagctgc ttccaaaacc atggtttaca gggtggttgc   60
atctccccct actgtacacc ac                                            82

SEQ ID NO: 209             moltype = AA   length = 4
FEATURE                    Location/Qualifiers
REGION                     1..4
                           note = Synthetic construct
source                     1..4
                           mol_type = protein
```

-continued

```
                                organism = synthetic construct
SEQUENCE: 209
QWSG                                                                   4

SEQ ID NO: 210          moltype = AA   length = 4
FEATURE                 Location/Qualifiers
REGION                  1..4
                        note = Synthetic construct
source                  1..4
                        mol_type = protein
                        organism = synthetic construct
SEQUENCE: 210
RSNG                                                                   4

SEQ ID NO: 211          moltype = AA   length = 4
FEATURE                 Location/Qualifiers
REGION                  1..4
                        note = Synthetic construct
source                  1..4
                        mol_type = protein
                        organism = synthetic construct
SEQUENCE: 211
SRSG                                                                   4

SEQ ID NO: 212          moltype = AA   length = 4
FEATURE                 Location/Qualifiers
REGION                  1..4
                        note = Synthetic construct
source                  1..4
                        mol_type = protein
                        organism = synthetic construct
SEQUENCE: 212
QWSG                                                                   4

SEQ ID NO: 213          moltype = DNA   length = 16
FEATURE                 Location/Qualifiers
misc_feature            1..16
                        note = Synthetic construct
source                  1..16
                        mol_type = other DNA
                        organism = synthetic construct
SEQUENCE: 213
gataaacccc ctccaa                                                     16

SEQ ID NO: 214          moltype = DNA   length = 15
FEATURE                 Location/Qualifiers
misc_feature            1..15
                        note = Synthetic construct
source                  1..15
                        mol_type = other DNA
                        organism = synthetic construct
SEQUENCE: 214
ataaaccccc tccaa                                                      15

SEQ ID NO: 215          moltype = AA   length = 35
FEATURE                 Location/Qualifiers
REGION                  1..35
                        note = Synthetic construct
source                  1..35
                        mol_type = protein
                        organism = synthetic construct
SEQUENCE: 215
ATHEDIVGVG KQWSGARALE ALLTDAGELR GPPLQ                                35

SEQ ID NO: 216          moltype = AA   length = 35
FEATURE                 Location/Qualifiers
REGION                  1..35
                        note = Synthetic construct
source                  1..35
                        mol_type = protein
                        organism = synthetic construct
SEQUENCE: 216
ATHEDIVGVG KQWSGARALE ALLTDAGELR GPPLQ                                35

SEQ ID NO: 217          moltype = AA   length = 5
FEATURE                 Location/Qualifiers
REGION                  1..5
                        note = Synthetic construct
source                  1..5
```

-continued

```
                           mol_type = protein
                           organism = synthetic construct
SEQUENCE: 217
KQWSG                                                         5

SEQ ID NO: 218            moltype = AA  length = 5
FEATURE                  Location/Qualifiers
REGION                   1..5
                         note = Synthetic construct
source                   1..5
                         mol_type = protein
                         organism = synthetic construct
SEQUENCE: 218
KRSNG                                                         5

SEQ ID NO: 219           moltype = AA  length = 5
FEATURE                  Location/Qualifiers
REGION                   1..5
                         note = Synthetic construct
source                   1..5
                         mol_type = protein
                         organism = synthetic construct
SEQUENCE: 219
KSRSG                                                         5

SEQ ID NO: 220           moltype = AA  length = 35
FEATURE                  Location/Qualifiers
REGION                   1..35
                         note = Synthetic construct
source                   1..35
                         mol_type = protein
                         organism = synthetic construct
SEQUENCE: 220
ATHEDIVGVG KQWSGARALE ALLTDAGELR GPPLQ                        35

SEQ ID NO: 221           moltype = AA  length = 5
FEATURE                  Location/Qualifiers
REGION                   1..5
                         note = Synthetic construct
source                   1..5
                         mol_type = protein
                         organism = synthetic construct
SEQUENCE: 221
KQWSG                                                         5

SEQ ID NO: 222           moltype = DNA  length = 16
FEATURE                  Location/Qualifiers
misc_feature             1..16
                         note = Synthetic construct
source                   1..16
                         mol_type = other DNA
                         organism = synthetic construct
SEQUENCE: 222
aataaacccc ctccaa                                             16

SEQ ID NO: 223           moltype = DNA  length = 16
FEATURE                  Location/Qualifiers
misc_feature             1..16
                         note = Synthetic construct
source                   1..16
                         mol_type = other DNA
                         organism = synthetic construct
SEQUENCE: 223
tataaacccc ctccaa                                             16

SEQ ID NO: 224           moltype = AA  length = 4
FEATURE                  Location/Qualifiers
REGION                   1..4
                         note = Synthetic construct
source                   1..4
                         mol_type = protein
                         organism = synthetic construct
SEQUENCE: 224
KRGG                                                          4

SEQ ID NO: 225           moltype = AA  length = 34
FEATURE                  Location/Qualifiers
REGION                   1..34
                         note = Synthetic construct
```

-continued

```
source                  1..34
                        mol_type = protein
                        organism = synthetic construct
SEQUENCE: 225
LTPDQVVAIA SHDGGKQALE TVQRLLPVLC QDHG                             34

SEQ ID NO: 226          moltype = AA  length = 4
FEATURE                 Location/Qualifiers
REGION                  1..4
                        note = Synthetic construct
source                  1..4
                        mol_type = protein
                        organism = synthetic construct
SEQUENCE: 226
SHDG                                                               4

SEQ ID NO: 227          moltype = AA  length = 6
FEATURE                 Location/Qualifiers
REGION                  1..6
                        note = Synthetic construct
source                  1..6
                        mol_type = protein
                        organism = synthetic construct
SEQUENCE: 227
ASHDGG                                                             6

SEQ ID NO: 228          moltype = DNA  length = 81
FEATURE                 Location/Qualifiers
misc_feature            1..81
                        note = Primer
variation               50..51
                        note = n is a, c, g, or t
variation               53..54
                        note = n is a, c, g, or t
source                  1..81
                        mol_type = other DNA
                        organism = synthetic construct
SEQUENCE: 228
tctcaactcc cccgcctccg tgagcaaggc ctccagagcg cgtgccccmn nmnntttgcc  60
gacgccaacg atgtcttcgt g                                           81

SEQ ID NO: 229          moltype = DNA  length = 84
FEATURE                 Location/Qualifiers
misc_feature            1..84
                        note = Primer
variation               47..48
                        note = n is a, c, g, or t
variation               50..51
                        note = n is a, c, g, or t
variation               53..54
                        note = n is a, c, g, or t
variation               56..57
                        note = n is a, c, g, or t
source                  1..84
                        mol_type = other DNA
                        organism = synthetic construct
SEQUENCE: 229
tctcaactcc cccgcctccg tgagcaaggc ctccagagcg cgtgcmnnmn nmnnmnnttt  60
gccgacgcca acgatgtctt cgtg                                        84

SEQ ID NO: 230          moltype = DNA  length = 80
FEATURE                 Location/Qualifiers
misc_feature            1..80
                        note = Primer
variation               43..44
                        note = n is a, c, g, or t
variation               46..47
                        note = n is a, c, g, or t
variation               49..50
                        note = n is a, c, g, or t
source                  1..80
                        mol_type = other DNA
                        organism = synthetic construct
SEQUENCE: 230
cccgcctccg tgagcaaggc ctccagggcg cgtgcgccgg amnnmnnmnn gccgacgcca  60
acgatgtctt cgtgtgtcgc                                             80

SEQ ID NO: 231          moltype = DNA  length = 90
FEATURE                 Location/Qualifiers
```

-continued

```
misc_feature           1..90
                       note = Primer
variation              53..54
                       note = n is a, c, g, or t
variation              56..57
                       note = n is a, c, g, or t
variation              59..60
                       note = n is a, c, g, or t
variation              62..63
                       note = n is a, c, g, or t
source                 1..90
                       mol_type = other DNA
                       organism = synthetic construct
SEQUENCE: 231
ggcaccgtc agtgcattgc gccatgcatg cactgcctcc actgcggtca cmnnmnnmnn    60
mnntgcaatc ttgagaagtt ggcctgtgtc                                    90

SEQ ID NO: 232          moltype = DNA   length = 71
FEATURE                 Location/Qualifiers
misc_feature           1..71
                       note = Primer
source                 1..71
                       mol_type = other DNA
                       organism = synthetic construct SEQUENCE: 232
agagagagaa gaaaatgaga tctcctaaga aaaagaggaa ggtgcaggtg gatctacgca    60
cgctcggcta c                                                        71

SEQ ID NO: 233          moltype = DNA   length = 71
FEATURE                 Location/Qualifiers
misc_feature           1..71
                       note = Primer
source                 1..71
                       mol_type = other DNA
                       organism = synthetic construct
SEQUENCE: 233
aggaagaaga gaagcatgag atctcctaag aaaaagagga aggtgatggt ggacttgagg    60
acactcggtt a                                                        71

SEQ ID NO: 234          moltype = DNA   length = 44
FEATURE                 Location/Qualifiers
misc_feature           1..44
                       note = Primer
source                 1..44
                       mol_type = other DNA
                       organism = synthetic construct
SEQUENCE: 234
aagagaagaa gaagaagcat tgcgccatgc atgcactgcc tcta                    44

SEQ ID NO: 235          moltype = DNA   length = 17
FEATURE                 Location/Qualifiers
misc_feature           1..17
                       note = Primer
source                 1..17
                       mol_type = other DNA
                       organism = synthetic construct
SEQUENCE: 235
cccgccaccc accgtgc                                                  17

SEQ ID NO: 236          moltype = DNA   length = 23
FEATURE                 Location/Qualifiers
misc_feature           1..23
                       note = Primer
source                 1..23
                       mol_type = other DNA
                       organism = synthetic construct
SEQUENCE: 236
tgctctatgc atgcactgcc tcc                                           23

SEQ ID NO: 237          moltype = DNA   length = 68
FEATURE                 Location/Qualifiers
misc_feature           1..68
                       note = Primer
source                 1..68
                       mol_type = other DNA
                       organism = synthetic construct
SEQUENCE: 237
agagaagaga agagaaggcg cccgcggccc aggcggcctc gggatcccct cggcctccgc    60
gcgccaag                                                            68
```

-continued

```
SEQ ID NO: 238          moltype = DNA   length = 65
FEATURE                 Location/Qualifiers
misc_feature            1..65
                        note = Primer
source                  1..65
                        mol_type = other DNA
                        organism = synthetic construct
SEQUENCE: 238
agagagagag agagagtcta gaggccggcc tggccgctca tcccgaactg cgtcatggcc    60
tcatc                                                                65

SEQ ID NO: 239          moltype = DNA   length = 27
FEATURE                 Location/Qualifiers
misc_feature            1..27
                        note = Primer
source                  1..27
                        mol_type = other DNA
                        organism = synthetic construct
SEQUENCE: 239
gccccagatc ctggtacgct ctagagg                                        27

SEQ ID NO: 240          moltype = DNA   length = 70
FEATURE                 Location/Qualifiers
misc_feature            1..70
                        note = Primer
source                  1..70
                        mol_type = other DNA
                        organism = synthetic construct
SEQUENCE: 240
atcttagcac ctggttggag ggggtttatt gggttttccc aataaacccc ctccaaccag    60
gtgctaagat                                                           70

SEQ ID NO: 241          moltype = DNA   length = 70
FEATURE                 Location/Qualifiers
misc_feature            1..70
                        note = Primer
source                  1..70
                        mol_type = other DNA
                        organism = synthetic construct
SEQUENCE: 241
atcttagcac ctggttggag ggggtttata gggttttccc tataaacccc ctccaaccag    60
gtgctaagat                                                           70

SEQ ID NO: 242          moltype = DNA   length = 70
FEATURE                 Location/Qualifiers
misc_feature            1..70
                        note = Primer
source                  1..70
                        mol_type = other DNA
                        organism = synthetic construct
SEQUENCE: 242
atcttagcac ctggttggag ggggtttatc gggttttccc gataaacccc ctccaaccag    60
gtgctaagat                                                           70

SEQ ID NO: 243          moltype = DNA   length = 70
FEATURE                 Location/Qualifiers
misc_feature            1..70
                        note = Primer
source                  1..70
                        mol_type = other DNA
                        organism = synthetic construct
SEQUENCE: 243
atcttagcac ctggttggag ggggtttatg gggttttccc cataaacccc ctccaaccag    60
gtgctaagat                                                           70

SEQ ID NO: 244          moltype = DNA   length = 20
FEATURE                 Location/Qualifiers
misc_feature            1..20
                        note = Primer
source                  1..20
                        mol_type = other DNA
                        organism = synthetic construct
SEQUENCE: 244
ttaaaagcca ggacggtcac                                                20

SEQ ID NO: 245          moltype = DNA   length = 20
FEATURE                 Location/Qualifiers
misc_feature            1..20
```

-continued

```
                            note = Primer
source                      1..20
                            mol_type = other DNA
                            organism = synthetic construct
SEQUENCE: 245
tgtagggagc ccagaagaga                                              20

SEQ ID NO: 246              moltype = DNA  length = 22
FEATURE                     Location/Qualifiers
misc_feature                1..22
                            note = Primer
source                      1..22
                            mol_type = other DNA
                            organism = synthetic construct
SEQUENCE: 246
acagtttgca ttcatggagg gc                                           22

SEQ ID NO: 247              moltype = DNA  length = 20
FEATURE                     Location/Qualifiers
misc_feature                1..20
                            note = Primer
source                      1..20
                            mol_type = other DNA
                            organism = synthetic construct
SEQUENCE: 247
ccgagcgagc aagctcagtt                                              20

SEQ ID NO: 248              moltype = DNA  length = 27
FEATURE                     Location/Qualifiers
misc_feature                1..27
                            note = Primer
source                      1..27
                            mol_type = other DNA
                            organism = synthetic construct
SEQUENCE: 248
cgcggatccc cgcccagtgg gactttg                                      27

SEQ ID NO: 249              moltype = DNA  length = 27
FEATURE                     Location/Qualifiers
misc_feature                1..27
                            note = Primer
source                      1..27
                            mol_type = other DNA
                            organism = synthetic construct
SEQUENCE: 249
ccggaattca cctgttagag ctactgc                                      27

SEQ ID NO: 250              moltype = DNA  length = 54
FEATURE                     Location/Qualifiers
misc_feature                1..54
                            note = Primer
source                      1..54
                            mol_type = other DNA
                            organism = synthetic construct
SEQUENCE: 250
agagagagag agaggcggcc gccctaccag ggatttcagt cgatgtacac gttc        54

SEQ ID NO: 251              moltype = DNA  length = 58
FEATURE                     Location/Qualifiers
misc_feature                1..58
                            note = Primer
source                      1..58
                            mol_type = other DNA
                            organism = synthetic construct
SEQUENCE: 251
aagaagaaga aggaagagaa gtaggcctgt catcgtcggg aagacctgcg acacctgc    58

SEQ ID NO: 252              moltype = DNA  length = 138
FEATURE                     Location/Qualifiers
misc_feature                1..138
                            note = Primer
source                      1..138
                            mol_type = other DNA
                            organism = synthetic construct
SEQUENCE: 252
actgctatcc gagtataaac cccctccaac caggtataaa ccccctccaa ccaggtataa  60
acccctcca accaggtata aaccccctcc aaccaggtat aaaccccctc caaccaggat   120
ctgcgatcta agtaagct                                                138
```

-continued

```
SEQ ID NO: 253              moltype = DNA   length = 128
FEATURE                     Location/Qualifiers
misc_feature                1..128
                            note = Primer
source                      1..128
                            mol_type = other DNA
                            organism = synthetic construct
SEQUENCE: 253
ttaattaaga gtctagatta gcacctggtt ggaggggggtt tattgcttca tccaaaacca    60
tggtttacag ggttccaata aaccccctcc aaccaggtgc taaagatcta ggaggaattt   120
aaaatgag                                                             128

SEQ ID NO: 254              moltype = DNA   length = 128
FEATURE                     Location/Qualifiers
misc_feature                1..128
                            note = Primer
source                      1..128
                            mol_type = other DNA
                            organism = synthetic construct
SEQUENCE: 254
actgacctag agaagctttt agcacctggt tggagggggt ttattgcaac cctgtaaacc    60
atggtttggg atgaagcaat aaaccccctc caaccaggtg ctaactgcag ttatttgtac   120
agttcatc                                                             128

SEQ ID NO: 255              moltype = DNA   length = 128
FEATURE                     Location/Qualifiers
misc_feature                1..128
                            note = Primer
source                      1..128
                            mol_type = other DNA
                            organism = synthetic construct
SEQUENCE: 255
ttaattaaga gtctagatta gcacctggtt ggaggggggtt tatcgcttca tccaaaacca    60
tggtttacag ggttccgata aaccccctcc aaccaggtgc taaagatcta ggaggaattt   120
aaaatgag                                                             128

SEQ ID NO: 256              moltype = DNA   length = 128
FEATURE                     Location/Qualifiers
misc_feature                1..128
                            note = Primer
source                      1..128
                            mol_type = other DNA
                            organism = synthetic construct
SEQUENCE: 256
actgacctag agaagctttt agcacctggt tggaggggggt ttatcgcaac cctgtaaacc    60
atggttttgg atgaagcgat aaaccccctc caaccaggtg ctaactgcag ttatttgtac   120
agttcatc                                                             128

SEQ ID NO: 257              moltype = DNA   length = 128
FEATURE                     Location/Qualifiers
misc_feature                1..128
                            note = Primer
source                      1..128
                            mol_type = other DNA
                            organism = synthetic construct
SEQUENCE: 257
ttaattaaga gtctagatta gcacctggtt ggaggggggt tatggcttca tccaaaacca    60
tggtttacag ggttcccata aaccccctcc aaccaggtgc taaagatcta ggaggaattt   120
aaaatgag                                                             128

SEQ ID NO: 258              moltype = DNA   length = 128
FEATURE                     Location/Qualifiers
misc_feature                1..128
                            note = Primer
source                      1..128
                            mol_type = other DNA
                            organism = synthetic construct
SEQUENCE: 258
actgacctag agaagctttt agcacctggt tggaggggggt ttatggcaac cctgtaaacc    60
atggtttttgg atgaagccat aaaccccctc caaccaggtg ctaactgcag ttatttgtac   120
agttcatc                                                             128

SEQ ID NO: 259              moltype = DNA   length = 144
FEATURE                     Location/Qualifiers
misc_feature                1..144
                            note = Primer
source                      1..144
                            mol_type = other DNA
                            organism = synthetic construct
```

```
SEQUENCE: 259
actgctatct cgagctataa accccctcca accaggctat aaaccccctc caaccaggct   60
ataaacccc tccaaccagg ctataaaccc cctccaacca ggctataaac ccctccaac   120
caggatctgc gatctaagta agct                                        144

SEQ ID NO: 260           moltype = DNA  length = 144
FEATURE                  Location/Qualifiers
misc_feature             1..144
                         note = Primer
source                   1..144
                         mol_type = other DNA
                         organism = synthetic construct
SEQUENCE: 260
actgctatct cgagcaataa accccctcca accaggcaat aaaccccctc caaccaggca   60
ataaacccc tccaaccagg caataaaccc cctccaacca ggcaataaac ccctccaac   120
caggatctgc gatctaagta agct                                        144

SEQ ID NO: 261           moltype = DNA  length = 144
FEATURE                  Location/Qualifiers
misc_feature             1..144
                         note = Primer
source                   1..144
                         mol_type = other DNA
                         organism = synthetic construct
SEQUENCE: 261
actgctatct cgagccataa accccctcca accaggccat aaaccccctc caaccaggcc   60
ataaacccc tccaaccagg ccataaaccc cctccaacca ggccataaac ccctccaac   120
caggatctgc gatctaagta agct                                        144

SEQ ID NO: 262           moltype = DNA  length = 144
FEATURE                  Location/Qualifiers
misc_feature             1..144
                         note = Primer
source                   1..144
                         mol_type = other DNA
                         organism = synthetic construct
SEQUENCE: 262
actgctatct cgagcgataa accccctcca accaggcgat aaaccccctc caaccaggcg   60
ataaacccc tccaaccagg cgataaaccc cctccaacca ggcgataaac ccctccaac   120
caggatctgc gatctaagta agct                                        144

SEQ ID NO: 263           moltype = DNA  length = 25
FEATURE                  Location/Qualifiers
misc_feature             1..25
                         note = Primer
source                   1..25
                         mol_type = other DNA
                         organism = synthetic construct
SEQUENCE: 263
tcagaaacag ctcttcttca aatct                                        25

SEQ ID NO: 264           moltype = DNA  length = 80
FEATURE                  Location/Qualifiers
misc_feature             1..80
                         note = Primer
source                   1..80
                         mol_type = other DNA
                         organism = synthetic construct
SEQUENCE: 264
ttaattaaga gtctagagga ggcgtgtcca aaaccatggt ttacagcacg cctccagatc   60
taggaggaat ttaaaatgag                                              80

SEQ ID NO: 265           moltype = DNA  length = 80
FEATURE                  Location/Qualifiers
misc_feature             1..80
                         note = Primer
source                   1..80
                         mol_type = other DNA
                         organism = synthetic construct
SEQUENCE: 265
actgacctag agaagcttgg aggcgtgctg taaaccatgg ttttggacac gcctccctgc   60
agttatttgt acagttcatc                                              80

SEQ ID NO: 266           moltype = DNA  length = 86
FEATURE                  Location/Qualifiers
misc_feature             1..86
                         note = Primer
source                   1..86
                         mol_type = other DNA
```

-continued

```
                           organism = synthetic construct
SEQUENCE: 266
ttaattaaga gagatctgct gatgcagata cagaaaccaa ggttttctta cttgctgctg    60
cgcgatctgc atctcaatta gtcagc                                        86

SEQ ID NO: 267            moltype = DNA   length = 82
FEATURE                   Location/Qualifiers
misc_feature              1..82
                          note = Primer
source                    1..82
                          mol_type = other DNA
                          organism = synthetic construct
SEQUENCE: 267
caccaccacg gatccgcagc agcaagtaag aaaaccttgg tttctgtatc tgcatcagca    60
atttcgataa gccagtaagc ag                                            82

SEQ ID NO: 268            moltype = DNA   length = 65
FEATURE                   Location/Qualifiers
misc_feature              1..65
                          note = Primer
source                    1..65
                          mol_type = other DNA
                          organism = synthetic construct
SEQUENCE: 268
caccaccacg cgcgcaagct tagatctggc ccaggcggcc accatgctga ttggctatgt    60
aaggg                                                               65

SEQ ID NO: 269            moltype = DNA   length = 35
FEATURE                   Location/Qualifiers
misc_feature              1..35
                          note = Primer
source                    1..35
                          mol_type = other DNA
                          organism = synthetic construct
SEQUENCE: 269
caccaccaca ccggttcccg atttaggtgg gcgac                              35

SEQ ID NO: 270            moltype = DNA   length = 21
FEATURE                   Location/Qualifiers
misc_feature              1..21
                          note = Primer
source                    1..21
                          mol_type = other DNA
                          organism = synthetic construct
SEQUENCE: 270
gttcctgcca ggatccacta g                                             21

SEQ ID NO: 271            moltype = DNA   length = 21
FEATURE                   Location/Qualifiers
misc_feature              1..21
                          note = Primer
source                    1..21
                          mol_type = other DNA
                          organism = synthetic construct
SEQUENCE: 271
gcatgtgtcc agatgcatag g                                             21

SEQ ID NO: 272            moltype = DNA   length = 20
FEATURE                   Location/Qualifiers
misc_feature              1..20
                          note = Primer
source                    1..20
                          mol_type = other DNA
                          organism = synthetic construct
SEQUENCE: 272
caccttctcc caggataagg                                               20

SEQ ID NO: 273            moltype = DNA   length = 20
FEATURE                   Location/Qualifiers
misc_feature              1..20
                          note = Primer
source                    1..20
                          mol_type = other DNA
                          organism = synthetic construct
SEQUENCE: 273
gttggcctgt attcctctgg                                               20

SEQ ID NO: 274            moltype = DNA   length = 22
FEATURE                   Location/Qualifiers
```

-continued

```
misc_feature          1..22
                      note = Primer
source                1..22
                      mol_type = other DNA
                      organism = synthetic construct
SEQUENCE: 274
aatgaagttc ccttggcact tc                                         22

SEQ ID NO: 275        moltype = DNA  length = 23
FEATURE               Location/Qualifiers
misc_feature          1..23
                      note = Primer
source                1..23
                      mol_type = other DNA
                      organism = synthetic construct
SEQUENCE: 275
ctgaagggtt ttaagtgcag aag                                        23

SEQ ID NO: 276        moltype = DNA  length = 22
FEATURE               Location/Qualifiers
misc_feature          1..22
                      note = Primer
source                1..22
                      mol_type = other DNA
                      organism = synthetic construct
SEQUENCE: 276
tgacgtcaat gacggtaaat gg                                         22

SEQ ID NO: 277        moltype = DNA  length = 122
FEATURE               Location/Qualifiers
misc_feature          1..122
                      note = Primer
source                1..122
                      mol_type = other DNA
                      organism = synthetic construct
SEQUENCE: 277
actgacctag agaagctttt agcacctggt tggagggggt ttataaccct gtaaaccatg   60
gttttggaag ctataaaccc cctccaacca ggtgctaact gcagttattt gtacagttca  120
tc                                                               122

SEQ ID NO: 278        moltype = DNA  length = 140
FEATURE               Location/Qualifiers
misc_feature          1..140
                      note = Primer
source                1..140
                      mol_type = other DNA
                      organism = synthetic construct
SEQUENCE: 278
actgacctag agaagctttt agcacctggt tggagggggt ttatagcaac cgcaaccctg   60
taaaccatgt ttttggatga agctgaagct ataaacccc tccaaccagg tgctaactgc  120
agttatttgt acagttcatc                                            140

SEQ ID NO: 279        moltype = DNA  length = 12
FEATURE               Location/Qualifiers
misc_feature          1..12
                      note = Synthetic construct
source                1..12
                      mol_type = other DNA
                      organism = synthetic construct
SEQUENCE: 279
gcgggaggcg tg                                                    12

SEQ ID NO: 280        moltype = DNA  length = 17
FEATURE               Location/Qualifiers
misc_feature          1..17
                      note = Synthetic construct
source                1..17
                      mol_type = other DNA
                      organism = synthetic construct
SEQUENCE: 280
tcttcattac acctgca                                               17

SEQ ID NO: 281        moltype = DNA  length = 15
FEATURE               Location/Qualifiers
misc_feature          1..15
                      note = Synthetic construct
source                1..15
                      mol_type = other DNA
                      organism = synthetic construct
```

-continued

```
SEQUENCE: 281
cagtcagtat caatt                                                        15

SEQ ID NO: 282        moltype = DNA   length = 17
FEATURE               Location/Qualifiers
misc_feature          1..17
                      note = Synthetic construct
source                1..17
                      mol_type = other DNA
                      organism = synthetic construct
SEQUENCE: 282
cctgcagctc tcatttt                                                      17

SEQ ID NO: 283        moltype = DNA   length = 16
FEATURE               Location/Qualifiers
misc_feature          1..16
                      note = Synthetic construct
source                1..16
                      mol_type = other DNA
                      organism = synthetic construct
SEQUENCE: 283
attcttccag aattga                                                       16

SEQ ID NO: 284        moltype = DNA   length = 17
FEATURE               Location/Qualifiers
misc_feature          1..17
                      note = Synthetic construct
source                1..17
                      mol_type = other DNA
                      organism = synthetic construct
SEQUENCE: 284
cagaattgat actgact                                                      17

SEQ ID NO: 285        moltype = DNA   length = 16
FEATURE               Location/Qualifiers
misc_feature          1..16
                      note = Synthetic construct
source                1..16
                      mol_type = other DNA
                      organism = synthetic construct
SEQUENCE: 285
tcattacacc tgcagc                                                       16

SEQ ID NO: 286        moltype = DNA   length = 18
FEATURE               Location/Qualifiers
misc_feature          1..18
                      note = Synthetic construct
source                1..18
                      mol_type = other DNA
                      organism = synthetic construct
SEQUENCE: 286
cttccagaat tgatactg                                                     18

SEQ ID NO: 287        moltype = DNA   length = 15
FEATURE               Location/Qualifiers
misc_feature          1..15
                      note = Synthetic construct
source                1..15
                      mol_type = other DNA
                      organism = synthetic construct
SEQUENCE: 287
ataaaccccc tccaa                                                        15

SEQ ID NO: 288        moltype = DNA   length = 74
FEATURE               Location/Qualifiers
misc_feature          1..74
                      note = Synthetic construct
source                1..74
                      mol_type = other DNA
                      organism = synthetic construct
SEQUENCE: 288
ttagcacctg gttggagggg gtttatatcc aaaaccatgg tttacagtat aaaccccctc       60
caaccaggtg ctaa                                                         74

SEQ ID NO: 289        moltype = DNA   length = 74
FEATURE               Location/Qualifiers
misc_feature          1..74
                      note = Synthetic construct
source                1..74
```

-continued

```
                              mol_type = other DNA
                              organism = synthetic construct
SEQUENCE: 289
ttagcacctg gttggagggg gtttataagg ttttggtacc aaatgtctat aaaccccctc    60
caaccaggtg ctaa                                                      74

SEQ ID NO: 290           moltype = DNA  length = 74
FEATURE                  Location/Qualifiers
misc_feature             1..74
                         note = Synthetic construct
source                   1..74
                         mol_type = other DNA
                         organism = synthetic construct
SEQUENCE: 290
tataaacccc ctccaaccag gtgctaactg taaaccatgg ttttggatta gcacctggtt    60
ggaggggggtt tata                                                     74

SEQ ID NO: 291           moltype = AA  length = 6
FEATURE                  Location/Qualifiers
REGION                   1..6
                         note = Synthetic construct
VAR_SEQ                  2..3
                         note = X can be any naturally occurring amino acid
source                   1..6
                         mol_type = protein
                         organism = synthetic construct
SEQUENCE: 291
KXXGAR                                                                6

SEQ ID NO: 292           moltype = DNA  length = 83
FEATURE                  Location/Qualifiers
misc_feature             1..83
                         note = Synthetic construct
source                   1..83
                         mol_type = other DNA
                         organism = synthetic construct
SEQUENCE: 292
tggaaattct tccagaattg atactgactg tatggaaaat gagagctgca ggtgtaatga    60
agaccttctt tttgagatct ggt                                            83

SEQ ID NO: 293           moltype = DNA  length = 77
FEATURE                  Location/Qualifiers
misc_feature             1..77
                         note = Synthetic construct
source                   1..77
                         mol_type = other DNA
                         organism = synthetic construct
SEQUENCE: 293
tggaaattct tccataattg atattgactg tatggaaggc tgcgggtgta atgaatacct    60
tctttttgag atctggt                                                   77

SEQ ID NO: 294           moltype = DNA  length = 77
FEATURE                  Location/Qualifiers
misc_feature             1..77
                         note = Synthetic construct
source                   1..77
                         mol_type = other DNA
                         organism = synthetic construct
SEQUENCE: 294
tggaaattct tccagaattg atactgactg tatggaaaac tgcaggtgta atgaagacct    60
tctttttgag atctggt                                                   77

SEQ ID NO: 295           moltype = DNA  length = 77
FEATURE                  Location/Qualifiers
misc_feature             1..77
                         note = Synthetic construct
source                   1..77
                         mol_type = other DNA
                         organism = synthetic construct
SEQUENCE: 295
tggaaattct tccagaattg atactgactg tatggaaagc tgcaggtgta atgaagacct    60
tctttttgag atctggt                                                   77

SEQ ID NO: 296           moltype = DNA  length = 76
FEATURE                  Location/Qualifiers
misc_feature             1..76
                         note = Synthetic construct
source                   1..76
                         mol_type = other DNA
```

-continued

```
                               organism = synthetic construct
SEQUENCE: 296
tggaaattct tccagaattg atactgactg tatggaagct gcaggtgtaa tgaagacctt   60
cttttttgaga tctggt                                                   76

SEQ ID NO: 297            moltype = DNA  length = 73
FEATURE                   Location/Qualifiers
misc_feature              1..73
                          note = Synthetic construct
source                    1..73
                          mol_type = other DNA
                          organism = synthetic construct
SEQUENCE: 297
tggaaattct tccagaattg atactgactg tagagctgca ggtgtaatga agaccttctt   60
tttgagatct ggt                                                       73

SEQ ID NO: 298            moltype = DNA  length = 72
FEATURE                   Location/Qualifiers
misc_feature              1..72
                          note = Synthetic construct
source                    1..72
                          mol_type = other DNA
                          organism = synthetic construct
SEQUENCE: 298
tggaaattct tccagaattg atactgactg tatgctgcag gtgtaatgaa gaccttcttt   60
ttgagatctg gt                                                        72

SEQ ID NO: 299            moltype = DNA  length = 70
FEATURE                   Location/Qualifiers
misc_feature              1..70
                          note = Synthetic construct
source                    1..70
                          mol_type = other DNA
                          organism = synthetic construct
SEQUENCE: 299
tggaaattct tccagaattg atactgactg tgctgcaggt gtaatgaaga ccttcttttt   60
gagatctggt                                                           70

SEQ ID NO: 300            moltype = DNA  length = 83
FEATURE                   Location/Qualifiers
misc_feature              1..83
                          note = Synthetic construct
source                    1..83
                          mol_type = other DNA
                          organism = synthetic construct
SEQUENCE: 300
tggaaattct tccagaattg atactgactg tatggaaaat gagagctgca ggtgtaatga   60
agaccttctt tttgagatct ggt                                            83

SEQ ID NO: 301            moltype = DNA  length = 79
FEATURE                   Location/Qualifiers
misc_feature              1..79
                          note = Synthetic construct
source                    1..79
                          mol_type = other DNA
                          organism = synthetic construct
SEQUENCE: 301
tggaaattct tccagaattg atactgactg tatggaaaga gctgcaggtg taatgaagac   60
cttcttttg agatctggt                                                  79

SEQ ID NO: 302            moltype = DNA  length = 78
FEATURE                   Location/Qualifiers
misc_feature              1..78
                          note = Synthetic construct
source                    1..78
                          mol_type = other DNA
                          organism = synthetic construct
SEQUENCE: 302
tggaaattct tccagaattg atactgactg tatggaagag ctgcaggtgt aatgaagacc   60
ttcttttga gatctggt                                                   78

SEQ ID NO: 303            moltype = DNA  length = 77
FEATURE                   Location/Qualifiers
misc_feature              1..77
                          note = Synthetic construct
source                    1..77
                          mol_type = other DNA
                          organism = synthetic construct
SEQUENCE: 303
```

-continued

```
tggaaattct tccagaattg atactgactg tatggagagc tgcaggtgta atgaagacct   60
tctttttgag atctggt                                                  77

SEQ ID NO: 304          moltype = DNA   length = 74
FEATURE                 Location/Qualifiers
misc_feature            1..74
                        note = Synthetic construct
source                  1..74
                        mol_type = other DNA
                        organism = synthetic construct
SEQUENCE: 304
tggaaattct tccagaattg atactgacta tgagagctgc aggtgtaatg aagaccttct   60
ttttgagatc tggt                                                     74

SEQ ID NO: 305          moltype = DNA   length = 73
FEATURE                 Location/Qualifiers
misc_feature            1..73
                        note = Synthetic construct
source                  1..73
                        mol_type = other DNA
                        organism = synthetic construct
SEQUENCE: 305
tggaaattct tccagaattg atactgactg tagagctgca ggtgtaatga agaccttctt   60
tttgagatct ggt                                                      73

SEQ ID NO: 306          moltype = DNA   length = 72
FEATURE                 Location/Qualifiers
misc_feature            1..72
                        note = Synthetic construct
source                  1..72
                        mol_type = other DNA
                        organism = synthetic construct
SEQUENCE: 306
tggaaattct tccagaattg atactgactg agagctgcag gtgtaatgaa gaccttcttt   60
ttgagatctg gt                                                       72

SEQ ID NO: 307          moltype = DNA   length = 72
FEATURE                 Location/Qualifiers
misc_feature            1..72
                        note = Synthetic construct
source                  1..72
                        mol_type = other DNA
                        organism = synthetic construct
SEQUENCE: 307
tggaaattct tccaggattg atactgactg agagctgcag gtgtaatgaa gaccttcttt   60
ttgagatctg gt                                                       72

SEQ ID NO: 308          moltype = DNA   length = 72
FEATURE                 Location/Qualifiers
misc_feature            1..72
                        note = Synthetic construct
source                  1..72
                        mol_type = other DNA
                        organism = synthetic construct
SEQUENCE: 308
tggaaattct tccagaattg atactgactg agagctgcag gtgtaatgaa gaccttcttt   60
ttgagatctg gt                                                       72

SEQ ID NO: 309          moltype = DNA   length = 72
FEATURE                 Location/Qualifiers
misc_feature            1..72
                        note = Synthetic construct
source                  1..72
                        mol_type = other DNA
                        organism = synthetic construct
SEQUENCE: 309
tggaaattct tccagaattg atactgacta ggagctgcag gtgtaatgaa gaccttcttt   60
ttgagatctg gt                                                       72

SEQ ID NO: 310          moltype = DNA   length = 83
FEATURE                 Location/Qualifiers
misc_feature            1..83
                        note = Synthetic construct
source                  1..83
                        mol_type = other DNA
                        organism = synthetic construct
SEQUENCE: 310
tggaaattct tccagaattg atactgactg tatggaaaat gagagctgca ggtgtaatga   60
agaccttctt tttgagatct ggt                                           83
```

-continued

```
SEQ ID NO: 311            moltype = DNA   length = 81
FEATURE                   Location/Qualifiers
misc_feature              1..81
                          note = Synthetic construct
source                    1..81
                          mol_type = other DNA
                          organism = synthetic construct
SEQUENCE: 311
tggaaattct tccagaattg atactgacta tggaaaatga gagctgcagg tgtaatgaag   60
accttctttt tgagatctgg t                                             81

SEQ ID NO: 312            moltype = DNA   length = 80
FEATURE                   Location/Qualifiers
misc_feature              1..80
                          note = Synthetic construct
source                    1..80
                          mol_type = other DNA
                          organism = synthetic construct
SEQUENCE: 312
tggaaattct tcctcaattg atactgatat ggaaaatgag agctgcaggt gtaatgaaga   60
ccttcttttt gagatctggt                                               80

SEQ ID NO: 313            moltype = DNA   length = 74
FEATURE                   Location/Qualifiers
misc_feature              1..74
                          note = Synthetic construct
source                    1..74
                          mol_type = other DNA
                          organism = synthetic construct
SEQUENCE: 313
tggaaattct tccagaattg atatggaaaa tgagagctgc aggtgtaatg aagaccttct   60
ttttgagatc tggt                                                     74

SEQ ID NO: 314            moltype = DNA   length = 83
FEATURE                   Location/Qualifiers
misc_feature              1..83
                          note = Synthetic construct
source                    1..83
                          mol_type = other DNA
                          organism = synthetic construct
SEQUENCE: 314
tggaaattct tccagaattg atactgactg tatggaaaat gagagctgca ggtgtaatga   60
agaccttctt tttgagatct ggt                                           83

SEQ ID NO: 315            moltype = DNA   length = 79
FEATURE                   Location/Qualifiers
misc_feature              1..79
                          note = Synthetic construct
source                    1..79
                          mol_type = other DNA
                          organism = synthetic construct
SEQUENCE: 315
tggaaattct tccagaattg atactgactg tatgatgaga gctgcaggtg taatgaagac   60
cttctttttg agatctggt                                                79

SEQ ID NO: 316            moltype = DNA   length = 79
FEATURE                   Location/Qualifiers
misc_feature              1..79
                          note = Synthetic construct
source                    1..79
                          mol_type = other DNA
                          organism = synthetic construct
SEQUENCE: 316
tggaaattct tccagaattg atactgactg tatggtgaga gctgcaggtg taatgaagac   60
cttctttttg agatctggt                                                79

SEQ ID NO: 317            moltype = DNA   length = 78
FEATURE                   Location/Qualifiers
misc_feature              1..78
                          note = Synthetic construct
source                    1..78
                          mol_type = other DNA
                          organism = synthetic construct
SEQUENCE: 317
tggaaattct tccagaattg atactgactg taaatgagag ctgcaggtgt aatgaagacc   60
ttctttttga gatctggt                                                 78

SEQ ID NO: 318            moltype = DNA   length = 78
```

-continued

```
FEATURE              Location/Qualifiers
misc_feature         1..78
                     note = Synthetic construct
source               1..78
                     mol_type = other DNA
                     organism = synthetic construct
SEQUENCE: 318
tggaaattct tccagaattg atactgactg tatgtgagag ctgcaggtgt aatgaagacc  60
ttcttttttga gatctggt                                                78

SEQ ID NO: 319       moltype = DNA   length = 74
FEATURE              Location/Qualifiers
misc_feature         1..74
                     note = Synthetic construct
source               1..74
                     mol_type = other DNA
                     organism = synthetic construct
SEQUENCE: 319
tggaaattct tccagaattg atactgaaaa tgagagctgc aggtgtaatg aagaccttct  60
ttttgagatc tggt                                                     74

SEQ ID NO: 320       moltype = DNA   length = 74
FEATURE              Location/Qualifiers
misc_feature         1..74
                     note = Synthetic construct
source               1..74
                     mol_type = other DNA
                     organism = synthetic construct
SEQUENCE: 320
tggaaattct tccagaattg atactgactg tatggactgc aggtgtaatg aagaccttct  60
ttttgagatc tggt                                                     74

SEQ ID NO: 321       moltype = DNA   length = 74
FEATURE              Location/Qualifiers
misc_feature         1..74
                     note = Synthetic construct
source               1..74
                     mol_type = other DNA
                     organism = synthetic construct
SEQUENCE: 321
tggaaattct tccagaattg atactgactg tgagagctgc aggtgtaatg aagaccttct  60
ttttgagatc tggt                                                     74

SEQ ID NO: 322       moltype = DNA   length = 73
FEATURE              Location/Qualifiers
misc_feature         1..73
                     note = Synthetic construct
source               1..73
                     mol_type = other DNA
                     organism = synthetic construct
SEQUENCE: 322
tggaaattct tccagaattg atactggtat gagagctgca ggtgtaatga agaccttctt  60
tttgagatct ggt                                                      73

SEQ ID NO: 323       moltype = DNA   length = 71
FEATURE              Location/Qualifiers
misc_feature         1..71
                     note = Synthetic construct
source               1..71
                     mol_type = other DNA
                     organism = synthetic construct
SEQUENCE: 323
tggaaattct tccagaattg atactgactg tagctgcagg tgtaatgaag accttctttt  60
tgagatctgg t                                                        71

SEQ ID NO: 324       moltype = DNA   length = 83
FEATURE              Location/Qualifiers
misc_feature         1..83
                     note = Synthetic construct
source               1..83
                     mol_type = other DNA
                     organism = synthetic construct
SEQUENCE: 324
tggaaattct tccagaattg atactgactg tatggaaaat gagagctgca ggtgtaatga  60
agaccttctt tttgagatct ggt                                           83

SEQ ID NO: 325       moltype = DNA   length = 75
FEATURE              Location/Qualifiers
misc_feature         1..75
```

-continued

```
                          note = Synthetic construct
source                    1..75
                          mol_type = other DNA
                          organism = synthetic construct
SEQUENCE: 325
tggaaattct tccagaattg atactgactg tatggaaact gcggtgtaat gaagaccttc   60
tttttgagat ctggt                                                    75

SEQ ID NO: 326            moltype = DNA  length = 76
FEATURE                   Location/Qualifiers
misc_feature              1..76
                          note = Synthetic construct
source                    1..76
                          mol_type = other DNA
                          organism = synthetic construct
SEQUENCE: 326
tggaaattct tccagaattg atactgactg tatgagagct gcaggtgtaa tgaagacctt   60
ctttttgaga tctggt                                                   76

SEQ ID NO: 327            moltype = DNA  length = 74
FEATURE                   Location/Qualifiers
misc_feature              1..74
                          note = Synthetic construct
source                    1..74
                          mol_type = other DNA
                          organism = synthetic construct
SEQUENCE: 327
tggaaattct tccagaatta atactgactg tgagagctgc aggtgtaatg aagaccttct   60
ttttgagatc tggt                                                     74

SEQ ID NO: 328            moltype = DNA  length = 73
FEATURE                   Location/Qualifiers
misc_feature              1..73
                          note = Synthetic construct
source                    1..73
                          mol_type = other DNA
                          organism = synthetic construct
SEQUENCE: 328
tggaaattct tccagaattg atactgactg gagagctgca ggtgtaatga agaccttctt   60
tttgagatct ggt                                                      73

SEQ ID NO: 329            moltype = DNA  length = 72
FEATURE                   Location/Qualifiers
misc_feature              1..72
                          note = Synthetic construct
source                    1..72
                          mol_type = other DNA
                          organism = synthetic construct
SEQUENCE: 329
tggaaattct tccagaattg atactgactg agagctgcag gtgtaatgaa gaccttcttt   60
ttgagatctg gt                                                       72

SEQ ID NO: 330            moltype = DNA  length = 68
FEATURE                   Location/Qualifiers
misc_feature              1..68
                          note = Synthetic construct
source                    1..68
                          mol_type = other DNA
                          organism = synthetic construct
SEQUENCE: 330
tggaaattct tccagaattg atactgactg ctgcaggtgt aatgaagacc ttctttttga   60
gatctggt                                                            68

SEQ ID NO: 331            moltype = DNA  length = 65
FEATURE                   Location/Qualifiers
misc_feature              1..65
                          note = Synthetic construct
source                    1..65
                          mol_type = other DNA
                          organism = synthetic construct
SEQUENCE: 331
tggaaattct tccagaattg atactgactg tatgtgtaat gaagaccttc ttttgagat   60
ctggt                                                              65

SEQ ID NO: 332            moltype = DNA  length = 39
FEATURE                   Location/Qualifiers
misc_feature              1..39
                          note = Synthetic construct
source                    1..39
```

```
                          mol_type = other DNA
                          organism = synthetic construct
SEQUENCE: 332
tggaaattct tccagaattg atactttttg agatctggt                              39

SEQ ID NO: 333           moltype = AA   length = 24
FEATURE                  Location/Qualifiers
REGION                   1..24
                         note = Synthetic construct
source                   1..24
                         mol_type = protein
                         organism = synthetic construct
SEQUENCE: 333
RNNRNNRNNR NNNNYNNYNN YNNY                                              24

SEQ ID NO: 334           moltype = AA   length = 24
FEATURE                  Location/Qualifiers
REGION                   1..24
                         note = Synthetic construct
source                   1..24
                         mol_type = protein
                         organism = synthetic construct
SEQUENCE: 334
RNNRNNRNNR NNNNYNNYNN YNNY                                              24

SEQ ID NO: 335           moltype = DNA   length = 20
FEATURE                  Location/Qualifiers
misc_feature             1..20
                         note = Synthetic construct
source                   1..20
                         mol_type = other DNA
                         organism = synthetic construct
SEQUENCE: 335
tccaaaacca tggtttacag                                                   20

SEQ ID NO: 336           moltype = DNA   length = 20
FEATURE                  Location/Qualifiers
misc_feature             1..20
                         note = Synthetic construct
source                   1..20
                         mol_type = other DNA
                         organism = synthetic construct
SEQUENCE: 336
tccaaaacca tggtttacag                                                   20

SEQ ID NO: 337           moltype = DNA   length = 20
FEATURE                  Location/Qualifiers
misc_feature             1..20
                         note = Synthetic construct
source                   1..20
                         mol_type = other DNA
                         organism = synthetic construct
SEQUENCE: 337
tccaaaacca tggtttacag                                                   20

SEQ ID NO: 338           moltype = DNA   length = 20
FEATURE                  Location/Qualifiers
misc_feature             1..20
                         note = Synthetic construct
source                   1..20
                         mol_type = other DNA
                         organism = synthetic construct
SEQUENCE: 338
tccaaaacca tggtttacag                                                   20

SEQ ID NO: 339           moltype = DNA   length = 20
FEATURE                  Location/Qualifiers
misc_feature             1..20
                         note = Synthetic construct
source                   1..20
                         mol_type = other DNA
                         organism = synthetic construct
SEQUENCE: 339
tccaaaacca tggtttacag                                                   20

SEQ ID NO: 340           moltype = DNA   length = 38
FEATURE                  Location/Qualifiers
misc_feature             1..38
                         note = Synthetic construct
```

-continued

```
variation            17..18
                     note = n is a, c, g, or t
variation            21..22
                     note = n is a, c, g, or t
source               1..38
                     mol_type = other DNA
                     organism = synthetic construct
SEQUENCE: 340
ggaggcgtgt ccaaaannat nntttacagc acgcctcc                    38

SEQ ID NO: 341       moltype = AA  length = 144
FEATURE              Location/Qualifiers
REGION               1..144
                     note = Synthetic construct
source               1..144
                     mol_type = protein
                     organism = synthetic construct
SEQUENCE: 341
MRLFGYARVS TSQQSLDIQV RALKDAGVKA NRIFTDKASG SSCDRKGLDL LRMKVEEGDV  60
ILVKKLDRLG RDTADMIQLI KEFDAQGVSI RFIDDGISTD GEMGKMVVTI LSAVAQAERQ  120
RILERTNEGR QEAMAKGVVF GRKR                                         144

SEQ ID NO: 342       moltype = AA  length = 141
FEATURE              Location/Qualifiers
REGION               1..141
                     note = Synthetic construct
source               1..141
                     mol_type = protein
                     organism = synthetic construct
SEQUENCE: 342
MLIGYVRVST NDQNTDLQRN ALVCAGCEQI FEDKLSGTRT DRPGLKRALK RLQKGDTLVV  60
WKLDRLGRSM KHLISLVGEL RERGINFRSL TDSIDTSSPM GRFFFHVMGA LAEMERELII  120
ERTMAGLAAA RNKGRIGGRP P                                            141

SEQ ID NO: 343       moltype = DNA  length = 44
FEATURE              Location/Qualifiers
misc_feature         1..44
                     note = Synthetic construct
variation            2..3
                     note = n is a, c, g, or t
variation            5..6
                     note = n is a, c, g, or t
variation            8..9
                     note = n is a, c, g, or t
variation            11..16
                     note = n is a, c, g, or t
variation            21
                     note = n is a, c, g, or t
variation            24
                     note = n is a, c, g, or t
variation            29..34
                     note = n is a, c, g, or t
variation            36..37
                     note = n is a, c, g, or t
variation            39..40
                     note = n is a, c, g, or t
variation            42..43
                     note = n is a, c, g, or t
source               1..44
                     mol_type = other DNA
                     organism = synthetic construct
SEQUENCE: 343
rnnrnnrnnr nnnnnnaaab nwwnvtttnn nnnnynnynn ynny               44

SEQ ID NO: 344       moltype = DNA  length = 44
FEATURE              Location/Qualifiers
misc_feature         1..44
                     note = Synthetic construct
source               1..44
                     mol_type = other DNA
                     organism = synthetic construct
SEQUENCE: 344
gctgatgcag atacagaaac caaggttttc ttacttgctg ctgc               44

SEQ ID NO: 345       moltype = DNA  length = 44
FEATURE              Location/Qualifiers
misc_feature         1..44
                     note = Synthetic construct
source               1..44
```

-continued

```
                            mol_type = other DNA
                            organism = synthetic construct
SEQUENCE: 345
gtggatggag cagccaatag gttccttttcc tcccccttag cccc                      44

SEQ ID NO: 346          moltype = DNA   length = 44
FEATURE                 Location/Qualifiers
misc_feature            1..44
                            note = Synthetic construct
source                  1..44
                            mol_type = other DNA
                            organism = synthetic construct
SEQUENCE: 346
agggaagtca atccagaaac catcctttat cccttcctgt cctt                       44

SEQ ID NO: 347          moltype = DNA   length = 44
FEATURE                 Location/Qualifiers
misc_feature            1..44
                            note = Synthetic construct
source                  1..44
                            mol_type = other DNA
                            organism = synthetic construct
SEQUENCE: 347
ggaaatgtaa aagtagaaac taaagtttct gctttcattc ttcc                       44

SEQ ID NO: 348          moltype = DNA   length = 44
FEATURE                 Location/Qualifiers
misc_feature            1..44
                            note = Synthetic construct
source                  1..44
                            mol_type = other DNA
                            organism = synthetic construct
SEQUENCE: 348
ggaagaagga tgagagaaac taacctttgt ggaacccctg cagc                       44

SEQ ID NO: 349          moltype = DNA   length = 44
FEATURE                 Location/Qualifiers
misc_feature            1..44
                            note = Synthetic construct
source                  1..44
                            mol_type = other DNA
                            organism = synthetic construct
SEQUENCE: 349
aacggcagaa gaagaaaaat tatactttct tttccattgt tttc                       44

SEQ ID NO: 350          moltype = DNA   length = 44
FEATURE                 Location/Qualifiers
misc_feature            1..44
                            note = Synthetic construct
source                  1..44
                            mol_type = other DNA
                            organism = synthetic construct
SEQUENCE: 350
gaggtaaata cttgataaat gttgctttttt tcccccatta ccct                      44

SEQ ID NO: 351          moltype = DNA   length = 44
FEATURE                 Location/Qualifiers
misc_feature            1..44
                            note = Synthetic construct
source                  1..44
                            mol_type = other DNA
                            organism = synthetic construct
SEQUENCE: 351
attgtggatg gagtaaaaat gatcctttaa tacatttcta catt                       44

SEQ ID NO: 352          moltype = DNA   length = 44
FEATURE                 Location/Qualifiers
misc_feature            1..44
                            note = Synthetic construct
source                  1..44
                            mol_type = other DNA
                            organism = synthetic construct
SEQUENCE: 352
ataggagaaa atttggaaag tataattttt cagactactc tttt                       44

SEQ ID NO: 353          moltype = DNA   length = 43
FEATURE                 Location/Qualifiers
misc_feature            1..43
                            note = Synthetic construct
```

-continued

```
source                    1..43
                          mol_type = other DNA
                          organism = synthetic construct
SEQUENCE: 353
acagaagaca ttaagaaaac ctaacttgac ctcctatggt tcc                      43

SEQ ID NO: 354           moltype = DNA  length = 44
FEATURE                  Location/Qualifiers
misc_feature             1..44
                         note = Synthetic construct
source                   1..44
                         mol_type = other DNA
                         organism = synthetic construct
SEQUENCE: 354
ggcaggacag ctaactaatg aaaggtttgg tgtgtgtctg tctt                      44

SEQ ID NO: 355           moltype = DNA  length = 44
FEATURE                  Location/Qualifiers
misc_feature             1..44
                         note = Synthetic construct
source                   1..44
                         mol_type = other DNA
                         organism = synthetic construct
SEQUENCE: 355
agggatgagg cctcataaag taaagttttt tgtttgtttg tttc                      44

SEQ ID NO: 356           moltype = DNA  length = 44
FEATURE                  Location/Qualifiers
misc_feature             1..44
                         note = Synthetic construct
source                   1..44
                         mol_type = other DNA
                         organism = synthetic construct
SEQUENCE: 356
acagtcaaag tatttgaaag ttaacttttt tcgtcagctc ttcc                      44

SEQ ID NO: 357           moltype = DNA  length = 44
FEATURE                  Location/Qualifiers
misc_feature             1..44
                         note = Synthetic construct
source                   1..44
                         mol_type = other DNA
                         organism = synthetic construct
SEQUENCE: 357
gaaattgtgg acaattaaat tatcctttct gggcccctta tttc                      44

SEQ ID NO: 358           moltype = DNA  length = 44
FEATURE                  Location/Qualifiers
misc_feature             1..44
                         note = Synthetic construct
source                   1..44
                         mol_type = other DNA
                         organism = synthetic construct
SEQUENCE: 358
gaaattggaa ggaaaaaaat tatcctttat ggtgtaatac ttat                      44

SEQ ID NO: 359           moltype = DNA  length = 44
FEATURE                  Location/Qualifiers
misc_feature             1..44
                         note = Synthetic construct
source                   1..44
                         mol_type = other DNA
                         organism = synthetic construct
SEQUENCE: 359
aaaacagctg gctttgaaag gaaacttta actactatcc tgcc                       44

SEQ ID NO: 360           moltype = DNA  length = 44
FEATURE                  Location/Qualifiers
misc_feature             1..44
                         note = Synthetic construct
source                   1..44
                         mol_type = other DNA
                         organism = synthetic construct
SEQUENCE: 360
atagtaagtg ctcaataaat gttcgtttat atcatcattg tggc                      44

SEQ ID NO: 361           moltype = DNA  length = 44
FEATURE                  Location/Qualifiers
misc_feature             1..44
```

-continued

```
                        note = Synthetic construct
source                  1..44
                        mol_type = other DNA
                        organism = synthetic construct
SEQUENCE: 361
aaagatggaa caaacaaaat taaggtttag tacattataa ttcc                      44

SEQ ID NO: 362          moltype = DNA  length = 43
FEATURE                 Location/Qualifiers
misc_feature            1..43
                        note = Synthetic construct
source                  1..43
                        mol_type = other DNA
                        organism = synthetic construct
SEQUENCE: 362
gcgggaggcg tgtccaaacc atggtttaca gcacgcctcc cgc                       43

SEQ ID NO: 363          moltype = DNA  length = 44
FEATURE                 Location/Qualifiers
misc_feature            1..44
                        note = Synthetic construct
source                  1..44
                        mol_type = other DNA
                        organism = synthetic construct
SEQUENCE: 363
gctgatgcag atcgagaaac caaggttttc ttacttgctg ctgc                      44

SEQ ID NO: 364          moltype = DNA  length = 44
FEATURE                 Location/Qualifiers
misc_feature            1..44
                        note = Synthetic construct
source                  1..44
                        mol_type = other DNA
                        organism = synthetic construct
SEQUENCE: 364
gtggatggag cagccaatag gttcctttcc tcccccttag cccc                      44

SEQ ID NO: 365          moltype = DNA  length = 44
FEATURE                 Location/Qualifiers
misc_feature            1..44
                        note = Synthetic construct
source                  1..44
                        mol_type = other DNA
                        organism = synthetic construct
SEQUENCE: 365
agggaagtca atccagaaac catcctttat cccttcctgt cctt                      44

SEQ ID NO: 366          moltype = DNA  length = 35
FEATURE                 Location/Qualifiers
misc_feature            1..35
                        note = Synthetic construct
source                  1..35
                        mol_type = other DNA
                        organism = synthetic construct
SEQUENCE: 366
agatacagaa accgttttct tacttgctgc tggcc                                35

SEQ ID NO: 367          moltype = DNA  length = 38
FEATURE                 Location/Qualifiers
misc_feature            1..38
                        note = Synthetic construct
source                  1..38
                        mol_type = other DNA
                        organism = synthetic construct
SEQUENCE: 367
tcagggaagt catcctttat cccttcctgt ccttagct                             38

SEQ ID NO: 368          moltype = DNA  length = 20
FEATURE                 Location/Qualifiers
misc_feature            1..20
                        note = Synthetic construct
variation               8..9
                        note = n is a, c, g, or t
variation               12..13
                        note = n is a, c, g, or t
source                  1..20
                        mol_type = other DNA
                        organism = synthetic construct
SEQUENCE: 368
```

-continued

```
tccasssnna tnnsssacag                                        20

SEQ ID NO: 369          moltype =    length =
SEQUENCE: 369
000
```